US009717778B2

(12) United States Patent
Tachas

(10) Patent No.: US 9,717,778 B2
(45) Date of Patent: Aug. 1, 2017

(54) COMBINATION THERAPY

(71) Applicant: Antisense Therapeutics Ltd, Toorak, Victoria (AU)

(72) Inventor: George Tachas, Kew (AU)

(73) Assignee: Antisense Therapeutics Ltd., Toorak, Victoria (AU)

( * ) Notice: Subject to any disclaimer, the term of this patent is extended or adjusted under 35 U.S.C. 154(b) by 0 days.

(21) Appl. No.: 14/376,390

(22) PCT Filed: Feb. 4, 2013

(86) PCT No.: PCT/AU2013/000095
§ 371 (c)(1),
(2) Date: Aug. 1, 2014

(87) PCT Pub. No.: WO2013/113074
PCT Pub. Date: Aug. 8, 2013

(65) Prior Publication Data

US 2014/0378379 A1 Dec. 25, 2014

Related U.S. Application Data

(60) Provisional application No. 61/594,532, filed on Feb. 3, 2012.

(51) Int. Cl.

| | |
|---|---|
| ***A61K 45/06*** | (2006.01) |
| ***A61K 48/00*** | (2006.01) |
| ***A61P 5/08*** | (2006.01) |
| ***A61K 38/27*** | (2006.01) |
| ***A61K 31/7088*** | (2006.01) |
| ***A61K 31/7115*** | (2006.01) |
| ***A61K 31/712*** | (2006.01) |

(52) U.S. Cl.
CPC .......... *A61K 38/27* (2013.01); *A61K 31/7088* (2013.01); *A61K 31/712* (2013.01); *A61K 31/7115* (2013.01); *A61K 45/06* (2013.01)

(58) Field of Classification Search
USPC ........... 435/6.1, 91.1, 91.31, 455, 458, 6.11; 514/1, 2, 44, 8.6, 8.7; 536/23.1, 24.5
See application file for complete search history.

(56) References Cited

U.S. PATENT DOCUMENTS

| | | | | |
|---|---|---|---|---|
| 5,534,617 A | 7/1996 | Cunningham et al. | | |
| 2005/0123558 A1 | 6/2005 | Ross et al. | | |
| 2013/0316948 A1 * | 11/2013 | Longo | G01N 33/574 | 514/7.6 |
| 2014/0296145 A1 * | 10/2014 | Cho | A61K 38/21 | 514/11.4 |

FOREIGN PATENT DOCUMENTS

| | | | |
|---|---|---|---|
| EP | 1156123 A1 | | 11/2001 |
| JP | 11-512298 | | 10/1999 |
| JP | 2005-525106 | | 8/2005 |
| JP | 2007-524373 | | 8/2007 |
| JP | 2009-539803 | | 11/2009 |
| WO | WO/2004/078922 | * | 2/2004 |
| WO | WO 2004/078922 A3 | | 9/2004 |

OTHER PUBLICATIONS

"Positive New Animal Data on ATL1103: Data presented today at the Thirteenth International Pituitary Congress", report published on Jun. 14, 2013 by Antisense Therapeutics.
International Search Report and Written Opinion issued for PCT/AU2013/000095 on Apr. 17, 2013.
International Preliminary Report on Patentability issued for PCT/AU2013/000095 on Aug. 14, 2014.
Extended European Search Report issued for corresponding European application No. 13743020.3 on Oct. 1, 2015.
ATL1103 Summary Background and Development Update (2011) Antisense Therapeutics.
ATL1103 in clinical development for diseases associated with growth hormone/IGF-I activity (2011) Antisense Therapeutics.

* cited by examiner

*Primary Examiner* — Jane Zara
(74) *Attorney, Agent, or Firm* — Knobbe, Martens, Olson & Bear, LLP

(57) ABSTRACT

The present disclosure relates to a method for treatment or prevention of diseases have an increased level of insulin-like growth factor I (IGF-I). The method comprises administration of a growth hormone (GH) variant having antagonistic activity in combination with an oligonucleotide targeted to growth hormone receptor (GHR) to a subject in need.

21 Claims, No Drawings

COMBINATION THERAPY

This application is the U.S. National Phase under 35 U.S.C. §371 of International Application No. PCT/AU2013/000095, filed Feb. 4, 2013, which claims priority to the U.S. Patent Application No. 61/594532, filed Feb. 3, 2012.

FIELD OF THE INVENTION

The present disclosure relates to a method for treatment or prevention of diseases caused by and/or associated with an increased level of insulin-like growth factor I (IGF-I) that relies on administration of a growth hormone (GH) variant having antagonistic activity in combination with an antisense oligonucleotide targeted to the growth hormone receptor (GHR).

BACKGROUND OF THE INVENTION

Growth hormone (GH), released by the pituitary, is a member of a cascade of hormones that regulate growth of the body and its organs. Secretion of GH into the bloodstream is followed by binding to growth hormone receptor (GHR) on many cell and organ types. Growth hormone signaling is mediated by this interaction. Growth hormone signaling causes the production of another hormone, insulin-like growth factor I (IGF-I), which is produced in the liver, adipose tissue, kidney and other organs and secreted into the bloodstream. About 75% of serum IGF-I is produced in the liver in response to GH stimulation. Many disorders are caused by and/or associated with increased GH levels and/or increased IGF-I levels in plasma and/or tissues including acromegaly, gigantism, retinopathy, macular degeneration, nephropathy, diabetes and cancers. The role of GH and IGF-I in these and other disorders is well recognized. The role of IGF-I in mediating many GH effects is well recognized and this interrelationship is referred to as the GH/IGF-I axis. In a normal feedback loop, IGF-I also causes the production of GH by the pituitary to be reduced. There is a need for treatments that reduce IGF-I levels in a subject, for example, more effectively, safely, conveniently and/or at reduced cost.

Somavert, a GH variant having antagonistic activity is approved in the treatment of acromegaly for its ability to reduce serum IGF-I levels in a patient. For a review of current practices for the treatment of acromegaly see Guistina et al., 2011. Briefly, in acromegaly, surgery is first used in treatment to debulk the tumor and reduce the pituitary tumor's GH secretion and reduce production of IGF-I in the serum. Medicinal treatments are also used to reduce serum IGF-I and in some cases also reduce GH release. All treatments use a medicinal monotherapy or a combination therapy where the combination is directed to two different biological targets. First line medicinal treatment is with a somatostatin (SST) agonist, and this treatment is started initially at low doses and escalated to doses that reduce GH and normalize the patients serum IGF-I. When an SST agonist treatment fails, a dopamine agonist is used in combination with a SST agonist, or Somavert is used in combination with a SST agonist or Somavert is used as a monotherapy. Somavert doses typically start with a loading dose of 40 mg on the first day, and 10 mg daily doses, and these daily doses are escalated until normalization of serum IGF-I, with up to 30 mg daily doses approved. There are failures with the highest approved daily doses of Somavert, and clinicians have escalated beyond approved doses. Somavert is however, prohibitively expensive, requires inconvenient daily (once or twice daily) injection, is a lyophilized powder and needs reconstitution, has safety issues causing injection site reactions and an increase in liver enzymes, and produces undesirable increases in GH. Thus, clinicians typically do not seek to use Somavert in different combination therapies to those outlined above. In patients where first line therapy using SST has failed or in patients where Somavert monotherapy or combination with SST has failed, clinicians are seeking new more effective monotherapies. Combination therapies using, for example, Somavert are only considered with a drug directed to a different biological target and typically an SST agonist, as SST agonists have potential to reduce tumor size.

SUMMARY OF THE INVENTION

The present inventors have now made the surprising finding that a growth hormone (GH) variant having antagonistic activity and an antisense oligonucleotide targeted to GHR act synergistically to reduce insulin-like growth factor I (IGF-I) levels in a subject. In other words, the combined administration of the GH variant and the oligonucleotide to GHR exhibits greater than additive effect. This is surprising, particularly considering that there are no expected synergies with using drugs to the same target, and one can just escalate the dose of the drug to the target. Accordingly, the present disclosure provides a method for treatment or prevention of a disease caused by and/or associated with an increased level of IGF-I, the method comprising administering to a subject in need thereof, a GH variant having GH antagonistic activity in combination with an oligonucleotide 8 to 80 nucleobases in length targeted to a nucleic acid encoding GHR so as to inhibit expression of the GHR, thereby reducing the level of IGF-I in the subject. In one embodiment, the level of serum/plasma IGF-I is reduced.

In one embodiment, the method further comprises identifying a subject in need of a reduction in said subject's GHR and/or IGF-I levels, for example serum/plasma IGF-I levels.

In one embodiment, the disease is acromegaly, diabetic retinopathy, diabetic nephropathy, or an IGF-I positive and/or IGF-I and/or GH responsive cancer such as prostate, myeloma, lung, breast, or colon cancer.

In one embodiment, the GH variant is a human GH variant in which amino acid Gly120 is deleted or substituted with an amino acid, for example, Arg, Trp, Pro, Lys or Leu. In one embodiment, the Gly120 is substituted with Lys.

In a further embodiment, the human GH variant comprises the following set of amino acid substitutions: H18D, H21N, R167N, K168A, D171S, K172R, E174S, I179T.

In one embodiment, the nucleic acid encodes human GHR. The nucleic acid may have a nucleotide sequence as shown in SEQ ID NO:4 or SEQ ID NO:5.

In one embodiment, the oligonucleotide is from 12 to 50 nucleobases in length. In another embodiment, the oligonucleotide is from 15 to 30 nucleobases in length.

In one embodiment, the oligonucleotide is a DNA oligonucleotide. In another embodiment, the oligonucleotide is a RNA oligonucleotide, for example, a short interfering RNA (siRNA). In another embodiment, the oligonucleotide is a chimeric oligonucleotide.

In one embodiment, the oligonucleotide has at least 70% complementarity with the nucleic acid encoding GHR. In another embodiment, the oligonucleotide has at least 80% complementarity with the nucleic acid encoding GHR. In another embodiment, the oligonucleotide has at least 90% complementarity with the nucleic acid encoding GHR. In another embodiment, the oligonucleotide has at least 95% complementarity, for example, 96%, 97%, 98%, or 99% complementarity with the nucleic acid encoding GHR.

In one embodiment, the oligonucleotide comprises at least an 8 consecutive nucleobase portion of SEQ ID NO: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

In another embodiment, the oligonucleotide consists of the nucleobase sequence of SEQ ID NOs: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

In one embodiment, the oligonucleotide consists of the nucleobase sequence of SEQ ID NO:6.

In one embodiment, the oligonucleotide specifically hybridises with a region encoding GHR, wherein the region comprises a translation initiation codon, a termination codon, a coding region, a 5' untranslated region, a 3' untranslated region, an intron:exon junction or an exon:intron junction. In one embodiment, the region comprises at least an 8 consecutive nucleobase portion of a sequence selected from SEQ ID NOs: 84-154.

In one embodiment, the oligonucleotide comprises at least an 8 consecutive nucleobase portion complementary to a region of SEQ ID NO:4 selected from the group consisting of nucleotides 260-339, 332-351 and 344-423 of SEQ ID NO:4.

In one embodiment, the oligonucleotide inhibits the expression of GHR and/or growth hormone binding protein (GHBP) by at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45%.

In one embodiment, the oligonucleotide comprises at least one modified internucleoside linkage, sugar moiety, or nucleobase. The oligonucleotide may, for example, comprise at least one 2'-O-methoxyethyl sugar moiety and/or at least one phosphorothioate internucleoside linkage and/or at least one 5-methylcytosine.

In one embodiment, the oligonucleotide consists of 20 linked nucleosides, wherein the oligonucleotide consists of a nucleobase of SEQ ID NO:6; and wherein the oligonucleotide consists of a ten deoxynucleotide region flanked on both the 5' end and the 3' end of said ten deoxynucleotide region with five 2'-O-(2-methoxyethyl) nucleotides, and wherein each internucleoside linkage in the oligonucleotide is a phosphorothioate linkage, and wherein each cytosine in said oligonucleotide is a 5-methylcytosine.

The present disclosure also provides a method of reducing the level of IGF-I in a subject, the method comprising administering a GH variant having GH antagonistic activity in combination with an oligonucleotide 8 to 80 nucleobases in length targeted to a nucleic acid encoding GHR so as to inhibit expression of the GHR, thereby reducing the level of IGF-I in the subject. In one embodiment, the level of serum/plasma IGF-I is reduced.

In one embodiment, the method further comprises identifying a subject in need of a reduction in said subject's GHR and/or IGF-I levels, for example serum/plasma IGF-I levels.

The GH variant, the GHR and the oligonucleotide may be further characterized by any one of the above features.

The present disclosure also provides for use of a GH variant and an oligonucleotide 8 to 80 nucleobases in length targeted to a nucleic acid encoding GHR in the manufacture of a medicament for the treatment or prevention of a disease caused by and/or associated with an increased level of IGF-I. In one embodiment, the level of serum/plasma IGF-I is reduced.

In one embodiment, the disease is acromegaly, diabetic retinopathy, diabetic nephropathy, or an IGF-I positive cancer such as prostate, myeloma, lung, breast, or colon cancer.

The GH variant, the GHR and the oligonucleotide may be further characterized by any one of the above features.

The present disclosure also provides for use of a GH variant and an oligonucleotide 8 to 80 nucleobases in length targeted to a nucleic acid encoding GHR in the manufacture of a medicament for reducing the level of IGF-I in a subject.

The GH variant, the GHR and the oligonucleotide may be further characterized by any one of the above features.

The present disclosure also provides for a composition comprising a GH variant and an oligonucleotide 8 to 80 nucleobases in length targeted to a nucleic acid encoding GHR for the treatment or prevention of a disease caused by and/or associated with an increased level of IGF-I.

The GH variant, the GHR and the oligonucleotide may be further characterized by any one of the above features.

The present disclosure also provides for a composition comprising a GH variant and an oligonucleotide 8 to 80 nucleobases in length targeted to a nucleic acid encoding GHR for reducing the level of IGF-I in a subject.

The GH variant, the GHR and the oligonucleotide may be further characterized by any one of the above features.

Any embodiment herein shall be taken to apply mutatis mutandis to any other embodiment unless specifically stated otherwise.

The invention is hereinafter described by way of the following non-limiting Examples and with reference to the accompanying Figures.

Key to the Sequence Listing

SEQ ID NO:1 Wild-type human growth hormone (hGH) nucleotide sequence

SEQ ID NO:2 Wild-type hGH polypeptide sequence

SEQ ID NO:3 Somavert polypeptide sequence

SEQ ID NO:4 Human growth hormone receptor (hGHR) cDNA sequence

SEQ ID NO:5 hGHR gene sequence

SEQ ID NO:6-83 Oligonucleotides targeted to hGHR

SEQ ID NO:84-154 Target sequences of hGHR

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in antisense technology, recombinant technology, cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory (1988), and J. E. Coligan et al. (editors), Current Protocols in Immunology, John Wiley and Sons (including all updates until present).

The term "and/or", for example, "X and/or Y" shall be understood to mean either "X and Y" or "X or Y" and shall be taken to provide explicit support for both meanings or for either meaning.

As used herein, "about" or "approximately" shall generally mean within 20%, more preferably within 10%, and even more preferably within 5%, of a given value or range.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, group of steps or group of compositions of matter.

Treatment and Prevention of IGF-I Positive Diseases

The present invention provides methods useful in the prevention and/or treatment of a disease, disorder, or condition caused by and/or associated with an increased level of insulin-like growth factor I (IGF-I). As used herein, the term "treatment" refers to administering a pharmaceutical composition to effect an alteration or improvement of a disease, disorder, or condition. As used herein, the term "prevention" refers to administering a pharmaceutical composition to stop or hinder the development of at least one symptom of a disease, disorder, or condition. The subject targeted for treatment is a mammal, preferably a human. As used herein, "an increased level of insulin-like growth factor I (IGF-I)" includes a level above the normal range or in the normal range, for example, at the high end of the normal range, adjusted for age and sex.

The methods involve administration of a growth hormone (GH) variant having GH antagonistic activity and an oligonucleotide targeted to growth hormone receptor (GHR) to a subject. The "subject" can be any mammal, preferably a human. Although not wishing to be limited to the theory, the oligonucleotide acts to inhibit GHR expression in said subject, whilst the GH variant acts to prevent GH binding to the GHR, thereby reducing the level of IGF-I (which is produced in response to GH signalling) in the subject. Insulin-like growth factor I is a ubiquitous polypeptide important in proliferation, having potent mitogenic effects on a broad range of cells, and important in cell survival, regulating apoptosis on a broad range of cells.

Although not wishing to be limited to theory, the antisense oligonucleotide inhibits GHR expression at the RNA level whilst the GH variant may increase GHR RNA by feedback inhibition. In one embodiment, the oligonucleotide also acts to reduce growth hormone binding protein (GHBP) expression. The GHBP is the soluble extracellular portion of the GH receptor, derived by alternative mRNA splicing of the mRNA transcript (in for example, mice and rats) or proteolytic cleavage of the GHR (in for example, humans, cows and pigs).

In one embodiment, the treatment reduces or prevents occurrence of one or more symptoms of acromegaly, for example, reducing the increased serum IGF-I levels in acromegaly to normal levels, or reducing soft tissue swelling, enlargement of internal organs, extremities like overgrowth of the jaw, enlargement of hands and feet, deepening of the voice, thickening of skin, offensive body odor, articular cartilage problems, hyperphosphatemia, peripheral neuropathies, higher blood pressure, diabetes, heart disease, and cancer.

In another embodiment, the treatment reduces or prevents occurrence of one or more symptoms of retinopathy, for example, reducing new blood vessel formation and/or edema, blurred, double, or distorted vision, or difficulty reading, floaters or spots in vision, loss of vision or a shadow or veil across field of vision, pain, pressure, or constant redness of the eye.

In another embodiment, the treatment reduces or prevents occurrence of one or more symptoms of diabetic nephropathy, for example glomerula filtration, microalbuminuria, proteinuria, renal damage, swelling in the legs, nausea and vomiting, malaise, fatigue, headache, itching, frequent hiccups, unintended weight loss, swelling of the face, unintended weight gain due to fluid buildup, and high blood pressure.

In another embodiment, the treatment reduces the size and/or growth of a tumor or cancer (such as prostate, myeloma, lung, breast, or colon cancer) and/or delays progression of the tumor or cancer (such as prostate cancer) from androgen responsive/dependent to androgen unresponsive/independent. Tumor or cancer size and/or growth may be reduced, for example, by reducing the proliferation rate of the tumor/cancer cells, increasing the apoptotic rate of the tumor/cancer cells, modulating tumor/cancer cell signaling, chemosensitization, and/or inhibiting adhesion, anchorage, metastasis of the tumor/caner cells and/or transformation of cells, for example, prostate cells. The treatment may, for example, reduce IGF-I levels at the high end of the normal range to lower levels, and/or from the top quartile to the $2^{nd}$ quartile, $3^{rd}$ or $4^{th}$ quartile, and/or from the $2^{nd}$ quartile to the $3^{rd}$ or $4^{th}$ quartile as adjusted for age and sex. The treatment may reduce endocrine, autocrine or paracrine levels of IGF-I as antisense oligonucleotides and the GH variant may work in the tissues.

Growth Hormone Variant Having Growth Hormone Antagonistic Activity

The methods of the present disclosure rely on the use of growth hormone (GH) variants having GH antagonistic activity. In one example, the GH variant is a peptide or protein having a similarity in sequence and/or secondary structure to a vertebrate GH, including but not limited to, mammalian growth hormones such as human and bovine growth hormones.

GH is synthesized and secreted by the somatotroph cells of the anterior pituitary gland. The GH gene consists of 5 exons and 4 introns encoding a 217-amino acid precursor protein. The amino-terminal signal peptide is removed by proteolysis, yielding the mature single chain 191-amino acid polypeptide, with a molecular mass of 22 kDa. The 3-dimensional structure of human (h) GH and of GH from other mammalian species was established by X-ray crystallography (Ultsch et al., 1991; Ultsch et al., 1993; de Vos et al., 1992). The protein consists of four α-helices, with 20-30 amino acid residues bound together by stretches of non-helical chains which are packed together in an antiparallel bundle (Ultsch et al., 1994). It has been demonstrated that the 4 alpha helix bundle GH possesses two non-identical binding surfaces, but binds to similar receptor binding sites in an ordered sequence, with the initial binding site possessing a higher affinity (Site 1) (WO 92/21029). Site 2 binding is stabilized by a further inter-receptor interaction involving the "dimerization domain" in the lower of the two cytokine homology modules (Cunningham et al., 1991; de Vos et al., 1992; Chen et al., 1997).

In one embodiment, the GH variant comprises an alpha helix having an amino acid sequence homology of at least about 50% with the third alpha helix of a vertebrate GH. The other alpha helices of the wild-type GH may be omitted if this can be done without loss of GH antagonist activity. The use of the term "antagonist" is in a functional sense and is not intended to limit the disclosure to compounds having a particular mechanism of action. Suitable GH variants are described in U.S. Pat. Nos. 5,350,836 and 5,849,535.

Variant GH sequence notation defines the actual amino acid substitutions in the GH variant. For a variant, substitutions are indicated by a letter representing the wild-type residue (in single-letter code), a number indicating the amino acid position in the wild-type sequence, and a second letter indicating the substituted amino acid residue. For example, G120K indicates a mutation in which glycine at position 120 is substituted with lysine. Multiple mutants are indicated by a series of single mutants separated by commas.

In one embodiment, the growth hormone variant is an hGH variant. The DNA (SEQ ID NO:1) and amino acid (SEQ ID NO:2) sequences of wild-type hGH have been reported (Goeddel et al., 1979; Gray et al., 1985).

In one embodiment, the hGH variant comprises a mutation at amino acid Gly120. Gly120 may be deleted or substituted with an amino acid. In one example, the amino acid is selected from the group consisting of Arg, Trp, Pro, Lys and Leu. In a preferred example, the amino acid is Lys. This mutation disrupts Site 2 binding. An hGH variant comprising this mutation acts as an hGH antagonist.

In a further embodiment, the hGH variant comprises the following set of amino acid substitutions: H18D, H21N, R167N, K168A, D171S, K172R, E174S, I179T. These substitutions increase binding affinity for the hGH receptor at Site 1. An hGH variant including this set of amino acid substitutions acts as an hGH agonist in the absence of an additional modification that disrupts binding to the hGHR at Site 2.

In one embodiment, the hGH variant comprises a G120 amino acid deletion or substitution and amino acid substitutions H18D, H21N, R167N, K168A, D171S, K172R, E174S, I179T. In one embodiment, the hGH variant includes the following set of amino acid substitutions: H18D, H21N, G120K, R167N, K168A, D171S, K172R, E174S, I179T. In one embodiment, the hGH variant is Somavert® (Pegvisomant for injection) (SEQ ID NO:3) which is a protein with 191 amino acid residues to which several polyethylene glycol (PEG) polymers are covalently bound (van der Lely et al., 2001).

Mutagenesis

The DNA sequence encoding GH can be mutated at one or more selected codons. A mutation is defined as a substitution, deletion, or insertion of one or more nucleotides in the DNA encoding the GH that results in a change in the amino acid sequence of the GH as compared with the wild-type sequence of the GH. Preferably, at least one amino acid is substituted with any other amino acid in one or more regions of the protein.

Site-specific mutagenesis (Carter et al., 1986; Zoller et al., 1987), cassette mutagenesis (Wells et al., 1985), restriction selection mutagenesis (Wells et al., 1986), or other known techniques can be performed on GH DNA to produce the variant DNA that encodes for the changes in the amino acid sequence.

Oligonucleotide-mediated mutagenesis is the preferred method for preparing substitution, deletion, or insertion variants of GH. The technique is well known in the art as described by Zoller et al., 1987. Briefly, an oligonucleotide encoding the desired mutation is hybridized to a DNA template which comprises the single-stranded form of the wild-type DNA sequence for GH. After hybridization, a DNA polymerase is used to synthesize an entire second complementary strand of the template, and thus incorporates the oligonucleotide primer and codes for the selected alteration in the GH DNA.

Generally, oligonucleotides of at least 25 nucleotides in length are used. Although smaller oligonucleotides can be employed, an optimal oligonucleotide has 12 to 15 nucleotides that are complementary to the template on either side of the nucleotide(s) coding for the mutation(s). This ensures that the oligonucleotide hybridizes properly to the single-stranded DNA template molecule. The oligonucleotides are readily synthesized using techniques known in the art such as that described by Crea et al., 1978.

The DNA template can only be generated by those vectors that are either derived from bacteriophage M13 vectors (the commercially available M13mp18 and M13mp19 vectors are suitable), or those vectors that contain a single-stranded phage origin of replication as described by Vieira and Messing, 1987. Thus, the DNA that is to be mutated must be inserted into one of these vectors in order to generate single-stranded template. Production of the single-stranded template is described in sections 4.21-4.41 of Sambrook et al., supra.

To alter the wild-type DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form, and the other strand (the original template) encodes the wild-type GH. This heteroduplex molecule is then transformed into a suitable host cell, usually a prokaryote such as *Escherichia coli* JM101. After the cells are grown, they are plated onto agarose plates and screened using the oligonucleotide primer radiolabeled with 32-phosphate to identify the bacterial colonies that contain the mutated DNA.

The method described immediately above can be modified such that a homoduplex molecule is created wherein both strands of the DNA contain the mutation(s). The modifications are as follows: The single-stranded oligonucleotide is annealed to the single-stranded DNA template as described above. A mixture of three deoxyribonucleotides, deoxyriboadenosine (dATP), deoxyriboguanosine (dGTP), and deoxyribothymidine (dTTP) is combined with a modified thio-deoxyribocytosine called dCTP-(aS). This mixture is added to the template-oligonucleotide complex. Upon addition of DNA polymerase to this mixture, a strand of DNA identical to the template except for the mutated base(s) is generated. In addition, this new strand of DNA contains dCTP-(AS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s)

to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acids to be substituted can be generated in one of several ways. If the amino acids are located close together in the polypeptide chain, they can be mutated simultaneously using one oligonucleotide that codes for all of the desired amino acid substitutions. If however, the amino acids are located some distance from each other (separated by more than about ten amino acids), it is more difficult to generate a single oligonucleotide that encodes all of the desired changes. Instead, one of two alternative methods can be employed.

In the first method, a separate oligonucleotide is generated for each amino acid to be substituted. The oligonucleotides are then annealed to the single-stranded template DNA simultaneously, and the second strand of DNA that is synthesized from the template encodes all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing substitution, deletion, and insertion variants of DNA encoding GH. The method is based on that described by Wells et al., 1985. The starting material is a plasmid (or other vector) comprising the GH DNA to be mutated. The nucleotide(s) in the GH DNA to be mutated are identified, optimally, there is a unique restriction endonuclease site on each side of the identified mutation site(s); however, this is not a requirement. If no such restriction sites exist, they can be generated using the above-described oligonucleotide-mediated mutagenesis method to introduce them at appropriate locations in the GH DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of GH.

Of course, other methods can be employed to produce GH variants such as the in vitro chemical synthesis of the desired GH variant (Barany et al., The Peptides, E. Gross and J. Meienhofer (editors), Academic Press, New York (1979) Volume 2, pp. 3-254).

Production of GH Variants

The GH variants can be conveniently produced by standard recombinant techniques. More specifically, a GH variant can be expressed using a vector-host cell system.

The GH DNA can be inserted into an appropriate plasmid or vector that can subsequently be used to transform a host cell. Prokaryotes are preferred for expressing DNA sequences to produce the GH variants. For example, *E. coli* K12 strain 294 (ATCC No. 31446) can be used, as well as *E. coli* B, *E. coli* X1776 (ATCC No. 31537), *E. coli* c600 and c600hfl, and *E. coli* W3110 ($F^-$, $\gamma^-$, prototrophic, ATCC No. 27325), Bacilli such as *Bacillus subtilis*, and other Enterobacteriaceae such as *Salmonella typhimurium* or *Serratia marcescens*, and various *Pseudomonas* species. A preferred prokaryote is *E. coli* W3110 (ATCC 27325). When expressed intracellularly in prokaryotes, the GH typically contains an N-terminal methionine or a formyl methionine and is not glycosylated. When expressed extracellularly into the medium or the periplasm, the GH does not contain a N-terminal methionine. These examples are, of course, intended to be illustrative rather than limiting.

In addition to prokaryotes, eukaryotic organisms, such as yeast cultures, or cells derived from multicellular organisms, can be used. In principle, any such cell culture is workable. However, interest has been greatest in vertebrate cells, and propagation of vertebrate cells in culture has become a repeatable procedure. Examples of such useful host cell lines are VERO, HeLa, Chinese hamster ovary (CHO), W138, BHK, COS-7, and MDCK cell lines.

In general, plasmid vectors containing replication and control sequences that are derived from species compatible with the host cell are used. The vector ordinarily carries a replication site, as well as sequences that encode proteins that are capable of providing phenotypic selection in transformed cells. For example, *E. coli* can be transformed using pBR322, a plasmid derived from an *E. coli* species (Mandel et al., 1970). Plasmid pBR322 contains genes for ampicillin and tetracycline resistance and thus provides easy means for selection. One preferred vector is pBO475. This vector contains origins of replication for phage and *E. coli* that allow it to be shuttled between such hosts, thereby facilitating mutagenesis and expression. "Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector can be a plasmid, a phage particle, or simply a potential genomic insert. Once transformed into a suitable host, the vector can replicate and function independently of the host genome, or can, in some instances, integrate into the genome itself. In the present specification, "plasmid" and "vector" are sometimes used interchangeably as the plasmid is the most commonly used form of vector at present. However, use of other forms of expression vectors which serve equivalent functions and which are, or become, known in the art fall within the scope of the present disclosure.

"Operably linked" when describing the relationship between two DNA or polypeptide regions simply means that they are functionally related to each other. For example, a presequence is operably linked to a peptide if it functions as a signal sequence, participating in the secretion of the mature form of the protein, most probably involving cleavage of the signal sequence. A promoter is operably linked to a coding sequence if it controls the transcription of the sequence; a ribosome binding site is operably linked to a coding sequence if it is positioned so as to permit translation.

Host cells containing a GH variant expression vector are cultured under conditions suitable for cell growth and for expression of the GH variant. In particular, the culture medium contains appropriate nutrients and growth factors for the host cell employed. The nutrients and growth factors required for growth of a selected host cell are, in many instances, well known or can be readily determined empirically by those skilled in the art. Suitable culture conditions for mammalian host cells, for instance, are described in Mammalian Cell Culture, J. P. Mather (editor), Plenum Press (1984) and Barnes and Sato, 1980.

In addition, the culture conditions should allow transcription, translation, and protein transport between cellular compartments. Factors that affect these processes are well-known and include, for example, DNA/RNA copy number; factors that stabilize RNA; nutrients, supplements, and transcriptional inducers or repressors present in the culture medium; temperature, pH, and osmolality of the culture; and cell density. The adjustment of these factors to promote expression in a particular vector-host cell system is within the level of skill in the art.

The cell culture procedure employed in the production of a GH variant can be any of a number of well-known procedures for large- or small-scale production of proteins. These include, but are not limited to, the use of: a fluidized bed bioreactor, a hollow fiber bioreactor, a roller bottle culture system, and a stirred tank bioreactor system. A GH variant can be produced, for instance, in a batch, fed-batch, or continuous mode process.

Methods for recovery of recombinant proteins produced as described above are well-known and vary depending on the expression system employed. For example, if, as is typical, the expression vector contains a signal sequence, the GH variant is recovered from the culture medium or the periplasm. Conveniently, the variant is secreted into the periplasmic space as a fully processed protein (i.e., lacking the secretion signal sequence). However, the GH variant can also be expressed intracellularly and recovered from cell lysates.

The GH variant can be purified from culture medium or a cell lysate by any method capable of separating the variant from components of the host cell or culture medium. Typically the GH variant is separated from host cell and/or culture medium components that would interfere with pegylation, if desired, or with diagnostic or therapeutic use of the GH variant.

As a first step, the culture medium or cell lysate is usually centrifuged or filtered to remove cellular debris. The supernatant is then typically concentrated or diluted to a desired volume or diafiltered into a suitable buffer to condition the preparation for further purification. Further purification of the GH variant typically includes separating deamidated and clipped forms of the GH variant from the intact form.

In one variation of this embodiment, the GH variant is purified (1) to a degree sufficient to obtain at least 15 residues of N-terminal or internal amino acid sequence, using a spinning cup sequenator, or (2) to homogeneity by SDS-PAGE under non-reducing or reducing conditions using Coomassie blue stain.

Any of the following exemplary procedures can be employed for purification of a GH variant: affinity chromatography; anion- or cation-exchange chromatography (using, e.g., DEAE SEPHAROSE); chromatography on silica; reverse phase HPLC; gel filtration (using, e.g., SEPHADEX G-75); hydrophobic interaction chromatography; metal-chelate chromatography; ultrafiltration/diafiltration; ethanol precipitation; ammonium sulfate precipitation; chromatofocusing; and displacement chromatography.

Conjugates

GH variants useful in the methods of the present disclosure may be covalently attached (hereinafter "conjugated") to one or more chemical groups. Such conjugation produces a GH variant conjugate having a greater actual molecular weight than the unmodified GH variant. As used herein, the term "actual molecular weight" refers to the molecular weight, as measured by mass spectrometry (e.g., matrix-assisted laser desorption ionization mass spectrometry). The actual molecular weight of the hGH variant conjugate is usually at least about 30 kDa; preferably, in the range of about 35 kDa to about 55 kDa; and more preferably, in the range of about 40 kDa to about 50 kDa. Generally, the actual molecular weight of the hGH variant conjugate does not exceed 100 kDa.

Chemical groups suitable for use in a GH variant conjugate are preferably not significantly toxic or immunogenic, i.e., any toxicity or immunogenicity observed with a GH variant conjugate is not significantly greater (i.e., less than 50%) than any toxicity or immunogenicity observed with the corresponding unmodified GH variant. Typically, a chemical group is selected that reduces toxicity and/or immunogenicity associated with the unmodified GH variant. In addition, the chemical group is conveniently selected to produce a GH variant conjugate that can be stored and used under conditions suitable for storage and use of the unmodified GH variant. Exemplary chemical groups include carbohydrates, such as, for example, those carbohydrates that occur naturally on glycoproteins, and non-proteinaceous polymers, such as polyols.

A polyol, for example, can be conjugated to a GH variant molecule at one or more amino acid residues, including lysine residues, as disclosed in WO 93/00109. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to a GH variant is termed "pegylation." However, those skilled in the art recognize that other polyols, such as, for example, poly(propylene glycol) and polyethylene-polypropylene glycol copolymers, can be employed using the techniques for conjugation described herein for PEG.

The average molecular weight of the PEG can range from about 500 to about 30,000 Da; preferably, from about 1,000 to about 25,000 Da; and more preferably, from about 4,000 to about 20,000 Da. In one embodiment, pegylation is carried out with PEG having an average molecular weight of about 5,000 Da (hereinafter "PEG(5000)"). The reaction conditions are adjusted to maximize production of GH variant molecules conjugated to between about four and about six molecules of PEG(5000). In another embodiment, pegylation is carried out with PEG having an average molecular weight of about 20,000 Da (hereinafter "PEG(20,000)") under conditions adjusted to maximize production of GH molecules conjugated to one molecule of PEG(20,000). In a variation of this embodiment, a branched-chain PEG having two chains of about 10,000 Da each is employed.

PEG preparations that are commercially available, and suitable for use in the present methods, are nonhomogeneous preparations that are sold according to average molecular weight. For example, PEG(5000) preparations typically contain molecules that vary slightly in molecular weight, usually ±500 Da.

A variety of methods for pegylating proteins have been described (see, for example, U.S. Pat. No. 4,179,337), disclosing the conjugation of a number of hormones and enzymes to PEG and polypropylene glycol to produce physiologically active non-immunogenic compositions. Generally, a PEG having at least one terminal hydroxy group is reacted with a coupling agent to form an activated PEG having a terminal reactive group. This reactive group can then react with the α- and ϵ-amines of proteins to form a covalent bond. Conveniently, the other end of the PEG molecule can be "blocked" with a non-reactive chemical group, such as a methoxy group, to reduce the formation of PEG-crosslinked complexes of protein molecules.

For pegylation of a GH variant, the activated PEG is one that can react with the variant under conditions that do not destroy Site 1 binding activity. Furthermore, activated PEGs that introduce a toxic linking group into the conjugate are usually avoided.

Suitable activated PEGs can be produced by a number of conventional reactions. For example, an N-hydroxysuccinimide ester of a PEG (M-NHS-PEG) can be prepared from PEG-monomethyl ether by reaction with N,N'-dicyclohexylcarbodiimide (DCC) and N-hydroxysuccinimide (NHS), according to the method of Buckmann and Merr, 1981.

In addition, a PEG terminal hydroxy group can be converted to an amino group, for example, by reaction with thionyl bromide to form PEG-Br, followed by aminolysis with excess ammonia to form $PEG-NH_2$. The $PEG-NH_2$ is then conjugated to the protein of interest using standard coupling reagents, such as Woodward's Reagent K. Furthermore, a PEG terminal $—CH_2OH$ group can be converted to an aldehyde group, for example, by oxidation with $MnO_2$. The aldehyde group is conjugated to the protein by reductive alkylation with a reagent such as cyanoborohydride.

Alternatively, activated PEGs suitable for use in the present methods can be purchased.

The degree of pegylation of a GH variant can be adjusted to provide a desirably increased in vivo half-life, compared to the corresponding non-pegylated GH variant. It is believed that the half-life of a pegylated GH variant typically increases incrementally with increasing degree of pegylation. At higher degrees of pegylation, the increase in half-life of a pegylated GH variant is believed to be partially offset by an increase in the dissociation constant (Kd) for Site 1 binding, indicating a decrease in Site 1 affinity. It is believed that this decrease in affinity is accompanied by a corresponding decrease in potency, which is reflected in an increase in the concentration of conjugate required for 50% maximal effect (EC50). As Site 1 binding is essential for GH antagonist activity of the GH variant, increased pegylation reduces the potency of the GH variants. However, the increase in half-life generally compensates for the reduction in potency, so that the in vivo efficacy of pegylated GH variants is believed to be comparable to, or better than, that observed with the corresponding non-pegylated GH variants. Accordingly, one skilled in the art can readily determine a suitable degree of pegylation for a GH variant to produce a conjugate having a desirably increased half-life, compared to the non-pegylated protein, yet retaining sufficient potency to be efficacious in vivo.

Usually, the half-life is increased at least about five-fold; preferably, at least about 10-fold; more preferably, at least about 50-fold; and most preferably, at least about 100-fold. In addition, the degree and sites of pegylation are such that the PEG-GH variant conjugate is capable of binding GHR at Site 1, typically with a Kd of about 400 nM or lower; preferably, with a Kd of 150 nM or lower; and more preferably, with a Kd of 100 nM or lower, as measured by an equilibrium binding assay, such as that described in Spencer et al., 1988.

The degree and sites of pegylation of a protein are determined by (1) the number and reactivities of pegylation sites (i.e., primary amines) and (2) pegylation reaction conditions. For example, wild-type hGH contains ten primary amines that are theoretically available to react with an activated PEG: the α-amino group of the N-terminal phenylalanine and the ϵ-amino groups of nine lysines. However, because some of the primary amines in hGH and the hGH variants are relatively unreactive, standard pegylation reactions typically result in less than complete pegylation (e.g., seven or eight PEGs per molecule for wild-type hGH).

The sites of pegylation of a protein are also somewhat constrained by the reactivities of the various primary amines. For example, a potential lysine in the Site 1 hormone-receptor binding interface of a given hGH variant may be relatively unreactive with a PEG. Thus, such moderately pegylated hGH variants, having of the order of four to six PEGs per variant molecule, may retain the ability to bind GH receptor at Site 1, despite the presence of a potential pegylation site at this binding interface. In one embodiment, the hGH variant comprises a phenylalanine at position 1 and lysines at positions 38, 120, 140 and 158 conjugated to PEG.

Standard mutagenesis techniques can be used to alter the number of lysines in the protein. Thus, to the extent that amino acid substitutions introduce or replace lysines, GH variants of the present disclosure can contain a greater or lesser number of potential pegylation sites than wild-type GH. In one embodiment, the hGH variant comprises nine potential pegylation sites (Phe1, Lys38, Lys41, Lys70, Lys115, Lys120, Lys140, Lys145, Lys158).

Furthermore, amino acid substitutions introducing or replacing lysines alter the locations of potential pegylation sites. For example, the replacement of G120 with lysine provides an additional potential pegylation site in Site 2, which if pegylated is expected to impair any residual binding at this site.

The degree and sites of pegylation can also be manipulated by adjusting reaction conditions, such as the relative concentrations of the activated PEG and the protein as well as the pH. Suitable conditions for a desired degree of pegylation can be determined empirically.

A composition containing a pegylated GH variant for use in a therapeutic formulation can be heterogeneous or homogeneous, i.e., containing multiple or single pegylated GH variants. Typically, the composition contains at least 70% one or two forms of pegylated GH variants; preferably, at least 80% one or two forms; and more preferably, at least 90% one or two forms.

Antisense Compounds to Growth Hormone Receptor

The methods of the present disclosure rely on the use of an antisense compound to growth hormone receptor (GHR) to modulate growth hormone (GH) signalling or the GH/insulin-like growth factor-I (IGF-I) axis, particularly the expression of GHR and/or IGF-I. Preferably, the antisense compound is an oligonucleotide. However, other oligomeric antisense compounds, including but not limited to oligonucleotide mimetics are contemplated.

Hybridization of an antisense compound with its target nucleic acid is generally referred to as “antisense”. Hybridization of the antisense compound with its target nucleic acid inhibits the function of the target nucleic acid. Such “antisense inhibition” is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

“Hybridization” as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A “nucleoside” is a base-sugar combination. The base portion of the nucleoside is normally a heterocyclic base. The two most common classes of such heterocyclic bases are the purines and the pyrimidines. “Nucleotides” are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

“Specifically hybridizable” and “complementary” are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the expression of the target nucleic acid and there is a sufficient degree of complementarity to avoid non-specific binding of the antisense compound to non-target sequences under conditions in which specific binding is desired, for example, under physiological conditions in the case of therapeutic treatment.

The term “stringent hybridization conditions” or “stringent conditions” as used herein refers to conditions under which the antisense compound will hybridize to its target sequence, but to a minimal number of other sequences. Stringent conditions are sequence-dependent and will be different in different circumstances. Stringent condition under which the antisense compound hybridizes to a target sequence is determined by the nature and composition of the antisense compound and the assays in which it is being investigated.

“Complementary” as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid. For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present disclosure provides for use of an antisense oligonucleotide for inhibiting expression of a growth hormone receptor (GHR).

The term “inhibits” as used herein means any measurable decrease (e.g., 10%, 20%, 50%, 90%, or 100%) in GHR expression.

As used herein, the term “oligonucleotide” refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Antisense oligonucleotides useful in the methods of the present disclosure include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H therefore results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, 1995). Montgomery et al. (1998) have shown that the primary interference effects of dsRNA are posttranscriptional. The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). It has been shown that it is, in fact, the single-stranded RNA oligomers of antisense polarity of the dsRNAs which are the potent inducers of RNAi (Tijsterman et al., 2002).

A person having ordinary skill in the art could, without undue experimentation, identify antisense oligonucleotides useful in the methods of the present disclosure.

Modified Internucleoside Linkages (Backbones)

Antisense compounds useful in the methods of the present disclosure include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,194,599, 5,565,555, 5,527,899, 5,721,218, 5,672,697 and 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, 5,792,608, 5,646,269 and 5,677,439.

Modified Sugar and Internucleoside Linkages

Antisense compounds useful in the methods of the present disclosure include oligonucleotide mimetics where both the sugar and the internucleoside linkage (i.e. the backbone) of the nucleotide units are replaced with novel groups. The nucleobase units are maintained for hybridization with the target nucleic acid.

An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262. Further teaching of PNA compounds can be found in Nielsen et al., 1991.

The antisense compounds useful in the methods of the present disclosure also include oligonucleotides with phosphorothioate backbones and oligonucleotides with heteroatom backbones, for example, $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of U.S. Pat. No. 5,489,677, and the amide backbones of U.S. Pat. No. 5,602,240.

The antisense compounds useful in the methods of the present disclosure also include oligonucleotides having morpholino backbone structures of U.S. Pat. No. 5,034,506.

Modified Sugars

Antisense compounds useful in the methods of the present disclosure include oligonucleotides having one or more substituted sugar moieties.

Examples include oligonucleotides comprising one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In one embodiment, the oligonucleotide comprises one of the following at the 2' position: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Further examples include of modified oligonucleotides include oligonucleotides comprising one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—$CH_2CH_2OCH_3$ (also known as 2'-O-(2-methoxyethyl) or 2'-MOE) (Martin et al., 1995), that is, an alkoxyalkoxy group. In a further embodiment, the modification includes 2'-dimethylaminooxyethoxy, that is, a $O(CH_2)_2ON(CH_3)_2$ group (also known as 2'-DMAOE), or 2'-dimethylaminoethoxyethoxy (also known in the art as 2'-O-dimethyl-amino-ethoxy-ethyl or 2'-DMAEOE), that is, 2'-O—$CH_2$—O—$CH_2$—$N(CH_3)_2$.

Other modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, 5,627,053, 5,639,873, 5,646,265, 5,658,873, 5,670,633, 5,792,747, and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene $(—CH_2—)_n$ group bridging the 2' oxygen atom and the 4' carbon atom, wherein n is 1 or 2. LNAs and preparation thereof are described in WO 98/39352 and WO 99/14226.

Natural and Modified Nucleobases

Antisense compounds useful in the methods of the present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. Nos. 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, 5,681,941 and 5,750,692.

Conjugates

Antisense compounds useful in the methods of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the antisense compounds.

Representative moieties or groups are disclosed in PCT/US92/09196 and U.S. Pat. No. 6,287,860.

Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense compounds useful in the methods of the present disclosure may also be conjugated to active drug substances.

Oligonucleotide-drug conjugates and their preparation are described in U.S. Ser. No. 09/334,130.

Representative United States patents that teach the preparation of such conjugates include, but are not limited to, U.S. Pat. Nos. 4,828,979, 4,948,882, 5,218,105, 5,525,465, 5,541,313, 5,545,730, 5,552,538, 5,578,717, 5,580,731, 5,580,731, 5,591,584, 5,109,124, 5,118,802, 5,138,045, 5,414,077, 5,486,603, 5,512,439, 5,578,718, 5,608,046, 4,587,044, 4,605,735, 4,667,025, 4,762,779, 4,789,737, 4,824,941, 4,835,263, 4,876,335, 4,904,582, 4,958,013, 5,082,830, 5,112,963, 5,214,136, 5,082,830, 5,112,963, 5,214,136, 5,245,022, 5,254,469, 5,258,506, 5,262,536, 5,272,250, 5,292,873, 5,317,098, 5,371,241, 5,391,723, 5,416,203, 5,451,463, 5,510,475, 5,512,667, 5,514,785, 5,565,552, 5,567,810, 5,574,142, 5,585,481, 5,587,371, 5,595,726, 5,597,696, 5,599,923, 5,599,928and 5,688,941.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

Antisense compounds useful in the methods of the present disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds useful in the methods of the present disclosure may be formed as composite structures of two or more oligonucleotides, modified oligonucleotides, and/or oligonucleotide mimetics. Such compounds have also been referred to in the art as hybrids or gapmers.

Representative United States patents that teach the preparation of such hybrid structures include, but are not limited to, U.S. Pat. Nos. 5,013,830, 5,149,797, 5,220,007, 5,256,775, 5,366,878, 5,403,711, 5,491,133, 5,565,350, 5,623,065, 5,652,355, 5,652,356, and 5,700,922.

Exemplary Oligonucleotides

In one embodiment, the antisense compound is a second generation phosphorothioate backbone 2'-MOE-modified chimeric oligonucleotide gapmer designed to hybridize to GHR mRNA.

Exemplary oligonucleotides are shown in Table 1. "Target site" indicates the first (5'-most) nucleotide number on the particular target sequence to which the oligonucleotide binds. "% Inhib" indicates the inhibitory effect on hGHR mRNA levels by quantitative real-time PCR. Data are averages from three experiments in which MCF7 cells were treated with the antisense oligonucleotides.

TABLE 1

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 227452 | Coding | 4 | 332 | tcagggcattctttccattc | 79 | 6 |
| 227453 | Coding | 4 | 337 | cataatcagggcattctttc | 52 | 7 |
| 227464 | Coding | 4 | 947 | cctttaatctttggaactgg | 58 | 8 |
| 227468 | Coding | 4 | 1079 | tcatcaatatctagctcaat | 62 | 9 |
| 227469 | Coding | 4 | 1124 | cttagaagtctgtctgtgtc | 63 | 10 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 227475 | Coding | 4 | 1514 | cctgctggtgtaatgtcgct | 68 | 11 |
| 227480 | Coding | 4 | 1724 | atgtaaatgtcctcttggtt | 66 | 12 |
| 227481 | Coding | 4 | 1729 | tggtgatgtaaatgtcctct | 45 | 13 |
| 227482 | Coding | 4 | 1734 | ttctgtggtgatgtaaatgt | 53 | 14 |
| 227483 | Coding | 4 | 1739 | aggctttctgtggtgatgta | 75 | 15 |
| 227484 | Coding | 4 | 1744 | tggtaaggctttctgtggtg | 63 | 16 |
| 227488 | Coding | 4 | 1922 | agttggtctgtgctcacata | 86 | 17 |
| 227489 | Coding | 4 | 1927 | tgttcagttggtctgtgctc | 75 | 18 |
| 227490 | Coding | 4 | 1936 | gcatgattttgttcagttgg | 67 | 19 |
| 227499 | 3'UTR | 4 | 2656 | tataaaagggctttgtaaaa | 14 | 20 |
| 227500 | 3'UTR | 4 | 4043 | catagcagcaaagtagcaga | 69 | 21 |
| 227501 | 3'UTR | 4 | 4183 | gctatttttggctatagaaa | 64 | 22 |
| 227502 | 3'UTR | 4 | 4197 | gattgaggtatttagctatt | 56 | 23 |
| 272302 | Start Codon | 4 | 31 | gatccatacctgtaggacct | 60 | 24 |
| 272303 | Start Codon | 4 | 36 | ccagagatccatacctgtag | 55 | 25 |
| 272304 | Coding | 4 | 115 | tgctaaggatagctgctgtg | 48 | 26 |
| 272305 | Coding | 4 | 160 | ttgtctttaggcctggatta | 68 | 27 |
| 272306 | Coding | 4 | 170 | ttagaagaatttgtctttag | 13 | 28 |
| 272307 | Coding | 4 | 185 | gtgaatttaggctccttaga | 55 | 29 |
| 272308 | Coding | 4 | 274 | gctgtatgggtcctaggttc | 57 | 30 |
| 272309 | Coding | 4 | 362 | taacagctgttttccccagc | 85 | 31 |
| 272310 | Coding | 4 | 439 | tttcatccactgtaccacca | 76 | 32 |
| 272311 | Coding | 4 | 468 | ttgcactatttcatcaacag | 47 | 33 |
| 272312 | Coding | 4 | 480 | gggtggatctggttgcacta | 57 | 34 |
| 272313 | Coding | 4 | 564 | attgcgtggtgcttcccatc | 77 | 35 |
| 272314 | Coding | 4 | 652 | tagggtccatcattttccat | 56 | 36 |
| 272315 | Coding | 4 | 684 | caatgagtacactggaactg | 53 | 37 |
| 272316 | Coding | 4 | 752 | aactcgccataatttccaga | 64 | 38 |
| 272317 | Coding | 4 | 857 | agcccaaatattccaaagat | 65 | 39 |
| 272318 | Coding | 4 | 913 | tcagcattttaatcctttgc | 55 | 40 |
| 272319 | Coding | 4 | 979 | attttccttccttgaggaga | 67 | 41 |
| 272320 | Coding | 4 | 1000 | agattgtgttcacctcctct | 70 | 42 |
| 272321 | Coding | 4 | 1053 | aacccaagagtcatcactgt | 64 | 43 |
| 272322 | Coding | 4 | 1084 | ctggctcatcaatatctagc | 84 | 44 |
| 272323 | Coding | 4 | 1110 | tgtgtctgattcctcagtct | 67 | 45 |
| 272324 | Coding | 4 | 1236 | tatgtcattggcattgaaat | 53 | 46 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 272325 | Coding | 4 | 1302 | aaggcataagagatctgctt | 66 | 47 |
| 272326 | Coding | 4 | 1420 | actcagctccttcagtagga | 77 | 48 |
| 272327 | Coding | 4 | 1560 | ggacatccctgccttattct | 60 | 49 |
| 272328 | Coding | 4 | 1623 | ggcattgtccataaggaagt | 85 | 50 |
| 272329 | Coding | 4 | 1651 | actttttggcatctgcctca | 63 | 51 |
| 272330 | Coding | 4 | 1656 | gatgcactttttggcatctg | 47 | 52 |
| 272331 | Coding | 4 | 1861 | cagtcgcattgagtatgagg | 67 | 53 |
| 272332 | Coding | 4 | 1884 | ctctttgtcaggcaagggca | 75 | 54 |
| 272333 | Coding | 4 | 1913 | gtgctcacatagccacatga | 72 | 55 |
| 272334 | Stop Codon | 4 | 1949 | aagaaaggctaaggcatgat | 61 | 56 |
| 272335 | 3'UTR | 4 | 1973 | aaatacgtagctcttgggaa | 47 | 57 |
| 272336 | 3'UTR | 4 | 2196 | caatcactgctactaaacag | 69 | 58 |
| 272337 | 3'UTR | 4 | 2249 | aaacatagccattcaatgct | 39 | 59 |
| 272338 | 3'UTR | 4 | 2337 | gtgctatggtttgcattcaa | 78 | 60 |
| 272339 | 3'UTR | 4 | 2454 | gttttacatatccaaactat | 72 | 61 |
| 272340 | 3'UTR | 4 | 2853 | catcaaccaagatttggtga | 69 | 62 |
| 272341 | 3'UTR | 4 | 2988 | gaggctatagatcttatctc | 65 | 63 |
| 272342 | 3'UTR | 4 | 3271 | tagtgagaaagaaagtttct | 45 | 64 |
| 272343 | 3'UTR | 4 | 3765 | aatgctctcaagaatgatgt | 48 | 65 |
| 272344 | 3'UTR | 4 | 3980 | acactcaattctagcttttc | 60 | 66 |
| 272345 | 3'UTR | 4 | 4011 | catctattacaaataacatg | 24 | 67 |
| 272346 | 3'UTR | 4 | 4057 | ctcttggagaaaaccatagc | 67 | 68 |
| 272347 | 3'UTR | 4 | 4097 | tctacactgatgatacttta | 62 | 69 |
| 272348 | 3'UTR | 4 | 4120 | cacagctttgaattgaatta | 57 | 70 |
| 272349 | 3'UTR | 4 | 4133 | agtcttccaaacacacagct | 68 | 71 |
| 272350 | 3'UTR | 4 | 4156 | aggctgttgtgaaatagtaa | 67 | 72 |
| 272351 | 3'UTR | 4 | 4170 | atagaaatgttgtcaggctg | 57 | 73 |
| 272352 | 3'UTR | 4 | 4218 | ccaaaatgacattctgagac | 77 | 74 |
| 272353 | 3'UTR | 4 | 4245 | ataatggcttatgtggccac | 72 | 75 |
| 272354 | intron | 5 | 2571 | agttatgtgaccctgattga | 65 | 76 |
| 272355 | intron: exon junction | 5 | 6418 | ttgagtgttcctaaaatgaa | 24 | 77 |
| 272356 | intron | 5 | 8405 | atggaggctggaggttcaaa | 63 | 78 |
| 272357 | intron: exon junction | 5 | 22712 | tagggtccatctttcaagac | 62 | 79 |
| 272358 | intron | 5 | 25543 | tctccagatagaatctaaac | 53 | 80 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 272359 | intron | 5 | 29755 | tccaaatattctggtacttt | 72 | 81 |
| 272360 | exon: intron junction | 5 | 29935 | tattagttaccttgaggaga | 0 | 82 |
| 272361 | intron: exon junction | 5 | 30267 | attttccttcctagaaaata | 10 | 83 |

All oligonucleotides in Table 1 are chimeric oligonucleotides ("gapmers"), 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All uracils are 5-methyluracils ($^{Me}$U). Typically, the oligonucleotide is synthesized using 2-methoxyethyl modified thymidines not 5-methyluracils. All pyrimidines are C5 methylated (i.e., U, T, C are C5 methylated).

The oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucleotide utilizes phosphoramidite coupling chemistry followed by oxidative sulfurization and involves sequential coupling of activated monomers to an elongating oligomer, the 3'-terminus of which is covalently attached to the solid support.

Detritylation (Reaction a).

Each cycle of the solid-phase synthesis commences with removal of the acid-labile 5'-O-4,4'-dimethoxytrityl (DMT) protecting group of the 5' terminal nucleoside of the support bound oligonucleotide. This is accomplished by treatment with an acid solution (e.g., dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-$^{Me}$C amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding (O,O,O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n−1)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O,O,O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 hours. The temperature is increased to 300° C. and a secondary drying step performed for 5.5 hours. Following completion of the lyophilization process, the drug substance is transferred to high density polyethylene bottles and stored at −200° C.

Target Nucleic Acid

"Targeting" an antisense compound to a particular nucleic acid can be a multistep process. The process usually begins with the identification of a target nucleic acid whose function is to be modulated. In the present disclosure, the target nucleic acid encodes growth hormone receptor (GHR). The term "target nucleic acid" encompasses DNA encoding GHR, RNA (including pre-mRNA and mRNA or portions thereof) transcribed from such DNA, and further, cDNA derived from such RNA.

The cDNA encoding the growth hormone receptor has been cloned from many species. The receptor consists of an extracellular hormone-binding region (exons 2-7), a single membrane spanning region (exon 8), and an intracellular region (exons 9-10). There are also multiple alternative 5' untranslated regions which are alternative first exons of the gene, in both the human and mouse transcripts. Growth hormone receptor has no intrinsic kinase domain, but the intracellular region plays a major role in the signal transduction process. A truncated form of the receptor, known as growth hormone binding protein (GHBP), lacks the transmembrane and intracellular regions of GHR and is secreted into the serum. The truncated protein is produced by one of two different processes, depending on the animal species. In mice and rats, alternative splicing of GHR precursor messenger RNA replaces the transmembrane and intracellular regions with a very short hydrophilic tail (encoded by exon 8A). In humans, cows, and pigs (among others), no alternative RNA splicing is apparent but instead the GHBP is produced by proteolysis of the GHR. The GHBP appears to be to modulate the level of circulating growth hormone (GH).

In one embodiment the GHR is a human GHR (hGHR) having a nucleotide sequence as shown in NM_000163.4 (SEQ ID NO:4) or NG_011688 (4852-302955) (SEQ ID NO:5).

The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding, for example, GHR, regardless of the sequence(s) of such codons.

A "translation termination codon" also referred to as a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding the GHR, regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are targeted.

Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

In mouse, rat and monkey, GHBP, which is the soluble shortened form of GHR, is produced by alternative splicing of the GHR primary transcript. In some embodiments it may be preferable to target regions of the transcript which are present in both the GHR transcript and in the shorter GHBP transcript. In other embodiments it may be preferable to target regions of the mRNA which are only present in the longer GHR transcript. In humans, cows, and pigs (among others), no alternative RNA splicing is apparent but instead the shorter GHBP is produced by proteolysis of the GHR. It will be understood that in the context of this disclosure, "nucleic acid encoding GHR" includes nucleic acid encoding GHBP.

Variants can be produced through the use of alternative signals to start or stop transcription, that is, through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted. The human GHR has several transcript variants as can be identified from the National Center for Biotechnology Information http://www.nchi.nlm.nih.gov/guide/ and other web sites http://www.uniprot.org/uniprot/P10912#PRO_0000010958. There are additionally alternative sequences and natural variants sequences of these transcripts.

The location on the target nucleic acid to which the antisense compound hybridizes is referred to as the "target segment". As used herein, the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

In a further embodiment, the target segment identified herein may be employed in a screen for additional compounds that modulate the expression of the GHR gene (and thus expression of GHR). "Modulators" are those compounds that decrease or increase the expression of a nucleic acid molecule encoding GHR and which comprise at least a 8 nucleobase portion which is complementary to a preferred target segment.

The screening method comprises the steps of contacting a target segment of the nucleic acid encoding GHR with one or more candidate modulators, and selecting for one or more candidate modulators which decrease or increase the expression of a nucleic acid encoding GHR. Once it is shown that the candidate modulator or modulators are capable of modulating (e.g., either decreasing or increasing) the expression of a nucleic acid encoding GHR, the modulator may then be employed in further investigative studies of the function of GHR, or for use as a research, diagnostic, or therapeutic agent.

The target segment may also be combined with its respective complementary antisense compound to form stabilized double-stranded (duplexed) oligonucleotides.

Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Exemplary Target Nucleic Acids

Exemplary target sequences are shown in Table 2.

TABLE 2

Sequence and position of preferred target segments identified in growth hormone receptor

| SITE ID | TARGET SEQ ID NO | TARGET SITE | SEQUENCE | REV COMP OF SEQ ID | ACTIVE IN | SEQ ID NO |
|---|---|---|---|---|---|---|
| 144070 | 4 | 332 | gaatggaaagaatgccctga | 6 | H. sapiens | 84 |
| 144071 | 4 | 337 | gaaagaatgccctgattatg | 7 | H. sapiens | 85 |

TABLE 2-continued

Sequence and position of preferred target segments identified in growth hormone receptor

| SITE ID | TARGET SEQ ID NO | TARGET SITE | SEQUENCE | REV COMP OF SEQ ID | ACTIVE IN | SEQ ID NO |
|---|---|---|---|---|---|---|
| 144082 | 4 | 947 | ccagttccaaagattaaagg | 8 | H. sapiens | 86 |
| 144086 | 4 | 1079 | attgagctagatattgatga | 9 | H. sapiens | 87 |
| 144087 | 4 | 1124 | gacacagacagacttctaag | 10 | H. sapiens | 88 |
| 144093 | 4 | 1514 | agcgacattacaccagcagg | 11 | H. sapiens | 89 |
| 144098 | 4 | 1724 | aaccaagaggacatttacat | 12 | H. sapiens | 90 |
| 144099 | 4 | 1729 | agaggacatttacatcacca | 13 | H. sapiens | 91 |
| 144100 | 4 | 1734 | acatttacatcaccacagaa | 14 | H. sapiens | 92 |
| 144101 | 4 | 1739 | tacatcaccacagaaagcct | 15 | H. sapiens | 93 |
| 144102 | 4 | 1744 | caccacagaaagccttacca | 16 | H. sapiens | 94 |
| 144106 | 4 | 1922 | tatgtgagcacagaccaact | 17 | H. sapiens | 95 |
| 144107 | 4 | 1927 | gagcacagaccaactgaaca | 18 | H. sapiens | 96 |
| 144108 | 4 | 1936 | ccaactgaacaaaatcatgc | 19 | H. sapiens | 97 |
| 144118 | 4 | 4043 | tctgctactttgctgctatg | 21 | H. sapiens | 98 |
| 144119 | 4 | 4183 | tttctatagccaaaaatagc | 22 | H. sapiens | 99 |
| 144120 | 4 | 4197 | aatagctaaatacctcaatc | 23 | H. sapiens | 100 |
| 188518 | 4 | 31 | aggtcctacaggtatggatc | 24 | H. sapiens | 101 |
| 188519 | 4 | 36 | ctacaggtatggatctctgg | 25 | H. sapiens | 102 |
| 188520 | 4 | 115 | cacagcagctatccttagca | 26 | H. sapiens | 103 |
| 188521 | 4 | 160 | taatccaggcctaaagacaa | 27 | H. sapiens | 104 |
| 188523 | 4 | 185 | tctaaggagcctaaattcac | 29 | H. sapiens | 105 |
| 188524 | 4 | 274 | gaacctaggacccatacagc | 30 | H. sapiens | 106 |
| 188525 | 4 | 362 | gctggggaaaacagctgtta | 31 | H. sapiens | 107 |
| 188526 | 4 | 439 | tggtggtacagtggatgaaa | 32 | H. sapiens | 108 |
| 188527 | 4 | 468 | ctgttgatgaaatagtgcaa | 33 | H. sapiens | 109 |
| 188528 | 4 | 480 | tagtgcaaccagatccaccc | 34 | H. sapiens | 110 |
| 188529 | 4 | 564 | gatgggaagcaccacgcaat | 35 | H. sapiens | 111 |
| 188530 | 4 | 652 | atggaaaatgatggacccta | 36 | H. sapiens | 112 |
| 188531 | 4 | 684 | cagttccagtgtactcattg | 37 | H. sapiens | 113 |
| 188532 | 4 | 752 | tctggaaattatggcgagtt | 38 | H. sapiens | 114 |
| 188533 | 4 | 857 | atctttggaatatttgggct | 39 | H. sapiens | 115 |
| 188534 | 4 | 913 | gcaaaggattaaaatgctga | 40 | H. sapiens | 116 |
| 188535 | 4 | 979 | tctcctcaaggaaggaaaat | 41 | H. sapiens | 117 |
| 188536 | 4 | 1000 | agaggaggtgaacacaatct | 42 | H. sapiens | 118 |
| 188537 | 4 | 1053 | acagtgatgactcttgggtt | 43 | H. sapiens | 119 |
| 188538 | 4 | 1084 | gctagatattgatgagccag | 44 | H. sapiens | 120 |
| 188539 | 4 | 1110 | agactgaggaatcagacaca | 45 | H. sapiens | 121 |
| 188540 | 4 | 1236 | atttcaatgccaatgacata | 46 | H. sapiens | 122 |

TABLE 2-continued

Sequence and position of preferred target segments identified in growth hormone receptor

| SITE ID | TARGET SEQ ID NO | TARGET SITE | SEQUENCE | REV COMP OF SEQ ID | ACTIVE IN | SEQ ID NO |
|---|---|---|---|---|---|---|
| 188541 | 4 | 1302 | aagcagatctcttatgcctt | 47 | H. sapiens | 123 |
| 188542 | 4 | 1420 | tcctactgaaggagctgagt | 48 | H. sapiens | 124 |
| 188543 | 4 | 1560 | agaataaggcagggatgtcc | 49 | H. sapiens | 125 |
| 188544 | 4 | 1623 | acttccttatggacaatgcc | 50 | H. sapiens | 126 |
| 188545 | 4 | 1651 | tgaggcagatgccaaaaagt | 51 | H. sapiens | 127 |
| 188546 | 4 | 1656 | cagatgccaaaaagtgcatc | 52 | H. sapiens | 128 |
| 188547 | 4 | 1861 | cctcatactcaatgcgactg | 53 | H. sapiens | 129 |
| 188548 | 4 | 1884 | tgcccttgcctgacaaagag | 54 | H. sapiens | 130 |
| 188549 | 4 | 1913 | tcatgtggctatgtgagcac | 55 | H. sapiens | 131 |
| 188550 | 4 | 1949 | atcatgccttagcctttctt | 56 | H. sapiens | 132 |
| 188551 | 4 | 1973 | ttcccaagagctacgtattt | 57 | H. sapiens | 133 |
| 188552 | 4 | 2196 | ctgtttagtagcagtgattg | 58 | H. sapiens | 134 |
| 188554 | 4 | 2337 | ttgaatgcaaaccatagcac | 60 | H. sapiens | 135 |
| 188555 | 4 | 2454 | atagtttggatatgtaaaac | 61 | H. sapiens | 136 |
| 188556 | 4 | 2853 | tcaccaaatcttggttgatg | 62 | H. sapiens | 137 |
| 188557 | 4 | 2988 | gagataagatctatagcctc | 63 | H. sapiens | 138 |
| 188558 | 4 | 3271 | agaaactttctttctcacta | 64 | H. sapiens | 139 |
| 188559 | 4 | 3765 | acatcattcttgagagcatt | 65 | H. sapiens | 140 |
| 188560 | 4 | 3980 | gaaaagctagaattgagtgt | 66 | H. sapiens | 141 |
| 188562 | 4 | 4057 | gctatggttttctccaagag | 68 | H. sapiens | 142 |
| 188563 | 4 | 4097 | taaagtatcatcagtgtaga | 69 | H. sapiens | 143 |
| 188564 | 4 | 4120 | taattcaattcaaagctgtg | 70 | H. sapiens | 144 |
| 188565 | 4 | 4133 | agctgtgtgtttggaagact | 71 | H. sapiens | 145 |
| 188566 | 4 | 4156 | ttactatttcacaacagcct | 72 | H. sapiens | 146 |
| 188567 | 4 | 4170 | cagcctgacaacatttctat | 73 | H. sapiens | 147 |
| 188568 | 4 | 4218 | gtctcagaatgtcattttgg | 74 | H. sapiens | 148 |
| 188569 | 4 | 4245 | gtggccacataagccattat | 75 | H. sapiens | 149 |
| 188570 | 5 | 2571 | tcaatcagggtcacataact | 76 | H. sapiens | 150 |
| 188572 | 5 | 8405 | tttgaacctccagcctccat | 78 | H. sapiens | 151 |
| 188573 | 5 | 22712 | gtcttgaaagatggacccta | 79 | H. sapiens | 152 |
| 188574 | 5 | 25543 | gtttagattctatctggaga | 80 | H. sapiens | 153 |
| 188575 | 5 | 29755 | aaagtaccagaatatttgga | 81 | H. sapiens | 154 |

Compositions/Formulations

Antisense compounds useful in the methods of the present disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption.

Representative United States patents that teach the preparation of such uptake, distribution and/or absorption-assisting formulations include, but are not limited to, U.S. Pat. Nos. 5,108,921, 5,354,844, 5,416,016, 5,459,127, 5,521, 291, 5,543,158, 5,547,932, 5,583,020, 5,591,721, 4,426,330, 4,534,899, 5,013,556, 5,108,921, 5,213,804, 5,227,170, 5,264,221, 5,356,633, 5,395,619, 5,416,016, 5,417,978, 5,462,854, 5,469,854, 5,512,295, 5,527,528, 5,534,259, 5,543,152, 5,556,948, 5,580,575, and 5,595,756.

The antisense compounds may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure.

The antisense compounds may be pharmaceutically acceptable salts, esters, or salts of the esters, or any other compounds which, upon administration are capable of providing (directly or indirectly) the biologically active metabolite.

The term "pharmaceutically acceptable salts" as used herein refers to physiologically and pharmaceutically acceptable salts of the antisense compounds that retain the desired biological activities of the parent compounds and do not impart undesired toxicological effects upon administration. Preferred examples of pharmaceutically acceptable salts and their uses are further described in U.S. Pat. No. 6,287,860.

The antisense compounds may be prodrugs or pharmaceutically acceptable salts of the prodrugs, or other bioequivalents.

The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds are prepared as SATE [(S acetyl-2-thioethyl) phosphate]derivatives according to the methods disclosed in WO 93/24510, WO 94/26764 and U.S. Pat. No. 5,770,713.

Formulations of the growth hormone (GH) variants for therapeutic administration are prepared for storage by mixing a GH variant having the desired degree of purity with an optional pharmaceutically acceptable carrier, excipient, or stabilizer (Remington's Pharmaceutical Sciences, 16th edition, A. Oslo, A (editor) (1980)) in the form of a lyophilized cake or an aqueous solution. Parenteral formulations can be prepared by mixing the GH variant in a unit dosage injectable form (solution, suspension, or emulsion) with a pharmaceutically acceptable carrier. Pharmaceutically acceptable carriers are non-toxic to recipients at the dosages and concentrations employed and are compatible with other ingredients of the formulation. For example, the formulation preferably does not include oxidizing agents and other compounds known to be deleterious to polypeptides. Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counterions such as sodium; and/or nonionic surfactants such as Tween, Pluronics, or polyethylene glycol (PEG).

Additionally, the GH formulation set forth in WO 89/09614 can be employed, wherein the GH variant is contained in a composition comprising glycine, mannitol and a buffer, such as a phosphate buffer. An exemplary version of this formulation is: 0.68 g/L glycine, 18.0 g/L mannitol, 5 mM sodium phosphate, pH 7.4. Alternatively, the GH variant can be contained in a liquid formulation that does not necessarily contain mannitol or glycine and comprises 0.1 to 5% (w/v) of a non-ionic surfactant, such as polysorbate, or a poloxamer. An exemplary version of this formulation is: 5 mg/ml GH variant, 8.77 mg/ml NaCl, 2.5 mg/ml phenol, 2.0 mg/ml polysorbate 20, and 10 mM sodium citrate, pH 6.0.

The GH variant is also suitably administered by sustained-release systems. Suitable examples of sustained-release compositions include semi-permeable polymer matrices in the form of shaped articles, for example, films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981; Langer, 1982), ethylene vinyl acetate (Langer et al., 1982) or poly-D-(−)-3-hydroxybutyric acid (EP 133,988). Sustained-release GH variant compositions also include liposomally entrapped GH variants. Liposomes containing GH variants are prepared by methods known in the art (see, DE 3,218,121; Epstein et al., 1985; Hwang et al., 1980; EP 52,322; EP 36,676; EP 88,046; EP 143,949; EP 142,641; JP 83-118008; U.S. Pat. No. 4,485,045; U.S. Pat. No. 4,544,545; and EP 102,324). Ordinarily, the liposomes are of the small (about 200-800 Angstroms) unilamellar type in which the lipid content is greater than about 30 mol. percent cholesterol, the selected proportion being adjusted for the optimal GH variant therapy.

The GH variant can also be formulated for local administration. Suitable formulations vary depending on the site of administration and do not differ from those known in the art. For example, GH can be formulated in a balanced salt solution for administration to the eye.

The GH variant formulation for therapeutic administration is sterile. Sterility is readily accomplished by filtration through sterile filtration membranes (e.g., 0.2 micron membranes). Therapeutic GH variant compositions generally are placed into a container having a sterile access port, for example, an intravenous solution bag or vial having a stopper pierceable by a hypodermic injection needle. GH variants ordinarily are stored in unit or multi-dose containers, for example, sealed ampoules or vials, as an aqueous solution or as a lyophilized formulation for reconstitution. As an example of a lyophilized formulation, 5-ml vials are filled with 2 ml of sterile-filtered 0.5% (w/v) aqueous GH variant solution, and the resulting mixture is lyophilized.

The infusion solution is prepared by reconstituting the lyophilized GH variant using bacteriostatic water-for-injection and the like.

The formulation of pegylated GH variants is carried out as described above for GH variants generally.

Administration

The methods of the present disclosure rely on the unsuspected synergy of combining a growth hormone (GH) variant having antagonistic activity with an oligonucleotide targeted to growth hormone receptor (GHR) to reduce insulin-like growth factor I (IGF-I) levels in a subject.

In a particular embodiment of the present disclosure, the GH variant the oligonucleotide are administered concomitantly. The GH variant and the oligonucleotide may be administered in the form of a composition comprising an admixture of both components. Alternatively, the GH variant and the oligonucleotide may be administered in separate compositions.

In one embodiment, the antisense oligonucleotide is administered systemically. As used herein "systemic administration" is a route of administration that is either enteral or parenteral.

As used herein "enteral" refers to any form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder), transdermal (diffusion through the intact skin), transmucosal (diffusion through a mucous membrane), inhalational.

The antisense oligonucleotide may be administered as single dose or as repeated doses on a periodic basis, for example, daily, once every two days, three, four, five, six seven, eight, nine, ten, eleven, twelve, thirteen or fourteen days, once weekly, twice weekly, three times weekly, or every two weeks, every three weeks, or every four weeks.

The antisense oligonucleotide to be used in the therapy is formulated and dosed in a fashion consistent with good medical practice, taking into account the specific condition being treated, the clinical condition of the individual patient, the site of delivery of the oligonucleotide, the method of administration, the scheduling of administration, and other factors known to practitioners. The "effective amount" of oligonucleotide for purposes herein is thus determined by such considerations. The term "effective amount" in this context refers to any dose of the antisense oligonucleotide sufficient to inhibit GHR expression, under the conditions of administration.

By way of example, a dose of 25-3400, more preferably 50-1600 mg oligonucleotide may be administered to a subject. A dose of 150-400 mg, for example, a dose of 250 mg is particularly contemplated for humans. In one embodiment, a dose of 250 mg per day is administered six times over 3 weeks, on days 1, 3, 5, 7, 14 and 21. In another embodiment, a dose of 250 mg is administered once weekly, or once a fortnight.

The GH variant may be administered by, for example, continuous infusion (using, for example, minipumps such as osmotic pumps), or by injection using, for example, intravenous or subcutaneous means. In one embodiment, the GH variant is administered subcutaneously. The administration can also be as a single bolus or by slow-release depot formulation.

The GH variant composition to be used in the therapy is formulated and dosed in a fashion consistent with good medical practice, taking into account the specific condition being treated, the clinical condition of the individual patient, the site of delivery of the GH variant composition, the method of administration, the scheduling of administration, and other factors known to practitioners. The "effective amount" of GH variant for purposes herein (including an antagonist effective amount to counteract, for example, acromegaly) is thus determined by such considerations. The term "effective amount" in this context refers to any dose of the GH variant sufficient to antagonize GH binding, under the conditions of administration.

As a general proposition, the total pharmaceutically effective amount of the GH variant administered parenterally per dose is in the range of about 1 μg/kg/day to about 100 mg/kg/day of patient body weight, although, as noted above, this is subject to therapeutic discretion. Usually, this dose is between about 0.01 and about 10 mg/kg/day, and more usually for humans between about 0.01 and about 1 μg/kg/day. If given continuously, the GH variant is typically administered at a dose rate of about 1 μg/kg/hour to about 50 μg/kg/hour, either by one to four injections per day or by continuous subcutaneous infusions, for example, using a mini-pump. An intravenous bag solution can also be employed. The key factor in selecting an appropriate dose is the result obtained, as measured for antagonists, for example, by reduction in serum GH, serum insulin-like growth factor I (IGF-I), and tumor growth, etc.

In general, a pegylated GH variant can be administered by any of the routes of administration described above. However, it is presently believed that a pegylated GH variant need not be administered as frequently as a non-pegylated GH variant. Non-pegylated GH and GH variants are typically administered at least three times a week and often daily. The pegylated forms of these proteins can be administered between about once every three days to about once a month, or more typically between about once every 6-7 days to once every two weeks. However, the pegylated GH variant Somavert is typically administered daily at doses ranging from 5 to 80 mg or more typically 10 to 30 mg per day after a loading dose of 40 mg on the first day. Somavert 30 mg/day is the highest approved daily dose regimen for acromegaly. Higher daily doses are desired in some acromegaly patients and in cancer.

The GH variant may be administered as single dose or as repeated doses on a periodic basis, for example, daily, once every two days, three, four, five, six seven, eight, nine, ten, eleven, twelve, thirteen or fourteen days, once weekly, twice weekly, three times weekly, or every two weeks, every three weeks, or every four weeks.

In one embodiment of the present disclosure, the GH variant is Somavert and the oligonucleotide is ATL1103 (SEQ ID NO:19) and the compounds are administered sequentially. In one embodiment, the ATL1103 oligonucleotide is first administered at a dose of 250 mg/day on days 1, 3, 5, 7, 14 and 21, and once weekly thereafter (for 5 to 12 weeks) and the GH variant Somavert is subsequently administered on the same days at 30 mg/day. Alternatively, the ATL1103 oligonucleotide may be administered once or twice weekly (for 8 to 12 weeks) at doses of 250 mg together with once or twice or three weekly Somavert doses of 30 mg.

After 5 to 12 weeks, treatment may be continued (cycle 2) with the same or increased or lower doses of Somavert, and with the same or increased or lower doses of ATL1103, and with the same or increased or lower dosing frequency to achieve the desired target IGF-I levels. Post 5 to 12 weeks, the Somavert dose modification may be in about 5 to 10 mg increments and monitored at about 1 to 4 weeks to assess IGF-I levels. Post 5 to 12 weeks, the ATL1103 dose modification may be in about 25 or 50 mg increments and monitored at about 1 to 8 weeks to assess IGF-I levels. Cycle 2 can be continued if the target IGF-I normalization is achieved or a new cycle started to further optimize dosing to achieve IGF-I normalization on a patient by patient basis.

In another embodiment, a repeat 21 day treatment cycle may be used, for cancer or retinopathy treatment. The ATL1103 oligonucleotide is first administered at a dose of 250 mg/day on days 1, 3, 5, 7, 14 and 21, and the GH variant Somavert is subsequently administered on the same days at 30 mg/day. Alternatively, in a repeat cycle, the ATL1103 oligonucleotide dosing may be once or twice weekly 250 mg together with once or twice weekly Somavert doses of 30 mg on the same days or once weekly 80 mg Somavert on the same day. Alternatively, treatments may be on different days.

After 5 to 12 weeks, treatment may be continued (cycle 2) with the same or increased or lower doses of Somavert, and with the same or increased or lower doses of ATL1103, and administered the same or increased or lower dosing frequency to achieve the desired target IGF-I levels and treatment outcomes in cancer or retinopathy. Post 5 to 12 weeks, the Somavert dose modification may be in about 5 to 10 mg increments and monitored at about 1 to 4 weeks to assess IGF-I levels. Post 5 to 12 weeks, the ATL1103 dose modification may be in about 25 or 50 mg increments and monitored at about 1 to 8 weeks to assess IGF-I levels. Cycle 2 can be continued if the target IGF-I normalization is achieved or a new cycle started to further optimize dosing to achieve IGF-I normalization on a patient by patient basis.

In another embodiment, the ATL1103 drug may be dosed once or twice weekly at doses of 100, 200, 250, 300, 350, or 400 mg/day and Somavert may be dosed daily, every other day, or once or twice weekly at 5, 10, 15, 20, 25, 30, 35, 40, 50, 60, 70 or 80 mg/day.

In another embodiment, the ATL1103 oligonucleotide is first administered at one of the above doses once every other week and the GH variant Somavert is subsequently administered on alternative weeks, so that the patient is on a once weekly alternative dosing regimen, first of ATL1103 and then of Somavert. In a similar embodiment, the patient is on a twice weekly dosing regimen, first of ATL1103 and then of Somavert, a few days apart, or one day apart. Somavert may also be given first and then ATL1103 dosing may follow. Somavert and ATL1103 may also be combined in a mixture and given on the same day. For example, the ATL1103 in a solution in a pre-filled syringe, may be added to the lyophilized Somavert, the Somavert reconstituted into solution, and the ATL1103 and Somavert mixture administered to the subject.

EXAMPLES

Phase I Trial of the GHR Targeting Drug ATL1103

The primary objective of the Phase I trial was to assess the safety, tolerability and pharmacokinetics (pK) of ATL1103.

The Phase I trial was a randomized, placebo controlled, double blind study of single ascending doses and multiple doses of ATL1103 in healthy adult male subjects aged between 18 and 45 years. In the single ascending dose stage of the trial, 24 subjects were administered four dose levels of ATL1103 as a single injection starting at 25 mg and escalating to 75, 250 and 400 mg or placebo. The multiple dose stage was undertaken in 12 subjects, 8 who were to receive six subcutaneous doses of 250 mg of ATL1103 and 4 subjects who received placebo administered on days 1, 3, 5, 7, 14 and 21. Subjects were monitored out to day 35.

Importantly, no serious adverse events were reported in this trial. Two subjects in the multiple dose arm withdrew from the study for reasons not related to safety. All adverse events were reported as "mild to moderate". Injection site reactions represented the majority of all the adverse events reported in the trial. There was one elevation in the liver enzyme ALT reported as an adverse event in the multiple dose stage. Importantly, the ALT levels in this subject returned to normal during the dosing phase, suggesting no residual or cumulative effect of the drug on this safety parameter.

A secondary objective of this study was to obtain data on the pharmacodynamic effects of ATL1103 on the IGF-I levels in the blood of the trial subjects. Reduction of increased levels of serum IGF-I to normal is the therapeutic endpoint in the treatment of the growth disorder acromegaly, and reducing the effects of IGF-I has a potential role in the treatment of diabetic retinopathy, nephropathy and certain forms of cancer.

As defined in the statistical analysis plan, the effect of ATL1103 on serum IGF-I was assessed as a change in IGF-I levels versus baseline (starting point) readings for those subjects who received treatment (ATL1103). Pre-dose baseline levels of IGF-I were recorded prior to the commencement of dosing and then measured at weekly intervals until the end of the monitoring period. This treated group showed a trend in reduction in IGF-I levels from day 14 to day 28, with a significant effect ($p=0.034$ one sided t-test) at day 21 with a 7% reduction in mean IGF-I levels versus baseline.

Other exploratory objectives of the study investigated the drug's mechanism of action and broader pharmacological profile, including the pharmacodynamic effects on levels of growth hormone binding protein (GHBP), insulin-like growth factor binding protein 3 (IGFBP-3), acid labile subunit of the insulin-like growth factor binding protein complex (ALS), and growth hormone (GH), as well as in vitro mitogenic and apoptotic parameters.

Notably, ATL1103 had a significant effect on reducing GHBP by 16% ($p=0.007$) at day 21 and 19% ($p<0.05$) at day 28, one week past the last dose. As circulating GHBP is produced by cleavage from the GHR, the reduction of circulating GHBP levels suggests that GHR expression is being reduced. ATL1103 also significantly reduced IGFBP-3 and ALS, both consistent with its effect on IGF-I and the fact that they are regulated by GH. There was no effect on GH levels. Specific trial details and outcomes are summarized in Tables 3-6.

TABLE 3

| Summary of ATL1103 Phase I clinical trial | |
|---|---|
| Title | A randomised; placebo-controlled, double-blind, single ascending dose and multiple dose study to assess the safety, tolerability, pharmacokinetics and pharmacodynamics of subcutaneous doses of ATL1103 in healthy adult male subjects |
| Trial description | Phase I trial of subcutaneous administration of ATL1103 in healthy males |
| Objectives | Primary objectives:<br>To assess the safety and tolerability of single subcutaneous doses (Stage A) and multiple subcutaneous doses (Stage B) of ATL1103 in healthy male subjects.<br>To determine the single dose and multiple dose pharmacokinetic (PK) profiles of ATL1103 by the subcutaneous route of dosing |

TABLE 3-continued

| Summary of ATL1103 Phase I clinical trial | |
|---|---|
| | Secondary objective:<br>To assess the pharmacodynamic (PD) effects on IGF-I levels following subcutaneous administration of ATL1103<br>Exploratory objective:<br>To assess the PD effects on circulating levels of (i) growth hormone (GH), (ii) insulin-like growth factor binding protein 3 (IGF-BP3), (iii) insulin-like growth factor acid-labile subunit (ALS), (iv) insulin-like growth factor II (IGF-II) and (v) growth hormone binding protein (GHBP) and on (vi) mitogenic and apoptotic activity following subcutaneous administration of ATL1103 |
| Main selection criteria; number of subjects | Males 18-45 years of age, BMI: 19 to 30 kg/m2, healthy (determined by medical and drug history, physical examination and ECG). IGF-I levels in the normal range<br>Stage A: 24 subjects (four groups of six subjects): randomized for 4 on ATL1103, 2 placebo<br>Stage B: 12 subjects (one group): randomized for 8 active, 4 placebo |
| Test Drug, Dose and Mode of administration | Subcutaneous administration of ATL1103 in the following doses:<br>Stage A (single dose): 0 mg (placebo); 25,75,250, 400 mg.<br>Stage B (multiple doses): 0 mg (placebo); 250 mg. Six doses administered over 3 weeks (on days 1, 3, 5, 7, 14, 21). |
| Criteria for assessment | Safety and tolerability: Physical examinations , vital signs, adverse event monitoring and ECGs. Blood sampling for clinical safety (haematology, biochemistry), coagulation (PT, APTT and TT), urinalysis and complement assessments (Bb)<br>Pharmacokinetic: Blood sampling for plasma ATL1103 levels at various time points over 7 days (Stage A) and 35 days (Stage B)<br>Pharmacodynamic:<br>IGF-I: Serum samples collected at least weekly to day 35. Exploratory PD: Blood sampling for GH, and the following for Stage B only: IGF-BP3, ALS, IGF-II, GHBP and in vitro mitogenic and apoptotic parameters on Days 1, 7, 21 and 28 of the study |
| Subject withdrawals | Two subjects withdrew form the study after the fifth dose of ATL1103 due to 1) withdrawal of consent 2) subject lost to follow up. No subject withdrew or was withdrawn for safety reasons. |
| Outcomes | Primary objective outcomes<br>ATL1103 was considered safe and generally well tolerated at the doses used in the study<br>There were no serious adverse events reported<br>There were 24 treatment-emergent adverse events (TEAE) in Stage A (19 in the 16 ATL1103-treated subjects, 5 in the 8 placebo-treated subjects), all reported as mild or moderate. In the ATL1103-treated subjects most common adverse events reported were pain at injection site (6), headache (5), influenza-like illness (2).<br>There were 25 TEAEs in Stage B (18 in the 8 ATL1103-treated subjects; 7 in the 4 placebo-treated subjects). All were reported as mild. In ATL1103-treated subjects the most commonly reported adverse events were injection site reactions (13).<br>Notably, although influenza-like illness (inc muscle aching and fever) was seen in two subjects after single doses of 400 mg ATL1103, this was not seen after repeated doses of 250 mg.<br>Increased ALT levels were reported for one subject in Stage B at day 11. ALT levels returned to the normal range by pre-dose day 21 and remained within normal range throughout the rest of the study period.<br>A summary of the pharmacokinetic parameters is shown Table 1.<br>Secondary & Exploratory objectives outcomes<br>The effect of ATL1103 on serum IGF-I levels and on the exploratory PD markers were determined as change from baseline levels.<br>For IGF-I there was a clear trend for mean levels to be lower than baseline on days D 14, 21, 28, 35 of the study with a statistically significant effect reached by day 21 (Table 2)<br>No treatment-related effects were apparent in growth hormone levels (data not shown)<br>The inhibitory effect of ATL1103 on other exploratory PD markers is shown in Table 3.<br>Of particular note is the ATL1103-related inhibition of circulating GHBP. GHBP is produced by cleavage from the GHr receptor so reduction of circulating GHBP levels suggests that GHr expression is reduced. This provides support for ATL1103 working via an antisense mechanism of action.<br>IGF-BP3 and ALS reductions are consistent with the effect of ATL1103 on IGF-I (Table 3). |

TABLE 4

Summary of pharmacokinetic parameters (mean ± SD)

| | n | Cmax (ng/mL) | Tmax (hr) | AUClast (hr*ng/mL) |
|---|---|---|---|---|
| Single Dose | | | | |
| 25 mg | 4 | 466 ± 136 | 3.25 ± 0.5 | 3711 ± 822 |
| 75 mg | 4 | 3139 ± 1576 | 3.25 ± 0.96 | 21342 ± 4755 |
| 250 mg | 4 | 12383 ± 3000 | 2.5 ± 1.29 | 88942 ± 11295 |
| 400 mg | 4 | 14343 ± 2823 | 3.25 ± 0.96 | 151123 ± 29434 |
| Multiple dose (250 mg; Pharmacokinetic population) | | | | |
| Day 1 | 6 | 8318 ± 2623 | 3.84 ± 1.49 | 58400 ± 11220 |
| Day 21 | 6 | 8557 ± 1431 | 3.00 ± 0.63 | 91870 ± 16795 |

TABLE 5

Serum IGF-I levels in ATL1103-treated subjects in Stage B
Pre-dose IGF-I: 36.57 ± 13.16 nmol/L mean ± SD

| Study day | Change from pre-dose<br>Mean ± SD (% change from pre-dose) | Probability < (−t)* |
|---|---|---|
| Day 3 | +2.65 ± 9.47 (12%) | >0.500 |
| Day 5 | +0.32 ± 7.42 (6%) | >0.500 |
| Day 7 | +0.77 ± 7.51 (6%) | >0.500 |
| Day 14 | −1.43 ± 7.19 (−2%) | 0.323 |
| Day 21 | −3.40 ± 3.59 (−7%) | 0.034 |

TABLE 5-continued

| Serum IGF-I levels in ATL1103-treated subjects in Stage B Pre-dose IGF-I: 36.57 ± 13.16 nmol/L mean ± SD | | |
|---|---|---|
| Study day | Change from pre-dose Mean ± SD (% change from pre-dose) | Probability < (−t)* |
| Day 28 | −3.43 ± 7.53 (−7%) | 0.157 |
| Day 35 | −1.9 ± 5.08 (−1%) | 0.201 |

*1-sided t-test on change from pre-dose at each time point; alternate hypothesis is suppresion
Per protocol population; (n = 6 at each time point)

TABLE 6

Exploratory PD assessments of ATL1103 subjects in Stage B

| | Pre-dose value/Mean change from pre-dose (% change from pre-dose) | | | |
|---|---|---|---|---|
| | GHBP (pmol/L) | IGF-BP3 (ng/ml) | IGF-II (ng/ml) | ALS (mU/ml) |
| Pre-dose | 1053.8 ± 664 | 2906.2 ± 320.8 | 722.3 ± 113.8 | 1710.2 ± 305.4 |
| Day 7 | −31.2 (0%) | −310.5** (−10%) | −101.8*** (−14%) | −115.3 (−5%) |
| Day 21 | −169.5** (−16%) | −228.3** (−8%) | −57.5 (−8%) | −160.7 (−9%) |
| Day 28 | −233.3* (−19%) | −160.5 (−5%) | −29.2 (−5%) | −188.7* (−10%) |

*P < 0.050,
**P < 0.010,
***p < 0.001;
1-sided t-test on change from pre-dose at each time point; alternate hypothesis
Per protocol population; (n = 6 at each time point)

Example 2

Co-administration of an Antisense Oligonucleotide and Somavert Including in Subjects in Need of Serum IGF-I Reduction ATL1103 is to be subcutaneously administered at 250 mg per day, six times over 3 weeks on days 1, 3, 5, 7, 14 and 21.

Somavert will be dosed subcutaneously at 20 mg per day for 7 days starting on day 1 or day 24.

Although not wishing to be limited to theory, ATL1103 is cleared from the blood after each dose and accumulates in the liver and other organs because of its long tissue half life. ATL1103 will be working to decrease GHR protein on the cell surface of hepatocytes and other liver cells and other organs and decrease the resultant soluble form of GHR in the blood (GHBP) which is cleaved from the cell surface GHR protein.

Control groups: Somavert is to be administered alone for a similar 7 or 24 day period or ATL1103 is to be administered for a similar 21 day period to normal volunteers or subjects in need of reduction of serum IGF-I.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I levels, and optionally, GH levels.

Example 3

Co-administration of an Antisense Oligonucleotide and Somavert for the Treatment of Acromegaly Groups of 15 acromegalics are to be dosed with ATL1103 as described in Example 1 and with additional once weekly dosing for 6 weeks and either (i) 30 mg once weekly Somavert or (ii) 80 mg once weekly Somavert for 6 weeks, starting on day 24.

Control groups: ATL1103 or Somavert is to be administered alone for a similar 9 week period or 6 week period, respectively, to acromegalic patients. It has previously been shown that serum IGF-I was reduced by 16% and 31% and 12.5% and 26.7% of patients were normalized for serum IGF-I levels when administered Somavert alone at 30 and 80 mg, respectively for 6 weeks at these doses. Somavert once weekly dosing was abandoned for daily dosing for acromegalics to normalize the serum IGF-I of a greater number of acromegalics.

Treatment is to be continued with the same or increased or lower doses of Somavert, and with the same or increased or lower doses of ATL1103, and administered with the same or increased or lower dosing frequency to achieve the desired target serum IGF-I levels.

Example 4

Co-administration of an Antisense Oligonucleotide and Somavert for the Treatment of Acromegaly Groups of 15 acromegalics are to be dosed with 200 mg ATL1103 once weekly dosing for 13 weeks and either (i) 30 mg once weekly Somavert or (ii) 80 mg once weekly Somavert for 13 weeks on the same days as ATL1103.

Control groups: ATL1103 or Somavert is to be administered alone for a similar 13 week period to acromegalic patients.

Treatment is to be continued with the same or increased or lower doses of Somavert, and with the same or increased or lower doses of ATL1103, and administered with the same or increased or lower dosing frequency to achieve the desired target serum IGF-I levels.

Example 5

Co-administration of an Antisense Oligonucleotide and Somavert for the Treatment of Acromegaly Groups of 15 acromegalics are to be dosed with 200 mg ATL1103 once or twice weekly dosing for 13 weeks and either (i) 30 mg once weekly Somavert or (ii) 30 mg twice weekly Somavert for 13 weeks on the same days as ATL1103.

Control groups: ATL1103 or Somavert is to be administered alone for a similar 13 week period to acromegalic patients.

Treatment is to be continued with the same or increased or lower doses of Somavert, and with the same or increased or lower doses of ATL1103, and administered with the same or increased or lower dosing frequency to achieve the desired target serum IGF-I levels.

Example 6

Co-administration of an Antisense Oligonucleotide and Somavert for the Treatment of Diabetic Retinopathy Groups of 15 patients with diabetic retinopathy are to be dosed with 200 mg ATL1103 once or twice weekly dosing for 13 weeks and either (i) 30 mg once weekly Somavert or (ii) 30 mg twice weekly Somavert for 13 weeks on the same days as ATL1103.

Control groups: ATL1103 or Somavert is to be administered alone for a similar 13 week period to diabetic retinopathy patients.

Treatment is to be continued with the same or increased or lower doses of Somavert, and with the same or increased or lower doses of ATL1103, and administered with the same or increased or lower dosing frequency to achieve the desired target IGF-I levels, and optionally GH levels and outcomes in retinal disease.

Example 7

Co-administration of an Antisense Oligonucleotide and Somavert for the Treatment of Cancer Groups of 15 patients with cancer associated with increased IGF-I are to be dosed with 200 mg ATL1103 once or twice weekly dosing for 13 weeks and either (i) 30 mg once weekly Somavert or (ii) 30 mg twice weekly Somavert for 13 weeks or (iii) 80 mg once weekly or (iv) 80 mg twice weekly Somavert.

Control groups: ATL1103 or Somavert is to be administered alone, with patients standard medication, for a similar 13 week period to cancer patients.

Treatment is to be continued with the same or increased or lower doses of Somavert, and with the same or increased or lower doses of ATL1103, and administered with the same or increased or lower dosing frequency to achieve the desired target IGF-I levels, and optionally GH levels and outcomes in cancer.

Example 8

Co-administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at, 250 mg per day, six times over 3 weeks on days 1, 3, 5, 7, 14 and 21.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

Example 9

Co-administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at 100, 150, 200, 250, 300, 350 or 400 mg over 3 weeks once or twice weekly or until a cumulative dose of ~1200-1800 mg.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

Example 10

Co-administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at 100, 150, 200, 250, 300, 350 or 400 mg over 4 weeks once or twice weekly, or over 6 weeks once or twice weekly, or over 8 weeks once or twice weekly, or over 12 weeks once or twice weekly.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Altschul et al., J. Mol. Biol. (1990) 215:403-410

Barnes and Sato, Cell (1980) 22:649

Buckmann and Merr, Makromol. Chem. (1981) 182:1379-1384
Carter et al., Nucl. Acids. Res. (1986) 13: 4331
Chen et al., J. Biol. Chem. (1997) 272:5133-5140
Crea et al., Proc. Natl. Acad. Sci. USA (1978) 75:5765
Cunningham et al., Science (1991) 254:821-825
de Vos et al., Science (1992) 255:306-312
Elbashir et al., Nature (2001a) 411:494-498
Elbashir et al., Genes Dev. (2001b) 15:188-200
Englisch et al., Angewandte Chemie, International Edition (1991) 30:613
Epstein et al., Proc. Natl. Acad. Sci. U.S.A. (1985) 82:3688-3692
Fire et al., Nature (1998) 391:806-811
Giustina et al., Pituitary (2011) 14:125-133
Goeddel et al., Nature (1979) 281:544
Gray et al., Gene (1985) 39:247
Guo and Kempheus, Cell (1995) 81:611-620
Hwang et al., Proc. Natl. Acad. Sci. U.S.A. (1980) 77:4030-4034
Langer et al., J. Biomed. Mater. Res (1981) 15:167-277
Langer, Chem. Tech. (1982) 12:98-105
Martin et al., Helv. Chim. Acta (1995) 78:486-504
Mandel et al., J. Mol. Biol. (1970) 53:154
Montgomery et al., Proc. Natl. Acad. Sci. USA. (1998) 95:15502-15507
Nielsen et al., Science (1991) 254, 1497-1500
Putski et al., Eur. Neurol. (2010) 63:311-317
Sidman et al., Biopolymers (1983) 22:547-556
Spencer et al., J. Biol. Chem. (1988) 263:7862-7867
Tabara et al., Science (1998) 282:430-431
Tijsterman et al., Science (2002) 295:694-697
Timmons et al., Gene (2001) 263:102-112
Timmons and Fire, Nature (1998) 395:854
Tuschl et al., Genes Dev. (1999) 13:3191-3197
Ultsch et al., J. Mol. Biol. (1991) 222:865-8
Ultsch M et al., J. Mol. Biol. (1993) 231:1133-36
Ultsch et al., J. Mol. Biol. (1994) 236:286-99
van der Lely et al., The Lancet (2001) 358:1754-1759
Vos et al. (1992)
Vieira and Messing, Meth. Enzymol. (1987) 153:3-11
Wells et al., Gene (1985) 34:315
Wells et al., Philos. Trans. R. Soc. London SerA (1986) 317:415
Zhang and Madden, Genome Res. (1997) 7:649-656
Zoller et al., Nucl. Acids Res., (1987) 10: 6487

The invention claimed is:

1. A method for treatment or prevention of a disease caused by and/or associated withan increased level of insulin-like growth factor I (IGF-I) the method comprising administering to a subject in need thereof, a growth hormone (GH) variant having GH antagonistic activity and comprising the following amino acid substitutions: H18D, H21N, G120K, R167N, K168A, D171S, K172R, E174S, I179T compared with the native GH amino acid sequence shown in SEQ ID NO:2, in combination with an oligonucleotide 15 to 30 nucleobases in length comprising at least one modified internucleoside linkage, sugar moiety, or nucleobase, targeted to a nucleic acid encoding human growth hormone receptor (GHR) so as to inhibit expression of the GHR, thereby reducing the level of IGF-I in the subject, wherein the disease caused by and/or associated with an increased level of IGF-I is acromegaly, diabetic retinopathy, diabetic nephropathy, or an IGF-I positive cancer such as prostate, myeloma, lung, breast or colon cancer.

2. The method of claim 1, wherein the nucleic acid is as shown in SEQ ID NO:4 or SEQ ID NO:5.

3. The method of claim 1, wherein the oligonucleotide is a DNA oligonucleotide.

4. The method of claim 1, wherein the oligonucleotide is a RNA oligonucleotide.

5. The method of claim 4, wherein the oligonucleotide is a short interfering RNA (siRNA).

6. The method of claim 1, wherein the oligonucleotide is a chimeric oligonucleotide.

7. The method of claim 1, wherein the oligonucelotide has at least 70% complementarity with the nucleic acid encoding human GHR.

8. The method of claim 1, wherein the oligonucelotide has at least 80% complementarity with the nucleic acid encoding human GHR.

9. The method of claim 1, wherein the oligonucelotide has at least 90% complementarity with the nucleic acid encoding human GHR.

10. The method of claim 1, wherein the oligonucelotide has at least 95% complementarity with the nucleic acid encoding human GHR.

11. The method of claim 1, wherein the oligonucelotide comprises at least an 8 consecutive nucleobase portion of SEQ ID NO: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

12. The method of claim 1, wherein the oligonucelotide consists of the nucelobase sequence of SEQ ID NOs: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

13. The method of claim 12, wherein the oligonucleotide consists of the nucleobase sequence of SEQ ID NO:6.

14. The method of claim 1, wherein the oligonucelotide specifically hybridises with a region encoding human GHR, wherein the region comprises a translation initiation codon, a termination codon, a coding region, a 5' untranslated region, a 3' untranslated region, an intron:exon junction or an exon:intron junction.

15. The method of claim 14, wherein the region comprises at least an 8 consecutive nucleobase portion of a sequence selected from SEQ ID NOs: 84-154.

16. The method of claim 1, wherein the oligonucelotide comprises at least an 8 consecutive nucleobase portion complementary to a region of SEQ ID NO:4 selected from the group consisting of nucleotides 260- 339, 332- 351 and 344- 423 of SEQ ID NO:4.

17. The method of claim 1, wherein the oligonucelotide inhibits the expression of GHR and/or growth hormone binding protein (GHBP) by at least 15%.

18. The method of claim 1, wherein the oligonucleotide comprises at least one 2'-O-methoxyethyl sugar moiety.

19. The method of claim 1, wherein the oligonucleotide comprises at least one phosphorothioate internucleoside linkage.

20. The method of claim 1, wherein the oligonucleotide comprises at least one 5-methylcytosine.

21. The method of claim 1, wherein the oligonucleotide consists of 20 linked nucleosides, wherein the oligonucleotide consists of a nucleobase of SEQ ID NO:6; and wherein the oligonucleotide consists of a ten deoxynucleotide region flanked on both the 5' end and the 3' end of said ten deoxynucleotide region with five 2'-O-(2-methoxyethyl) nucleotides, and wherein each internucleoside linkage in the oligonucleotide is a phosphorothioate linkage, and wherein each cytosine in said oligonucleotide is a 5- methylcytosine.

* * * * *

SEQUENCE LISTING

```
<160> NUMBER OF SEQ ID NOS: 154

<210> SEQ ID NO 1
<211> LENGTH: 586
<212> TYPE: DNA
<213> ORGANISM: Homo sapiens

<400> SEQUENCE: 1

cgatatgttc ccaactattc cactgagtcg cctgttcgat aacgcgatgc tgcgtgcgca      60

tcgtctgcac caactggctt tcgacactta ccaggagttc gaagaagcat acatcccgaa     120

agaacagaaa tacagcttcc ttcagaaccc acagacctcg ttgtgtttct ctgaaagtat     180

cccgacccct tctaaccgcg aagagaccca gcagaaatcg aaccttgaac tgcttcgtat     240

ctcgctgctt ctcattcagt cgtggctgga gccagtacag ttcctgcgtt cggttttcgc     300

aaactcactg gtttacggtg cgtctgacag taacgtttac gacctgctga aagaccttga     360

agaagggatc cagaccctga tgggtcgcct ggaagatggt tcaccacgca ctggtcagat     420

cttcaaacag acttactcca aattcgatac taactctcat aacgatgatg ctctgctgaa     480

aaactacggc ctgctgtact gtttccgtaa agatatggat aaagttgaaa ctttcctgcg     540

tatcgttcag tgtcgttctg ttgaagggtc gtgtggcttc taatag                   586


<210> SEQ ID NO 2
<211> LENGTH: 192
<212> TYPE: PRT
<213> ORGANISM: Homo sapiens

<400> SEQUENCE: 2

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60
```

-continued

```
Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 3
<211> LENGTH: 191
<212> TYPE: PRT
<213> ORGANISM: Artificial Sequence
<220> FEATURE:
<223> OTHER INFORMATION: Somavert

<400> SEQUENCE: 3

```
Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Gln Gln Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe
            180                 185                 190
```

<210> SEQ ID NO 4
<211> LENGTH: 4563
<212> TYPE: DNA
<213> ORGANISM: Homo sapiens

<400> SEQUENCE: 4

-continued cggcggcggc ggcggcagcg gcagcagcag ctgctacagt ggcggtggcg gcggcggctg 60
ctgctgagcc cgggcggcgg cggggacccc gggctggggc cacgcgggcc ggaggccccg 120
gcaccattgg ccccagcgca gacgcgaacc cgcgctctct gatcagaggc gaagctcgga 180
ggtcctacag gtatggatct ctggcagctg ctgttgacct tggcactggc aggatcaagt 240
gatgcttttt ctggaagtga ggccacagca gctatcctta gcagagcacc ctggagtctg 300
caaagtgtta atccaggcct aaagacaaat tcttctaagg agcctaaatt caccaagtgc 360
cgttcacctg agcgagagac tttttcatgc cactggacag atgaggttca tcatggtaca 420
aagaacctag gacccataca gctgttctat accagaagga acactcaaga atggactcaa 480
gaatggaaag aatgccctga ttatgtttct gctggggaaa acagctgtta ctttaattca 540
tcgtttacct ccatctggat accttattgt atcaagctaa ctagcaatgg tggtacagtg 600
gatgaaaagt gtttctctgt tgatgaaata gtgcaaccag atccacccat tgccctcaac 660
tggactttac tgaacgtcag tttaactggg attcatgcag atatccaagt gagatgggaa 720
gcaccacgca atgcagatat tcagaaagga tggatggttc tggagtatga acttcaatac 780
aaagaagtaa atgaaactaa atggaaaatg atggacccta tattgacaac atcagttcca 840
gtgtactcat tgaaagtgga taaggaatat gaagtgcgtg tgagatccaa acaacgaaac 900
tctggaaatt atggcgagtt cagtgaggtg ctctatgtaa cacttcctca gatgagccaa 960
tttacatgtg aagaagattt ctactttcca tggctcttaa ttattatctt tggaatattt 1020
gggctaacag tgatgctatt tgtattctta ttttctaaac agcaaaggat taaaatgctg 1080
attctgcccc cagttccagt tccaaagatt aaaggaatcg atccagatct cctcaaggaa 1140
ggaaaattag aggaggtgaa cacaatctta gccattcatg atagctataa acccgaattc 1200
cacagtgatg actcttgggt tgaatttatt gagctagata ttgatgagcc agatgaaaag 1260
actgaggaat cagacacaga cagacttcta agcagtgacc atgagaaatc acatagtaac 1320
ctaggggtga aggatggcga ctctggacgt accagctgtt gtgaacctga cattctggag 1380
actgatttca atgccaatga catacatgag ggtacctcag aggttgctca gccacagagg 1440
ttaaaagggg aagcagatct cttatgcctt gaccagaaga atcaaaataa ctcaccttat 1500
catgatgctt gccctgctac tcagcagccc agtgttatcc aagcagagaa aaacaaacca 1560
caaccacttc ctactgaagg agctgagtca actcaccaag ctgcccatat tcagctaagc 1620
aatccaagtt cactgtcaaa catcgacttt tatgcccagg tgagcgacat tacaccagca 1680
ggtagtgtgg tcctttcccc gggccaaaag aataaggcag ggatgtccca atgtgacatg 1740
cacccggaaa tggtctcact ctgccaagaa aacttcctta tggacaatgc ctacttctgt 1800
gaggcagatg ccaaaaagtg catccctgtg gctcctcaca tcaaggttga atcacacata 1860
cagccaagct taaaccaaga ggacatttac atcaccacag aaagccttac cactgctgct 1920
gggaggcctg ggacaggaga acatgttcca ggttctgaga tgcctgtccc agactatacc 1980
tccattcata tagtacagtc ccccacaggg ctcatactca atgcgactgc cttgcccttg 2040
cctgacaaag agtttctctc atcatgtggc tatgtgagca cagaccaact gaacaaaatc 2100
atgccttagc ctttctttgg tttcccaaga gctacgtatt taatagcaaa gaattgactg 2160
gggcaataac gtttaagcca aaacaatgtt taaacctttt ttgggggagt gacaggatgg 2220
ggtatggatt ctaaaatgcc ttttcccaaa atgttgaaat atgatgttaa aaaaataaga 2280
agaatgctta atcagataga tattcctatt gtgcaatgta aatattttaa agaattgtgt 2340
cagactgttt agtagcagtg attgtcttaa tattgtgggt gttaattttt gatactaagc 2400
attgaatggc tatgttttta atgtatagta aatcacgctt tttgaaaaag cgaaaaaatc 2460
aggtggcttt tgcggttcag gaaaattgaa tgcaaaccat agcacaggct aatttttgt 2520
tgtttcttaa ataagaaact tttttattta aaaaactaaa aactagaggt gagaaattta 2580
aactataagc aagaaggcaa aaatagtttg gatatgtaaa acatttattt tgacataaag 2640
ttgataaaga ttttttaata atttagactt caagcatggc tattttatat tacactacac 2700
actgtgtact gcagttggta tgacccctct aaggagtgta gcaactacag tctaaagctg 2760
gtttaatgtt ttggccaatg cacctaaaga aaaacaaact cgttttttac aaagcccttt 2820
tatacctccc cagactcctt caacaattct aaaatgattg tagtaatctg cattattgga 2880
atataattgt tttatctgaa tttttaaaca agtatttgtt aatttagaaa actttaaagc 2940
gtttgcacag atcaacttac caggcaccaa aagaagtaaa agcaaaaaag aaaacctttc 3000
ttcaccaaat cttggttgat gccaaaaaaa aatacatgct aagagaagta gaaatcatag 3060
ctggttcaca ctgaccaaga tacttaagtg ctgcaattgc acgcggagtg agttttttag 3120
tgcgtgcaga tggtgagaga taagatctat agcctctgca gcggaatctg ttcacaccca 3180
acttggtttt gctacataat tatccaggaa gggaataagg tacaagaagc attttgtaag 3240
ttgaagcaaa tcgaatgaaa ttaactgggt aatgaaacaa agagttcaag aaataagttt 3300
ttgtttcaca gcctataacc agacacatac tcatttttca tgataatgaa cagaacatag 3360
acagaagaaa caaggttttc agtccccaca gataactgaa aattatttaa accgctaaaa 3420
gaaactttct ttctcactaa atcttttata ggatttattt aaaatagcaa aagaagaagt 3480
ttcatcattt tttacttcct ctctgagtgg actggcctca aagcaagcat tcagaagaaa 3540
aagaagcaac ctcagtaatt tagaaatcat tttgcaatcc cttaatatcc taaacatcat 3600
tcatttttgt tgttgttgtt gttgttgaga cagagtctcg ctctgtcgcc aggctagagt 3660
gcggtggcgc gatcttgact cactgcaatc tccacctccc acaggttcag gcgattcccg 3720
tgcctcagcc tcctgagtag ctgggactac aggcacgcac caccatgcca ggctaatttt 3780
tttgtatttt agcagagacg gggtttcacc atgttggcca ggatggtctc gatctcctga 3840
cctcgtgatc cacccgactc ggcctcccaa agtgctggga ttacaggtgt aagccaccgt 3900
gcccagccct aaacatcatt cttgagagca ttgggatatc tcctgaaaag gtttatgaaa 3960
aagaagaatc tcatctcagt gaagaatact tctcattttt taaaaaagct taaaactttg 4020
aagttagctt taacttaaat agtatttccc atttatcgca gaccttttt aggaagcaag 4080
cttaatggct gataatttta aattctctct cttgcaggaa ggactatgaa aagctagaat 4140
tgagtgttta aagttcaaca tgttatttgt aatagatgtt tgatagattt tctgctactt 4200
tgctgctatg gttttctcca agagctacat aatttagttt catataaagt atcatcagtg 4260
tagaacctaa ttcaattcaa agctgtgtgt ttggaagact atcttactat ttcacaacag 4320
cctgacaaca tttctatagc caaaaatagc taaatacctc aatcagtctc agaatgtcat 4380
tttggtactt tggtggccac ataagccatt attcactagt atgactagtt gtgtctggca 4440
gtttatattt aactctcttt atgtctgtgg attttttcct tcaaagttta ataaatttat 4500
tttcttggat tcctgatagt gtgcttctgt tatcaaacac caacataaaa atgatctaaa 4560
cca 4563

<210> SEQ ID NO 5
<211> LENGTH: 304901
<212> TYPE: DNA

-continued

<213> ORGANISM: Homo sapiens

<400> SEQUENCE: 5

```
atggttttct ttaatcagca cttcagtgat ttacttatta tgtttattgt tcattgtctc     60
tcctaactag aatgcaagcc ccatgagggc agcatctttg tagatatgtg gtataaattt    120
tgttccctga tgcatgctaa gtttttagaa cgaagtctgt catagtgtag gctcaccaac    180
atttgtatga atgaaagaac atggtgaatg ggaattcagt gttagtttaa aaaaaattca    240
ttaaagggat aatattttat tagaatctta ttaattttac cagtaaatat tgtattaatc    300
agggagatat atatatatat atatgtcata ttcatgagat atatatatat atatatatgt    360
catattcatg agatatatat acagagactt attttgagaa atttgctcac ataattgtga    420
aaactgaaaa gtcaaaaatc tacagggtaa attggttaca gatttaggga atagttgata    480
tgcagtttga atccaaaggc tgcctgctga cagaattttc tcttctttgg gataggtcag    540
ttttttctc ttaatgcctt caactgatcg attgaggccc acctacatta tgtagagcaa    600
tatgatttac tcaaagtcta ttgatttaaa tgttaatctt accataaaaa tgcctttgcc    660
aaaaaaatct aaaataatat ttgaccaaat atctgggtac catggtctag caaaattgac    720
acataaaatt aaccatctca atgtgtcaac tttgctaggg catggtaccc ggacatttgg    780
tcaaatatta ttcaaataaa tttagaattt atcacaaatg tttgatatca taatttgatt    840
tacaaatatc aatctaatac tttattttac agctgaatga tctcagagag caacccttc    900
cttctatagg ccaagaaatg gagtcattgt gagattagta actaatttac ccaaaatcac    960
agaggaccca cacaggatcc caaggctcct gactaacaat cctatgttct tcaactacaa   1020
atgctataaa acaaaacagc tataaaatgc tactttaagt gttttggcct cttttgtttt   1080
gttttgagaa gaagctttgg cattttatag tacaacagag tgactaaagc catgctctaa   1140
cctcagataa ctgtagattt aggaagttta tactgtggtg ttttatggtt tggggagatg   1200
gcgatctgac ctagatatct gcacttgaat atatataatc agaattattt tctaattgtt   1260
tctattgtct tcaaggcagt ttatattttt tgctaagccc tactggggat gtataaaaga   1320
ctggggaagg gtgggccata ataaggtaag gccataataa ggtaaaatag gttggacaag   1380
ataagttagc caatatctga gtaaagactt caaggaactg taggaggaag caaatgaata   1440
tttgtggaag tgtgtttaaa tcagagagaa aagccagcaa aaagccttca agttaggagt   1500
ctgcctggcc tgcttaagaa acagcaggga ggccggtgtg ctgggagcag aatggatgac   1560
ccagtgatgg ggaaattcat gggagatgag gtgtggggca aaggtacata gctcacgtag   1620
ggtctcatgg gccattttga attttattct gatttgaatg gggaaccatt ggagggtttt   1680
gagctgagga atgacatgat attaatttta aaaggaatga ctatggcaac tgaatttata   1740
ctttgggttg ttgttggtgt tggttgggga ttaggggtgg ggtttgtcaa agcaagcaga   1800
ccagttgagt tgagagacta ctgcagtaat ctgagaaatt ctggtggttc agaccaggtg   1860
tctctggacc tctccaagaa aatagacaga gttttgaatg tggaatgtga ttggcagaga   1920
agaagtaagg atgatttcaa aggtttgtgg cctgggtaac tggcaggaag tagttgccat   1980
ctactgagat ggaaatgtca cccactgtga ttggagtatg tttaaggaga aagaaccaga   2040
gttcagatgt ggacatgtca agtttcagag gtctgttaga catccaaatg gagataccca   2100
gttgttagcc tggagctctg tggagagatc tgggttagag atataaatcc aagagataca   2160
acttttcatt caatttgatt atttattgga cgctttataa actctgtaaa tactgggcac   2220
taacctagac attgcaggta cagatattaa gaatatatag tttctccctc agaaatctct   2280
```

```
taattaatga gaaaagcaga catgtcaaca aaactgcaat atttaataaa agaagatata   2340
aaggcctata aaggtgctga tacagggaga attaattaat tccaccctgg ggaatagtca   2400
ggaagacctt cagagagaaa gtaaacaatt gattggaact ttaagattaa gaaggatttc   2460
tctgggtgga caaagtagga tcttccaagc agagtggaaa ccatgagcaa atgcagtttc   2520
attcttcaga aggtaaatgt gctctggcat gccttaactt ataacaaatt aatcaactca   2580
atacctgcta cattttccct cacaatttgg aatatataaa gaggcacata ctactatgga   2640
ccaatacctg gtcatatatg agattgaagg acctttactt acgaggctta aaaataaaga   2700
ctgcccttca tgtcagttgc aggtttatat ctagttctat agtattaact gaggtgtctt   2760
ttcctatgtt ttctgtgcat gatgactttt taaaaatcaa agacagagca gcagccagag   2820
tagtctagtt tcatggcaca cagaatggag gatattgctg aacccagatt taaaaaaaaa   2880
aagaagtcaa ttcttatttt tttaagtatg gccctgagct catctcagag cataaacaat   2940
agaatttaga atatctttta tgactccgtc tggcacctcc taaactagat caagattctc   3000
tagctcaggg aagaagggca aaggatgaga aggcacagag aggatataaa cagagaggtt   3060
ggtagtgcca ggctctgaag aaggtccaac ttggaaggtc atttcagaca ggcgtggagt   3120
cagcatttga ggcctgtctg gtctctactc ctgccaggac taccctgtca gccagcttgg   3180
caggtatgga ccacccagca ggagtttttc ttgactgtgc cctaatcttt tactttccca   3240
agtttctcta tatgggtacc tccccttta aaagctccag acacagccaa gcaccactat   3300
tgctccagca aagtatgaag ccccagaaat caatggtttg gggaagagtc ttaggggaac   3360
taaatgcctc cttattttta gatgccatag aacaagagca gttcaggatc aataaccatc   3420
ccaccccatg ataaaacacg ccccttccag aatctttcct ttttcgttca ttctaggtgt   3480
ctgtctggaa cagctggggt atttgagcca cagctgagct tctgaaagca ttctaaggaa   3540
cagtttttca cttatctgat tcctttgaaa ataggggtat cttatgtgat atctgctatc   3600
ccagagtctt tggtcctctg ttccttctca agtcttggct cccgtgtact acttcaaagc   3660
cctatagata ttttattcta aagaaaagaa acttggttcc tttaagttgt ttaaacattt   3720
ctttctgggt ataaacttgg gtttgtgtct gggagctctg ttaaaaaaaa aaagtcttta   3780
gtaagccaaa gctgttagaa gcttataagt aagtgacatt acaattgacc gtcagtaaat   3840
agtggaaaga ttgcatgact agctactcct tcagatctga gacaacctgg agctagattt   3900
ttgtactctc tactcagaaa agcatatagt gacttggggt ttgatgctgt acaaaaatga   3960
catgcttatg cacaacttta actttctgca acacttttac aacttcttgt gaatgaagta   4020
ggcagggctc gcatttgaca gatgagctat gtccagcgtg aggcagagtt aaaacccttt   4080
tcctggctca ggaacttcag gctggggcct gtgtctgctc tccctgcatc cctgtcctct   4140
agcagatacc tctctgctaa catgctgagt gtccttggta aattactcat tctctctgtc   4200
tccgtcttct aacctccaca ataaagtcct tcgtagtttt aactatcttt tcactgtgcc   4260
ccagtgagca ggagtttgga acttgattgt tgatggaaag gcaatatttg gatggctaaa   4320
cacgctttcc aaggtatctc gctgatcttc ctctcattcc tggagatagc taaccttttt   4380
gtaagtgttt ctttgagtct gtggactgca cttaacgctc ttgtaggtcc tgctttcatt   4440
tggaacgggc aggcggagag gaaggaagtg tattgcaact accaatattt tcctctagga   4500
ggagccgcgc agctcagttg agagtgacac gcaccaactc cagctcctcg ccgggaagac   4560
ttcatcccag caactcggaa tgcttggccc gggcggcact cggcctctcc gcagcagttc   4620
```

-continued

```
tcgaactggc ctccttgaac gtccgcttcg ccttcgcttc tgcaacctgg atctggggga   4680
ctgcgggcca ggcgcggcgt gacccctggt gaacggtggc cgccttttcc cacccctgcc   4740
ctcccatcct cccttcccgt ttcaccccgc cccctctctc ctccccaagc ctgacagccc   4800
gcgagctgcc aagcagggcg cagccatggg aagaggagga gggctaggga gcggcggcgg   4860
cggcggcagc ggcagcagca gctgctacag tggcggtggc ggcggcggct gctgctgagc   4920
ccgggcggcg gcggggaccc cgggctgggg ccacgcgggc cggaggcccc ggcaccattg   4980
gccccagcgc agacgcgaac ccgcgctctc tgatcagagg cgaagctcgg aggtactgga   5040
gtggggctcc gggagtctgg ctttattttc ctcctgttgt gccagggggc ctgagggtga   5100
accctgggac tctagttgtt tatgaaaacg ggaggatctg tcttatatat ttacacggat   5160
aattttttat tccggatgac ttggctgtgc tcccctcctc cttgcgaaga agttgttttc   5220
tgctggtggg ttgttgtaac ccaatctagt gtgtgtgtgt gtgtgtgtgt gtgtgtgtgt   5280
gtgtgtgtgt gtgtgtctgg aagttggtga gggcggcagg gagttgcggg cgacagacga   5340
accatcacac tctggcgtct gctctggccc gcgagtagtg tacgtggagg ggtttactcc   5400
ggagacagtt ttgttaaagt cataaaagtt ttgctagtgt gtttctgttt gccatcatct   5460
gcctggctgc ggcaggaact gccgaggctg ctgctgttgc gcggggaaga atccccggca   5520
gcgcgactgg agagactggg gaggtcgagc tgtgcgcgtg gacacagcgc gcagagcgcg   5580
cggtcttttg cgcgtttgtg cgggccgcag ccgcacgttg gcaccgatgg aactggggtc   5640
agtagagtga cagccaccag tccgcatgaa ctggggtaag tggaaattgt ggcgagccga   5700
cctcccccag cttttgacac actagtggtt gtaaaatcaa ccaggcttaa agttttgaca   5760
gaactgccag aggctgcggg tcaatggggt ggccgcgtgt ctagggagag ggcgctggcg   5820
gcgcagaggg tgcggggcag ggcacttgcg agtgcgtggg gaagtctatt tggggcgagt   5880
gctttatata tagcccgagg ggatgcctgc tgagaccgag ctgcgggggc tctcggtctg   5940
gcgcggactg tgtgtcctga atgagtgtac gtgtgcgctg tgtgtgcgcg cgcgagtgtg   6000
cgcctgggga ggcgtgtcgg cgcctgagcc agtagggtgt gcagggtgga agaggccaca   6060
gaggtgccgc ctgtctgttt gtgccgccag gagaccttgg aagggacaga gaaaggtaac   6120
ggaaggccaa agtgttggga agtcagagta gtttctgcat aggattaagt attaagggct   6180
ttaaaataac taaacgcatt gccctgagtg gctgaggact ggaagtgagg ttttggggag   6240
ttctcaggag aactgcatgg gagggcgttt gggaggtcta agggatgtgt aatatgtgtg   6300
agtacagaac ttcggagaca gacacaggtt ggagctatga atttgaaatt ttcagggtgc   6360
tgctgtccac agtccaggga ctggctggtt tcagaggtat tcaggctccc tggtgtgtgt   6420
gcctgggaag acactcatct tttcttgcag acatgggata ttgtggcagg tcaggctctg   6480
tttcctgagc aactggtgtt ccaggctagt ttccacctga atcaccctag aagtgtcttt   6540
tttctgatga taaatgttga aacctttcca gaaattaaaa tgctggatag aaacaaaatt   6600
gatgcagcag acaggattgt tgattctatt tattcagtga ttgggagctc tttttccttt   6660
tgagaaaagc aaagctcagt gtttccagat tagatttcaa ggagtcttca gctatctaca   6720
gcttcccttc tgggcctttg gatggagctg gaaggatgtg ttttggccta aagacctttg   6780
gaagacatca tgtgtagctt aaagaggttg tcccgtctct catcatcttc ttccaccctt   6840
ataaactttt tgttttgcat taatctaagg aaagttggtg tgtcaacatt tagctttttt   6900
ttattggagt aaatatatca cagtgaaatt atagttatgg tctcctgaag cccatggaaa   6960
gccaacactt aatgggcaaa ggtgtgaaat gaaagtctat aaatgcaatg acaaagtgac   7020
```

-continued

```
gagatgagtg cattcttttt tcaaaatgaa cataactgtg ctcacaaaaa tttgttttag   7080
ccaggctttg ggcccatgtt ttttattatt agtttttaaa cagcagactc cacatcataa   7140
accactttaa aatggatact agaggcctcc tgtatgctat ctctggcgcc tgcttaaaca   7200
gatgtttaca gtgcttggta acctatggga ttgtcatgtt gagtatcttg ttagctcagg   7260
acataatgtt tatagcataa tataataaat ggagccacag ttgcagcgtg cttcttccaa   7320
gtgcatgaag caaatcttgc agcagggaaa caaatcttgc agttggtcca acttggctag   7380
ccttctttgg ctatctcctg gtgagcaatg ttaatgtaaa gataaatgtg agtgacgtag   7440
tgagaaagtg ggacagtaaa ttgtttagct tagtgaaaaa agcatggatt atgtttttta   7500
aatctgctaa cctgaagatt acacttctca ggtcgtacca ctggcaaatt gcacaactat   7560
gggaatttgg tttgctttta aagagcaatt tttaaaaagt atgtcagtaa tgaaaataac   7620
ttatatttct taatgtgttt atgtgtgtcc atacaagcca atactttttc ttctttaaaa   7680
agaaccctat aatttctgtg gtaattattt aaatattatg agcattcaaa tctcctaatc   7740
accttttcaa tcttcaattg ataagaatcg aagtttggta agactggagt catccctcag   7800
ccaattgtgt aaacaagaca gtacagaatg tctttctggc aagtaatttt tttcaacctg   7860
aaacagataa tataaataat atgtcccata aaagaattac ttaagatgat aattacttta   7920
gaggtaatta tctggtgcat gaacctctat ctgtgaaaat ggtctagtct atctcttatt   7980
ggaaataatc agttggaaat ctcccttttt cattggtcag tccattctag gaaagattca   8040
tttctagaaa gttcttatac tgaatcaaca ttttcttcca tccacttgcc tatccttcag   8100
cagctgacca caatgaatct agtctctttt ccctgtgttt accatacttg aaaacaaata   8160
ttatcctcct tgccgaatcc ccttttgcct actcttggag cagtttttca tccactatag   8220
ggttccaccc tcctctgcct tgaacaagat gcccttgatt gtacattctc attgtattag   8280
tctgttctca tgctgctaat aaagacatac gtgagactgt gtaatttata aagaaaaaga   8340
ggtttaatgg attcacagtt ccacatggct ggggaggcct cacaatcatg gcggaaggtg   8400
aaggaggagc aaaggcatgt cttacatgac agcaggcaag aaagcatgtg caggggaact   8460
gccctttata gaaccatcag atctcattag acttattcac tatcatgaga acaacatggg   8520
aaaaacccac ttccatgatt taatcaactc ctactgggtc ccttccacca catgtgggaa   8580
ttatgggaac tacaattcaa gatggcattt gggtggagac aaagccaaac catatcattc   8640
cgctcctagc ccctcctaaa tctcatgttc tcacatttca aaaccaatca taccttccca   8700
acagtccccc aaagtcttaa ctcatttcag cattaactca aaaatccaca gtccaaagtc   8760
tcacctgaac caaggcaagt cccttccacc tatgagcctg taaaatcaaa agcaagttag   8820
ttactttcta gatacaatgg aggtacaggc attgtgtaaa tatgcccatt ccaaatggga   8880
gaaattggcc aaaacagagg ggctataggt gcaagtccaa agtctaatag ggcagtcatt   8940
aaaccttaaa gttctgaaat gaactccttt gacttcatgt ctcacatcca ggctgttttc   9000
atggctggca ttgactgtgg cttttccagg cacatggtgc taactgtcag cccctaccat   9060
tgggggtgct ggggaatggt ggccctcttc tcttagctct actaggcagt gacccactgg   9120
ggactctgtg tagaggatcc aaccccacat ttcttttcct cattgcccta gcaagggttg   9180
tttatgaggg ctctgcccct gcaggacaac tctgcctgga catccaggca tttccataca   9240
tcctctgaaa tctaggtgga agttcccaaa cctcagttct tgtcttctgt gcacctgcag   9300
gaccaacacc acatggaagc ttccaagact tggggctttc accctttgca gccatggcct   9360
```

-continued

```
gagctgtacc ttggcccctt ttagacatgg ctagaggggc tgggacacag ggtaccaagt   9420
acctaggctg cacctagcag gcccagaaaa ccatttttcc ctcgtaggcc tctgggcctg   9480
tgatgtgagg ggctgccata aaggcctctg acatgttctg gagacatttt ccctattgtc   9540
ttggtgacca acatttggct tctcattact tatgcaaatt tctgcagcag tcttgaattt   9600
ctccccagaa aatgggtttt tcttttctat ggcatcatca gcttgcacat tttccaaact   9660
tttatgctct tttcacctct tgaatgcttt gctgcttcta aatttcttct gccagatacc   9720
ctaaataatc tctctcaagt ttaaagttcc acagatctct aggacagggg aaaaatgcca   9780
ccagtctctt tgctaaagca ttaacaagag tcacctttgc tccagttccc aacaagttct   9840
tcatcttcat ctgagaccac atcagcctgg actttattgt ccatatcact ataagcattt   9900
tggtcaaagc cattcaacaa gtctctagga agttccaaac tttcccacat cttcctgttt   9960
tctgagccct ccaagtctct agaaagttcc aaactttccc acattttcct gtcttctttt  10020
gagccctcca tactgttcaa acctctgcct gttacccagt tctaaagttg cttccacatt  10080
tttgggtatc tttacagcag caccaactct accattacca acttactata ttagcccatt  10140
ctcatgctgc taacaaagac atacccaaga ctgggtaatt tataaagaaa attaggttta  10200
atggtcgcac agttccacat ggctgggagg cctctcaatc atggcagaag gtgaaggagg  10260
aataaggcac tcttacatgg tggcagacaa taaggcatgt gcgggggaac taccctttat  10320
aaaaccatca catctcatga gacttaatca ctatcgcaag aacagcatgg gaaaaactcg  10380
ccctcttggt tcaatgacct cccactgggt tcctcccatg acacatgggg attatggtag  10440
ctacaattca agatgaaatt ggggtgggga cacagcaaaa ccatattact gactgtccct  10500
cctaatgtgt gttttctaaa caaaagattt ataatttgta gttctgaaca ttctatatct  10560
attaagacag tttaatatta atgaaattct ttagccattt cattacgctc ttgattaatt  10620
tcatacctat aaacaagata acttgttctt ttcagattat taatcatcca tagtcaaagc  10680
atttttataa tagcttcaaa acattttttc atgcctgaat gtactataaa tttatggaaa  10740
gtataatact gtgtgggtaa ataaaattct ataaacagtg caaatagtga cttaatttct  10800
ccctatcaag gaatatcaac cccaaatata ccgaaagtag aatgttccaa agataaacaa  10860
gttgaaacta catgttatag acaggtaggg actatgatgt attttttca taggcctcat  10920
tgtgtctgct tccatgaaca tgagtcagta ctagcaatca ggcatttatt gaaggcttgt  10980
tctgccaaag tcccagagag tatgccatct ggccttaaat gaagtgaaag tacatcaaat  11040
aaagatactt ccttgggcaa ctgggattta agatgtgcat gcaggacatg tctaagtcag  11100
ccatctactt tttctcagga ggtaaatggc ttgccaatgc cacaggaaag tctaaagtgt  11160
tcacactcca taagcaggtc ccatgtcctg ttgtaggtct ggacaggagc tggacaaagg  11220
ccctgttact cttagcttac caagtcttag ctgccttgga agaagatagc aaatctggct  11280
tatccagagg agaggcctga agtgtgcatt gggcacctac ctggtgtgac tgatttctct  11340
tttatgtatc tgtcttgggc ttccagctaa attgtgaatt ccccttgcca ccaagctaag  11400
aatctgccac agcattgtct tcctgcacac acacacacat acacacacac aaaaacatat  11460
atgttggatg atgaagagac aatgtcagtt tttcagcaag tctgaatgtg aaacaaatgg  11520
ctatgtttct tggtgcagtg gggtgggagg atgagagaga aaaaacaaac ctgtgatata  11580
aactgacatc tgagcctacc aaaagccctt tgagagacct ttgatcaaga caaggggata  11640
atcatagtgt tgtgcactta gataaaattg tccatgctag tcccgtgtgt gtgtgtgtgt  11700
gtgtgtgtgt gtgtatgtgt gtgtttcttc actttatccc cagcattatg gtctcaattc  11760
```

-continued

```
atacacattt gctttttgc tttattctag tctgatatga agggaagaaa taagcaatga  11820
ttcagttcct ttttttacat ttcaaacatt catttcacta ctccccacct cccagtcctc  11880
accccccaaa attacaagag acccattggc aagtacttgg acatgcaatt ttcaaaccaa  11940
aggtttactt tgctataaga aacgtctaag ttaggatgat ataatatgaa ataatagtaa  12000
attagatgtc aagaaacttg ggtcctctcc aagctctgcc tttaatgggc tttgcagttt  12060
ttgccaacta tttaaccttc ctgggcttca tatttcttgt atgttaaaaa caagcaaaaa  12120
ggagaagtaa acaaaatgac cccttagaat tctcttcagg gctattgttt gaatccattt  12180
aattatcaaa tttctctctt cttttaaatg taagcatcaa aaaatgtttg cctattttat  12240
tctctcatca ttaattttta atcaattaaa taaaatagat aaaaatttta tcaaaaccat  12300
gcttcttgct ttcattctaa aacaatgcaa ctcatcacta tctgatgcag aaagtctttc  12360
tgaaatattg tttttctctt ttgttgttgt tttttctttt gtgctaaaga aaattcattg  12420
atgagtacca ggttcttcaa agaaggatgg aaaagtcatt gtttttttagt ctcaacttct  12480
ttcttcagtg cttcttccta ccttttaata taggcaaata aagccttagg ccaggcacta  12540
attttactta gtaatgattc ataagaaggt agtgattttg tcagaaattg ctggctgcat  12600
gcttttaatc agcatctaaa cttaccttca aatactccat tccaaaatca gcagataact  12660
tcttctacag agtctttcaa acttccagat gtgtttactg ttttgattag ggctttcttc  12720
ttttgttgtt gataagactt cagccagttt tctttaggct aacattatta tattcccaat  12780
gaattatact tcttaggttg tgaatttgtt taaagataaa tctatctcca gctggctggc  12840
ttctaagtaa aaaggggtat cctagggaag aagtgcactt cacagggatt cagtacaggt  12900
gtagagaatt ccctgataga gaattggaac acatcaagag tttgcaaatt gaaaaggtac  12960
ttttatgtac ttatccatgg tggacaacct gtgtcctagg gaagaagcgc atttcacagg  13020
gattcagcac aggtgtagag aattccctga tagggaactg gaacacatca agattttgca  13080
atctgaacag gtacttttat gtacttatcc atggttgaca acctactgtg ctagacattt  13140
gctgtagtaa ctccttgatt ttttcctcgg ttgtttataa aattaaacat ttgaagtagc  13200
ctattgaaaa gtcttaaaag aagcatctcc tctattcctt tagaatacag tatattaaac  13260
aagtgataaa gtccaaagaa aaatccttat tcttttcttg ctttaaaaaa tgcactttat  13320
tttattaagc attatatcta tcttttaaaa ctttgaattg ccatatcaat gaaagtagag  13380
tgttatcatt acaaaacaga atcgcagata gttctttccc tgtgcttatt gagagaaaag  13440
gtgcataatt gatgctgtaa atgatcatct tgaatttgat gatggctggt gagaaacctc  13500
agtcagacat tcaattttga ttgccattgg tcagaaaggc agcctttgtt cttcgtcact  13560
atgtggcaca tgatcctaat tcaccctatc agctgcttct ctgcacactt tcaagctatg  13620
tgattgttat actagaaagc ctctaagttg gccaaactaa tgaagactaa tctgacaaag  13680
catatgtgaa tgataaattc tgtaaagacc gtggagatag agcctctgca gtggcttctt  13740
cccctgggga tagaagaaga taccagaatc cctgggcaag atgaaataga taaaggaaag  13800
gcatcatttt tatacctagg aaatcagaaa gattaaagaa agagaagcaa gaataaagaa  13860
gaactactac tttcatagtt cattctttca atgtagcacc ttatttccca tagagacatt  13920
ggtgaagcca tgcttttctt tgccatagaa taggtgttca gtaaatattt tgcaggtggc  13980
cttaatatgt agtaaaacat acagaaatat ggaagcattg acaagaagtt tgtggataat  14040
ttgagggcaa aaggatgtag ataggatcag gttcataatg caaatttgct attattctcc  14100
```

-continued

```
ttagattaat gatgtcactc aaacttcatg acctgctttc caaggtgtat gctgttcaca  14160
gccttggaaa catttagaag tttttagtac ttggagcaag atggatatat gtttcacatt  14220
ttatctagga cttagtagga cttgggagac atatctactt tgccagatct tagtatactt  14280
attatggagc atgacatttt aattctcttt gcttttgtcc tacaaagttt agtgttttaa  14340
tttatttttc tcggtgcata tagggagaga attatttata taatctgaaa agtactttga  14400
aaactacttg ggaaaatatg ttgaataaat aagttttttt ttaaattagc ctacaggatg  14460
taagtctggc caggctagtg gtatttttgg tatcattgtg aaaaatcaaa aacagaacat  14520
gtatttatca atccattagt gtgttcccag gaatgtgcta gacactaggg aattaaaaca  14580
tgactcttga ctttagtacc aagcattcaa gctagaaggc aacactatta atgtacattc  14640
atggtgtgat tatggaacag tcgatgactg tacaacttaa tgaaaagttc attagagact  14700
ataaatgcta catttattta gagagaagga caatctgttt ggactgaggg attggaagag  14760
tggccttcat gggcaacatg gctcctgagc cagtacttaa gatatggtat tttttttttt  14820
tttttttttt tttggttagg tagaagggtt ggagaggttt catgcaagga gttaggaact  14880
gaggaccagg aggcgtatct tgagttcact ggggttactg gtaataggga ggaggcagag  14940
agtaccaggc tgtggatttg ttatccgttg gaagctcttc ccattgctta ttatggtcgc  15000
tgcatatagg ctcatccctt gggtagggct attggagtgg ccaccctgac cctattgctg  15060
attggatagt ggtggctgct gtgtggtatt tcagcacatt tatcttttct gaacattatg  15120
taaattcagt ctgaaaactt ctttcttaaa caatgttcca agaggcctat taaagatgcc  15180
aacaatatga cttccattca agaatatgat cttgaatggg ctttacaatg gcagagctga  15240
cctgagatta cctcctctgc tcctgctctc aagccatgtg ctgatgctga cagtcctggc  15300
ccaatagagc catagggcct cacagaactt gagatcatct accagtggct gtcaaccaag  15360
ccactccttt ctgctaggta gtgcataggg acattgggaa atacagttat tataagaact  15420
ggaaagagtt gtaggctttt ggtgcctgaa gtcagaaatg ctaaatttct gtgatgccag  15480
gggcagtcct atataagaaa ttattgtgcc tcctcaaatg ccagtagatc cctattgaaa  15540
tacttgagtc tcatatcctc actttattta taggtgagga aatgggaggc cctgagaagt  15600
gacaaaactt tcttctagga ttaaacttca cagtctcagt gacagattta taactcaatt  15660
cttttagttt tctttcaaga gctcttgttg cagcaccaca gtccctccta ttaacatggg  15720
ctataactat ggaatagcat gttgtttatc tctgccattt ttatagaagg atgatagtta  15780
gctatgttaa ctatctgaat gggtggaatg tgaattgaga taactggtac ttgaccagca  15840
gttctttcgc ctgggaacac acacagattc acctgtaaat tagggttggc agatgcctgt  15900
tgagatgtca accatagcca aagcttacaa attggttgac tttttggaaa gggcatggag  15960
taggctttgg attcacacaa atctgcttgt ctgaccggat ttgaatacaa cccttcttat  16020
ctttactatc tttgtgactc tcagccaatt aaactctctg agctttatct gcaaaaaaac  16080
agttgattat tcttatttca caagcaatga gtcaaaatag tgcctggcac atattgggca  16140
ctgcagatat agagaattcc ctacagtatc tttttgagca taaagacttg aaaccttcac  16200
ttataaaaga ccctcttgat aacagtcgct atttttttct cctcctttcc ccaaacaacg  16260
aaactagggc ttcagtgagt ccctgaagtg tttactttgt ttgaactgtt gagatttccc  16320
tcctccagaa gagtcctgct ggccagagat gagttccttt tgacttctct gtcaacgtgc  16380
ctgtattatt gtcacatagt aaaaatgaaa gatatatcta gatgattatt agcaggttat  16440
gaaacttaga ttttaaagtc aataataaaa gccattcctg ggtagagaag tttttcagag  16500
```

agatttctac cttgccagcg atgagagagc ctacttaggt gaggtgaata ctttaggcaa 16560
gttaagggat aacacaatat aatttattta agtaagtttt ttatctggga ctaatttcag 16620
gtttgcagaa aagttgcaaa aattttagag gtcctgtata ttcctcacct agtttcccat 16680
gttgacatcc ataatcatga tatatttgtc aacactaaga aaccaatgtt agtacagtac 16740
tattaactaa aatccagact tcatcctaat tcccccagag cttccactca catcttcttt 16800
tctgttccag gattcaatcc agaagcgtgc actgcttttg attttatgat ttttaaatac 16860
tgtgcatgtg ctttttttaat ttgggccctc tcatgtgtta aacttaccgg cctttgtaac 16920
cagatagcaa gttctgtaac agaaaataca atgatgttga atccaacatc atgctgggca 16980
caaagtatgt tctccaaact aattaaattt atcacagcaa caagaacaaa gttttactca 17040
gcgtacatat gtagctgagt cctcattggt aagctaagag gtagtcataa gagtgggata 17100
acttggaaga aatttgattt tgaatgtgtg ccctgaacat tggtataaaa caggaccccc 17160
taaatcatat atgaactgag tctgtacact gtgcctagca ttgtgtgtgc atatcacact 17220
tactcctgat aactgtaagg cacatagcct tgagtaactt agctgaggaa atgagaccaa 17280
gggaagttaa gttacttggc cagggattca cagctagtaa cacagctgag attaaaacat 17340
atgtttttct ggcttcagag cctacactcc taatgctgta ttcaattact cccacacttc 17400
tccacttgct taacccctat tcttggtgtc ctttttctag gtatacagaa tttgaaaact 17460
atattgtcaa actacagcag acctggatgc atggtataca cttctttgtg agctggatta 17520
agtttcagcc ttgaatttgt ggattatttt caaaacctgc ctaacatctg taaaacatgt 17580
tgttttttta atatgtagat atccacataa attgaccaca atgctcttca gaaagtccca 17640
taatccaata ataaataaat ttttgataca tggctaataa caggcacaga agcatctcca 17700
aaggacagga cattgatatt gtgtaataat ttaaagtatt ttatgattgt ataatgtgcc 17760
tgagttttgg atagttgacc tctatttctc agtctttaca tagttactgc ttttttaagt 17820
gttacatgag ggatgtggaa tattcagtgt aacatttgac taatctttat gttttgagtg 17880
gcccaactga aaattaccct tggttgcctt ggaactctgg gcatgatgtt caaaactaga 17940
aattcttgca aattatttga gctttggctc tgggaagata aacaacatga ataactaggt 18000
taaccagggc tgaaatttct ctaacctata attctaaatt cagaaaagaa tgggctttag 18060 ggtttttgt ttatttttgc tttgattaca agttgttgga agcctagagt tagtatctaa 18120
taacacaatc tatgtaaaac acaaattatt ggctcagaat gatatctaat ttctaagaag 18180
atatgaggag gcaatcatgt aaaaacgtgc ttttcttcct agaaggaata agctgggatt 18240
ggccaaaagg taatcccttt agagtctaat gtttagagca ttgcatattt ttaaagaaga 18300
catattacct tttagaacat atgtaggaaa ccattttctt tgcttatatg gctacataaa 18360
gttgtcatgg ttttaaaccg tgaccttaga taccttatag aagtaattac aggcacaatc 18420
tgtgaatgaa gatttgcaaa ctatgcttca ccaagcctca gggactattg gatgtccaga 18480
ggacagagcc atgttggatg tcttatgggc cttcagtcct gcaaagtggt gtgctttcat 18540
gttttacaca cagcagttct gagaaaattt aagttgaaaa aacagcctct cttcttatta 18600
tttttatatt tatttattta tttatttatt tatttattta tttgaaacga aatcttgctg 18660
tgtcaccagg ctggagtgca gtggcgtgaa cttggctcac tgcaacctct gcctcccagg 18720
ttcaagcgat tctcttgcct ctgcctcctg agtaggtggg actacaggtg caggccacca 18780
cgcccagcta atttttgtat atatgtattt ttaatagaga cagggtttag ccaggttgcc 18840

-continued caggctgatc ttgaactcct gagctcaagt gatcagccca cctcagcctc tccaagtgct 18900
gggattacag gtgtgaggca ccgtgccgag ccatcctgtc ttctgaaaaa aaaaaaaaag 18960
caaacaaaaa tgtttaagcc tggtatatat tttcttatat tgcataagct acttttctga 19020
ctgcctctct ttagaaattc ctctgatttc tagagaaaaa aaaatcgcat tagctttttg 19080
gtttctaaat tcaggctcac tttagtaact gctagattat aaactcttag aaggcaaagg 19140
gctatgtatt ctctacttgt ggacactcaa ttagtttgct taagcaatta cttctgtgta 19200
agcaacatta atgaagtgct tactatgatc aagggctata ccaagtcctt ttttatatta 19260
tttaatccca cacaaaaccc atgatcgacc taattgtaca cttggtgaaa ctatgatgta 19320
gggaggttaa ataatttgtt caagaaccca cagctggtaa gtcgcacagt gtattcaaac 19380
ccagatcttc ctaattgcaa atgtgtccaa ctcccatgct tctaaccact gcctatgtga 19440
tggttctttg aaattcctcc ctccaagaag tggaatttaa ttccccccgt ccattgaatg 19500
tgggccaaac tcaggtgact catttctatt aaatggagta aagtggaagt gaagatgtgt 19560
ggctttagcg actaggtcat tcaaagtggc tcctgtcttg gttgttctgt ctcttatacc 19620
tattgggcat ttaatctggg gaaaaccagc tgccatgttt tgagctgctc tgtggaaagg 19680
ctaacatgaa aagatactgt ggatcctaca gacagcttca aatgaggacc tgaggccctc 19740
agaccagtag ccagtatgaa actgaagcct cttgaccaca gcctccatga gagtaatgga 19800
atcttgaccc cctagtgaac cacagcctcc atgagagtaa aattcaagat ggagccttga 19860
cacccagtgg agcctcgaga tgactgcagt cttccaccaa cagcttgatt catgaaagac 19920
catcagccag agccacccag ctaaggtgat tctaggcccc tactcctaga aaataaatat 19980
ttgctgtttt gactgccaag tgtttgatta atttgttacg cagcaataga taaataatgc 20040
agcctaacac tgtcctggtc atttttaaaa aagaaattgt tttaatttta ctaaatcaca 20100
aattttaaaa cattgataca gcaaggagaa actttccaga aaaaaaatgc tgccaaattt 20160
aagtagtaaa atattaatgt ccaaaaaaca tcatagttac aatgacatct ctaggattga 20220
ggattttgta agtcaaaggt cagctgctta aaaaacccat aattttaaaa ggaaggatat 20280
taataataac tgcattattg aacatagata gcattttgaa cttttaagaa atcctcatgg 20340
gaaaactcag gaaataatct gtttggtaag ttatcactca taatcttaaa ttgttaggtg 20400
catgtttgca ctttccatga tttgaagagg aatataaagc aaagttgaat tttaacctct 20460
tccctaatga ttttactcag cttttcaaag gggtcctaaa agctcagagg tcaagtcatt 20520
tcttggtttg ctctacctga caaattgcat taactctgct ttatagccac ttgcagttta 20580
ataaatgact tggactttga ttaatatctt tagtgcttaa gcccaagaat ttgtataaga 20640
ctttgggata tagtactgta aatttatcta aagatggaca ctggaaggta gaaggagata 20700
tattagtgtt ggtttgggta catgtctagg tactgaattt ggatcatcat aagtccttac 20760
agaagatact tgttgacttg tcttttaaaa aatatgtgaa agtgattttt taatatattt 20820
acaaagtgat ctaagtgatt taaggaattc attcatgaag tggatatgac tagttcttgt 20880
ttagtattca gaatgactgt aaaatagaaa tgctgatttt ccttgcccag attgtagaac 20940
acagatcaaa ccctcctagt ccttccctta aatgtttttt ctccatacag cttatgccct 21000
gagttctcaa aacatttttt atattgaact ggactgtata gtatatgcct gaccctgatt 21060
catgggatta tgctgcaagg gaatataaag atgaatattg atagcctgag tgtgaaaatt 21120
catcattact ctcatcctca ttcattaatt catttgttca ttaactcata aacacactaa 21180
ttgattcaac agatatttat tgaacgttta cactttgccc agtggagcac tggactaggt 21240
gctagcatag tataataagc aacccagaaa tagcctctgc cttgctgcat ttcatagtct 21300
aggacggaga aaggcattaa ccaagtataa tttaaaattg ttttaagtaa tgtgaaataa 21360
acatatatga gaacttgact caggttggta tatttgatgg ttagggaaag cttcaaaaat 21420
gggatatttg agatctaagt aagagggaaa agaaagagca taatgggtag agaaaaaata 21480
ggatccagga agatacttag tacttctgag aactaaaaac agtcaagtca gtgtagtcag 21540
agttcaaaga aggagaaaga acatgatcca agaagaagcc agaaaagtaa gcagggacta 21600
catcttacac gatgatgtag gctgtatttt agtttttact tatcttaaga gcaatagaaa 21660
accattgaag ggtttgaagc aggggagtga cataatcagg tctgcatttt aaggaggtca 21720
cctgctctat tatgaagcat gaatggagga ggatggaaag agatattcag ggagctggtt 21780
tatgagtctg ttgtaggcca gaggtattgg tagcttggac cagggtgatg atgctgaaga 21840
ttgaaaggag ttaatagatt tataatatat ttgtgaagta aagttgactg tacttagtgc 21900
tgacttagat agtactggtg agggatgtca tggtaaactc caaggtactg ggcttcttca 21960
actgagtgga aaacactaga gggagaccag gtaaaggttg aaggaaagtg aggaacagta 22020
gttcagtttg gggatatttt gatttggagg ccttttttaag acttcctcaa agagacacag 22080
tgcagtcttg agtcctggat cagaggagat acctcaatgt ataaatttgt aagacaatgg 22140
tttatacaca ctattaaagc cactgaggta agtgagatca tgtacagagt gaaaatgaag 22200
tgagagaaga aagcataagt ctgagccatg agaactccaa catttaaagg ccaagtggaa 22260
aagttgacaa gagtgggaat tgtgactggg gtagatgcta gaggggcatc tcagaggcca 22320
aggaaagaga atcatttaag gtgctgatga ggggtaaagt aagaaggtcc tgtaaatgtc 22380
ctcttggatt aataaatttg atgttttgaa ggactttagg gagaatgagt ttgttgtagt 22440
gatgggggca gaagccagaa tgaagtgtca tgggaaatgg gtggaagtct tgaaagagag 22500
acaatgaata tagataactc aagatatgtg gtcaagggaa acaaaaagga taaggcttta 22560
actagaggag gaaatggagt taaaggagga gttttttttt ttttgagacg gagtctcgcc 22620
atgtcgccca ggctggagtg cagtggcacg atcttggctc actgcaagct ccgcctcctg 22680
ggttcacgcc attctcctgc ctcagcctcc tgagtagctg ggactacagg tgccctccac 22740
cacgcccagc taattttttta tatttttagt agagacgggg tttcaccgtg ttagccagga 22800
tggtctcgat ctcctgacct catgattcgc ctgccttggc ctcccaaagt gctgggatta 22860
caggtgtgag ccaccactcc cagccaggag gagtattttt taaagatggg agacttgagc 22920
acatttgaac aataatgggg aagaccagtg gggaggatca ggggtggcct gaagatagac 22980
agagggtgga taaataatca tgtaggattc ctgagaagat agaagaagtt ggatccagag 23040
cacagcaggg ggaattagct ggccttggag aggagagatg atctctatcc tctattctag 23100
aaggaagcca aaggtgatgt gtgcagatgc agaggtgtgt ttgatgtggt gaagccaagt 23160
caaaggagtt tttgttcgat gccttatatc tgctccagaa agcagttgag tcaccaactg 23220
agacagggag agagaaaggg gctggcatac taggaaggaa aggggatcat ttcagatatt 23280
tgaggaggac agagtaagtt ggaatatgaa agggaataaa tgagtgaaat ttagtaggac 23340
tgctagtcac tgcttgaagg ctcagctgag gctgatgatc atgaattcat ggtactactg 23400
ttagaattat tataaaatat atgagccttt ttggaggtgc tcagcagttt accagacaca 23460
gaaaaacagg ttcatctagg cttaggattt tgtcagagag gtatgatgaa aagattgcaa 23520
aggagtttag gatattggca tgggcaaggg agcttctgga gtgataaacc aggaatctaa 23580

-continued

```
gcctgctagg gagggacata tagacaggag aaggagagta tagagatctt tctgaaggtt  23640
agaggaaatt tgtaatcaaa gtggttgatt aaacaagaca gaagtatagc agtcagtgat  23700
cagcccagga tgctgcaccc cagatcaatt aaatctgtat ttctgggtgt agggcccatc  23760
ccagtttctc aggagattcc agtgctttcc ttaagggaga atattgatat aactgttatt  23820
aagactattg tgaaaaaaca tattagcaat gtgaaatcaa gacaaaaaca caaacacaga  23880
aagaagttag acaaaaacaa aaaacactga aattacacat tttctttttc acaaatcaaa  23940
gtcaaattca cggaccttct tccctgactc attctccctg acattagaag tccaaaggga  24000
gcaagtaaag tctttatggg gaagatggta taattaagca ccaattacct agggaccaga  24060
tgctttggga tttgactgat gaaaacagat tagaagcatg gtgaatttgt tcactactgt  24120
ctttttggag gggcaacact cctggctcac ttggcatgag gtaatgtcag tctggctaca  24180
aagatttgaa tgtggggctt gagtttctaa aaggggactg attggacttc tcttagccag  24240
gatacttgga cttggtggct atatcatggc tcacagtgtc ttggaatggt cttgagccta  24300
gttgaaattt gttgaaatta catatgaata ttcattaatg tattacttgg aactcagtga  24360
gaaggatcat cactgccaga tttcctagtt aggaaaactt accttcattc cttccagtta  24420
aatagaagac cattgtatag ttcattttgg gctaagtgga gtgtttatga aatgtgtagg  24480
gcttataggc ataactattg ctaaagaaag cccagtaaag cttgacatcc cctctgttgc  24540
ccttgtctgt cattccataa atttaatgtc aagggcattt ttagagaaga tgatcacagg  24600
atgattcagg tagacatgga gcaggttgtg aaaacactgg catgtttcac caatgtatta  24660
gggtttccag agaaacagga ccagtagggt gtgtgtgtgt gtgtgtgtag atttatttta  24720
agagattggc tcacacaatt atggagactc gcaagttcaa aatgtgcaaa gtgggctagt  24780
aggttggaga cccagagaag agctcatgtt gcaagtcaag tccaagtccg ctgcagaatt  24840
tccctttgct tgggaggtca gtctttggct ctattaaggc attcaactga ttggagggca  24900
gtttacttta ctcagagtac atcatttaaa attttaatat catctaagaa cactctcata  24960
gaaacattta gggtaatgtt tgacaacata tctgggcacc atggcccagc caaggtgata  25020
tagatataga tatagataga tatagatata gatatagata tagatataga catagacata  25080
gatagatata gatatagata tagataatgg atatatataa tggatatata atggttatat  25140
aattaaacat tacacctggg aagttacagc actatcttct ctggattaaa caacaacaac  25200
aaaaatactc agtccaattc atgatttgtt gagggtctgt gtagaatata gaaattatac  25260
tacaagtttg gttttcttta ggatggtgag cattttataa aatatgtata tataaagaga  25320
ggcattctct tgtaacactt agaatagtcc tgtacacata gaaggcacac agaatgtcca  25380
gtgccagtga catgagactt cataatgagt ttgaagccaa agctttgtgt agtaaaaagc  25440
catgagcagt taataaattt ccatttgatg gcagctataa atattaacca gaagactcat  25500
aactgtgttt tcaactcaca tacctgggtt ggggcagaag caatagtttc agcagctttt  25560
atttatctgc ttttaattcc atctcaccat tgttaaattt acctgaaata attgccattt  25620
tgacaatgcc ctcaaaaatc atcttattgc ctggggactg attttcagat tcctgagccc  25680
agtattcaga atcctatata ttccctcaac ctatctttcc atgtgtattt tctgttgagc  25740
ttcaaactga actacctctt tgctctcaac atattctatt tgttaacttt tgttcatgtt  25800
attccctcta aaatgacttt tctctaattt ttttcattct ctcattcttc ttgtctttcg  25860
aggtggaact caaatgccac aacgtcaaat gccacagtat ctgctatgat ccttcccctt  25920
tccagctaca aattcctctt tcctctacca cttctttggc acatttatta agactcgcga  25980
```

-continued

```
tttctctcat ctaagtctct tgtgcaatgt cttactgtat gtggcctgaa ttcaggatct  26040
atgtctacag cctccccttt agcctcactc cagtatcttg caggtgggca gtcctctgta  26100
aacacttgtt aaaaaagtca aaacacattt ttcaaatcag aaagaaccta acatacaaag  26160
cctcattgtc atttttaaat ttcatcgaag agctatacat tgaatttttt gtgtgttctc  26220
tatagtacct agccatgtgc tggacagtgg acccacagtg gacattcagt aattagtaat  26280
agatggattt attctgtatt taacaaaatt ttctggatgc ttttagactg aaggagattg  26340
gtttgatgac acaagtttca aaagacaatg ttattgctaa tgcacattat gagggaacta  26400
tgatatattt tgaagtccaa caaatagaaa aatgaatcaa tcacgagtca gatttattga  26460
tggaattgtg ccaccatcaa gtcctaaagc attagtagtg atgttatcag aaaatatccc  26520
actctgagat catctgtagc cagctttata ctctaaaaga atagtctgag tatgttctgc  26580
ctggaaaagg gctcagtggt ctaggaatta ttgtttttac tttttcaaag tttataaact  26640
tggcatgact gtgcttttct gtggcttcca atctctggtg ataagttttc tcaaaatatt  26700
cctgatttat cctgatgtaa atcacaattc ataaatatca agagagactg cctacagtac  26760
catcttctga tttaaaaaca catttgaatc aatatttact tatatataat gcattctgct  26820
gaataaggaa gttctgactt gttaagctca gtatgcttcg ataagaaagc aaaatttttt  26880
tgttgggttt ttaaaatgta ttttaaggtc cttgtctctt ggtgatagtt ctttacatat  26940
tgaagtgcca gggaataact gtccagtagc tggacaagag agactcataa tatggcagtt  27000
gaagccaaag cattaagcaa aaacagttat taatattaac aggctcactg tagagagaag  27060
ccatagttgt caggggaggc agaactgccc aggaaaccca tctttgtcct tttgtctaca  27120
caggttgggg caaaagcagc agttatttga actcagcaaa cctgtgttcc atattgaagg  27180
cctgcataag tcagggacca gggatgtaat gaagaccaga catggacttt aggagcacaa  27240
agtgtagaga taaaactgca ctcataatgt aagctaatgg gaggcaggaa cgatggaagc  27300
agcaaagact cgctacagtg ggaggagtta tgagagactt cccagaagat atggcatctg  27360
agctgattct taaaagttct gtaagaggcc aacaggcaga gaaaaaaatga aaaaatgcta  27420
ttaaacagta tagcccataa ccgtggggat ataccagagg atgatgtgtt agggaaatgg  27480
taagtacttt aaagtggcta gatcagagaa tgttcgaggg caggtgaagg gaaaagtagg  27540
cagggttctt atatttatat cagtgatctt ggactttgtc tggggacctg caggtagctg  27600
ctaccagaat ttcttatgtc agtaagtaac atgatcagat ttgttatttt agcaagacaa  27660
cttacactat aaagtataga gaggtgtttg gagtgcactg attgaacagt agtgtggaga  27720
tgtgtttttt aataataaac caaatgagta ataacatgtc ttactcttac ataattagta  27780
agatcttgcc agcatctttg ttggatgaaa ggaagcctag tgtttatcac caaatctttt  27840
gagatgtcag tataacacaa cactgtattc cacttttgaa aacagccatc cctatagtgt  27900
gtgaagagaa tacttaaagt gcagacagac aagtgaacac cgcacttctt tgtcacatgc  27960
agtcaagaaa ccagacaaga tatttaagct atgattatta gtgttggcaa gggttcagct  28020
ccagggaaaa taaatacatt gagttagtgg tggtgatgag attgacacga atagagttgt  28080
attttccttt tcatgctgtt gcaagggaaa tgaagcttta aacataatga aattggttct  28140
tgtgaacagc aaatctgcta tttcttcact ttttatggct ttgtcaacag tgatctaagt  28200
tttgctttac ttatttattt taaattttgt tttattttaa tagtttttgg ggaagaggtg  28260
gtttttggtt ccacgaataa gttctttagc ggtgatgtct aagattgtgg tgcacccatc  28320
```

```
acccaagcag tatacactgt acccagtgtg tagtctttta tccttcaccc cctcccaccc  28380
ttctccctga gttgccaaag tctattatat tattcttatg actttgcatc ctcagagctt  28440
agttcccact tacaagtgag aacatacaat atttggtttt ccattcctga gttactttca  28500
gctccatccg ggttgctgca aatgccatta ttttgttcgt ttttatggct gagtagtatt  28560
ccatggtata tatatatcac attttcttta tccactcatt ggttgatagg catttaggct  28620
tgttccatat ttttgcaatg gcaaactgtg ctgctgtaca aatgcatgtg caagttgtgc  28680
aactgcctcc ctccctccat ctctctctct ttcctttctt ccttccttcc ttcttttctt  28740
ctttccttgt tttctccctc cctccctccc tccctctatc tctccctccc tccctccctc  28800
tctctctctt tctttctttc ctttctttct ttcttttctt tctctctctc tctttctttc  28860
ctctttctct agccctgcca cccaggctgg agtgtggtgc catgatctca gctcactgca  28920
acgtccaacc tctgcctccc aggttcaagc aattctcctg tctcagcctc tgggattaca  28980
ggtgcccaca accatgccta gctacttttt ctatctttag tagagatggg gtttcatcat  29040
gttggcctgg ctggtctcaa actcctgacc tccagtgatc cacccacctc agtctcccaa  29100
agtgttggga ttacaagcat gagtcaccat gccccgcaca agtgtctttt tcatataatg  29160
acttcttttc cttcgagtag atacccagta gtgggattgc tgaatcgaat ggtatttcta  29220
cttttagttc tttaaggaat ctccctactg ttttccatag cggctgtact agtttacatt  29280
cccaccagta gcgtaaaagg gttccctttt cactaccttc atgccaacat ctattatttt  29340
tttatttttt aataatggcc attcttgcag gtgtaaggtg atatcacatt gtggttttaa  29400
tttgcatttt cctgataatt agtgatgtca agcatttttt tccatgtttg ttgggcattc  29460
gtatatcttc ttttgagaat tgtctattca tgtcctttgc ccactttttg atgggattat  29520
ttgttttttt cttgctaatt tgtttgagtt ccttgtagat tctggatatc ttgccgattc  29580
tggatattag tactttgtca gatgcatagt ttgcgaagat tttctcccaa tcggtgggtt  29640
atctgtttac tattattatt attattatta ttattattat tattattatt gctgtgcaga  29700
agctttttaa ttaattaggt ccaatttgtt tatttttatt tttgttgcat ttgctttggg  29760
gtttttgctc atgagttctt tgcctaagcc aatgttgaga agagtttttt tgatgttatc  29820
ttctagaatt ttaatgattt caggttctag atttacatct ttggtccatc ctgaattgat  29880
ttttatataa ggtgagggat gaggatccag tttcatcctt ctacatgggg cttgccaatt  29940
atcccagcac catttgttga ctagggtgtc ctttccccac ttcatgtttt tgtttgcttt  30000
gttgaagatc agttggctgt aagcatttgc ctttatttct gggttctcta ttctgttcca  30060
ttggcctatg tgactatttt tataccagtg ccatgctgtt ttggtgaata tggccttata  30120
gtgtagtttg aaatcaggta gtgtgatgcc tccagatttg ttctttttgc ttagtcttgt  30180
tttggctatg tgggctcttt tttggttcca tataaatttt atgatttttg ttccagttct  30240
gtgaagaatg atgatggtat tttgatggga attgcattaa atttgtagat tgcttttggc  30300
agtatgttca ttttcacaat attgattcta cccatccaca agtgtgggat gtgtttccat  30360
ttgtttgtgt catctattat ttctttcagc aatattttgt agttttcctt gtagagatct  30420
ttcaactcct tcgttaagta tattcctaag tattttattt ttatttttgc agctgttgta  30480
aaaggaattg agttcttgat ttgactctca gcttggtcat tgttggtgta tagcaatgct  30540
actgatttgt gtacattgat ttttgatcct gaaactttac tgaattcatt tatcagatct  30600
aggagctttt tggaggagtc tttaggattt tctaggtata caatcatgtc attggtgaac  30660
agtgacagtt ggacttcctc ttttctgatt tggatgcctt tatttctttc tcttgtctaa  30720
```

tcactctggc taggacttct agaactacgc tgaatagaag tggtgacagt gggcatgctt 30780
gtcttgttcc agttctcagg cagaatgctt tcaacttttc cctattcagt acaatgtggg 30840
tttctcctag atggttttta ttactttgag ttatgtccct tctatgccaa ttttgttgag 30900
ggtttttatc ataaaagtat gctggatttt gtcaaatgct ttttctgtgt ctagtgagat 30960
gatcatatga tttttgtttt taattctgtt tatgtggtgt atcacattta ttgactcggg 31020
tatggtaaac ctacatccct ggtatgaaac cactatatcc ctagtatgaa acccgcttga 31080
tcatgatgtg ttatcttttt tgaaatgctg ctggattcag ttagctacta ctttgttgag 31140
gatttttgca tgtatgttca ttagggatat ttgtactttt agttttctgt tatgtccttt 31200
ccaagtttag gtattagggt gatactggct tcatagaatg atttcctctt tttctatctt 31260
tttgaatagt ttcagtatcc aattcttctt taaatgtcag atagaattca gctgtgaatc 31320
catcgctctt ggactttttt tgttggcact tgttttttta ttactgtttc agtctcacta 31380
cttgttattg gtctgtccag agttcctgtt tcttcctgat ttaatgtagg agggttgtat 31440
atttgcagga atttgtccat ctcctctaga ttttctagtt tgtgtgcata taggtgttta 31500
taatagcctt gaatgatctt ttgtatttct gtgatatcgg ttgcaatatc tcgtttcatt 31560
tcttattgag cgtattcgga tcttctctct tcttggttaa tttcactaat ggtttttcaa 31620
tcaattttat ttatattttc aaagaaccag ctttttgttt cacttgtctt ttgcattttt 31680
gttgttgttg ttgttgtttc agtttcattt agttcttctc ttatttggtt atatcttttc 31740
ttctgctttg tttgggtttg tttttttctt gtttccctag ttccttgagg tgtgacctta 31800
gattgtctat ttgtgctctt tcagactttt tgatttaggc atttaaaact atgaaatttc 31860
ctcttagcat cacttttgtt gtatcccata ggttttgata agttttgtca tcattatcat 31920
tttgaaagaa tttttaattt tcatcttgat ttcattgttg acccaaagat cattcaagag 31980
cagattattt aatgtccatg tatttctata gttttgaagg tttcttttgg agttaatttt 32040
catttttatt ccgcagttgt ctgagaggat acttaatatg attttgtttt tcttaaattt 32100
attgagactc gtttagtggc ctatcatatg gtctgtcttg gagaatgttc catgtgctga 32160
tgaaaagaat gtatattcta catttttagg tagactgttc tgtaagtacc tattaagtca 32220
atttgttcca gggcatagtt taagcccatt gtttctttgt tgactttctg tcttgatgac 32280
atgtctagtg ttgtcaatgg agtactgaaa tcccacacta ttattatgtt actgtctatc 32340
ttgtttctta ggtctagcag taattgtttt attaatttgg gagctccact gttagatgca 32400
tatatattta tgattgtgat attttcctgt tggactaatc cttttatcat tatataatgt 32460
ccctctttgt cttttttttt ttccactgtt gttgctttaa agtctgtttt gtctgatata 32520
agaatagcta ctcctagact ggccgcagtg gctcacacct gtaatcccag cactttggga 32580
ggccaagatg ggcagatcac aaggtcagga gttctactaa aaatacaaag aaattagcca 32640
ggtgtggtgg tgtgcgcctg cagtcccagc tactcaagag gctgtggcag gagagtcact 32700
tgaacccagg aggtggaggt catagtgagc caagattgca ccactgactc cagcttgggc 32760
aacagagcaa gactctgtca aaaaaaaaaa aaaaaaccta ctcctgctca cttttagttt 32820
ccatttgtgt gaaatatctt tttccacttc tttaccttaa gtttatgtga gtccttatgt 32880
gttacgtggg tctcttgaca acagcggata cttggttgtc ggatttctct ccattctgtc 32940
attctgtatc ttttaagtgg agcatttagg ccatttgctt tcaatgttag tattgacata 33000
taaggtactg ttctattcat tatgttagct gttgcctaat actttttaaa attatgttat 33060

-continued

```
tgctttatag gccctgtgag atttatgctt taagaaggtt ctgtttgggt gtatttcaag  33120
gttttgtttc aagatttaga acacccttaa gcagttcttg tagtgctgat ttggtagtgg  33180
caaattccct caacatttgt tagtctgaaa aagactatct ctccttcata tctgaagctt  33240
agttttgctg gatgcaaaat ttttgactga caattatttt gtttaagggg gctaaagata  33300
ggaccctgct cccttctgat tggcaaggtt tctcttgaga agtctgctgt taatctgata  33360
ggtttttctt tataggttac ctgatgcttt tgtctcacag ctcttgattt tttcctttgt  33420
cttgacttta gataaactga tgactgagtg tctaggtgat tatctttgca atgaattttc  33480
caggagttct ttgagcttcc tgtatttgga tatctaggtc tccagcaagg ccagggaagt  33540
tttccttaat tattccctta aataagtttt tctaattttt agatttcact tcttcctcag  33600
gaacaccatt tattcttagg tttgactgtt taatatagtc ccaaatttcg tggaaacttt  33660
gttcattttt aaaaattctt ttttctttgt ctgattgggt taattcaaaa gtcttatctt  33720
tgagctctga agttctttct tcttcttgtt ctagtttgtt gctgaaactt tccactgaat  33780
tttatatttc cctaagtgta tctttcattt ccagaagttg tggatgtttt tctttatgat  33840
atctatttct ctggagaaaa tttcgttcat attttgtact agtttttaaa tttatttaaa  33900
ttgtttttttg cctttttctg gtaactcctt gagtagctta ataattgacc ttctgaattc  33960
tttgtctgga aattcagaga tttcttcctg gttcggatcc attgttgtgg aactacagta  34020
atctttgggg gttttataga actctgtttt gtgatattac cagaattact tttctggttc  34080
cttctcattt gggtagacta ttacttaaaa ttgtttttgt ggactgtgtt tttttttaa  34140
tttcttattt tttctttctt aagaatcaga ctctaatgtt tattttagcc taattggagt  34200
cttggtgctt gtaggggtga agactctgta cgagatcctt agttacagaa tcttcctgca  34260
ctggttttcc ccaatgctga ttttagtagt tacatacttg gtgtgtgggt gaattctctg  34320
tctcctgtga agctggaatg gcagggatcc cttgacgctt atgtcctcct ctcatggtat  34380
acagtttatt tactggtctt ttatttactg agttgatgat tcaggcttca ggacaattgg  34440
ggaggtatcc cccggcaggc accagttgtg gctaaggcaa gtgggtagat gtaataccca  34500
atggcgagcc gaggtcacag ccttgatgag ggtggctgga ggagctctca attaggtgtg  34560
ctgaaatttt atcaaggtga aaagtgggag cttcctcagc tcccctgcca agtcagaaag  34620
aaaactattc acctcacagc ctcactcctg tcctagcatt tcagctattc agatcagaca  34680
ggcatctctt ttcatctata ggaatgttgt tgttccaagt agggaggaac tgtgactctg  34740
cctctcatgc aggcctgaat ctggggtttg ctcctcttgt gggcgatact caccctggag  34800
tgttccagaa aggctgtcta caggtgtatc catgtgtgtt cctgtggggg aagccccagc  34860
tgtgtctgca gtggagtgcc agggggaaca aggactcctt ttccaaggcc cttcatggtc  34920
acagaggctg cttgcctatt ggggtatagg tgcagacttt ccctactgca cctggcactg  34980
caattgggtc tctgctgtga gaaactaccc actagcagaa agatctgaaa ctcctactat  35040
tcagattatt ttgtctcact tagtgattcc ttgatgtggt gttctcctct ttcccctagg  35100
gatgggcttc ctgagagcca gattgcagtg actgttattg ttcttctggg tctagccacc  35160
caatggagtt accaggctct gggctggtgc tggcgaatgt ctgcaaagag accggtgatc  35220
tgatcagtct tcaggtctcc tagccatgta taccagcacc tgctctggtg gaggtgacag  35280
gatagggatg tagactctgt gagaatccct gattgtagat aggtgtagtg tgctggcttt  35340
ctcaaatgct agttatgcta gtattgaagt tgccacgtgg acagactaag gacctctggt  35400
tagccaggat gttgcaggca gtgatattag ctgttgtttt ctccttcctg ggagcaatat  35460
```

-continued

```
tattgtcatg agtatggcct gagttggttg gcctccagcc aggaggtggt gtcttttgtg  35520
ttcggctgcc aaggcagata gaaaaatacc atcaagtggg ggcaggatta ggcgggtctg  35580
agctgagact cttcttgggc tagtcttgcc acagccacta tgtaggatgg ggaggatggt  35640
tttcaggctg atggggttat gttccagagg ggattatggc tgcctctgtg gcacagaata  35700
gttcaccagg gaagtggaga atagccagta gtgaaaggct tcacccagct cccacacagt  35760
tggtgagccc aatctcactc ttgcaatgct gtgttaacag caccaagttt agatccacgc  35820
ctcctgcttg tggaactcag tcttactcca ggccatacac ttccccactg agaaagcaag  35880
caaggctttc aggccacacc cctccctgtc tgcccacaag gttcctgtgc tcatatctgc  35940
tgcagttccc attcacccac cagattctgt tcacgcaggt tcatgccccc tcaaaattat  36000
cacaaaattc atttggaagc ttctttcacc ttgtgccccc tccctaattc tgctggctgc  36060
cttccctgag ggcccctgtg agatatagtc aggcatggct tccctgggtt tgagctggag  36120
actgggagtg cctacaagac tcttcctgct gctgcttcta cttttgtgtt tcacgtggct  36180
ccctaaatct gttccagctc taggtaaggt taaatccttc tctcatgatc tggattttca  36240
gattccccag tgaggatatg tgtttggagg caggttttcc cccattcaca ctttgggaac  36300
tcattgcttt ttgcctgtct cacagagttt gcagcagcct gtcacttctt tcaaaggatc  36360
tgtgaattct ttccattttc ctgatatgat cctgtggtgg ttcttggaaa aaaggttcac  36420
agtctgagtc tccacacact gttctgtcca tccaagcagg agatgtatgt tagccctgcc  36480
tgctatctgc catctttctt ctgtccccaa tccttctctt tagatagctg agataccatc  36540
ttttgtttct tctgacttgg ttctattcac tgacattcct ctctatcaag tagatttttg  36600
aactttcatg gaaatttatt cccaatttat atggaaataa ttcccaattt atatgaaaag  36660
cttataaagt gattcattaa ccaagtattt actgaggtgc taaaagtata ctctgaagca  36720
ggagtggcaa gtcctttgcc ttcatggaga ttgcattctc ttgtaaatct tacatgatgg  36780
tcactagatt taggaataaa ggactccagc ataaaacact gacacttctg ctggagaaat  36840
attttacaaa ctatatatat tgaagcccaa actctggttt attggtaaag gagtagcact  36900
gatactagaa ttttgtgatc aacatgttgg aataagaagt cagaagactt agatctgtgt  36960
tctttttctc ccgctggcta taggttgctt taatctctga gctgcagttt cctcatctac  37020
agaataggtt agaccagatt agtggtcttc aactttggct gtatattaga attatcttac  37080
tcttgaccaa ttaggttaga aatttcgggc cacacacaat ggcttacgcc tgtaatccca  37140
gcattttggg aggcagatac gggcagatca caaggtcaag agatggagaa catcctggcc  37200
aagatggtga aaccccatct ctactaaaaa tacaaaaatt agctgggtgt ggtggtacac  37260
acctgtagtc ccagctactc aggaggctga ggcaggagaa tcgcttgaac ctgggaggcg  37320
gaggtggcag tgagccgaga tcgtgccact gcactgcagc ctggtgacag agcgagactc  37380
cgtctcaaaa taaataaata aataaaaatt aaaattagaa atttcctggt ggagaggaaa  37440
gcagaggtat ttttaaagct ctcaggtgat atatttctgt tttaaggtag gactaaaaat  37500
catgggacta cgtcagaagt tctaattata aatctatagg ttagttttct ccaggcatgg  37560
gtatagtgct taaatgcctt ttaaatttgt taccaacata gaaaaaaaaa ggtttccggc  37620
ttctcttgaa aaatggaaat attaggcaac agttgggctt atgtttctga gtggtaaaaa  37680
ttaaacaaag taaacgagtc tccgtttcat ttgttcctgt tgccttcctg gctcttgaag  37740
gcattgtcat ttgtgaaaac taaactagat ggtctttaaa atctccaatt atttgaattg  37800
```

-continued

```
cttatttcca catccagaaa agagacggta aacaaactat acctttatct gtaagctagt  37860
tggtttgtga aatcaaaggg aacttaatct ttgaatatgg aaaaatccca gggtccaatg  37920
gaagagaaac tccatctcat taatagcagg actccacaga ctgctatgga aaagacaccc  37980
acccggggct aagagggagg gaggcggaag aggacttaat tcattttctg ggcattttta  38040
atgaagcttt cccctctttc attatttctt atttgggagc tggatcatta gttgggatgt  38100
gactggcttt ccctggggag caaaaaggag attaacagag gttttgctcg cttcttcctg  38160
tgatttactg tgggaagtct cccaggttct tcccttcgct tctctgtggc cttcatcttc  38220
atggtttctt gctgtgtctc tctgagagca agtacctggg tgaaaaaggc tgagtgtgtg  38280
gtttttggc aactgcctgg cattggattt aagtgggtat atttgaatta ctagaatttt  38340
acattttata ggttcaaaat atgcacttga attctgtagg acctcttacc caaattgaat  38400
aatcctttgt gccttgttaa attttaaaaa gtcacactat caacattatg acatatggca  38460
tatatgatgg caataataaa aataacacac ttattgtcca ctttaatgtg ccagcagtgt  38520
tccaagtgat ttgcgtaaat atcaaatttg ttccacacaa ttatcctatg aactaaatgt  38580
tattatttcc tggtttatag gtgaggaaca cagaggctca aagcagctat ttgatttctc  38640
ttatttcaaa attaggggaa gtgagataca ttaacctgta taaccagacc ttgttaactg  38700
tttttggtaa attccaatgt gtattgattt tcacaaagac aaatcacacc attgttatat  38760
taaatattaa ttttttcata gtccctcaag gtgcttactg gctatattgt tactgtcttt  38820
tgatgttgtt tatacatggt ggattacaga attccatgaa cataaaaaat cttgacttta  38880
tcctagccta tttcctattc ttaccccctg caaagtaaaa agttcaaaat agcgttagta  38940
agccaagcaa actacttact agccacatga acctactagc ctctctgcct cagtttcttt  39000
gttgggaaaa tggacaatac ctaactcaac tcataaggat atttctagaa tcaggtgtaa  39060
tatcaaataa aaatatattt ccttttttcct agaagatacc catgtatatc ttaggtactg  39120
atgtattcat agtgatgcag aacataaaat gtttattctt ttgcttagca acaactatcc  39180
atagagattt ttccacttta gagatttaat cccattaaag gtttttagat tgattggaca  39240
atgagaatgt ttttgtctct ctgaaactga ggctgaaagt tgatttcatt ctctcacttc  39300
aaatcatact acaaggctac agtaaccaaa acagcatgtc actggcacaa aaacagacac  39360
atagacaaat ggaacagatt agagagccca gaaataatgc cacacaccta caacaatctg  39420
atctttgata aagttgacaa aaacaagaaa tggggaaagg actctctatt caataaatgg  39480
ggctgggaag ctagctagcc atatgcagaa gattgaagct ggacccctcc ttacaccata  39540
taaaaaaatc aacttgagat agattaaaaa cttaaatgta aaacctaaaa ctataaaaaa  39600
ccctggaaga taacctagga aatggcattc tcgacatagg acctggcaaa gattccatga  39660
caaagatgtc atgacaaaga tgtcaaaagc aattgcaaca aaagcaaaaa ttgagaaatg  39720
gaaacagatt aaactaaaga gcttctgcac agcaaaagaa ctatcaacag agtaaacagc  39780
ctacaggatg ggagaaaata tttgcaaact atacatccga caaaagtctg gtattcagaa  39840
tctataacaa acttgaacaa atcaacaagc aaaaaacaac ccaattaaaa agtgagcaaa  39900
ggacattaac agacattttt caaaggaaga catacatgtg gccaacaagc atatgaaaaa  39960
atgctcaata tcactaatca ttatggaaat gcaaatcaaa accacaatga gataccatct  40020
cacaagtcag aatggctatt accaaaaagt aaaagaaaaa cagatgcctg tgaggttgta  40080
gagaaaaggg aatgcttata cactgaaaag ggaatgctta tacactgctg gtgggaatgt  40140
aaattagttc agcaattgtg gtaagcagtt tggtaatttc tcaaagaact caaagtagaa  40200
```

ttaccattag acccaataat cccattattg gatataaacc caaaggaata taaatcgttt 40260
taccataaag acacatgcat atgtattttc actgtggcac tataacagag acacaataac 40320
aaagacatgg aaccaaacta aatgtccttc aatagtagac tggataaaga aaatgtgata 40380
catatatacc atggaatacc atgcagccat aaaaagaaat gagatcatgt cctttgcagc 40440
aacatggatg aagctggagg ccattatcct aagtggacta acacaggaac agaaaaccaa 40500
ataccacatg ttctcattta taagtggaag ctaaacattg ggtacatatg aacacaaaga 40560
agagagcaac agacagtggg gcctacttgt gggtagaggg agggaagagg atgaggatta 40620
acaaactacc tatcagatac tatgcttatt acctgagtgg caaaataatc tgtacaccaa 40680
acccctctga catgccattt acctatgtaa caaacctgca tagtaccccc gaacttaaaa 40740
gttaaaagaa aaaaaaatga ttaatgagcg tgataccaga acaatattat gatgcagggc 40800
tattttttgt gtgtttgcta gctgggcttg agatttgata aataagtccc attgtcctaa 40860
tccgctagtg atgatgttct agcctttgaa attcaaacta ctactactcc actttgagag 40920
agactgcatg agaattggac ccagcctggg gctttagaca ccatggttca aatcttggct 40980
cttatcattt tttagccacg tgtcatggac tcaatgtttt tgtctcccag ctccccagat 41040
tcacaggttg aagccctaac ctccaatgtg gctgaatttg agattagggc ctgtgaggag 41100
ctggtaaaag ttaaatgaat tcttaaggat aggtctccaa tcctatagag ttggtgctct 41160
tacaagaaga ggaacagaca cccgagttct ctctctttgc tatatgagga catggtgagg 41220
agtggccatc tgcaagctca gaagagagcc ctcaccagga acttaagtgt ctggcacctt 41280
gatcgtggac ttcccgacct ccagaactgt gagaaataat tttttgttgt ttaaatcacc 41340
caaactgtag tattttgttg tggcagccca agccaattat tataccatgt aagcaggtta 41400
cttaaattta ctaaatatgt aagttactta aaatttcaaa tcctggttct aactttacta 41460
gctatcactt ttactagcta acacattaca ttttcttcaa cttgccgcat gcttttgctg 41520
tgagttttaa atgaaattgc ttaagtactt tgcttatcat actgctgatc catagtaagc 41580
acttaaagtt agtttccagg aagtttggaa tggatctcac ttatgcaaat ggttgacttt 41640
gacggtgctt gttcctctct ggaaagggtt cacctcccat tagaatagtc ctgtgactgc 41700
agtaattttg tatgttaaac ttacatgtat atctgcagaa tgttaaatct gcaaacacca 41760
tccatcaacc caaaagcaaa aaaagagtgt ttcctaatag ttaatagttg gtagcttaat 41820
aggaaatcta gaaaaaaaat gtttaataat gaaggctata ttaataccaa gtctcatttg 41880
agttcctgtc agtaaggaaa tagttatctt tcgttgttaa tcaatgaaga ccagttgcca 41940
taattagggc tctggtgtgt tttcttcaca tggtcttcta ggacctaatg taatatcatt 42000
tgagaggctc aaagaggatc ccatattccc aaaggtatct tagagtcctt agctgcccaa 42060
catcccacca ttaatcatgc tttgcagatg aaaaattgaa gactccttgt ctctgaatat 42120
ctgggatatg ctttcattcc taggatggac atttttcttc ttccccaata aggaagaaaa 42180
agggacagag gtgatttata agagcagttc tactgagtga aatgtgggtc ctagcaaagg 42240
aggacacagc tgccccttgt aatagtggag ggaaggaagg aggcaggctg gctgtacttt 42300
gccctcctca accctaaacc ctatctgttt accacagtgg acctttttttc tgaactctaa 42360 cctcattatt tcattcatta tccacgtaat attcattaat gttctccaag gctcttagaa 42420
taaatcttta acatttcccc aaaaagtcac aaggtctgac acctgccttc ctttttccag 42480
cttcctatca taatcctcct ttttggcagt ggccacactg atcttctttc aggttcccaa 42540

-continued gctcagcatt tgcttttcat tgggagcccc ttacatcatg actgtcagcc tgattgtcat 42600
ttctttgggg aggccttccc tgaaccctgg aactggatca tataccccta tcatgtgctt 42660
tcatagcacc atgaatgtct ccttggtggc agtccccagt aggagaattc tgtgtttatc 42720
tgtatggctg tttcataaat gtttatcttc ctcccaatag tctgtcagca ctttggcagc 42780
cagttgtgtt ttgctgttga ttctacctcc agcacagaat gtctcttagt atttatggaa 42840
ggggacatga aaaaagaaaa agtccactgc atgaagattt aatccagcga cactgaggcc 42900
tgaacatcta gctttaggga agccagcttc tagcaggaca gactggtagg gactaggtaa 42960
ggagaatgga aaaacacagg gaatgagcat cactttcttt aagactttgc ctctggcaga 43020
cccctccaag taacagattc caaagagatt gtgaatgttc tccctctggt atgcagtctc 43080
ctgtcctgtc agaaacatgg tacccagagg ccaaagctgc tgcataagca agttatcatg 43140
aaactattcc aggacaggtt tcagaagcag ggtcttaaaa atgagtatta aatctaatgt 43200
tcacccagat acatttccaa cccacatata gacaccgaat ttaacgatga aagtggaagt 43260
tactctgttg aggatttatt tgaaatgttg gttttctctt gtccatctga tacaggtcat 43320
agctctgttt ctgtcattag attgattttc atgtttctca gcacagactc tctgtgagtc 43380
agagataagt ttaatttttc agcatggcca taggaatgat gaagtcattc ctcattaaaa 43440
tgaagctaag caaaatttaa tagtacttgt ttaagattcc ttatttactt ttctacacaa 43500
aaagagttgc aaggggaaaa caaaaacttt agctttgagt aatttcctta attcaaatat 43560
agatttaaac cactttgtca taatatgtaa atgaactatt gctttttttca ccacaggtct 43620 gttttcaaat agataatgag attatataaa taattacctt atataaacat aaggttactc 43680
attattgaaa gcaatttttct ttttttgttt ctggtttatt atggttaaga gtgagccttt 43740
gttttagata tttgaaaaca aaatgtgtgt gtgcgtgtgc ttttgtgtgt gtgtgtggat 43800
atgtgtatct agggaggtcc tcaaattcaa aaattataat acaaggttgt aatgtcagca 43860
cttcctattg catagtttta taatggggat atatagctat gcattaaaat gcattattga 43920
aatggaaaat caggatgtgt taaaaatgaa ttagtaatta tattaagatc tgaatgggaa 43980
ctagcataca atgtaactta agcttttgaa aaataaaaaa aaacagaaaa taattaatga 44040
taagttagtt tcagtattac attgataaat atttccagaa taagctataa aaaataagga 44100
ggtagattta ttattttaag gttcatacta aaagattgta atatttactt aacctttctt 44160
tatttaattt agaataagat tactgtcatc tctctaagca tctatgtaat agtgttttat 44220
ttacttttcc attaaatatt actgagataa ataaggagtc ctggtgaatg aaatataatt 44280
taataagcag agttttctta ggtgaaaact aatcatgtcc tgctataaat gtatattgag 44340
agagaagctg aatagacaag ctccatgatt tagtcaatga tacgacttca gggaaaatgt 44400
ttttatgcct tgttggccat atcttttaat acttgcattg aaaataaaat tacatcccaa 44460
gattatgagg gttgtgaaat tttataatta gatatttaag tcctgaattg attagcagca 44520
gtataaacat agacatggat tttgggttaa atctgagaac tattttttttg tactaaaatt 44580 tgcgtgcaga tgacaatggg aaaatcaaat gttttcctgg aaaattttca aatgggacaa 44640
atagtcatct ttctggaaat atgaaataaa gggagtggta gtggttggac tataaacctc 44700
tttgaaggcc ttttaatctt tagctgtaat tcatgtttta tcaccattgg attttcaaaa 44760
cggaaaatac cttagaaata atttagtggg ccgggcgcgg tggctcacgc ctgtaatccc 44820
agcactttgg gaggccgagg cgggtggatc acgaggtcag gagatcgaga ccatcccggc 44880
taaaacggtg aaaccccgtc tctactaaaa atacaaaaaa ttagccgggc gtagtggtgg 44940

-continued

```
gcgcctgtag tcccagctac ttgggaggct gaggcaggag aatggcgtga acccgagagg  45000
cggagcttgc agtgagccga gatcccgcca ctgcactcca gcctgggcga cagagcgaga  45060
ctccgtctca aaaaaaaaaa aaaaaaaaaa aaagaaaaag aaataattta gtgttacctt  45120
gttgatatta ccaaaaaaaa aaaaaaagtg ctcagagtca cataacttga ttcagtcaga  45180
gctggtacta gatgctcagt cttctgactt ctaatttagt ttgctttcat tatctactta  45240
ctacctgctg ctgactcaga gctcctcagc tatctgcaag tggatgtgtt tattgaacat  45300
ttacgatgta catgaactgc tctcaatgcg aagctcccat ggtgaatggg agcttacttt  45360
ctgactcaaa aattagtttt ctctctttgt gttctaaatg aaagtgtcct tttgctttat  45420
ctgaagcaga aagttgtaag tttgtttatt ttacttttga aattttggag aattggcagt  45480
ggggtcatgc catcagaaac acatacatgc aatgcatgga tgcacggtgt gaatgagctc  45540
tctggaagat ggtagattat gggaaagaag gaagctcaga aagagagtgg accaagtcaa  45600
gaggaaagag agaagaaaca ggcaagtgtg gagcagagga aaagtaggag ggtcatgaat  45660
ccattctgca ggtgtgtgct gagtgactgg aagaaggaaa agaaccaagg aagtctctgc  45720
catgttatct tagttttgtt aagggtataa agagattgaa gagagtttaa ctaggccatc  45780
tttaacccta ggacatccct agagtccctg gcagaactaa taatctaaat tatgaatggc  45840
tgtgtgtgca cacacacagg atgcacttac taatgtctat cattatgagt atcttctgac  45900
ttctccacta caaagaaagg aagggaatgt gaccctcttt ccaggttaga agtaactagg  45960
gcatagtaac acaaatggat gaattaaact gtttaaatgg tgcactggaa tatatttatt  46020
ttggggcaaa tcatgaagaa ataaaaaagg aagagattct cttttgagaa aaagtttgtt  46080
tcctattgtc aattgagcaa ctctgtgaac atcttaaaga taaagaatga ttattctgta  46140
aagtgctggg atttctggtg ctgtgtgaca aagtccggtt ccttttgtct aagttagtta  46200
taataatctt taatgaaaag cagaggggtc ccatggtttg gaacaagtat ctgagtcaag  46260
agttgacaag tagaatagct gggcgcagag gctgctgtca agttgacaaa gccagaacag  46320
tacatttgga cagaaagaat ttgattttct tatactgaat gtgatgatct tgaagaacag  46380
attttttttt tgcatgaaaa taaatcttta ttttcagtta ttacccacca gtaagagaaa  46440
gttaggttaa gggtataaag ggattgaaga ggtttctact tttgcccagt ccttattttg  46500
aatagccttc cactcatcca aagtcatctc ttttggaccc tcctctttta cctcttcaac  46560
ttcattctcc ttattttcag tgtctgccac tggatgatgt tcttcacctt caggtgtttc  46620
ctcagtcaca tttgattgat ccaagtcact gcaattataa gatatttgtt tctgaatgta  46680
tttgggggac tctgttaatt catctttgac aattccccag ttgtgagatc tgctacctcc  46740
acgttacagg tcctcgtgct tcaggccact gtaatgtgaa aaaaaagatc tatcacttcc  46800
actataccta tcaaattcac gtttgccacg agaatcaaat ccatctcctt ggcccatttc  46860
acgtccactg ccctctcgac ctcttccaag accaccatga ccttgaatag gtcggtcaat  46920
aatcagtcta tcaactgaaa attcgcctcc ttcacccctt tcatcaagtg gcttttcaag  46980
tcttcgttca caaggtggtc tcctttctgg tcttctatca gttattttcc cttcaccgtg  47040
aagttgttga gcaggtcttc ttccaacttg tcttattcct tcttcttttt gtgtttttta  47100
tttttcctct aggcaagctt tattctttga ttcctctatc caggaagggg gctgttggtt  47160
gcatcttacc caaatggaat gcaatgggaa ttgggagctt gagttgtgtg gaggaggagt  47220
tgtcaatctt aacaaatgac tatagctggc gtgtggtgtc catcaatcct tgagggcttg  47280
```

-continued

```
gccatgcaca ctagggaatg gtcagaacag actcaacaga ggtctccaga gctttacaat  47340
atctacaata tcaaggttca gggggtatag acagtaagga aaaaggccat ttcctgtttc  47400
tgtccatttt tggtacagta gacagttaag gttttttctt ttgactagct tttaaaaaat  47460
tacttagaaa atggaaagct tataaacatt cataagtgaa ttgttgaatt gctaccccaa  47520
gtggtttcct tacctagtca ccacttaacc agaaatacta gaatacacgg ttcaaccaga  47580
attcaaccag gcagataacc tgcctattgc tcaagcaatc atcagagttt ttaaaaacaa  47640
aattaagcaa aaaagacctt tccccaaata caatcattac tttgtatgac ccattcctaa  47700
gaaagctaca ttccatttca gaaaacatga ccacttaagg tacagttaaa acaaagtcgt  47760
tgccttcagg tgcttacttt ctgttttctt taaattaact gctgaaatgt ttatcttgtg  47820
ttttgtgctg cattcctgaa aactgtaact tttaaggaca taggcctcat ctttataaag  47880
gaagaagaaa acagcaaaga ggtgtctcat ttgggaggca gaaggttatg accaatgctg  47940
gaagtcttcc tcttccttac ttgttgttca acaagatggg ttctgtggtg tcgcatgagg  48000
tgtgagttgg aaatgaaagc tgcaccacac ttcttatatt catagggctt ctccccagtg  48060
tgggttctct ggtgcaccgt gaggctcaac ctctgtctga aggccttccc acactcatta  48120
cacatgtaag gtttttctcc attatggatt ctctgatgaa taagtaggta tgagctacat  48180
gtgaaggcct tcccacattc attacacaca aaaggaagat ctccactgtg aattctctgg  48240
tggacaaaaa ggcaagagag ctgactgaag gcttgcccac attcactgca gtcataaggt  48300
ttctctgcag tgtgaattat ctggtacata ataaggtgtg aaaaacaact aaaggttttc  48360
ccaaactcac actcatatgg cttctcacca gtatggcttc gctgatgtac aataagattt  48420
gcaatctgcg taaaggcttt gccagaatcg ttacaggcag agggcttctc cccagtgtgg  48480
atcctctggt ggacaatatg gtttgagctc ccagtaaatg ttttccgaca ctcattacat  48540
ttacagcatt tttctgtaat gtggagtttc tggtgccgag caagttgtga gctataacta  48600
aaggctttct cacatttact acgcctaaag gtttttttcta aggagaggtt tttttgatat  48660
acagtcagat ttgaactctg attgaaggct ttcccacatt ttgagcaaac ataaggtttc  48720
tgtccagtgt ggattctctg atgcacatcg agctttgcac tctgaatgaa ggccttccca  48780
cactcatgac attcaaaagg tttctccccg gtgtggattc tctgatgcac aacgaggttt  48840
gcactctgac taaatccttt cccacacatg ctacaatgta aaagactttc gcccaagctg  48900
ggttttcgga ttgttaacag tgtcagaatt aaggctgtat tttcccacag atttcttaca  48960
tttctggtct tcctcttctt tgaagctttc aggtaagtga cagtcattca ctatgactta  49020
tctgaaatct ttcctttccc tccttattct ctgcctcttt aacatgtttt ctttttcaca  49080
agcctctctt aactcaggtc cttaaggatc agctttctgg attcttccta atatgatgcg  49140
ggggttttca gcttcctcac gtatctcagt ttttggaacc agtaactgaa ggttcttggt  49200
ttcagcacct tttcttcctc ttctgatcca tcaaggcctg tctgacgaaa ctcccctggg  49260
gcccagactt tgatgttctc agagtgcact tgttggctgg atgcctgatc tgggaagttt  49320
tcttcttcct cctcctcctt tttcaccttc actgggcggc atgggcctag ggccatggct  49380
tctctcaatt ctgcagtcat cttctctgct cagcagggga acgcctatag ctgggagctg  49440
cccagcacag gtcaaacccc atctaagctt tatgtttcaa aagcttcttc ttgagtttcc  49500
tcccagggcc aagatgagta ttgcctacgt gcgcagctga gaggcccgac cagagttcac  49560
tggctctgca gcaggaggct gggggaccag gacctcagct cctactggca cgagaacaat  49620
gacccttatt ccttctttct taagcaccat ggacggctgc gtctcctctt tcctgtcaac  49680
```

```
cacgccaacg ctggagggca gcgggttctt gctgtctttc tgggactcct tgcgcagcta  49740
gctatttgcc tgccgccttg gagttggtct gggtcgcagc ctgagctgcc gctcttggcc  49800
ccagagacgc cgcccccgcc agcttctttt ttcttgttct ctcctgcctt cagcacctcg  49860
aaggggtccg attagttgtc aaataactgg tcgaatcggt tggtgaccag gcagctgaag  49920
ccttcctgta actgcccagg catgatggtt gctcggcggc acattcctcc acggattgca  49980
gcgggctgcg ccgagccaag agcgcgtgct tcagctcttc ccagaagatc gaagaacaat  50040
tttttgaaa tccgcctgta aatgtcaggc aaggtaaatt tcaaaatgaa tttttaaagt  50100
ctctaaaatg gagttatgtt taattatgac tttatgacaa attaaaagat agttctagat  50160
aatactattg tagaaagaag cttctcttgt tctgggaaag agagacagtt tggaaacttg  50220
agacaagacc cttattgtct gttttattat ttactgctaa caaactgcat tctctcactg  50280
ttcactggaa taggtgggtc cagggaactt aggaaagcct aatgggaagt gagaaaagta  50340
aattatttct tatattttta tgtatacaaa tagttgataa aggaggaagt gtagtggtgg  50400
ggtggatcat gcagattggg atacaagaga cagtataatt attcacaatt atagataagg  50460
agatctaggc ttcacatttt cacttctgga atattccact ttgacagaac agtctactgt  50520
ctgcctcagc ctatcctgga gatgtccttg tggtgggaga ggacctgctt tctccttgct  50580
gtgctcctac agtttgtctc tgccagtcat gtccaagccc cttgtcttag tgcctcacaa  50640
gacctcttcc tctgaccagg attcaggcac cttctcagaa ccttcattcc cctgacagca  50700
ggaccagcca gtctcccaga cccggggtag tgcgaagagg agagcagact ccttagaccc  50760
agagtcccag gacacttggc ctcaattccc gtgacaccta tatcacccag acaactggga  50820
aatggaggtg ctggtgccag aacaaaagca taagctgtgt ttctcaagtt tggactttac  50880
ctgggctgtt gctttatttt ctagctgttt actgattttt agaagcataa aggtttcttt  50940
ctgtgaagtt cctagggaca cttaacggag tggggacagg tattcctttt gtctttcaga  51000
aaggcatgtt aagagttagt ctcacagtaa tttaagtctc acctcctaaa tggggtaaga  51060
gtggggagaa atatatgtgt gtatatttgt gtgtgtatat aaataatata tatatactac  51120
taatataatt aataatgtgt gtataaataa tatgtaaata acatattata ttatatgtca  51180
ataataaaat attatattaa tatatgttat tacattaata tactatatat tataatatat  51240
aagatataat tatatattat atactattat attatatcta taacataata tattatatat  51300
ttatatatca ttatataatg tattacatgt attaatatat attatctata tagtaaatat  51360
atggggtgtg tatttgtgta tacacacaca cacgcacata tatatcctgc attgtttgct  51420
tagaatcatg ctttgcaatt attaactgct ttttcttcct tcccttcatc taatacacct  51480
gaagaatatt tcagttagcc aaaggtgaga atccgaattc atatttgtat tcccaataga  51540
tttcccgcag aatcttgggt tatcatttca tcaataacag ttatgcagat gttctattgc  51600
tgtgtccaat gcttgcttcg ttcatatgaa atttgacttt tggccattca aaaagcaatc  51660
agtgccttct tgttgattag cactaatcac cacaagatcc ttccaatagt aaattttcca  51720
gagcaaaatt ctaaacttac agattagttt gccgcagccc ctagccctac actgtaagga  51780
tcttgctttc catgaggtcc attgttaaat ggaaatgttc ccctggctct atgcagtgct  51840
caggtgtttc ttactcagct gaaggactaa tgaatttagt ttgaatctaa atttggagta  51900
aaaaatgcca ctcaggagag ctgcttctgt gactgcattg ccttccaacc tgcttttcca  51960
tttttcctta ttactccatg tccttgagga gtttattcct ttatagcttt tgtgatctgg  52020
```

-continued

```
ctgtaattat tttgaaaaaa attttcatta tactggacat tttggattaa gtcctccaaa  52080
ttttcttatt tgtgagagta caagtcacta tttacactat ggtaaactgc atgcaaacat  52140
ctgagtacct ttctgttcct gtcttcagct gggccagcac taagctggaa tagcctatac  52200
tttgatgttt ttctgaggaa gtacattttc cttttccctc agattcctgg tgcctggtat  52260
agcacttttt tgatttgctc ttgttctggc aataggtcaa ctggctttca tggtccttaa  52320
cgtttcaggt aaataattcc aacagttgtg actggaagga attcaaatca actcaaggca  52380
tccactctat gttcaaaatg ccatgttttg agtgatttgt cctttggtta gtaactttaa  52440
aaaatatgag gactggaagg agaagctact atttgaggaa ctaatggaaa atcaagcagt  52500
ttttgatgta ctaacatata cacttatgat gcaaggagtg tgatcgttga ccttcctact  52560
tatctaaaca ttatgctctc agagcatgtg gataggtagc atagcctagt ggttaacaca  52620
catagaaaag tcagactgcc tagttcgaat cccagcttca tcacttgcta gctatataat  52680
ctttattaaa ttagttaact ttcctgtgcc tcagtctggt tttcctgagg attaaatgat  52740
tttatatttg ttaagtgcct agaactgtag ctggtctgca acaagtacta tacgtctttg  52800
tttaaataat aaataaaatg acagtattgt tcatatggag aaacaggggt cttaggcagc  52860
ttaggagttt ttctaaagta acagaatcat ttaatggcag gaacaacaat attatcactg  52920
cccagaaccc taatggagaa ctatagctct taagggtgat gtggggagaa atacactgat  52980
gaaaaacaat caacattatt aaagacagga tgggagagag tgggaactcg tcattcattt  53040
atctaatggc ttagtcagca agtaactaat gcctactttg ggccttgaca ctataccaac  53100
attgtgcaga aagtgattaa aatgcaaaag aacattcact taggctggga taaacaagag  53160
gtcttttgca aaatctgatg atgagcttgt tgatgttgag ttgacaaact atgcagcagg  53220
tcagtggggg ggtgattatc ataaaattcc atcccttaaa catctacagg aagatgatta  53280
ttttaagatg ctttacttct ggagatgtat gctttacttc tacttagaga atctggctta  53340
tgttctcatg ttctggtttt atatgtaatt ggtcatgagc ttaatttgag ccaagcattt  53400
gacacagttg cccccagaag ttaactcatt tgtggattgt ataaatgcta ttgcacaaaa  53460
aagaagtata tatatacaaa tagtcatagt agaccacatc tcagttaatg gcttcaagtc  53520
tagatgaaat gttttaagag ggatattgac aaattagaga acattagaag catttgccag  53580
aatactggca gggcaagaaa ttatgccaaa tagtagaaag agaattagat gcctaagtgg  53640
aacatggtgt atagcccata agaatttgaa ggattgtcac tggtagaata agatgttatt  53700
cttggctgct tccagctgag gagtggtgga tgggtgacta aggcctataa gagagcaaat  53760
ataaggaaga gtttctagat attaaaatca atttccaaag aaacagcctg gcctctaagg  53820
gaaagagctt cttgtgagta gatgtgttta ggtggggcca gatgaacaag ctcctgagct  53880
ctagggatta gactccttct gctggatagg aggtacaacc aggtcatccc agaggttcct  53940
tgtgttccaa gattctgtta ctctatgatt tcatgacttg gatgtcacct cccttaggtt  54000
ggttactcta aataatgtta aaagtcagtg tatgccttaa gattgggtga attgctatga  54060
cagaatgaga tttaccagag aagcagttaa gtctaagaat gaaactactg tttctaagtg  54120
aaagaggtat gaataaccta aagataatat ttttctctgt agatagaaag aatttgtatt  54180
ataagtctgt gttgggtgta tagtagggca tcaccagaat tcaccctaac tgggtgaatt  54240
catggcagtg atcagtagaa tatgtagttt aacaatgagg ccttatcatt tctaagtagt  54300
ttctttttga gacggagtct caccctgtca accagagctt tgccctggaa ctcttggagt  54360
gcaacggcgc gatctcgggt ccctgcaacc tccgcctccc aggttcaaac aattctcttg  54420
```

```
actcagcctc ccgatttcta agtggagagt tatgaatggc ccaaagataa tatttttctc  54480
tatagataga aataatttgt atgctaggta tgtgttggat atatagcagg acattaccag  54540
aattcagcct aactcggtga attcatggca gtgaacactg caatatgtgg tttaataatg  54600
aggccttatt cttaaggcaa agctcagaaa agctgataag caaattagaa aggtctattg  54660
aaaagtgtct gttggccggg cgcagtggat cacgcctgta atcccagcac tttgggaggc  54720
tgaggcgggt ggatcatgag gtcaagagat tgagaccatc ctggccaaca tggtgaaacc  54780
ccgtctctac tacaaataca aaaattagct gggcatggtg gcatgcgcct gtagtcccag  54840
ctactcggga ggctgaggca ggagaatcgc ttgaaccatg gatgcagagg ttgcaatgag  54900
ctgagattgt gccactgcac tccagcctgg tgacagcaag actttgtctc aaaaaaaaaa  54960
aaaaaaagaa aagtgtctgt ctagccaggc gtggtggttc atgcctgtaa tcctagcact  55020
ttgggaggcc aaggtgagtg gatcacttga ggtcaggagt tcaaaaccag cttggccaac  55080
atggcgaaac cttatctcta ctaaaaacac aaaaaattaa caggatgtgg tggtgcacac  55140
ctataatccc agctacttgg gaggctgagg tagaagaatc gcttgaaccg aggaggcaga  55200
ggtagtagtg agccaagatt gtgccacagc actccaacct gagcaacaga acaagactca  55260
gtctctgaaa gagagagaga gatgaaagag agagagagag aaagaaaaag aaagaaagag  55320
agagaaagac agacagaaag aaagaaagaa agaaagaaag aaaaagagaa agagaaagaa  55380
agaaagaaag aaagaaagaa agaaagaaag aaagaaaaga aataaagaaa gaaagcaaag  55440
tgtctgtctg ccaacctgct tccacaaagg cccctcttct gattgtagaa gtgcctggtt  55500
taggatggca gtgtgctcta cctgctgtct ggtgagtagt caggattgga cttctataag  55560
acaccctctg agaggcttgc aaataccttc agaatcaggc agaggtcttt ggccagttat  55620
ttctgaataa agcatatctg cgtgtctgtc tgacctaagc ctgggaacca cgatggaaga  55680
tactgtttga acaacaacaa caacaaaaaa aggcagggaa cttaagagag aaatggattt  55740
tagtcactaa gaacacgaag aggaacattt tgataatatg tactctatac aaacagaatg  55800
cttatacaag acaatcaaag aggaatgggt agtttctaa agagtaaaac ctgtattttt  55860
aggaacatat atttgtttac aatatatttt ttcttttttc acccttgatt tttaactatt  55920
taataatttt ctacaacatt tttttctttt ttttttttttg cccttttttt tttttttttta  55980
aacagagtct cgctctgttg cccaggctgg agtgcaatgg tgctatcttg gctcattgca  56040
acttccgcct cctgggttta agtgattctc ctgcctcagc ctcccgagta gcttggatta  56100
taggcacctg ccaccacacc tggctaattt ttgtatttgt agtagtgacg gggtttcacc  56160
acgttggcca ggcttgtctg gaactcctga cctcaaggcc caccttagcc tcccaaagtg  56220
ctgggattac aggtgtgagc caccgcgccc agcctgccct tgatttttaa ctatccctcc  56280
tgtgaaaatt taagtctttc tgtgggttaa agggaactgg taaagagcac tggatttatg  56340
cttgggctgg aatttccctc taggtttgga tgtaatgaag gcagtagaga tttgggttta  56400
taacagaggc agatttgtga aactatagga gttgaagcct gagggtccct cacttgcaga  56460
gacccccttcc agggtcctgg aaggaaccct gctaatgtgt tattatggtc atttttttta  56520
taaaaattgc aaaacataat gtgtttcagc catgactggt taagatcatt gtcttcttcc  56580
aattcaactt tccctccttt ctccttccct ttctagttgg gtggcattaa agtggtcatg  56640
cgcattttgt atttgtaatt atgtattttt tttttttctt aaaaaggacc cccccaccaa  56700
attgtataag tttcaggccc taaaaacatg gatcttccac tgggtgtagg aatggaatga  56760
```

-continued

```
gtaacaattt ggaaattgcc tgtgtagcag aatcagcgaa aagtcagagt cagcagtcaa  56820
aatgtgatgg ggagagtgag agtaaattgg aatccataat cccaacagca tttgacagtg  56880
ggaaaatgga gctttttccc ccctctttag ggttcatttt aaagaattcc atgcaaagga  56940
tatcatgaat tgagaaatat acatcagatt catcagatta aaaatttttt tttttttttt  57000
gagacggagt ctcgctctgt caccaggctg gagtgcagtg gcgggatctc ggctcactgc  57060
aagctccgcc tcccaggctc acgccattct cctgcctcag cctcccgagt agctggaact  57120
acaggcgcca accaccatgc ccggctaatt ttttgtattt ttaatagaga cgcggtttca  57180
ccgtgttagc caggatggtc tgatctcctg acctcgtgat ttgcccgcct cagcctccca  57240
aagtgctggg attacaggcg tgagccaccg cgcccggctt tttgttgtgt tttttgtttt  57300
tgtttttgtt tttttgagat ggagccctgc tctgtcgccc aggctggagt gcagtggcac  57360
aatctcggct cactgcaacc tccgctccca ggttcaagtg attcccctgc ctcagcctcc  57420
cgagtagctg ggattacagg cacgcgccac catgcccggc taaatttttt gtttttttagt  57480
agagacaggg tttcaccatt ttggccagga tgatctccat ctcctgacct cgtgatgtgc  57540
ctgccttggc cttccaaagt gctgggatta caggcgtgag ccactgcacc tggcctaaat  57600
tctttttaaa aatagcaaat tcttaaaaat aatgcaaatt gatgatgaat tatgaaaatc  57660
atgatgagaa actcctgact gaagagagaa attgttggaa aatgattctc cttttcctct  57720
actactttat gtaattataa agccttttttc taaagttcct ttctgacaca gaaatactgg  57780
ccaacagaaa ttcaaaggaa agttgagact tttgaagttc aggcaattta tatggtgttt  57840
caggtgttac tacctctaat agtctatcag taaaaccctg ataggggatg gtctctcctt  57900
tttgccttct actccatctc ttctcacaca cacttgtgat tctttttcttt tttttaaaaa  57960
attttattat tataatactt taagttttag tgtacatgtg cacaacgtgc aggtttgtta  58020
catatgtata catgtgccat gttggtgtgc tgcacccatt aactcgtcat ttagcgttag  58080
gtgtatctcc taatgctatc cctcccccct ccccccaccc cacaacagtc cccagtgtgt  58140
gatgttcccc ttcctgtgtc catgtgttct cattgttcaa ttcccaccta tgagtgagaa  58200
catgcggtgt ttggtttttt ttccttgcga tactttgctg agaatgatgg tttccagttt  58260
catccatgtc cctacaaagg acatgaactc atcattttta tggctgcata gtattccatg  58320
gtgtatatgt gccacatttg cttaatccag tctatcattg ttggacattt gggttggttc  58380
caagtctttg ctattgcgaa tagtgccaca ataaacatac gtgtgcatgt gtctttatag  58440
cagcatgatt tataatcctt tgggtatata ccccagtaat gggatggcag gttcaaatgg  58500
tatttttagt tctagatccc tgaggaatcg ccacactgac ttccacagtg gttgaactag  58560
tttacagtcc caccaacagt gtaaaagtgt tcctatttct ccacatcctc tccagcacct  58620
gttgtttcct gactttttaa tgatcgccat tccaactggt gtgagatggt atctcatagt  58680
ggttttgatt tgcatttctc tgatggccag tgatgatgag cattttttca tgtgtttttt  58740
ggctgcataa atgtcttctt ttgagaagtg tctgttcata tccctcaccc actttttgat  58800
ggggttgttt gtttttttct tgtaaatttg tttgagttca ttgtagattc tgcatattag  58860
ccctttgtca gatgagtaca ttgcaaaaat tttctcccat tctgtaggtt gcctgttcac  58920
tctgatggta gtttcttttg ctgtgcagaa gctcttgagt ttaattagat cccatttgtc  58980
aatttttgct tttgttgcca ttgcttttgg tgttttagac atgaagtcct tgcccatgcc  59040
tatgtcctga atggtattgc ctcggttttc ttctagggtt ttcatggttt taggtctaac  59100
atgtaagtct ttaatccatc ttgaattaat ttttgtataa ggtgtaagga agggatccag  59160
```

```
tttcagcttt ccacatatgg ctagccagta ttcccagcac catttattaa atagggaatc  59220
ctttccccat ttcttgtttt tgtcaggttt gtcaaagatc agatagttgt agatatgcgg  59280
cattatttct gagggctccg ttcggttcca ttggtctata tatctgtttt ggtaccagta  59340
ccatgctgtt ttggttactg tagcctagta gtatagtttg aagtcaggta gcatgatgcc  59400
tccagctttg ttcttttggc ttaggattga cttagcgatg caggctcttt tttggttcca  59460
tatgaacttt aaagtagttt tttccaattc tgtgaagaaa gtcattggta gcttgatggg  59520
gatggcattg aatctataaa ttaccttggg cagtatggcc attttcacaa tattgattct  59580
tcctacccat gagcatggaa tgttcttcca tttgtttgta tcctctttta tttccttgag  59640
cagtggtttg tagttctcct tgaagatgtc cttcacatcc cttgtaagtt ggatttctag  59700
gtattttatt ctctttgaag caattgtgaa tgggagttca ctcatgattt ggctctctgt  59760
ttgtctgttg ttggtgtata agaatgcttg tgatttttgc atattgattt tgtatcctga  59820
gactttgctg aagttgctta tcagcttgag gagattttgg gctgagatga tggggttttc  59880
tagatatata atcatgtcct ctgcaaacag ggacagtttg acttcctctt ttcctaattg  59940
aataccettt atttccttct cctgcctcat tgccctggcc agaacttcca acactatgtt  60000
gaataggagt ggtgagaaag ggcatccctg ttttgtgccc gttttcaaag ggaatgtttc  60060
cagtttttgc ccattcagta tgatattggc tgtgagtttg tcatagatag ctcttattat  60120
tttgagatat gtcccatcat tacctaattt actgagagtt tttagcatga agcattgttg  60180
aatttttaca aaggcctttt ctgcgtctat tgagataatc atgtggtttt tgtctttggt  60240
tctgtttata tgctggatta catttattga tttgcatatg ttgaaccagc cttgcatccc  60300
agggatgaag ccagcttgat catggtggat aagcttttttg atgtgctgct ggattcggtt  60360
tgccagtatt ttattgagaa tttttgcatc aatgttcatc aaggatattg gtctaaaatt  60420
ctctttttttg gttgtgtctc tgccaggctt tggtatcagg atgatgctag cctcataaaa  60480
tgagttaggg aggattccct ctttttctat tgattggaat agtttcagaa ggaatggtac  60540
cagcttctcc ttgtacctct ggtagaattc ggctgtgaat ccatctggtc ctggactttt  60600
tttggttcgt aagctattca ttattgcctc aatttcagag cctgttattg gtctattcag  60660
agattcaact tcttcctggt ttagtcttgg gaggatgtat gtgtcgagga atttatccat  60720
ttcttctaga ttttctagtt tatttgcgta aaggtgttta tagtattctc tgatggtagt  60780
ttgtatttct gtgggattgg tggtgatatc ccctttatca ttttttattg cgtctatttg  60840
attattctct cttttcttct ttattagtct tgctagcatt ctatcaattt tgttgatctt  60900
ttcaaaaaac cagctcctgg attcattaat ttttttgaat ggtttttttgt gtctctattt  60960
ccttcagttc tgctttgatc ttagttattt cttgccttct gctagctttt gaatatgttt  61020
gctcttgctt ttctagttct tttaattgtg atgttagggt gtcaattttg gatctttcct  61080
gctttctctg gtgggcattt agtgctataa atttccctct gcacactgct ttgaatgtgt  61140
cccagagatt ctggtatgtt gtgtctttgt tcttgttgct ttcaaagaac atctttattt  61200
ctgccttcat tttgttatgt acccagtagt cattcaggag caggttgttc agtttccatg  61260
tagtagagcg gttttgagtg agtttcttaa tcctgagttc tactttgatt gcactgtggt  61320
ctgagagaca gtttgttata atttctgttc tcttacattt gctgaggagt gctttacttc  61380
caagtatgtg gtcaattttg gaataggtgt ggtatggtgc tgaaaagaat gtatattctg  61440
ttgatttggg gtggagagtt ctgtagatgt ctattaggtc cacttggtgt agaactgagt  61500
```

-continued

```
tcaattcctg ggtatccttg ttaactttct gtctcgttga tctgtctaat gttgacattg  61560
gggtgttaaa gtctcccatt attattgtgt gggagtctaa gtctcttagt acgtcactaa  61620
ggacttgctt tatgaatctg ggtgctcctg tattaggtgc atatatattt aggatagtta  61680
gctcttcttg ttgaattgat ccctttacca ttatgtaatg gcattctttg tctcatttga  61740
tctttgttgg tttaaagtct gttttatcag agactaggat tgcaacccct gccttttttct  61800
gttttccatt tgcttggtag atcttcatgc gtccctttat tttgagccta tgtgtgtctc  61860
tgcatgtgag atgggtttcc ttaatacagc acgctgatgg gtcttgactc tttatccaat  61920
ttgccagcct gtgtctttta attggagcat ttagcccatt tacattcaaa gttaatatca  61980
ttatgtgtga atttgatcct gtcattatga tgtcagctgg ttattttgct cattagttga  62040
tgcagtttct tcctagcctt gatggtcttt acaatttggc atgtttttgc agtggctggt  62100
accggttgtt cctttccatg tttagtgctt ccttcaggag ctcttttagg gcaggcctgg  62160
tggtgacaaa atctctcagc atttgcttgt ctgtaaagta ttttatttct ccttcactta  62220
tgaagcttag tttggctgga tatgaaattc tgggttgaaa attcttttct ttaagaatgt  62280
tgaatattgg cccccactct cttctggctt gtagagtttc tgccgagaga ttagctttta  62340
gtctgatggg cttccctttc tgggtaacct gacctttctc tctggctgcc ctgaacattt  62400
tttcctgcat ttcaactttg gtgaatctgc caattatgtg tcttggagtt gctcttctcg  62460
aggagtatct ttatggcgtt ttctgtattt cctgaatttg aatgttggcc tgccttgcta  62520
gattggggaa gttcacctgg ataatatcct gcagagtgtt ttccaacttg gttccattct  62580
ccccgtcact ttcaggtaca ccaatcagac gtagatttgg tcttttcaca tagtcccata  62640
tttcttggag gctttgttca tttcttttta ttcttttttc tctaaacttc tcttctcgct  62700
tcatttcatt catcttccat cactgatacc ctttcttcca gttgatctca tcggctactg  62760
aggcttctgc atttgtcacg taattctcgt gccttggttt tcagctccat caggtccttt  62820
aaggacttct ctgcattggt tattctagtt atacattcat ctaatttttt ttcaaagttt  62880
ttaacttctt tgccattggc tcaaacttcc tcctgtagct cggattagtt tgatcgtctg  62940
aagccttctt ctctcaagtc atcaaagtca ttctccatcc atctttgttc cattgctggt  63000
gaggagctgc tttcctttgg aggaggagag gcactctgat ttttagagtt tccagttttt  63060
ctgctgtttt ttccccatct tggtggtttt atctaccttt ggtctttgat gatggtgacg  63120
tacagatggg tttttggtgt ggatgtcctt cctgttcatt agttttcctt ctaacagaca  63180
ggaccctcag ctgcaggtcc attggagttt gctagacgtc cactccagac cctgtttgcc  63240
tgggtatcag cagcggtggc tgaagaacag cggatattgg tgaaccgcaa atgctgctgc  63300
ctgatcgttc ctctggaagt tttgtctcag aggagtaccc agccgtgtga ggtgtcagtc  63360
cacccctgct ggggggtgcc tcccagttag gctactcagg ggtcagggac ccacttgagg  63420
aggcagtctg cctgttctca gatctcaagc tgcgtgctgg gagaaccact actttcttca  63480
aagctgtcag acaggtacat ttaagtctgc agaggttact gctgtctttt tgtttgtctg  63540
tgccctgccc tcagagaggg agcctacaga ggcaggcagg cctccttgag ctgtggttgg  63600
ctccacccag ttcgagcttc ctggccgctt tatttaccta atcaagtctc agcaatggtg  63660
ggcgcccctc ccccagcctc gctgccgcct tgcagttcaa tcttagactg ctgtgctagc  63720
aatgagcgag actccatggg cataggaccc tccgagccag gtgcgggata taatctcctg  63780
gtgtgccatt ttttaagccc attgggaaag tgcagtatta gggtgggagt gacctgattt  63840
tccaggtgcc gtctgtcacc cctttctttg actaggaaag ggaattccct gacctcttgc  63900
```

gcttcccagg tgaggcgatg cctcgccctg ctttggctcg cactcggtgt gctgcaccca 63960
ctgtcctgca cccactgtct ggcacacccc agtgagatga acccggtacc tcaattggta 64020
atgcagaaat cacccgtctt ctgtgtcact tatgctagga gctgtagact ggagctattc 64080
ctatttggcc atcttggctc ctcccccaga tcacacactt gtgattcttg ctggcattca 64140
cacttactct ctctttattt tttgagacag ggtctcactt tgtcatccag gctggagtgc 64200
agtggtgcca tctcagctca ctgcagcctc cacctctgga gctcaaggga ttcgagtagc 64260
taggactaca ggcgtgtacc tccacccctg gctaattttt gtattttttg tagagctggg 64320
gttttgccat gttgcccagg ctgatctcca acacctggga tcaagcagtc tgcccacctt 64380
ggcctcccaa agtgctgaaa ttacaggtat gagcctccat ggctgggcac ttactgtctt 64440
tttaattatc agcttgcaaa tgagaaatct gcccaaggag cctgagcttg gtgaatacaa 64500
gttcatttca gccccattgg tgagtttatg attctatgag actttaaaga tgtattttat 64560
ttggacatgt taaaaaaaaa aaaaaagaac cgtgtgtttc ttcacaacat ccaaaataat 64620
tattttattg gtattgataa ttattattga ggaataggga agtcatgtat gttatcaacc 64680
acttcctaaa tgatacctag ttaacacgtt aggggaggga atcgaatctg aaagtgatac 64740
ccatttagtg aagccaagca atgtagcaag agttgagaaa aacttataaa gggacctctt 64800
agcccatgtc cataacattg tcgttaacat aaagataggt tgccagagaa agggtaactg 64860
tatggtcaat ttagccaggt ctgaactctc aaaaatcaag cactctcatt ctgttagggt 64920
gaagtcagag aaaagaacct tcacaaggtt tgaaaacaca gttgtaacat actgggctgt 64980
gttccagggc tagcatttga ctctgatttt tatcttgtgc ttagaaccag cctactgttg 65040
tctctgtgca gagagagtac taagtaggta ctgaataata cttgctgtcc agcacatagc 65100
tctgtgcaga acgagcacta agtaggtact taataatgct tgctggccag cacatggatg 65160
gatcatgttt ataagtgtgt atcataaaca ctttgccttg aggaaattgt tttcttttta 65220
gagttttcat actgtggaca tccttaaaaa gcccagaaaa tgtatcttta tggattgaca 65280
tgtgacttct tacatatgaa gttagaagcc aatgaaatgc tgttctttgg actgaacttt 65340
caagactcat gtgtgtggtg tctaattcat taactaaaaa tatgattcat atttacctta 65400
tgtaggacta caggtatcca catatccacc attaggatat tctttaaatc tggtagtttg 65460
gaagatttcc agacattgta aagagtaaat gcatcagaaa taagcatttt ccagaagagg 65520
gaggtatgaa attgtaatga ttagcctgtt gcttagtcct ggaaatgtga aatcagataa 65580
aaatgaaaaa gatgctttcc ttgcattctc ttccagaaat atgcagcctg ctgctctttt 65640
gtcttcagtg tgaccatgct gccctgagga gagcccagaa ctgtttttaa attcaaaagg 65700
acagctgctt tctgctcact caggtccact gaggcatgct ccaagacagg aaaaaggtgc 65760
ttagcggggc tctttgatag agattcaata tatgaatttt actttgagaa taaaaagctc 65820
acccactttt aaaaggttaa tcaaaagctc attgtagtgt attcttcctt tcctatgcag 65880
tttcctatgg aaatggaatc agtttaaatt ctggcctcag aacagcaata tttttcacag 65940
aggcagtcct tctgccaagt ggctctagaa gtacccgtaa tatccatgtc aggagtatga 66000
aaaatgaaag ggatgaacac ttccttcaga aattatacct ttgattcctt tactttacgg 66060
ccaggcagga agaatcctga gagaggtctt tactgaaagt tcagtattta tgaactacat 66120
actgaaaaat gaaaaacgat tcctagcact gagttgctta ccctgtcaag tttacccatt 66180
attttcaggc tgttgagcat tgtttgaaaa atcgatctga gagctaaatg agactctgtc 66240

-continued

```
ccttaccatg gtcttgctgt tataaattca cactgggcta tttccattcc ctaagtttgc  66300
tttgcccttt cctacccttt acctctatgg tcttccatcc ggtaaatttt ctctcaccct  66360
tcctggtcta gctctatttc atcttcactt atgaaggctt ccttgttttc ctttttttaga  66420
attaattgct aattcctcac tgctctctaa gcattaatac cccatcata gccttcatca  66480
taatatgttt tgtgctgtag ttatttatgt acttacttgt ttttccccct tctttgctct  66540
ttgattaaat gcatgccaga tccaacttta cagatgagaa aaatgagctc tgaagttcaa  66600
taacttgccc aaggctaccc agttagaaga gttatggact tcactctgaa tatggtgact  66660
tttgttctag tgtgttgcct tctctagtct tcttaagaaa aaccttgtct tcttttcttt  66720
tttccttagg ttgacttatt ctatacatta gaagtttcta aattttaatc aaactgtcat  66780
tccagggtca tagtcagcca catgtaaatc agaatgcagt tttacataga ttcattatta  66840
ctgtgcatgg agattagaag ccagctcaca agaagactta atttggaaag atatgtaacc  66900
aacttcacgt aagtgctagc ctttcattga tttctcacct ccattctata ttcctcctgg  66960
cacttgtttt aaatctgttc tactgaagtc catactctac ccccttgctc tcagccgatg  67020
atctgtttac ctgctctgag aagatttaga tcagtagttc tcaaacttta atatgtataa  67080
aaatcacatg cagagctctt tctaacatag tttcccggga cttttcccag gaattctgat  67140
ttcagcaggt cagggtgggg ctcatgaatg ctccattcta acaagctccc aggtgatggc  67200
aacacagctg gtctgaggac tacactttga gaacctctga tttaggccat cctctgcaat  67260
aggatgtctt ctccaataca tcttctctgg atatttatcc ttcctctcct tctatgagaa  67320
ttcagtcgtt ctattctcag gctgaaccct ctcaccacga gcttttatcc catctcattt  67380
catctatttc aggaccttgc ttcaacttgg ctctctttga atcttttata tcaccctctc  67440
aattgctttt tattctctac tgctttacta ataaaactgt tcctttctca gttgtactat  67500
ttaagataca tctaatgatt gtaagcaaaa ttattttctc taagaatggt cgacaatttc  67560
agattcaact cagctggcta ggaactaagt ttctgtaatt tgggaattgg cttgtagaga  67620
gcaaaattaa gaaaccaagt ttggccgggc acggtggctt acgcctgtaa tcccagcact  67680
ttgggagtcc gaggcaggtg gatcacgatg tcaggagatc gagaccatcc tggctaacac  67740
ggtgaaaccc cgtctctact aaaaatacaa aaaattaacc gggcgtcgtg gcgggcacct  67800
gtagtcccag ctactcggga ggctgaggca ggagaatggt gtgaacccag gaggcggagc  67860
ttgcagtgag cggagatcgc gccactgcac tccagcctgg gcgacagagc gagactccgt  67920
ctcaaaaaaa aaaaaaaaaa gaaaccaaat ttaacttttt ttaatggatg tgagtggaag  67980
agactaatga gataacacaa aagagttaac ttcttacatt tctgtagtct aatacgagat  68040
agtttctcca ggaattaaca cagcacatct ggttcactga cctgagtttg tttcctggtg  68100
aggcattgca gtatcatcca tatctcaggc aaaggtactc cagcattttg tagttaagca  68160
gttggaggag gagtagggag aactgctgta ctttgaaaca tttcacagtg gactactttg  68220
cattctaatg atgttctcct tacttaagga ctttgttatg taaggatact ttgtccttct  68280
gataatcact tacacttttc ttctgtgttc atgtcacttc attaatcctg attacttgta  68340
atgaatcata atcttaccca cttattcttg tgtgactcat tcctacttgt attcttaata  68400
gtattttcta tgtctgataa cacattgtca attgactatg ctatttttaa cgtaagcgtt  68460
ggcaaaaagg tttacttaga gaaaagctct acatttaatt ccccggtgcc tcagttccca  68520
aatttgctaa taaagattat acttagctgt cactccacgt ttcatcagta ggattaaaat  68580
gaatagagat catgaaataa gacaatgaaa aaagataatt ataatggacc agattgagaa  68640
```

atccctacaa atcaacagaa gcgacctgcc atgtcagatt cctagatgca gtttatttac 68700
tcagtgggcc atatttcttc cttattcttt ctttttccat gatgccttcc aaaactatat 68760
tttaaccagg agggaaatac catttgtctt ctgatatagg aagatcctac tgagagatta 68820
tattcatata tttcgtccat cggcctgtag gtggaattgt atttaaaata ctaataaagg 68880
ttattattgc ttatatatct aaaaatgctc caactgtcca aacaaagctt atactgttga 68940
tgatatttat cagtggctct gaacacttgc atatcataaa attctccctc aaaatttaac 69000
cttaaactct ttcaggcttg tcttggtcac agtgggaact gaggacagct gctcatgttt 69060
tttgatagaa cagctcttaa catgcttttg ctcttgcctc ccactgccca acaccagctg 69120
catacacaca gtctacttgc tgtgtgcatg ctctggctcc tgtctccttt tccttcagcc 69180
tagttagcct ggttttgttt ggtttcatca tacaatgtat ctattagtaa aacttttatg 69240
aactctgatt atagtactaa actcataata aagtaatcag aacttcattt attaaaacac 69300
tgtcttgagc ttattttta atttagtaca catgacaatt tggtaaggta ggaattttca 69360
ttcccctttt atagatggga aaactgaggt ccaggatata ggtaacattt tcaaagttaa 69420
ctcgtaagta aatggcttag ctggaatttg aacccaggtt tctgcaattc taaagcccat 69480
ccttttaact gctatgctat gcgcacaatt actgtattct tatttgctct ctgaaataca 69540
acaccttatt ctcatttcat ctgctctttc tgccctgtac acttcagttt ctgctctata 69600
gatacctgct cgtattgtga catctcaatt ttttttgtac cttggcaggg ttttgattga 69660
tgtattggtg ttctgaactc tttagcatat gtattaatag ggaagaccta ccaaatattt 69720
catgtaatag ggattatttt gtctacctat tttatcttc tttataatgt aagtttgtag 69780
agggcagaaa ctataaattg ctcagttagg gactccacat tgagccaagc acatacatac 69840
ttgacccaga gaagtcatca ccatctttat cgccacagct aacatatggg tagtgctcac 69900
catctaccaa acatgtgcat ggattatttt atttactctt cacaataacc ctataaagta 69960
gactatgttg ccatccccaa ggttaaaaaa ctagcccaag ttcatcgagt tactgcatga 70020
tagagtttga gtctaaccaa caccaatcta cacgtctgtc aacacagtta actatcccac 70080
acttctcagt ggaatctaga gttccactta tttcctattc cttccattct tcactatatg 70140
tcctctttgc cttcttatcc tgtttctcta cttctcactt tctgccctat acgtatctgc 70200
tcaatcttca atcttctctg ccttaccctc tctttttcaa ttttgttctc gttctgtcct 70260
atcctgcctc cccactcttc ttacctcatt ttcctagtcc tcttttcttc tttttttcac 70320
ctttttacct cttacatatt tcttttttaa aagtaacttc aagcttgata atagattctt 70380
caacgctctt agcaatatcg tatcctaacc ataataaaat gatagtgtgc taggtgtaaa 70440
cagaagtaga atatgaaatt gaaatgaaga atctctttac tttttctatt agaaacataa 70500
ataatgagtg actgtaacat cttggtctcc ataatttcta agtgttaaat aaaacacatt 70560
tctttttttta tttaacacac acacatccac acacacataa acttgtttta tgcattgatt 70620
gccatttatt gagcagcata tttttggaaa tgcaacaact acaaaagaat ttttaagtta 70680
ttatcataca gtgacattaa taggctcatc actttgcctt ctttccttgt tctatcatgt 70740
agagggttgc tttagagatc attgtgtatt gatatgaatt atcattgaag ttttattagt 70800
ctggatgtct catcttgggc attttgataa atttcttttg ctccaaatcc agaagttatg 70860
gccattcatc tttataaata agactttta aaaaaggtaa agtcataaaa taaatatttc 70920
aaagcagtgt tggatatagc cagctgaata aactgccctt tctagttaac tttgaactct 70980

-continued

```
aaaccttatt taaatatcct cccttttttt ctgtaaagaa gacgagaaaa aaaaacaatt  71040
tcagtagatt ctaaaagaaa atatagcaag aacattttca taagagatat ctcacataaa  71100
aagctgtaaa aattgggcaa gtatttgcac ctaaccagta gaacttagaa gagaaaacat  71160
gaaatgaact tcttagctta tggaatggtg tggataggtt tgcattactt agatgttcac  71220
agagctctag catttactta ctgaaacact ggaatggttc atatccctgt ggtttccacc  71280
ttatttcttc cagaaggatt aggttttatg ctgccagaga ccacattgac tcttagtaat  71340
gggatcacta aattctggtt cacaattttg tgcatagaga gattgcacta atatctcaaa  71400
attgtagcta tgattataac cctggcatag aaatctgagc tatgctggca gtgtcatgct  71460
gtacaatcga atccacctga ttatctctgc atttgtgaca gctgggctgg ccttcattgg  71520
catatgcctc tttgctgtgc ccagggcttt gaatgcaaaa tgaaagatca gcatgatatt  71580
aggggcccat gatccataga tggagcttca caagtgaaca gcgtctcagc tttaacatgg  71640
cccccagtat cctgctttat ctttctggac tgaagttcct atgacagatt tgttgcttta  71700
aaaaagtaat tttgcagatt tgtccttttt taaaagaaat aaagattgcc ttccatttcc  71760
tactgaaagt gatatggtag tatccatctt ataattgcac agattcaaaa ataagccaca  71820
agtatgtgtg ctgaagtata actgtggact ataaaataca gatatcatag cctataaatat  71880
ggagggtagt gtgatgttat aaagccattt ttctgtgttt tacattatca taaaatttaa  71940
ctactgaagg gaaagtgaag gttttaatat ttaactaagc ctagcacttg aagagaaaca  72000
catatatttt acttggaaaa aaaggaagtt ccattttgga cactgcaaat gacagtgcca  72060
gctgttgtca taatatttct aacatccgct gaggattaat tccaggccca gcaaattcac  72120
tggatgagca gaaacagcca aagaagtaaa cactggagct tatgctgtga tattattaaa  72180
ttaggcatga gacttctaca gagttggata tgtagtgaac actggattat catgcctgag  72240
gatcgtttgc tttgtgtata tctgcagaaa attgaatcct gaacttgctt tcttctgcct  72300
cttggccctc ttcctctgta gaggtatact cagaaaatgt gatctcattt gaatataaac  72360
ttttctatta atattcatta agtactcata caatataagc tgaggaaaca aagtggtggg  72420
tgtaaaacac aggcctcatg taaagagctt actttcacta cagaggcaat gtagcataat  72480
gaagcagaga tgggtttcag aggcaggtag accagaattc aaatcctact tctcctaagt  72540
atggccttgg gcccatcact taaatttctg agactcagtt tccttttcta tgaaaggtag  72600
atactaatca tgctacagag ttctattaag aattagaaat atttaaagat acttagacca  72660
ctacaaggta gctatttttc tagaacaggc ataccttatt gtatacattc tatgtttcta  72720
gaacaggcat accttattgt atacattcta tgaaacagaa tatggaaagt gctaaatgaa  72780
aggcacaatc agagaattcc ccaggccctc aagaaggaag gcggaatgga tgaggaagtc  72840
tgctgtccaa ggggtgggcc agagctaagg caagatttgt gggtgggcct tcactaacca  72900
ggcacaggga gagggcattc caggagcaga tgtagatctg gccaaggaat taagacagga  72960
atgcaagtgg cgttttccag gcaaaagatt aggaagtttt agatcagcct ggatatggag  73020
accttgaata gcaagccgac tgaggaatgc atgaaagaat gactactagc tggaataaga  73080
gataaatctc aaggcctctt ttctctttca cctctcctct tgcccacatc atggacagat  73140
agttctggct tttccttata ctctgtttct gtaagcaatt ttaagaaggc agagtgcata  73200
atggtattac ttttatgtct gcgtgtgtat tgccaccatg aagcctatag ttttgctttt  73260
caaactacta gattgtgacc ttgtaatgat ctggcaaaag gctgaatttt taaaagcagt  73320
aaatccatat agtggataat attgggaaaa aattagggct aatactgagg aatgagaaga  73380
```

ttaggaaaga gataaataaa atatgggtgg tataaataaa aattaaagtg aaaatgtggg 73440
gaaaggactg cttatgattc accttacaaa atttctacct tatggggtct gttttcactg 73500
tcagttcttt ctgtgaatgc atgttcatga agatactgaa ggctgttttt ctataggcag 73560
ctggtggttt tctgctgtag gcagaagtgg ttgaggtaat cctagggagg tgatgctgaa 73620
tggggctgtg gttctacttt atgtaaggtt attatatgtg aaagaaagag taatttttaa 73680
aagtaattaa ctagtggtag attctgaact aacattagca aaggttgatt ataaatcaga 73740
ttttattttt actactgatt tagaaaaaat ctttggagaa atagatttgg aatggttaaa 73800
tatcacttta gggagcacat tttggtatca cagcttaaag gtactcttaa gagaaagctt 73860
tacaaatggg gcaacctgaa aagacacatt tcatgtgcat tcaaattcaa gataagaccc 73920
aaagctctgt tgccaaggta aaggttttga gagttaaatg ggaatttgga aaataatatg 73980
caaaaattga cttaaaatgt agataagcct acaagtattt acagggtgga gacatcagag 74040
aatgtaagaa atagtttgga tcactaacag gaatgtgtaa tgggaagtca aaatctatgc 74100
tgtcaggaaa aattcatatt attggataga aactgtatta tttggtacat ttaagataaa 74160
atgaaaattg tgttttcaaa gggttacgcc tcgcagtgga tgagtgattg gggcgttttc 74220
tggtttcagt gattctgtag gcagaaaaca gtttttactg ccaagtgtgt cagtggaggt 74280
ggggagacag agaccttgct gtgttaagtg aaatctgttg cttaagaata aagctgggat 74340
ttctgtagaa tggagaagga gtttggtatt atcatattat caaaaataac tgctctttga 74400
aaagtagatt ttttaaagtt tgattatcaa gtatttattt aaaatactgc ctaagtattt 74460
aaacactttc aggctctgat tttgtttttt ttacaaagga aacctatgcc taaaaattat 74520
tttaagtagt tatatggata catgagctac acagtttcag acctgtgtat atgactttct 74580
aagaggtcta tggtatccaa taataaatga ttttatgcag ggatttaaca cataatgggt 74640
catgcattat ctataccttg ttaatgggat ctatatagag tgatagcaga aaagaaagtt 74700
aattttagga tcctttaatg cctataaatt tagagcaaaa gaaatatttc taaaagttca 74760
acttttgtat acatatgccc aatcacaagt tttacagaca tttttacacg tttaggcctg 74820
aaatatttga ttccgctctt atttgtcaag atacaatata attacattag taaaatgcaa 74880
acagggcaga taagttttcc ttctttttcc tatgctatag tcatgctgca aaccctccat 74940
tacagttttt tggctgaggt aggtctagat gtctagaggc caactaatac agttttatat 75000
aatcaacata gggaagtcat ttcagagact ggcattgagc tcttggaggg aagaaaatga 75060
accttaaagc ttcttgggaa tatccctcac tgcagcagag tttatgtgct ctaatggatg 75120
ctccgtaaat gcttgagaga atataagtcc cataggttag catatactta attctaccta 75180
tcatggaaac ctctccatac attctatagc tgaaatattt taggagctca aaaggagtaa 75240
cagaaactaa agggaacacc agctccaaga ttggattttt aggctttctt tctagtgtaa 75300
cacttccctt cctgttgggc catcggcaac catatcctgg ctaattagaa gtgattttca 75360
ggggaaagga agaggtcata agttcttgcc tccctatttt ccttcttgtt gggtgctagt 75420
aacttacctt aagaagtaat gaagtcctag taaaactcct aatattcaga aaccaactct 75480
cattattcaa acatgttgag gaaaaaatgt ctccttgcgt cctcttctgc ttaaaactcc 75540
cccagtacca tcaagcatgg acggatatat gatagtggca gtatccagaa gacacaccat 75600
ctatgtaaca aaccctggaa ataaagtatg gtataatcct aagcattcgc tcagcactct 75660
tgcttctggg aatttgctat gagtcagcca caggcatctc tgtgtacctt caagcccaga 75720

-continued

```
ttagcacgta tgggaggata agagagaaag tgtacttcct gaatacatct tgggtagagt  75780
aaactaatcc ttagctaggt tgatgacatc cttacccaga atttaaaagt tcagtagaga  75840
ctcttcttga aatgttgaat ttttatttct gcttgttgcc ctctatagat gagtgaaatg  75900
caatgaagat attcatggct actataaaaa tgcattagtt ctttttggtg agctacttga  75960
ctatcagagc caaatatgta ggtagttgga attaaatttc caatttagca tcccccttag  76020
aagggtgatg gaagctccca tatcttggta tttctctttc tgagtatctg ctgtctcact  76080
gaggcaacat gctagcctcc atgttgtatt atttcacagg tatagaacta agtgacacat  76140
tgccaattcc cacgcccccc ccccatttc tttgatggag gtagattaca tttataaggt  76200
gtagatattg cttgaaggta cttgttcttt cttataagta agcaagaaag agagcagcaa  76260
ataatagcta ggaggaagat gtgcccacac cacattcagg ccacttagtc tatctagtaa  76320
gatagagtgt ttcaggcatc aagcatgtac tgggagacat gcatacagaa aaagaacaag  76380
caatagactc ctttgagagt gacatggtag gtctgaagag tgaatgtaac tttttgtctc  76440
catcccctca gtgattcatt aattattcat tagctgtttt tttccaccag gattacaatc  76500
attttacctt tgcttgccag cctagtgggt tattaacagt ggttactcta tttatttaca  76560
cattttcctt gtgtatgtta ttcatcctgt attagttcac ccccacccct agtcaccatt  76620
ctttttcttt ttgtttggcc tttcatggct accatattac catgtgatca gaaaaaaaat  76680
gcactggtgt cagaattagg ccaacacaga catatgggat ggtaggttca tttgggttgg  76740
atagagagct gtttgaaact tgtatacaca tttttcaatt tcaagaagaa acatctgcag  76800
taaaggaaga actgcatagt ttgcagtggt ctaatggagg tgaactcagg aatctcagat  76860
gcatttagct ctacaagtct ccattataca aatgatgttg aatgtttcat ctcttgctac  76920
agattagttt tgggccatca tgaaaaactt tcctgaagat taagtcaaac ttatctatgc  76980
atgccttctt tggatacata gatccacctt tgacagctac tctgtccact aattctgtca  77040
agtaggactg agctttcttg aacacctctc cttttgttaa caagaaggag aagaagaaaa  77100
ttaaacactc ctggcatctg cctggctgtg atttagccct tggtaaaaag tattacaaat  77160
tgagacggtg ccagactgct cctgtgattc atctcttctc ctgtcaagac cagttgaggc  77220
gatgcaattg ggaacctctc tagtttgtga agagacactt tatgttggaa gcaacagcat  77280
aagcacaata gtacttaggc attcaaagca gagagaattg gttcctcctg attgggtgaa  77340
caatcactgc aaattaaggt caaaagtatt gtcaaccaat tcagtgtact aggcttcttc  77400
atcatttccc atgacttgtt ctctcttagg agaaggttta gcaaattgga gcaatttttt  77460
tttttaaatc ttggtgcagc gttagtgata aaacacaaga aagtttaagg ctggatatag  77520
catgtgcatc tatatcaaga tgaagatcca tagagagatg tgcttgatct tgggatgctg  77580
gatgaaaatc caggcactgt gttgtgggag cctgatttct gaaagttggg gcatcattgt  77640
ttggcttatg acgtttataa gtgtcaggta cgtcttgtcc cacagaatac ttgttatagc  77700
tgttaaagga cagattgtct tcaagacaac tggtacccat gccagagtag ggtatattct  77760
gacagaaaat ccatttactc tcatctgtaa tttatcccct tagttgaaac atgatcccag  77820
tgtagggcat ttacttttca cactccgttt aaatcagtgt ggtttcttcc taccttaatg  77880
aattttacct catttctttg tcttgcaaaa acccagggca gaatggtaaa atttcaaaac  77940
aaatctttca caaggctgga actagacact ctgttgggtc acatgcaagt tatttgcaga  78000
agaggaacac tttgcatgtg aataagagaa agcaaagcac ttacaccagt attcagtgct  78060
cttggggcca ggagtgaggg gccttccatg tttgcaggac atctgtttgg gccttaagtt  78120
```

ctgctacagc cccaagtcct tatctcatat ctgcctggtg tcctattttt ctgcttaaag 78180
agtcaaagac tgaaattctt atccttgttt cccattcatt cctaagttac tttagccttc 78240
acatggagcc accatgctgt ggcccacaga gtgtgctatt cacttaaact tatttatctt 78300
aacctttttg tgaaatatgg ttgcattctt tgactttcct tgcttgtcac agtttacatt 78360
aatcctggaa cttttgagtc ttaagcgcta catgatagta ctctttctaa tggtttctaa 78420
tgttacacga atgcctctct ttcccatttc atccctttct ctctgttggt tttgacttta 78480
agctctctgg ctgtttcatg gcaatgatta ttggtgacag tattatctat taccaagtgt 78540
ttcttgttca gttttgcata gtttcaatgt ccttttaagc aaggattgcc aaactacagg 78600
ccacctgttt ttggagatgc catttaattg gaacactgcc atacccattc atttacatat 78660
cacctatggc tcctttctca ctacaagggc attgtttagt agttgaaaca cagaccttat 78720
gtaccttcac ctcaaaacct agaatattta ctatctgact ctttacagaa aaagtttgct 78780
gatctctact ttgaagaaga gaaagtcgtc agatacatac aatgccaaag aactgctggc 78840
tatgaaaggg atattgtaga attctgcaat tttcttaaag aatggaaaac attggaaaag 78900
agtcacctgt ttacaggtga tttgcatttc tataggtatc agaataatgt gggtgcttgt 78960
aggttgggga aggaatggca ggccttctct ctctgtcagt atcttcaggc cctgaagtca 79020
tacaatcaat ggattgcttt tcctcttcac ttttccattt tgccataatt ttgccaaggg 79080
ggaggttgga agtgggttaa tattttgcgt tagaagagca tttggataca tcctgataat 79140
tactttatct cagatattct tagattctct ctagtgaagg ccacaccttc tctgtgcctc 79200
aggctggcat ggcccaactg tgctacttac cttgggttcc tgctgctcag cttaaaggga 79260
atctctttca tatgcctaga gccttgttta ctcagttcag gtctgtacca gttgacacca 79320
agtcaaaaag cactttagac agaagcctgc tttgaaagtg ctagctagca gcaaataagt 79380
ctggcttaat tctcccttga gtctggagat ctgattggaa gggtaaaagg gagaaaggga 79440
tgatttattt gttgactgga ttgactactt tatattagta attatgaggc aattctaccc 79500
acattatctc atttaactcc ccataaaaac cctacaaggg aggtaatata ctttggaaaa 79560
ctgagactca gagaaattaa gtaaattgca aagtccccat gctataagca ttatagtctc 79620
ataagcaaat gtcatgagct tcttctagct ttttcttcat gctcacaaaa tggttgaagg 79680
agatccaagc atcatgtttc tagttaaaaa gaaggtgcag agtaaaaggc aaaaggcaaa 79740
cggacaagcc aaccaagttt gttctctttc ctagatgttc tacttggtga cttcagctta 79800
tatctcatta atgtgcatca taggattatc tctgcaaggg aacctggaaa atatagaaat 79860
ttgtttgtgt taagctgggc accttgccac ctccataaaa atgtgctcta taggtacaga 79920
gcaggagata atcattatta ataggcaact tatagtctct gtttcaagag gtcattctgg 79980
tacctgagaa aattgacaat ctctggtcta aactcttaca ggcctctctt gccttcattt 80040
aagatgaact tgatagaata aagattattg ttgttctcta atctcctggg tatgagacag 80100
agaggtaaca gatggaatga tttctttctg gcttccatag caaaccaaag catgtgccag 80160
tgaagagtgg caactgctac aaatacttag ccaaacgtgg ggaagagtgt tgatgctgta 80220
agtctcctag ctatgtcgag gcagcaggtg tctctgtaga tcagggcagc aatccctttg 80280
gtaagggcat gaagagggca cttgggacta ctggattgca tcatcttggc agagaaaaat 80340
gtagcatata ctggaactct agctgggtag ggaattgaca agttgaacca caagttgact 80400
actgttcagt cagcactagc ttttatcttc cagtcaccat tccctgtggc tcttcattga 80460
tcgtccacaa gctccaggcc tgggtggtgc ctgttgtgat ataagaaggg aagagtgatg 80520
gtttccaaaa tgtgaacact catgtgtaca gttttcatgt tgataatgaa atgctagaag 80580
gggaacagct agctgatgcc tatgtctttg tccatacctg gctacccatg acaaagttgt 80640
tgttgttgtg gttgttgttt cactccaggc acaggcacag agccgcaaga gtagaaaaca 80700
agaattccat cctgcaaaag aaaactgaat ccccccttgct tggtcactta gggaatcaag 80760
ttcaggaggg ctggacatgt tttctgttgc tctgtaatag gggctgaaac ttagttcaat 80820
tatggtgctt agctgaagca ccatgactga atcttttttt gagaaggaga aaggagaaga 80880
ttttaaaatg aaatgccata agtgtaacat agtacatata gaggtcacaa acttggaaag 80940
cctgtggtgt cttggaaggt cacataaatg tgtgaaacac gccagttgca cacaggcaag 81000
catatgtccc ttctagagaa attattgcca ctgaggaatg ctggttctaa tctccaccct 81060
cccttcccct cccctccact cctgtaaaaa ccagaggttt ggaattttgc gtgaataact 81120
cagtttgtta gtgttgacaa ccaggcatga cagtagctca tttggaccct ttgtccaaat 81180
caggaaacag cagcccttcc ttcatggcag ccctgtagct acgccagtcg agtgtgggct 81240
ggatttcagc ccttactctc ctccttagct gagactttgt gccagacaca agctgcccag 81300
ctgtagacag tgggcccaga agttatcagt gttacatgag caaaacaaaa catatctacg 81360
ggccatactc agcccatgga ttattatttt gcagcttctg tagctgcggt taaaacaaag 81420
ctctggggcc agatcacctg ggtttaaatc tgggttctgc ccttcaggca aatgactcag 81480
tatttcttgg cctcagcctc ctctatctgt aaaatgaaga taaatacttg tacttactta 81540
acagggttgt tacgaggata aaatcaatac tgtggggcaa acacttagct ctacagaggg 81600
tgacacatag cacttaatgt tatataatac caaaatcatg tgaaaatctg atttttttcac 81660 acttagagaa tatacagcat ataaaatgat gggagagtgc atgtcagacc ttcatgatta 81720
ttttctgctt cttggggaaa tgcttatgcc tctttggtca ctgtgaagac agagaactca 81780
aaatagtaag catcacttac tagctggcct actaaggcca caagaacaaa tgaagtaaac 81840
actctgcttg aaccactgat tttgtttgcc tgcatgaaac acttgcacag gttgacagct 81900
gacatccgta acaatgacat cctaaaacca ttaagaaatg attaaattaa gttcagtatt 81960
atctgttgca aaagacaaag atgtgtgagg tacgttttag aataacttac aatgaaaaca 82020
actaaaaagt gaggaagttt aaagtggtga gtattcaatt gcttgagttc atcttctaca 82080
ctggctcatt atctggaagc tgggccacag agttaatact ccatctttaa agactgtcac 82140
aggtgtttgc acctaagatg catcaggttc tgcagtaaaa atttggttcc tggcactgag 82200
acaatgctag gaggagggtg ttaacttagt actgaccata atgaaatctg tggttgactg 82260
caaggacctg ggttgaaata agactaaatc cagtagtatt gctccggtag gttcaatcat 82320
attcaagtgt tcaataatga ttataaagaa gtgtcaagct gtcatgctta ctttaaaaca 82380
tatccagaaa agagaatcca aggaagtgta tttagttcta cctgcattta aattagcttt 82440 ttttttatc attacatcaa tgtcattagg ccctaaatga tattaagagt gtctatgaga 82500
ccccaaagac aaagattgtc ccctaaactt ctattcttat ttgtttaaca tggacttggc 82560
ccagctacct ccaatctaaa gcttctttct ctagagtaag gtatctcaat ctatgcactg 82620
ttgacatttt gggccagata attctttgtt cttggggcta ccctgtgcat tttaggatgt 82680
ttagcagcat ctctggtctc tacccactag atgctagtga cttccttccc ctcaactcat 82740
gacaaccaaa aatatctgta tacattgctg taatgtcacc tggggagaaa atcttcctgg 82800
tgagaaacac tactctagac taagaaaagt agccagattt ttaaacacaa aagtgttttt 82860
cctcccagag gcaaaaagtg ccctagagat ggaagaattt tgaaaataag ctcttccaca 82920
aactatactg ccaaaatggt tagagaaaga tcctataatc accatgcttg acaaatggtg 82980
tttttgctaa gcctcacagc agctttgttc atgtattgtg ttaattgcaa ttaaataaac 83040
tagtctagaa gtgcgggtca tcatccagcc cattcatatc cctcctttac agtacacatc 83100
cagacttctt tcagagtttt gcttgcccat tggtgctcac atataaaaac tccgtgggtg 83160
ggagttaggg attcatagag cagagaggga cctcagctct tcatgtccac ttttcttgtt 83220
ttaaaggaca aggcactgag gtccagaaag tggaatttgc agcacaaatt gctatgataa 83280
acctcagtga ttcagcccct gggatcttca atgatatagg cacagaacat ataactatta 83340
ctgagtaaaa tgtttaaaat tatgttctta tggcaatgtt caaggtttta ggcataagta 83400
agacaaagca gagaaaaaat aaaaaatatt tttcaaattg aaggcttaaa aaattaagga 83460
taccctctat gtgccttctg ctttaggatc cagaatctta tgtttgtttg ctctttataa 83520
cacatgactg tgtaatatca gtcaattgtg actggtaaat ttccattaat ttgcctaatc 83580
atatttagaa attatgccta ctaaataaat tatggttgga acttgaaagg aataatggct 83640
taaataagtg atttgttctt tagtcagaaa aatattctca cgctctctct cataccctca 83700
tgaagcactg tcatctccat ctagtttata attaaggcaa tgggaccaaa gtcatcctgt 83760
tggcacagga tggccatctc tgcatccaaa tttcttttac taattggaga aaaccactaa 83820
ttgtacattt taaactcaaa atgtctttat gtatatatat atttaaaata tattttatta 83880
tttttattaa tttattaatt ataattatat ttattaaaat aataattatt tttattaatt 83940
tatacatatg tataatttat gttttctcca tgtggctagc tgttgatcta aaggagaagg 84000
agcaaggcag gaaaattatc aggttcagtg tttaactggg agatgaggac atcactaaaa 84060
gaaaggtaca gcaggttcta ctggtatgta caagttttga ttacaaggtg tactcttgcc 84120
acctggtgtg gtgtctcagc taactttagt ttctgattac cggggtctct gagacaactc 84180
tccagggtca ggtatagagc tccttttgcc cttggcatgt tccaaatcgc ttccttatgc 84240
tcaaccttct gagcaataca aggaaaaatt ccttgtattg gcatgttatg aaggttattg 84300
aaatacttta ggaaatgcct ttgaccttgt tttgtactta gaggatgatc tcattcagaa 84360
atgggtagtg tcaaaatatg gaatgtgcta gtaaaataag cacacaattc acttaaagaa 84420
acaaaaacaa gacaagacaa aacaaaacaa aacttgtttg ggatgggtga aaggcatggg 84480
gctgcaattc atcctggatt ttaaggttag aagtggttga aagaaatgtg atatttttac 84540
ctaaaccgtg gtcaactata cttttacttt ttagcaatga tgtgaatgaa gaatggcttt 84600
gaagactgtt ggtggatttg acaaatattt atcaagagcc tgctatgagt gtcaccatta 84660
taggtggtag agattccaca atgaacaaaa cagagtcctt tcttacattt tgtgaaggga 84720
gaccacctct aaacaaatat atatcatgtc aggtagagat aagtgccatg gggaaaaaca 84780
aaatagggta aggggctagg tggggcagga tcagaccaag gaatttatat tttatataag 84840
attgtcaggg aatgcctctc taattagatg actttttttt taatagaact gaaggacata 84900
aaaggacgag gcttatggat atctggggga agatgtcaga ggctgttata aaagttgcaa 84960
caggaaactg attaggactc ttagcagact tatatgtgct tagaatgaaa gggattggga 85020
taaaagaaaa gaggggagct ttgggaaagc attaaactgt ggccatagca ctgattggat 85080
aaaccataac attggattat gggtctgcaa atttcttaca ttttttttaa agtgtcagac 85140
ccatagccct agtaataagc aacatggtct tttctttgag catagctgta atgaacatgt 85200

-continued

```
tattcttttg gagttatcct gcaaagctta tcaaactcaa gaagcaatag tttatatgca  85260
ttgcccaggt tgaatattat taatttgggt tgggaagtga tatgaccaca ttctgactga  85320
ctataggccc tagttcagtt tacctgattt tatgcccaat ttttaatgag aagggagctt  85380
gctaggccag gcaggaagaa agaaatgggg acagtgtcaa gcaggaaatg cagaagagtt  85440
gagtgtaggt aaatcccatc tttcctggct ttacgttgcc ttcacatccc tcataatgat  85500
cttctacctc agtcttcagt ataagcagta tgttgttcta aaggtatgaa gtcttggcca  85560
ggcaccgtgg ctcacgcctg taatcccagc actttgggag gccgaggtgg gtagatcacg  85620
aggtcaggag attgagatca tcctggccaa catgatgaaa ccccatctct actaaaaata  85680
caaaaattag ctgggagtgg tggtgcacac ctgtagtccc agctactcgg gaggctgagg  85740
caggagaatc gcttgaaccc aggaggcgga ggttgcagtg agccgagatc gcaccactgc  85800
actccagcct gagaacggag cgagattccg tctcaaaata aaataaaata aaataaaagt  85860
aaaggtatga agtcttttcc aagctaaggc aagaatgctg aaacctcaat catagcactt  85920
ttccaaaaga gtcttacctt atattctgga tctcttcatt atctcaagag gggcttcttt  85980
ctctttaaat gtgaaaagaa gagaggcatc agctagccct attagcccag ggctaagaat  86040
tgctccagat ttttgaatgc ttaaccttaa acaaagtcac atgtaccagt ggaaagtggc  86100
tcccctgttt tcaaggacag gtcagatttt aactacgtgc ctcttaggct tgccctgtct  86160
tcggagttgt taaacatgca tgttgggagc tgttgactgt tttttttttt ttttctttct  86220
ttcttttttt gccttataat ttacttttat tttaaatcta ttatactttg aactgttgac  86280
tgttagagaa agcagtactg gcttaggatc agcagagaat atggttgaat tctatttctt  86340
aaactgagga gaatttctgt ttgagcccag tccaagtcat tacttgagca attttttgcg  86400
cattttgctg cttaagtgtt tatttttttt ttgcttttac aagtaatttt ttttaaaaaa  86460
gttatcatac actcagcaaa catttttttga gcacgtacac aatgcccagc cctgtgccat  86520
gcatgttcaa aaaaaaaaat aggtaacatt atatctgtgc ttgtgaaatt aatacatttg  86580
ttagaaagat aagacttcaa tcagtaaagc aatccaagaa ggaacaagta caaatccagg  86640
aaggagacat tagctcagtg gaaagagtcc actgaggtag gtagacttgg gtttgagtca  86700
gaagcaagag attgcttttg tgagatttcg cttatcctgt gtgggcctca gcttcctgtt  86760
atgtaaaatg ggataatagt acctattaca ttgtcacatt ggattgctgt gatgacttga  86820
taatatttat atacaaagca accagtataa tgcgtgctca tagtaagcac ttattatatt  86880
attattattt attggacata taattagaag gtctgggtta taatcttgat tctacaatta  86940
tttagttttg gtaagtcact taactttatc ataccattca tgcatattac ctataaagtg  87000
aaaggaacag aggttctaca atttatctcc caaattccat ggtattttga accaaaatgt  87060
attgaataag tatttgatgt ttgcttcccc ttcttgttag tgatatttac aatagcaata  87120
aaacatcaat atttatttag gacttgctct ggagccacga gccgtggtgt gttcttgaca  87180
ttatgttatt tactccatgc tgcatactca gtgagacaga taaccttgtc ttgtttccta  87240
gatcctaggc catattttat ccagtttaat atttctgaaa tcagaatgta ttatgtagta  87300
ttatgtagtt aataaatata tttaatgtgg aattttttttc ccaaaagccc tttctaagtg  87360
agatggaccc tcttatgatt taatgaggat gtcttccaag ggaaataaat atttttttcta  87420
tatttctgat ggtaaagttg aagcatagag aggataattt acatgaccaa gattaatgaa  87480
ctaacaaaag caaattcagg acttgaactt aggtttgttt tatttaacaa tgctcaccct  87540
accgtacttc ttgggagcaa aaaatttaaa aagtttctaa catatattca ttagttcttt  87600
```

ccatttttta tagcaaaata tatttgatct gtctctagaa tcaatgatag attcactatt 87660
tgttaacttt taacaggaat atattttagt ccctctagcc tgactttata ggctatgtac 87720
ccagtacatg aaaatatata gtagcctcag tttaatgttg atgtttattt gatgtcgaca 87780
tcactagtga cactggtcaa gcgtatcctt ttagataaga gcctattaga attatatatt 87840
ccctgtagaa atcttacctt gaccatagta catttaacag cagattttc tcagactttc 87900
aaaatcctga aagtctgggt cattacaaga aaacaaggat gtggtcataa acagttgatt 87960
attaagcaaa ttcattgaaa attaacagca gtattctttg acctcactct ttatagccaa 88020
actgctaatc ttgggtaaat tataagatta tattactaat ccattgacat ttagcacaaa 88080
ttagctatca aatgggtcag ttgttactgt tggaaactta tgaaaataca ttaaagttct 88140
tcccatttcc tgtatgtttc tttctctgac acagaatctt agaggctttt attaggctgg 88200
gagaacttcc caaataatct aatgactagt tgaataattg tttatgatat aaaatcagct 88260
ttgttgtcag aatgattaca gtttcagggt catagttaat agaaaaaatat ttcagtgaag 88320
gttaccatta gtcgttgtaa gtatcccttg attcaagaag tgaaactttt attgaaaaaa 88380
ctatttgcag agctggagcc ctgatgggcc tttctgaagt ttttaaaatt aagaaatcct 88440
atctctactt ttaacaagac atgaatgtta gtatattcac ccagactaaa tgaatgaatg 88500
aatgatcaca ttacacatgc ttgggatttg atttccttcc tctggtgttc actggactag 88560
cagcttcagt actcaagtgc gattgtaaaa ttacacatgg tggaattcaa aatggtgtac 88620
atcagtcagg tcctggaaag acacacaatc taactcagaa gtttcaagag acttcaaggg 88680
gaaatgtaca gaagtatggg taggattaaa gtagctagca aggaatgctg agtcactcgg 88740
accctagctg ccatgagaag ctattatctc ttctggacct ggagctgcag aagaaggaaa 88800
ccgtgttact ctagtcctga gagggccgga gccatggagg aggggtcttg tgacagaagc 88860
taaagttctg gagagacata ggctaggcca gagcatagga atgtggggaa gacatccctg 88920
acctctctgt caaccttcta atctccattg ttcaaaccca gtaggaagtt atccagcatt 88980
gagcctggag agtcagcccg cagcagtcag cctcctgagt gcagagcaga ggaagacctg 89040
gaatggatat gctataggag gagggccaaa cagagagtaa ctagtccaga tgggaaatgc 89100
tattttagac ctcatacact gccaaaaaag aatggcatat tcaaggaatc caggaccttg 89160
acctcatttg atcttggatt tgcatccatt ttctgatact ttcttccaaa tactcttgta 89220
agcatctgac agcagccagg agaattgctg gtcagttcag cctgtcccag cttcattgct 89280
gaggtacata tgtggttaag gagctgagag aactggtctg atagctcacc aaagggggcc 89340
tttcccaagg aaaataaaat aaagagaaaa ttcattgaga atctgtccag aaaggacagt 89400
aagtaggcat ggaatcatag tagtaaggaa gcatggagga ggcaggtgca taaaaatgac 89460
ttgtgatatt tttgaagcta tatgataatg ttctgaccca cactcttgcc agcctctgca 89520
atcttctgga ggcttcatat gaaagcagga ttggtatgct gtttattata aatagtgaga 89580
cctgagagat gattactgtc agcataaatg gatattacac attgcaccta tctcccagca 89640
ggaagtttgt ttgtttgttt gtttgtttta gacggagtct tgctctgtcg cccaggctgg 89700
agtgcagtgg cacgatctcg gctcactgca agctgcgcct cccgagttca cgccattctc 89760
ctgcctcagc ctgccaagta gctaggacta caagcgcccg ccaccacgcc cggctaattt 89820
tttgtatttt ttagtagaga cggggtttca ctgtgttggc caggatggtc ttgatctcct 89880
gaccttgtga tccacccggc tcggcctccc aaagtgctgg gattacaggc gtgagccacc 89940

```
gcgcccaacc agaagtttgt gtttgatgtc actgttgttt caccaattta aaagaaaatg  90000
aatattttta aaggaaaaga aaaaagttat cacactatgt gatgaaattt gtatctatgg  90060
gtggttattt gctacttggt aaataattaa agcctgtact ggttaccttt cctttagcag  90120
ctgacaacaa ataaacatcc tcacctcaca ccttatacac tttactccat ggttcatttt  90180
cagtattatt ttgtacttct cttgcttcat catactattg cctggcaaaa ttccaaccca  90240
gatttaatcc tgctttccat ctataccctg cctacacctg agagttcaat gttactgtgg  90300
aaaatgcaca ctgtggtgac ttgtttcact ttaaatgcat gggccctaac ctcactgagc  90360
catttattag taatgattgg caactctcca tatttcttga atccactcac tttcctagtc  90420
tcctggacaa ctatgtgaca actcctctat cctcaagcct ccaacaatta cttctcatac  90480
cctaactctg cgcagataac ctttttttcct atttcactgc aaaaagccca gaagtaatca  90540
aaagtgaatc tacaagcttc caccaccaca tctactcctc ccagtctcag tgaccatatg  90600
gtttgccttc cttctgttaa cagagagctt ctatcaaaga tgaacctctc cacttggcac  90660
tttatttccc tcttgcatat tcaaggacat tagctcagca attttctttc tttctccttt  90720
cttgcattat ttattttctc cctccaccag aagttgtcac cccaacttct attagaatga  90780
cttaggaagt gcaggcctca aacctttttt tttttttttt acacgtctac ctctattagc  90840
actccctgct cctattttag gaatccaggc tttaacgcta acagttacaa attaagccac  90900
aagctttgta agtatttgcc tgtgctctag ctgctagtgg gtttttggaa aatcagtatc  90960
tgatgggcat ttgaatacat ttgctcttgt ggctttaaac aatgtctgta caataaaaac  91020
ttgagaattt atctcctctg aattctagac atttctattc aactacctag ctggcatttc  91080
cacttgcatg ccttaaaggc cctcaatctt atctgtactg aatcgatcac ccccctaact  91140
gcctcatccg tcagttatcc ccattgcagt tggtgacatt ccatcctttg gttgcttggg  91200
ttaaaaaatg ttggagtccc ccttgactcc tttctttctc tcatttccca aagccaattc  91260
tttggcaaat agtaaccatt tatcacattt tccactgcta ctgttctggt ccaagccacc  91320
atcctcattc acttggatta ttgcaaagac ctttacctgt tctatatgct tttatatttg  91380
ctcatttttc tcccttcacc cctattttgc tttcagcaca gtatatcatc tcatgcatct  91440
actcaaagcc ttctaatgcc ttcccatttc atgatggcct ataaagccct ttgtgatctg  91500
gttccctgaa atccttgact tcatttgggc agatgtttct gctataacgc tatttatgtg  91560
ttctgtaaaa ctttttggtc tgcaagatgt actttgaaaa ataacaggtc ttatggtaaa  91620
attacgattg gaatagaaca ctcatatctt atacaacata aaaaactgta gcaataacca  91680
aagcaataat agataccttg ggagataaca ggaaggcagg cagctcagat tgactgaagg  91740
cgactcaagg aatattaaaa atgcacaaaa acagtagcat ggagatgccg gctggggagc  91800
tgagatgaga cagatgaatg gagctctgag ccagagggcc taccacaaaa gtggtcatag  91860
gaagaagttc agcctgcctt gagcagatag ctttgcctgg tgggagaggg cgtatttctt  91920
gggagacacc tctgggtgca ggcgctcatc tttaattccc ttaagagagc tgaaatcact  91980
gcagtctgtg cagcagccaa cttcagggat ttttcctttc ctgctaaggt tataattctg  92040
ttcttgctat tcttactcct cttgcctaag aaaaatcttg tttccatgta ataccaatat  92100
tatcccacta tttaccagta gcatatgagc tgcttgctgt tacagaaaca catgctgtaa  92160
tagaacagac tgcactcctt gggtcatctt tgttatttcc catgtgtcag gtgagcaccc  92220
accttgtgac ttttgctact ggtctttccc tgcctggaat gctttccctc cagaagtcct  92280
cacggatttc ttcttctatt tcagttcttt atttaaaaat atttttcata gtttgaacct  92340
```

ctctaaccag ctgatttaaa agaacaacac caccccaaca acgttctcta ctttacatca 92400
tagtttaatt ttctccatag tatttatcat catctgatat attataatac tcatgtattg 92460
gctgaaccac atccataagt attaagatcc gtgagggcaa gacttgtggg tttttaaact 92520
tgttttcctc ctttgttttt ctctattata tctttagtgt ctggaataag gttcagcaca 92580
tacaaggcat ttactaaatg ttgaatgaat gaatgaatga agctcaagct ccatctacaa 92640
acagtcctct gttttttgtt ttttgtttgt ttgtttgttt tttgtttttg ttagctgtta 92700
tctggctgtt ttttattaga taataatttg tcttccttta cttactgatt ttgtttatgt 92760
gtttgcaggt gtgtgtgtgt gtgtttgtgt gaaagaggag aatgactttt atcaaacctg 92820
gttttatgtc ttccttagga tgcatcagag tttcatgctg ttcacactac ccttcggggt 92880
attcagacat ttaaagtctt aatatttcag caataaagtc ttaatatttc tggcctggaa 92940
aaatactgtg atatgggttg aattcatctt tttgcacccc tctatcatca taaccactcc 93000
ctgctcccat tctaggaatc caagctctta tgctaacaat taaaaattaa gtccacagac 93060
tgcagataga ccctacgctt gagctgccgg tgggttgctg aaaaattaat atttgatgga 93120
aatttgaatt aattgcctct ttacccccta ccaatccctg tgtatggtca aaaaatagga 93180
cattccaata ctccacagtg atggccacag tgctggtttg tgctgatgtt ataaaggagc 93240
aggaagatgg taatgaactc cctctggtgc tggacaaggc ttcacaaggg tgctgatgaa 93300
aacaatgtga gaaaatggac tcaggggttc tcaaggcaga gaatggtggg gggatccagg 93360
aatccacata ttcaaagaca caaagaagta cagatttctg aggtgttcag ggaatggtga 93420
ttcattaggt atggggctgg gggtggggca cagggtaggc agaggagaga gcagtaggtg 93480
tatatgccat gaagattttg gaatcgatcc aactatacag ctatcaaagg tttttggtga 93540
tacaaccaga ttcgtcttct cactccttac ctttctcacc tgatccctcc ctggcttttc 93600
caaactgtca actataaggc tgtgtgacca gagagcatgc ccctgtcccc agtactcaga 93660
taagtgcctg acatatatat atatacatag acaacctact tgtttatgtg tctgaacaaa 93720
ctatcaatat tcatttctgc attttctttt cagcaatgct tacactgtct tcaaatcctt 93780
tagggcccta cacttgacta tcaggctgcc tattgaaaac taactttaca ggttgttcat 93840
tggttaccat gatggcacaa gtaaccattc agtaactttt tttttttttt taactagaat 93900
tgaaagcttt gatccattct ctttttctgg tctcatttcc cttctaccag atctgattca 93960
tggtgcaact tttggtggca tcacccctta atccagcaac atttttgtat accctgaggt 94020
tattactttg atgtcctgaa cttatggctc tgggggatat ttttttaaag gggtcagaga 94080
aataaggttg aattagagag attcttagaa gtttatgatt aaaacactat cccctctgat 94140
ctgagtccca gctctgccat tgacaggttg tgtatcatta gcaatagcaa gctacttcac 94200
atttctgaat ctcagttgat tgagcaaaat ttagataatc aaagactact ggagatgtga 94260
tgctttgaca caaagaaatc tacctctttg gtgaaatttc aattgtgtag gagcagttat 94320
ttgggagaaa agtgccctct caccttctta aatcatctcc tagggctata ataggaaata 94380
cgcagctttt gctgagaacc caaatgacat tgtggattat ccagctctag tcttctctct 94440
cccatataga ggccggttat ctttgtcact tcacagctca ttagcagccc cactcagggc 94500
catggagagg aaatagatga gatgaagctt aaatatgtca cattggttat ttcttagcag 94560
ctctgataaa aggcttagca ggggccaggc gcggtactgt acgtctgtaa tcccagcact 94620
ttgggaggcc gaggtgggcc gatcacctga ggagttccag cccagcctga ccaacatgga 94680

-continued gaaaccttgt cgctactgaa aatacaaaat tagccaggcg tggtggtgca tgcctgtaat 94740
cccagctact cgggatgctg aggcaggaga atcgcttgaa ctcgggaggc ggaggttgtg 94800
gtgagccaag atcgcgccat tgcactccag tctgggcaac aaaagcaaaa ctccgtctca 94860
aaaaaaaaaa gcttcagcag ggtgaggtta aaactcaaat aaagaggtct gaggattatc 94920
tgtgatgtta gctcatgtgt gttaccttcc tgtcttccct tctttgttct tatttctagg 94980
gattagttga ctgcaaacat taatgggtta aatataaaaa tgactgcaaa cattaatggg 95040
ttaaatataa aaaatctttt ctatcctgaa ggtctttgaa aaaatgattt tattacttac 95100
tggaaaagaa aaataaaaca aagcttgctt cacccagaat ttattttttc ttctagttaa 95160
aatgagcaac ttctttaacc agaactgacc ttgaagacaa atggctaaaa taaaacattt 95220
gctgaattca ctgggcgcat cttacaagta atttttggat tctgcattga ctacctacaa 95280
gtgccttctg ggtgcaagtc cacaggcaag atttgttctg caaatcttcc atgaccaagg 95340
tcacctcttt ggattggcag acccagggag tccatattgg gaagataaat tcacacttca 95400
ccccttgttg agatctccag ccttgctcct ctgataacca ggtctctctt ctgtcctatt 95460
ataatttatg acctttgaaa agttacttat atctggggct attcaaactc ccagctatct 95520
atgaccatat gcataaatgg ttctagattt aaaaaaaaaa agaagctatt cagagatatt 95580
gggataccct ataaccaata taaatgggta attcagcaga accagatgct ggggttgaga 95640
aatagatgtg gacaattggg gcagggccta agaaagatcg gaggcaaaga cagtgactag 95700
atggggagct ctgataaggt aatgcccagg cctgtgcttg gaattctgcc acagtgggga 95760
cattagtggg ggtctgtagt cattgcaggg tgagaggagg atagaaagaa aagattgtgt 95820
gaaggtcagt ggaaggtccc ccatttcatt gctaagagaa ctatgtatgc acgttttcct 95880
gtgtttagtc tcacacataa ttgtaccttt aagaactgat cacacactgc atttccctgg 95940
cagtttttgg catctcagat gaggaagagt gatgggcgac aggtgatggt gacaactatt 96000
aataagatct gaaagtaaac agtctcatga aaggtggcca ggagagggca gtcacctttt 96060
atcaggagca cagactgaat ttgcaaaggg tacttaagct acaagactat aaagcatgat 96120
gcaggcttaa ccaaaatgca gtgtcttgag catagtagac tcttagtgta tgtttgctaa 96180
atataccttta gctgctgctg ttccccagag ctcatcagag ttccatagaa acctggtccc 96240
ttccagaaaa ccaaagaatg actaaagaaa agtgattgca aatccagaaa gcagctttgc 96300
cttactggtt ggtaacagca ggattttctt ttccttgtag tttattttgg cttaggctag 96360
tgtctctttc atgaagacag ctactattta caattgttgt taacatgttt ttcctttttc 96420
atctcccaat atactctctt cctgtcgtta aacacagtca atttaccaat ggaatctgct 96480
ttataagctc ctgcattttc tttttccaca gatgggatta atgccattat gttctatgtc 96540
atccacatag tcttggcttc taggcaccaa ggtgttgttc tagaggaaag aagagtaatg 96600
gtcgacacag gcaggctgag ggctaaccta atgatttcat gcatttagtg gtaattctta 96660
attaagatcc caattttatt ctgttggatt tagtctataa cccgctgaaa atcattcttg 96720
aattaacact gggtggatat aaaagcagaa agccaaggac tttgcactgt tctcagctgt 96780
agctgtttat ttagctggag aaaatttagt gggtggtcca accttcataa ccaggaagaa 96840
taaaatagag gtgtaaaggc cttggtggaa ggagggcagt agcaaccttt ccatttcttc 96900
agttttatcg cagcctatga aattagttcc ttaggtatgt tgatcttgta ggagctagta 96960
ttttaacatt tgctccatca agttgtttgg tttaaatcta agaataagcc cactgaaaac 97020
tattcctaat ttgtgaaacg aataacaata atagatgtta atagaaacaa agacttcatt 97080
tggttagttt ttagaggggg cacagagaat gtagtaacat aataagttag atttttgttg 97140
ttttcttttt cttagttctt tgtagtcttt ataatctcta attggcattt gctcctgact 97200
tttctcagtg tacttccaca tggaagagac aaaagtctca aagctggtgt agaaaaaccc 97260
ttaataaatt gcccattaat tagccacctt gatttccacc tttaaagcag ttaattgaag 97320
taagaatttg ttagattttt ctcaagcata gcagaaatta agattaattt cttaggtgtc 97380
attgctactt gcctacttaa accaccagtt catctttatc ataaatactt aagccaaaag 97440
tcacattaga ggcaatatgg cacagtgatt gtggaccccg gagtcaggtg agctggttga 97500
aatcctggct tggctacttc ccagctatgt gatcctgggc ttcagggttc cctttttgcaa 97560 catgacatga ttgctgagct gcttcttagg gttgtgtgtg gctccggtaa gataatacag 97620
gaaaagagct gaaagcagta tctgaccctg gagagaaagt agggaagaga caatagagga 97680
aagaggacaa ggaagtggga gatgaagaga aagttcaaga aggaaagtgg aagaatctca 97740
aatagaaagt taattttcag tttttcctga gaagagatat atagacatct tcatgtggct 97800
ttggagagcc ttggagccca tcagcaagac ggttggaaat tatactgaaa cagaagtgta 97860
gacctatgtg acttatgtcc tggccagttg cctcatgtcc tctgtggtca ggttgatctc 97920
tactggcact gtcaaaagat tttttatgga cagctggttg gggtaaactt tgaaacctga 97980
ttgtttgcac ttgagtgcca gagtgtgtaa ttatttaccg gtgttcacta aggatgtcag 98040
tgtagatttt tagggggaga aaaaacttaa atttaaaatt tggaggcatc tttttcagtc 98100
tgcctgccct ggtgtttgtt ataacactta gtttggcatg taacagctga agctactggt 98160
taaatcatta agcatttatt attttaaaac tcctcttctc aaagcaaaaa ataactatca 98220
tgttgaagtt ctttcctcta agaatgacat ttactgtgag ttttatacca atggactaat 98280
tggagggttg agaaaataaa ttttggaaag acaacaataa cttcagaatt ttccttggat 98340
ggaggtttcc tttttaaaac ctgaactgag ctttatcaaa acagtaactg aactttgaaa 98400
cgaaacaaga gtgctgaatt gaaagctcca ggaaggcagg gatgtgtctg tgttgtttat 98460
gactataacc tctgggccta aatcagtacc tatcccatgg taggcactcg gtaaatactg 98520
aaggaatgag tacagtatga aaattagcat ggctgatcct tggaaaaaat ataagtcaaa 98580
agggaatagc atgcatgtgt aactaaaaca tcagtccaca tgcttgaaat gtcatcactt 98640
ttttatggtc aggacctgtt tttttctgct ccaattaaag aagaaaattg taatgtgaaa 98700
gaagcaagaa gtgaagtatt tggtattcat gtgttttgac atctgcagta agtttaaaat 98760
aaatttctaa atcttattgt attgaaattg tatgagtttc ttaagtggta ttattcattc 98820
agacttaaag tgaagttagg ttgctgtcac tcatagtgga cttttttttt tttggcatta 98880
ttaaaacaac atgtcttctg ggtgttgtct tgtattacaa aagcttgcgt gttttctctt 98940
gatgctgtgc cctgtctgtt gccattgagg ggtctaagga ccaaatgagg tcttgtttcc 99000
ttcctgatat tcttttgacc agtttagaat atgccaggtc cattcacaca actaagcggc 99060
tcagttctct cagttccctg gtcttctcat attagattgt tatctatgag cttgaagttt 99120
agacatgaaa aagaatggtt gtaatcctct tccttctctc accctcttcc cttttttttct 99180 taagttagcc ttttgaattc atgattctaa taattaatat atattattat ataatatagt 99240
atatattcat aataatgatt aatgatagta ttaataattc tgtgtgtgtg tgggcagcta 99300
ctcatacaga ggaaaacaga ttgattagtg gaaattacat taatttcata acttcttatt 99360
aaaagagttt gtgtgtgtgt tgttggttgt ttgttccctt tgcaactcaa catggtcttc 99420

-continued

```
ttgaggtgta gggaaaacat atgcttagga aacagagcct tcttttctcc ttttggtatg  99480
gaagacatat gcaaaaagaa tgaaggaact aattgtctct agccagggct ctgcaaaaat  99540
agtactggta gagaaaaagc tctaaaagaa gtaaaagttt atagtgcttt ctcctggcag  99600
agttaacctc atcttcatca gcttttcccc tgcctcagag aggcagtttt ggaatgacca  99660
aagcagagtg cccaacctct ctgttcagag ttagcgagca tttggatcac tctctctctc  99720
tgcctcagta tgagtggaat attgcatgac catttctgat ttctgccatg agcgcactcg  99780
gcctagatga ataaatcctc cttgaagaag gcggggcatt ttggcattca caagaaacca  99840
tgttgatatc tgatcctccc actggagaaa tgtggcaaag tgagaaagac tcactctttg  99900
ggactccaaa aatgtaaaca caagtaagca tgcaagctga agaagtcact tgaaatagaa  99960
aaaaaaagtg ttaaactctc tgttagtcat gtgacttttt cttggtattc gagagccagg 100020
aggctcttgt ggtctaatct ggaaagagtc gctaatcgct gtgtcacctt ggcaaattgg 100080
ttgatctccc tgtgctggag tgtttagtcc agctgctgga tgggatgaaa gcaagacctc 100140
actgaaacca gatgctgtct ctctgaaaag atttcagcaa taaataatat cgtatatact 100200
ttgttcctgg cagcaaatac tgaactgcta taaccctctg ttttcacttg cttctaaatt 100260
tctggaaata tctcctttgg gcttgaattt ttccatgctt gtcttcagcc caaaactttt 100320
tggaaagttt gaccaaaatt tcacttagct gtttttcctg aattatggga gaataagggc 100380
aatgcattgt ttttcagctc ataaattctc atttttccca ttattcctca gaaaaatagc 100440
tgctacattt aaagtgttta gaactagtaa aagaatcttg gtatggtaaa gaatactggc 100500
agaagacaaa tttaagtctc tcagtatttc cttctaactt taaacatgac tgcacacaat 100560
cagggcacac ataaaaagct ctgatgtagt tttatagatg gccaaagaga agattctgca 100620
aattctctca gtaactcatc ccaagttacc aagaggcaac tttagctacc atcagttgtt 100680
acctttctca accacttgct ctgtctgtgg atctgatttc taaaaaaatg tcatggttat 100740
atgttggcat tgacccctta tctacatttt aaataaagtt gaccatttct tttaggtagc 100800
cttcatgtgt gatgacctca gtcatatctg ctgacctact agactcaaaa ttcctttaca 100860
gcagggccta ggtctgtcta cctcaccatt gacactgtag tgctcagcag ggtatgacac 100920
atgtagtaaa aactgattgt tgaatgaatt aaatgaacat aagtacagtt gtttttgctg 100980
caatttgttc attgatttgt ccactaagac atgcatgcat gtattcagtg agtatcactg 101040
agtctctact ttatgccagg tattggtatg aatgttgtga atatttcttt gctttgatgg 101100
ataacacaga agttttgctg atacacaaca aaataattat attatttgag tacaattact 101160
atgcctatag ttggaatatt agtccaatat agctaaaggc aatcccaggg aatttatcac 101220
ttactgagcg tccatgatgt gcctggccct gtgttaggta ctgagaagag atcaattaga 101280
cagtttctgc aggaagtcac acataggtta acagtgccaa gacaaatcct aaagtaccta 101340
ttatacaagg ggaactataa taaagagcca ggtgagttga aggcaggaga ggtatcattg 101400
taccacaaga taccttgtga tcttgtgtaa atcccctgaa caatcaggaa aagctttatg 101460
gcatagcttt atggtcagag atctcatggg gacaggcagt tagttgcaat gccttttata 101520
gccacatcct tcactcctta accctgcact gtctgccatt cattctctct gtgctttcag 101580
ccttgagaag ctggccaaat ttctcaggac tggaaaataa actggaatga cactcaggca 101640
cttgatatca agattattag ggtcatgatt gtgtttaaga ccctaagacc tcttgatgct 101700
tttacaagaa tgggtacttt ttttgtccct gttttcttct tttgccccaa gtttcaagag 101760
catgttacag cagcagtata agcatacaca atcaaaggtg attgaagtga ggacaactgg 101820
```

ctcaatgagc tccagccact tcaactctcc tcctagtccc tgtccccttg cccggaatgc 101880
ttcaccctca gactttgaca tagcaggctt ctttttgtca ttcagatctc agctcaactg 101940
caaggatttc tctgacctga agttacatat gtgtcacccc ttctggtctc cgttgctctc 102000
tatcacatca cctattggac tacctttata gcatttatct ccacctgatt gtgtcctttt 102060
cactgttttt ctttaaactt tttattgtca attttctttc actagatgcc agttccatga 102120
agtaggaaac ctttaccact ggtcttgagt gctcttgaaa gtgtacgtgt gcaataggca 102180
ctcaaaaatg tttatggaat gatcagctgg atgcgtatat ggcaagtggc gagaagccaa 102240
gggaatagga caagagtcct attgtgctcc ttgcctgaag aaaacctctt gcaagaatca 102300
taggctgttc ttgagggtgc ctttgccttg gattcgccaa aaattcttct gtttcttttg 102360
tgtgaaaatt ttcccctcat acacagcaat gggcactaag aatgcatata tccagacttt 102420
tcaggttaca ggatggcatc tcagatatag tcttcctttg atctatatac tatgaagcca 102480
taattgctta gccagtatct ttttcaggat ttactccata tttcttattc taggcctttc 102540
aggtggcagc tgcactggct ttcagatata atttagaatt tagtttcgga tttgtaaagc 102600
tactcatgct gcagatcttc tctgaaacat ttctgtcaca ttttagaaag ctttacattt 102660
tcatctgcta acgattttca tctgccaaag agcccatcta cttaaaaagc agatcactga 102720
agccacactt ggcacatatt actttggctt attttctttt gatttttttg ctttgctggg 102780
attacttatt tatgaagaaa gagagaatat tgacttctta ttttagaaga gaggatatta 102840
cttgggttga gagttctagt tatataaaat gtatttatct aagttgttaa ctatatcaaa 102900
aatggagcag tcaatctttg gaaatagttc agggtgaaat gtttttagca tgttcacata 102960
ttctctttgc tgtttttaaa taatttggca aagcttattt gcatttccca aattaacaat 103020
tttggccaag aggaaaagct aaagtgttgg tttttctcag ctcaactttt tgggtgtaat 103080
taatttataa gcaagatttt atgaagggag aacagatagg acctttctac aaagtccctg 103140
agccaaaata aacaccccat tgttccatcg ttttgtattg cacataggaa aacatccatc 103200
cctatcatta ttctgttaaa gggacacaga ttaccagatt tgtaatttta aaaaaggcca 103260
tttgttgatt gagccacttt gcgtataaag ggtggtatat gttgcctgcc gaatttctgt 103320
acaagaaaaa aatcatatat caaaaaaatt tttctcattc atcatataag aaatttatgc 103380
attttagtat gtaccagaag aaatggcttt ggcattttct gtttttagca gtctgttgaa 103440
atttcttcat taaagacatt ttctgtttga aggttaaaat gaccatataa atacagatta 103500
attcagtttt aataggtgca tcttcctgtc atttaccact ttctctcctc aatatcagct 103560
acagtgatca acatatattt agcagtgaaa ctgatatatt ctgtttatct tcaaatcata 103620
agctttttgt ttaaatacaa aggaaaatct tatacctctg attttaatat gacaaatcaa 103680
aaagtccaca ccaaactccc aactcatccc aaaaaagaga ttgctatcta ctcatcactg 103740
ttctctgctt ctaagatttg tttcccttgg ggttactgtt tgagcaactt ttcttacttc 103800
caagattgtt tttgtggttt taagaaagaa tctgaattcc aagattattt ttctggtttt 103860
aagaaagagt ctgaaaatct agagattact taccttgtgg tgaggtggtt gtctatgctt 103920
ctgttcaaca aaggcctcat gtactgaatg gaaaaaaagc atcaggacct ataattttct 103980
aggcattatg caagataata gaggagacaa aaatgatgtc ttgcttcaaa gtcttagatc 104040
tatttccctt tgggggttga ggaatgagaa agagattttt agatgaaaaa caggaagccc 104100
aatgaggacg tgtggcaata gttcctaaaa tgagcaaaga gataaattta ctcttttata 104160
tgattacaac caaatcacac actggtgagt ttcaaaacag tagttttcat ttagaaagca 104220
aattaagtgg aataattcaa ctgagtttca ctgcaatggg attcattcta gatggttcaa 104280
ctctggaatt agaaacaata tctaaggatg ttgctgatag tagtcagcag ataaatacca 104340
gtaagtcgta tacaggtata catcatttta ttgtgatttg ctttattgtg ttttgtagat 104400
aattgtgttt ttacaaattg aaggtttgtt gcaaccctgt aacgagcaag tcttctggct 104460
ccatttttcc aatgacttgt gctcattttg agtctctgtg ttacatattg gtaatccttg 104520
caatgtttca aactttttta ttattattat atctgttttg gtgatctgtg atgagtgacg 104580
tttgatgcta ttattatgtt gttttggcac accatgaatt gcacccatat aaggtgggga 104640
acttaatcac taaatgttgt gtgtgttctg actgcttcac tgaatggctc ttcccctatc 104700
tctctccctc tcctctggct tccctattcc ctgaaacaca acaatattga aattaggagc 104760
gttaataatg ctacaatgac ctctacgtgt ctgatatggt ttggttgtgt ccccaaccaa 104820
atctcaactt gaattgtatt tcccagaatt tccatgtgtt atgggaggca cccagggggt 104880
ggtaattgaa tcatgggagc cagtctttcc catgctattc tcatgattgt gagtaagtct 104940
cactagatct gatgggttta tcaggggttt ccacttttgc ttcttcctca tttttctctt 105000
gccaccacca tgtaaaaagg gccttttgcc cccagccatg attctgaggc ctcccaaggc 105060
atgtggaact gtaagtccca ttaaagctat ttttgttccc agtttctggt acgtctttat 105120
ctgcagcatg aaaacaaact aatacagtaa attggtacca gtagagtggg gtattgctga 105180
aaagataccc aaaaatgtgg aagtgacttt ggaactgggt aactggcaga gtttggaaga 105240
gtttggaggg ctcagaagaa gacaggaaaa tgtgggaaag tttggaactt cctagggact 105300
tattgaataa ctttgaccca acagcctgat aacgatatgg acaataaagt ccaggctgag 105360
gtggtttcag atggagatga ggaacttgtt gggaactgga gaaaatatga ctcttgttat 105420
gttttagcaa aaagactggc agcattttgc cctagagatt catggaactt tgaaagtgag 105480
agatgattta gggtaactgg cagaagaaat ttctaaacaa caaagcattc aagaggtgaa 105540
tgcttgggtg ccattaaaag catttcattg tgaaagggaa acagagcata aaagttcaga 105600
aaatttgcag catgacaatg cagtagaaaa ggaaaaccca ttttttgagg agaaattcaa 105660
gccggctgca gaaatttgca tgagtagcaa ggagcctaat gttaatcccc tagaccatgg 105720
ggaaaatgtc tccaggccat gtcggagacc ttcatggcag acctcccatc acagacccag 105780
aggcccagga ggaaaaattg tttttctggg ccaggcccag ggtccctgtg ctgtatgcag 105840
cctaaggact tggtgctcta tgtcccacct gctccagctg tggctgaaaa gggccaacac 105900
agagctcagg ctgtggcttc agagggtgga agccccaagc cttggcagct tccatatggt 105960
attgagcctg tgggtgcaca aaagtcaaga actgaggttt gggaacctcc gcctagattt 106020
cggaagatgt acggaaatgc ctggatgccc aggcaaaagt ttgctgcaga gttggggccc 106080
tcatggagaa cctgtgctag ggcagtgcag aaaggaaatg tggggtcaga gcccccacac 106140
agagtccctg ctggggcact gcctagtgaa gctgtgagaa gagggccact gtcctccaga 106200
ccccagaatg gtagatccac caacagcttg cactgtgctg ctggaaaagc cgcagtcact 106260
caatgccagc ccatgaaagc agacaggagg gagactgtac tctgcaaagc ctcagagtag 106320
agccgcccaa gaccatggga acccacctct tccatcagcg tgacctggat gtgagacatg 106380
gagtcaaagg agatcatttt tgagctttaa agtttgactg ccctgcggca tttcagactt 106440
gcatggaccc tgtaatccta atcctattgt tttgtccaat ttcttccatt tggaacagct 106500
gtatttaccc aatacctgtt gtatctagga agtaactagc ttgcttctga ttttacaggc 106560
ttataggcag aaaagatttg ccttgtctaa ggtaagactt tggactgtgg acttttgggt 106620
taatgctgaa atgaattaag actttggggg actgctgaga aggcattatt ggttttaaaa 106680
tgtgaagaca tgagatttgg aggggccagg gccagaatga tatggtttgg ctgtgtcccc 106740
acccaaatct caccttgaat tgtatctccc agaattccca caggttgtgg gagggaccca 106800
gggggaggta attgaatcat gggggccagt ctttcctgtg ctgttctcat gatagtgcat 106860
aagtctcctg agatctgagg ggtttatcag aggtttctgc tttcgcttct tcctcatttt 106920
tctcttgccg ccaccatgta agaagagtct tttgcctcct gccatgattt ggagggctcc 106980
catacatgtg gaactgtaag tccaattaaa cctctttttg tttccagttt cagatatgtc 107040
tttatcagca gcatgaaaac aaactaatac agtgtccaag ggaaaggaaa agtcacatgt 107100
ctctcacttt aaattaatta agcttagtga ggaaggcatg ttgaaagcca atataggcta 107160
aaagctaggc ctcttgcacc aaagagttat ccaagttgtg aatgcaaagg aaaagttatt 107220
gaaggaaatt aaaagtctac tccagtgaat acataagtta ttaaaaaaaa aaaagtgaca 107280
cagccttagt gctgatatgg agaaagtttg agtggtctgg atagaaaatc aaaccagcca 107340
caacattttc ttaagccaaa gcctaatcca gagcaaggcc ctgactctct tcagttttat 107400
gtaagctgag agagaaagct acagaagaaa tgttggaagc tagcagaggt tggaaattta 107460
agaagccatc tgtgtaataa cataaaagta caagatgaac cagcaggtgc taatttagaa 107520
ggtgcagaaa gttatccaga agatatagct aagatcagtg atgaagatta ctaaacaaca 107580
gattttcagt atagataaaa tagccttcta ttggaagaat acgtcaatag aagatctaag 107640
actttcatag ttagaaagaa aaagtcaatg ctgggcttta agacttcaaa acttcaaagg 107700
gaaggctgat ccttttttta tgagttgatg aagttggtga ctttaagttg aagccattct 107760
ccccagcctt gctagagaaa ccaaaagtca aattcaggaa atacagagaa cccctgcaag 107820
attctacaca agaagatcat accccagaca cataatcatc agattttcca aggtcaaaat 107880
aaaagaaaga atgttaaaat cagctagaga gcaagggcag gtcacctaca aaaggaaccc 107940
catcgggcca acaacagacc tctcagctaa aaccctataa gccagaagag attgggggcc 108000
tatattcaac attcttaaag aaacaaatct tcaaccaaga atttcatatc cagctgaact 108060
aagtttccta tgtgaaggag aaagaagatt cagagaagca aatgttgtgg gagtttgtta 108120
gtaccagacc tcccttataa gagatcttga aaggagcact aaatatagaa aggaaagaca 108180
gctaccatct aatactaaaa cacacttaaa tacacagacc agtgacacta taaagcaacc 108240
acaaaagcaa gccagcataa ccagctaaca acacaatgac actatcaagt tcacacatat 108300
caatactaac cctgaatgta aatgggctaa atgcctcact taaaaggcac agagtggcaa 108360
gctggataaa aaagaaagac ccaatggtat cctgtcttca atagacccat ctcacatagc 108420
ctcaaaataa aggggtggag gaaaatctac caggcaaatg gaaaacagga aaaagcaggg 108480
gttgcaatcc taatttcaga caaacagact ttaaaccaac aaagatcaaa aaagacaaag 108540
aagggcatta cataatggta aacggttcaa ttcaacaaga agacctaact accctaaatg 108600
tatatgtacc caacacaaga gcactgtatt cataaggcaa ggtcttagat acctacaaag 108660
agacatagac tccctcacaa tattagtggg agacttcaac actccactga cagtattaga 108720
tcatcaaggc agaaaattaa caaagacatt taggacctga actcaacatt ggactaaatg 108780
gatctgatag acctttacag aactctccac ctaaaaataa caaaatatac attcttctca 108840
tcaccacgtg gcacatactc taagattgat cacataattg gaaacaaaac aatcctcagc 108900

-continued aaatgcaaaa gagctgaaat catacaattt caaaaatcag agggccctta agaattatgc 108960
taaatctact ctgtctatac tctataaatg gaacacaata catgtgtaat agtacacctg 109020
tttacagtat ggcttgctga atattttaag gccacagttg agacctcctg cacagaaaaa 109080
aaagattttt ttctaaatat tagtcctcat tgagaaagca cccagtgacc aaagggctct 109140
gatggagatg tacaaggagg ttaatgtagt tttcgtgcct gttaacacaa tgtccattct 109200
gcagcctatg tatcaaggag taattttggc ctttaagtct tattatttaa gaaatacatc 109260
ttgtaaggct atagttgcca tagatagtca ttcttctgat ggatctaaga aaaatacatt 109320
aaaaacctta tggaaaggat ttaccatcct agataccatt aaaaacattt atgattcata 109380
ggaggaggtc aaaatatcaa ccttaacagc agtttagaag aagttgattc caattctcat 109440
agattacttt gaattgattc aagacttcag tggagaaagc cgctgcaagt gtagtggaaa 109500
tagcaagaaa acttgaatta gaagtggagc ctgaagatgt gactgaattg ctacagtctc 109560
atgataaaac ttgaacagat gaggaatcac ttcttatgga tgaacaaaaa aatagtttct 109620
tgagatggaa tctactcctg gtgaagatgc catgaacact gttgaaatgg caaaagattt 109680
agaatatgac ataaacttag ttgataaagc agcagccaga tttgagaaga ttgactccaa 109740
ttttaaaaga agttctgtgg gtaaaatgct gtcaaggagt atcacatgct acacagaaat 109800
cttttatgaa aggaagaatc aatcagtgtg tcaaacttta ctgttgcctt attttaagaa 109860
attatcacag ccaccccaga cttcagcaac caccaccatg atcactcaga aggtgtcaac 109920
attgagacaa gactctccac cggcaaaaag attatgactc actaaaggct cagatgatga 109980
ttagcatttt tagcaataaa gtatttttaa attaaagtat atacattgtg ctctttttag 110040
acataatgct cttgcacact tactagacta caacagatta tacacgtaac tttttttttt 110100 tttttgaga cagagtcttg ctctgtagcc cagtctggtg tgcagtggtg caatcttggc 110160
tcactgcaag ctctgcctcc cgggttcacg ccattctcct gcctcagcct cccgagtagc 110220
tggaactaca ggtgcccacc acaatgccca gctaattttt tgtattttca gtagaaacgg 110280
ggtttcacca tattagccag gatggtcttc atctcctgac cacgtgatcc accctcctca 110340
gcatcccaaa gtgctggtat tacaggtgtg agccaccgcg cctggccaga cataactttt 110400
atatacagta ggaaaccaaa aaattgtgtg gcttgcttta ttgagatatt tgcttcattg 110460
cagtggtccg gaactgaact gcagtatctt caaggtatgt ctgtattcaa gtttatattt 110520
tgacatacat tcttctttac ttgttaaaat catggtcacc tcattattat atgactgatc 110580
agaatttgca gggttgcttt gaccatatac cattgttcta caactacgca gatgtctgag 110640
tcctaaaggt gaatctgtct ggccagttct gggtttaacg gcctatataa aaagtagatg 110700
ttacacacct tgtataactg aagcgcccta tcacggacac agcttaactc ttgggtgggt 110760
cacttagtct gcttggttga ggtttcagtg cttttcacat ctacagaaat gtcctatttg 110820
tctaaggcaa ttttatgaag taaatttact cttgtcatcc tttccaacct gaaaatagag 110880
gatatataat ttttagcatt ccattattac ctaggggatg gtcttcagtc attcttccct 110940
gaatttatta cactggccct atcttcttca cctgaaataa gttaaatgta gaattagcac 111000
taaagagaaa tagaatgaac ttcttccgga atgggaatag gaaatgaaag agagtaaatc 111060
agaagtgaat cacttctttt tttttttttt tttttttttt gctttgcaaa tctatatttt 111120
tttccagctt tatttaggta tgatcagcaa ataaaagttg tatatattca aggtgtatga 111180
catgatgatt tgatatatgt gtacatttta taatgatcac catgatcaaa ttaattaaca 111240
catccttcac cacacagtta ccatttgtgt gtgtgtgtgc aagaggaggt aagggagttt 111300
aatcattttt gaacactagc tacaacataa ttcaattaaa attctgagaa agaagaaaaa 111360
ttgtcatgca gctgtttaat tttagaagca ttaactgaca aaatccaagt cttatgatga 111420
atactcagtc aaattttcat gaatgaatgg gagcctttac ctctgaaatt gttgtcatgg 111480
aagaaaacac taacactgtc ttacacagta attcaagtta ccaattgagt taaagtagca 111540
agatgagcca tggttgtaat tgagaatggc aactatggtg ttcttatcta atctgctacc 111600
tagtttgcct ttttgctcta aaatggtgac tatgttagaa ttcaaagaat aaaaggcctt 111660
tatcctttca ggggaaatac aagtaacaag cttaattttt tttttcttaa cactgatgaa 111720
actcatttgg ggctgtggaa attgctgcta gcattgaacc tcttattaac attcaaggtg 111780
tgccagtttt gcacaagctg tgtcatattc agagatagat tgttggcaca aactaaggca 111840
cttattctct tgttttttca cttctttcaa taagaacaga taaatatact atttctagat 111900
aagcagttga aactgttctg ctcatctctt tggaataggt ttgtgggggt atcactgtat 111960
gacatgccga agaaatatac aagggaaatg ctcccgcata cattgagata taaatgaatg 112020
cctattttag aatacgtcat ttcttaaaag taaaataagt tttggctggg cgcagtggct 112080
cacgcctgta atcccagcac tttggaggcc aaggtgggtg gatcacctga ggtcaagagt 112140
tcaagactag cctcgccaaa acagtgaaac cccatctcta ctaaaaatac aaaaattagc 112200
cagacatggt ggtgtgcgcc tgtaatccca gctactcaga ggatgaggca ggagaattgc 112260
ttgaacccag gtgatggagg ttgcagtgag ctgagatagc accattgcac tccagcctgg 112320
gcaacagagt gagagtccat ctccaaaaaa aaaaccaaaa agtaaaataa gtttttaaag 112380
tcactgattc tgtttctaag gaattctcag ctggggcttc tgagtcaatt ctcgatggtt 112440
agaacttatg agtagcagaa aaagaaaact actatggatt ttctctacaa tgatttgaga 112500
cagtgaatgg ggctttctgg caggttagca gttaggaact cagatgacca tagacttttt 112560
ttttttaga gtgggtctcg gtctcactct atcacccaag ctggagtgcc gtggtgtaat 112620
catagctccc tgaagcctcg acctgggctc aagcaatcca cagatttttg aagttcaccc 112680
tggattgttg tgttctacac agaggttcca ccttttgctg ccttttatgg ttactatatt 112740
attattttga tgtttcttaa ccagctgaat cacattgtag tatatgaaat atgttttggc 112800
tcttgtttta atggttattt gctagcagat ttcacaatgg cccaatgaaa caacccattc 112860
attgctattt gttgcaattc atggtgacta aacatgactc catggtacgg ctcaccaaag 112920
tcttggttta tgtgtgactt ccaggggaga gagattgaga accatctgtt aatcattttg 112980
tccctaaact agagttttc aatggagtac ttgggcagtt gaattagtat gtttctcgta 113040
ggctagtgag aaaaatagct tttttttttt ttggcattaa tcagactgct gacccacatc 113100
tctgggaata cttgtgacaa gatccagcct gacaatatca catatgattt gcttttcttc 113160
ttggaaggga cacattgtgg cttttctctg gaatctgtga agaaaatgct cctgagccta 113220
gaaactggaa ctgagaaagc tcttcctgat catataacaa taagtcttgt gagggtcaac 113280
ccttgagcca tgagggcagc ttgaaggaac atggggttga gagtcaagtc atcagaactt 113340
ctgtttattt ttctgtgtaa tatttaggga cttgttatgt ttaactctag gcaaaggtat 113400
agatttggag gtctttgata tagatgatag atagatagat agatagatag atgaaatata 113460
ttttagcata caaaggaggc tacaatacac actcatgtac ctgtcactcc aatgaattca 113520
tcaaatgtaa acattttccc caaatctgct tcttagctgt tattcgtaaa gaaacaaatt 113580
gtacagaaaa atttgaaggc ccccgtttta ccttccccag tctcattatt ttctctgcca 113640

-continued ccccagagaa aacaactgtc ttgcataggt atttatataa ttctgtttta tactttgcca 113700
cttttactac atatatgaag catgcttgtt acatacatga acataaaata tacatgtttt 113760
actgtaagtg tggaatgtat tctagaattt gctactttta ctacaaatat tttattttca 113820
gaatttaccc ttgttattat ataaccctag ttcatttttt aattgccata tattactcca 113880
tcttatgaaa ataccacaat ttatttattc ccatactaat cagaatttga attgatacaa 113940
tttttaatta aaattaataa tgctgaaaga aatgttcttt ttatacattt ccctcagggt 114000
gcatgtgata gagttcttct cacatatata tcagtgtact tgctgtgtct taggatatgt 114060
acaattgcat gtctattaga tatgccaaat tgctctgcaa agtactcata ccagtttcca 114120
ctcctaccag caatgaatga gaactttgtt tcgcaggtca ttgccaacac ttgattatta 114180
tcagatttaa ttatttgcca gttgatggat gtgaattgct ctatcactgt tttaatattc 114240
attactttga ttatttataa cattaggtat acttttcata gggccattta aatttcctct 114300
catctgaatt gcctatttct cctcttcgtt gattcttcta ttatcttttc ttctctttat 114360
taatttatag aaatgtatgt gtgatcctaa tatgtgtcat aatatctatg ttcatatttc 114420
atatataaat ataatgaaat acttgtctct gttatatata ggttgaaaag tttgctccct 114480
atctgctgat tgcattttaa ttttgttcat ggcatctttt aacacacgtg atttttaatt 114540
ttgatatagt taatattttt tattactcta gattttgaga attgctcaag aaatgacttt 114600
attttgcata gtcatatgct ctaatttttt taatctactt acaatagttt tatgttaaat 114660
atgtcaacct ttgtttcacc cggaattttt tatatgtatg gtataaagca taaatcaatt 114720
ttttttacta ttgagaatgc ttttattata ttatatctta ttctattcta ttttttattt 114780
tccataagtt attggggtac aggtggtatt tggttacttt agtggtgatt tgtgagattc 114840
tagtgcaccc atcacccaag cagtatacac tgcaccatat ttgttttctt ttatccctca 114900
tccccctccc acccttcccc caaagtcccc aaattccatt gtatcattct tatgcctttg 114960
catcctcata gcttagcccc cacatatcag tgagaacata tcatgtttgg ttttccattc 115020
ctgagttact tcacttagaa taatagtctc cagtctcatc caagtcactg ccattaattc 115080
attcctttct atggttgagt agtattccat catatatata tagtatatgt atgtatatat 115140
atgtacgtat gtatatatgt atatatgtaa gtatatatgt acgtatgtat atatgtatgt 115200
atatatatgt acatatgtat atatgtatgt atatatatgt acatatgtat atatgtatgt 115260
atatatgtac atgtgtatat atgtatatat gtatatatgt acatgtgtat atgtgtatat 115320
atgtatatat gtacatgtgt atatgtgtat atatgtatat atgtacatgt gtatatgtgt 115380
atatatgtat gtatatatgt acatgtgtat atgtgtatat atgtatgtat atatgtacat 115440
gtgtatatgt gtatatatgt atgtatatat gtacatgtgt atatgtgtat atatgtatgt 115500
atatatgtac atgtgtatat gtgtatatat gtatgtatat atgtacatat gtatatgtgt 115560
atatatgtat gtatatatgt acatatgtat atgtgtatat atgtatgtat atatactata 115620
gtttctttat ccactcgttg attgatgagc atttgggttg gttccatgat ttttcaattg 115680
caaattgtgc tgctataaat gtgtgcaagt atcttttttct tataatgact tctttcctct 115740
gggtagatac ccagtagtga gattgctgaa tcaaatcgta gttctacttt tagttcttta 115800
aggaatctcc acgctctttt ccatagtggc tgtactagtt tacattccca ccagcagtgt 115860
agaagtgttc cctgatcacc gcattcatgc caacatctac tgttttatta ttattttttt 115920
tattatggcc atccttgcag gagcaacatg gtatcacatt gtggttttga ttgcatttcc 115980
cttatcatta gtgatattga gcattttttc acatatttct tggccatttg tatatcttct 116040
tttgagaatt gccttagccc actttttgat gagattgctt gttttttat tttcttattg 116100 atttgtttga gtttgttata gattccagat attagtcctt tttcagacgt atagattgtg 116160 aagattttc tcctactctg tgggttgccc atttactctg ctgactgttc cttttgctgt 116220
ccaaaagctc tttagtttaa gtcccaacta tttatctttt gtttttattt catttgcttt 116280
tgcgttcttg gtcatgaaat ccttgcctaa gccaatgtct agaagagttt ttccaatgtt 116340
atcttctagt atttttatag tttcacgttt tagatttaag tccttaatcc atcctgagta 116400 gatttttgt atgaggtaag agatgaggat ccagttttat tctcgtatat gtgactagcc 116460
aattatccaa gcaccatttg ttgaaaaggt gtcctttccc cactttatgt ttttgtttgc 116520
tttgtctaaa atcagttagc tgtaatattt ggatttattt ctgggttcaa tattctgttc 116580
cattggtcta tgtgcctatt ttcataccaa taccatgctg ttttggtgac tatggcctta 116640
gagtatagtt tgaaatcagg cagtgtgatt cctccagatt tgttcttttt ccttatttct 116700
tgctttggat atgcaggctc tttttggtt ccataagaat tttagaattg ttttttctaa 116760
ttctgtgaag aatgatggtg gtattttgaa ggagaaggtt ttgaatttgt aggttgcttt 116820
tggcagtgtg atcgttttca caatattgat tctacctatc catgagcatg ggatgtgttt 116880
ccatttgttt ggtcatctac gatttctttc agcagtgttt tgtagttttc cttgtcaagg 116940
tctttcaact cttttgttaa gtatattcct aagtatttta tttttattt ttttggcagc 117000 aattgtaaaa ggggttgagt tcttgatttg attctctgct tggtcgctgc tggtgtatag 117060
aagagctact gatttgtgta cattaatctt gtatctggac atgttgctga attcttttat 117120
cagttctggg aactttctgg aggattcttc agggttttca agttaaatga tcatatcatc 117180
agcagacagt gacagtttga cttccttttt accaatttgg atgctcttta tttctttctc 117240
tcatctgatt gctctggcta ggactcccag tactatgttg aagaggagtg gcgagagtgg 117300
gcatccttgt cctgtcccag tttccagagg gaatgctttc aactttccc cattcagtat 117360 tatgttggtt gtgggtttgt cataaatggc ttttattaca ttgaggtatg ccccttgtat 117420
gccaattttg ctgagagttt taatctgaaa gggatgctgg attttgtcaa atgcttttc 117480 tgcatctttt gagatgatca tgtgattttt gtttttaatt ctgtttatgt ggtgtatcac 117540
atttattgac ttgcatatgt taaaccatct ctgtgcccct ggtatgaaac ccacttggtc 117600
atggtggatt atctttttga tatgttgtca gattcagtta gctagtattt tgttaaagag 117660
tttagcatct atgtttatca aggatatcgg tctgtagttt tctttttgg ttatgtcctt 117720 tcctggtttt ggtattaggg tgatgctggc ttcatagaat ggattaggga gggttccctc 117780
tttctctatc ttgtggaata gcatcaaaag gattggtatc aattcttctt tgaatgtctg 117840
gtcaaattct gctgtgaatc catctggtcc tgggcttttt gtcggtaagc ctttaattac 117900
catttccatc tcactgcttg ctattggtct gttcaggtta tctaattttt cctgatttaa 117960
gctaggagag ttgtattttt ctaggaattt atccatctct tctaggtttt ctagtttacg 118020
tgcacaaagg tgttcatagt actcttgaat gatcttttat atttcagtgg tgtcagttgt 118080
agtatccccc attttgtttc ttaatgaggt tatttggatt ttctctcttc tattcttggt 118140
taatcttact aatggtctat tgattttatt tatcttttaa aataaccagc tttttgtttt 118200
atttatcatt tgtatttttt cttttaattt tatttagttc ttctctgttc ttggttatgt 118260
cctctcttct cctcggtttg ggtttggttt gtccttgttt ctctagttcc ttgaggtttg 118320
accttagaaa gtcactttgt gttctttcag tctttttgac ataggtgtta gggctatgaa 118380

-continued ctttcctctt agcactgcct ttgctgtatc ccaaaggttt tgataggttg tgtctttact 118440
gttgttcagt tcaaagaatt ttttaacttc catcttgact tcatttttga cccaatactc 118500
attcaggagt aacttattta gtttctatgt atttgcatgg ttttgacggt tccttctgga 118560
gttgatttcc aggtttattc aatgtggtct gagagagtac ttgatataat ttcaattttc 118620
ttaaatttat tgaggcttat tttatggcct atcatatggt ctattcttgg agaaagttcc 118680
atgcactgtt gaatagaatg tgtattctgc agttgttgga tgaaatgttc tgtatatatt 118740
tgttaagtcc atttgctcca agtacagttt aaatccattg tttctttgtt gtctttttgt 118800
ctggatgacc tgtctagtgc tgtcagtgga atattgaagt ccccactatt attgtgttgc 118860
tgtttctctc atttcttagg tctattagta attgttttat aaatttggaa cctccagtgt 118920
taggcgcata tatgtttagg attgtgatat tttcctgttg cacaaggctt tttaccatta 118980
tatagtgtcc ctgtttgtct cttttaactg ctgttgcttc aaagtttgtt ttgtctgata 119040
caagaattgc taccccctgct ggcttttggt gtccatttgc atgaaatgcc tttttccacc 119100
cctttacttt aagtttatgt gagttcttat gtgttaggtg agtctcctga aggcagcaga 119160
tacttggttg gtgagttctt atctattctg ctgttctgta tcttttaagt ggagcattta 119220
gggcatttac attcaatgtc agtatgagat gtgtggtact gttgcattca tcatgctgtt 119280
tgctgcctgt gtaccttggt tttttgtttt tggtgtttgg tttttaactt gtatttttgt 119340
ttataagtcc tatgtgattt aggctttaaa gaggttctgt tttaatgttt ccaggatttg 119400
tttcaagatt tagagctcct tttagcagct cttgtagtgc tggcttggca ggggccaatt 119460
ctctcagcat ttgttcgtct gaaaatgact gtatctttcc ttcatatatg atgcttagct 119520
tgctggatag aaaatttttgg actaataatt gttttgtttg aggaggctga agataggggc 119580
ccaatcttat ctagcttgca gggtttctga tgagaaatct gctgctaatc tgatagattt 119640
tcctttatag gttacccagt gcttttgcct cacagctctt agaattcttt cttttgtctt 119700
aactttagat aacctggtaa caatgtgcct aggtgatgat ttctttgcga tgaatttccc 119760
aggtgttctt tgtgcttctt atatttagat atctaggtct ctagcaaggc tggggaagtt 119820
ttcctcaatt attccctcaa atatgttttc ccaaactttt agatttctct tcttcctcag 119880
gaacaccaat tattcttagg tttggtcgtt taacataatc ccagacttct tggaaccttt 119940
gttcatattt tcttattttt ttctttgtct ttgttgaatt gggttaattc aaagaccttg 120000
tcttcaagtt ctgcatttct ttcttctact tgttcaattt tattgctgag actttccaga 120060
gcgttttgca tttctataag cttgtccaat gtttcctgaa gttttgattt tttttcttta 120120
tgctacctat ttccttaaat ttttctcctt tccctgcttg tatcatttcg ttgtatcaga 120180
tttccttgcg ttgggcttca cctttctcta gtgcctccct gattagctta ataactaacc 120240
tcctgaattc tttctcaggt aaatcagaga tttttttctt ggtttggatc cattgctagt 120300
ggactagtat tacttttggg gggtgttaaa gagccttgct ttgtcatatt accagagttt 120360
gttttctggt tccttctcat ttggaagctc tgtcagaggg aaggtccagt gctgaaggct 120420
gttgttcaga ttcttttgtc ccttaatgta gtactctccc tattttccta tggatgtggt 120480
ttcctgtgag ctgagctgaa gtgattgtta tctctcttct gggtctagcc acacaaccag 120540
tctacctggc tctgagctgg tactgagggt tgtctccaca gagtcctgtg atgtgaacca 120600
tctatgggtc tctcagccat ggataccagc acagtatttg gggtgtctcc tgcatcctgc 120660
aggagcagtc cacttccttc tgtgggtcct ctcgggattc ctgtttcatt cttgaagtct 120720
agatctattt tttgacagtc taatcctaac accatttact gaggaacact cttttttca 120780

-continued ttgttctgta atgcctcctc tgttgtaaat taagatccca taaatgcctt ggtatttgct 120840
agactttctt tttcttctgt tgttttaaaa ttttctctcc caacaagata aaatattgtg 120900
taaatattat atgtttatac taagcatttt tatcttgtac tgaataatag tgagaatgct 120960
tcaaaatttc actgtttttg ctattaagta tgatattaag tacgctatta agtactgtat 121020
aggtttttgg ctgacttatt tttgtcaggt taagaaaact gctctctatt tctagtttat 121080
taagacagtt tatcacaagt attagcctat aaataatggt ttttctgcac attcgaataa 121140
tcatttgatt cccactttta aattattaat gctgtagatt atattgatag atctgcctga 121200
tattaaacta tccttgcatt cttgatctaa atcttacttg aatgggatgt gttactgtat 121260
tctctctctc tctctctctc tctctctctc tctctctgta tctctcttcc tctcttcatc 121320
tctcttctgc aacatcttaa agcatatttt ggtaaatttg ctttttatag ttattgattt 121380
tcagaaatat ttctttgaga agctaaaaat gcaaaggttt tatttcacct tgtttcaaat 121440
atagtaatta tctaggaata agaattgtcc attttctacc tattgagaat caaaacattc 121500
acagaacata aacctacttg tttcaaatat ggtagttatc taggaataag gattgtccat 121560
tttctacata ttgagaaaaa aacattcaaa gaacataagc ctaaaacctc tctttctttt 121620
gtttctaacc tacgggaagc ctgtcacttt tctaaaagtt atgatcaggc tgagcttcac 121680
tccccccttcc tgggctctct ggtagaatat gccctcccaa gtcctcccta gtgtgagtcc 121740
gcccctgtcc ccacccatcc cctctatcca ccaccgcccc cgctctcagg ctgccctgca 121800
gttgtttctt aatgcagcag aaggctgcaa caaccacaaa ctacattgcc catgatcaac 121860
ccatgcccat gtccttctgc accccccagt cagactaccc actcccacaa caaccaatat 121920
cagtgttccc atatttcatg cattatctat ccttctctca aataaagcag atctagcaca 121980
ttttaattat cctttgtgac agtctctagt attttccttg tttttttttt tttgtctaga 122040
atttactttc atcttctgat tcacaggaaa tttgttccat attgtttttt tacaagcaat 122100
atctagttga attacccacc atgttttact tttttcctca ccattagttc attcacctaa 122160
taaattctta ttgcatgcct tgtgttttcc tgctattgta catgcctgga aatataggag 122220
tcaaccaaat cgtctctgag ctcatgtagt tgacaatcta gttagagaac agagatgata 122280
aacaagtaaa tatatatcaa aaataattgc catggagaaa aattaagtag tataaggatt 122340
attatttatc taggttgtca ggcaagagct tacagatggg tgacatttga atgcatactt 122400
gaaagaagtc tgggagaaaa gtatcccagg tagagggaat agcatatact atttgggatc 122460
ttcaaggaac atcaaagagg ccagtttgtt ggagcaggat gagcaagaag aacgtagtgg 122520
taaatggagg cagagatagt gggtgagagt ggggttggga aaaaatcaga taggactttc 122580
agaccactgt aaatacttgg tcatttactc taagtgagat aggataccat gacagtgtcc 122640
tggaaaaaaa aaagggacat gttcttattt tagtgagacc aatttgggtg ttgggaataa 122700
ggagattcaa aagcaaaagc aggtaggcca ttaagaaact gttataataa tccagataaa 122760
tgttggtgcc ttggttaagg gagataaaga tggagatggt aagaagtgat cgcattctgg 122820
atgtaatttg aaggcatgtc tgagaggatt agttgatgga gtgttactta tggggtatca 122880
gtgaaagaat agaggaaagg cctgagaatc tggaaagatg aaggtgatat ttactgaaat 122940
ggcctacact cttgaatgaa tagattagga agtaaaattg aaagtctggt tatgggtttt 123000
ataagtttga gacgcctata aaacattcaa agaaattatt aaatagtgaa ctggatatat 123060
gagcctgtag ttcaagaaag aggtctggat taaagttatg atttggacaa catcatcata 123120

-continued tatgtggcat tagtgtcatg attccaaatg agataatcca gggaataact atagagaaaa 123180
gaggagagga ggataatttc tggtgatatt tcaatgctaa gtggttggga aaatgaagag 123240
aacacagtga agttgaccag gatgaagtac ttactgaggt ggaagaatca atggagaagg 123300
gtgttcaaga tacaaaatta agacagtgtg tcagagaagt ggggagtgat ccattgtggc 123360
aagtgttatt cattggttaa ataagatgat taagaatttg ccacaatgtg gaagtcattg 123420
gtgactagag caaaagctat tccattgatg tagtggagat taaagcctga tttcaataag 123480
tttaagaaat tgggcaagga ggaattaaag aaaggagaat aagacaattt cttcaagaag 123540
ttttgattta gaggggagca gagaaatggg tcagtaactt catgagcagt aactgaaata 123600
ggagaaatta tcctttttct aaaaggagat aattttagtg cacacttaag gtgattctta 123660
tcttcctgca aaaatagctc ctttaggtat ttttcaaaat tttatacatg tatatttcta 123720
ttccaatcat ttttggggta caagtgattt ttggttacaa ggttgaattg tatggtggta 123780
gtgaagtctg agattttagt tcatccatca cccaagtaat gtacattgca cccaatatac 123840
accttttttt atccctcagc cacccctacc ccctcctcag tctccagtgt ccattatatc 123900
actctgtatg cctttgcata cccatagctt acctccccact tacaagcaag aacttcatgg 123960
tatttggttt tccattcctg agttacttct tttagaatag tggcctccag ctccatccaa 124020
gttgctgcaa aagacattat ttccttcttt tttatggctg agtagtattc catggtgtgt 124080
atatatcaca ttttatttat ccactcattg tttgatgggc atttaagttg tttctacatc 124140
tttgcaattg tgagctgtgc tgtgataaac atacatgagc aggtatcttt ttgatataat 124200
gacttatttt cctttaggtc gattcccagt agtgagattg ctggattgaa tggtagatct 124260
acttttagtt ctttgaggaa tttccatatt gttttccatg gaggttgtac taattgacat 124320
cactaccagc agtgtataag taatcctttt tcactacctc tacaccagca tttattgttt 124380
gtttttggga tttttttgtt tttgtctttt tataatggcc attctggcta ggaaaaggtg 124440
gcatatcatt atggttttaa tttgcatttc cctcctttag gtattattta atgagagtct 124500
tttggtggta aagtatctta gttttcatgt gtgctcacac acacatacac agagtcttta 124560
gtgacaggct agttgggtat caaattctga attgatgttt ttttctctaa tacttttaaa 124620
gtttatttgt gttctggcat ctgttgttac taaataaaaa tcttccacca gtccatttga 124680
gttcattagc aggtaatctg cctcttattt taagcacttt taaagatttt tctgtatctt 124740
gatgccatat gatagatcta ccttttatta tactttactc agtaattact gtgggctttt 124800
aatctgcaaa ctcaatcaat tattcgattt tataaaatta tcagtaataa cctttttctat 124860
aactgattat ttgcagttga attaaatcct ctctttctgg aattccaatc atatgtgtgt 124920
tggagcttct caatctgccc tccaaggctc gtaactgctc ttttaaattt ttcagtacta 124980
ctctcaattt ttttttaaa aaaacaacct aatattgcag tgtttggcac agaagaagtt 125040
caaagtacaa ctttgcactg ccacgttgac cagctattct ggcactggtt attctttaaa 125100
gttattttta aggttaacgt accttatcag gcagcaggtc tcaaaaccta gggaagctta 125160
aaagcctaaa ggcagcctgg caaaaatcaa gctgattaaa atgctctttc ccattttctt 125220
gtcctcctat gccctcatcc ctaaagaata gtgagagggc cttccttaaa aagatatgta 125280
taaaatagca gaaagaaaaa ggggatccag caagcgtgag aagacatact tagataattc 125340
acagtaaatg ttccaaataa tattcagcct cactaattct caaataaatg taaaacaatg 125400
gcagatcatt tttatccatt aaattagtga aaataggagg aaaagaacat tttgctgaca 125460
attgttaaca gtgaaactga aattctcttc ttgtctagtt tgaatctaaa ttaggacagt 125520
ttgaaagcaa ttgggtgata tctatgaaaa atctcataaa cattctaccc ttccatgtag 125580
caacattgct tctgtgaatc aaccattagg caaataaatg gaaataacaa accaaatttc 125640
cccccacctc ccaagagatg tttattgtaa cattactgat aatattgaaa aactagaagc 125700
gatctatatc agtgatccac ccttgttttg actgtcactc accgtaagaa aatattaggt 125760
atacaaagta acccaacaga cacacccatg catcaaaaag ttccatataa ggaaaccgtt 125820
caatccattc catttattta aacaagccaa tgaacaaagc tggctttgat ccactaaatt 125880
gatcctacaa cctaagagta ggttatgact cagtttgaaa agcaccaatc tgaatgtcct 125940
ataaaagata tatgatggaa tatgaattaa atttgatatt cacaattttt tacttttttt 126000
tgtttgaggg tagttggagg ggtactatgt ttcttcagcc agcaaggaag ataatgtttc 126060
tagataactc catataatgg agatttactg taatgatacc agatctgttc tactatgccc 126120
agccattctt atgtatctgt ctctcaatgc atcatgggtc ctttatggat tcttttgtga 126180
tgtcctcaag cttcctgtcc actccctagc aacttgccca aactgataga accggcctga 126240
atcagtcaac atctgatttc aagcattttc tcttggtcag cctttggtat taggacttta 126300
ttctcaatct aatcaattaa tattagctga gctaggttga tttcatttga atcaacaaag 126360
aattgctaaa agctgcattt cctagaaaat gtggcaatat aattggcagg tacttgagag 126420
tctttaatgt taaatggaaa aaaaataaaa aataataaga gacaactttt tatacggagc 126480
atgttttcgg ttttctttag atattttgtt agagacaaaa aaggaatcca gaatttattt 126540
tatactacat tagtacttaa cagatttcta cataagcaag tattatgcat ttgtaatcag 126600
aaaaaaatat caaaattagc tctgtggaaa atgatcatct tgcaagcaag catcatgtac 126660
ccctactttt gatttagctc atcttcttga tgtaaatatg aagtgtctgc gcttgaaatt 126720
ctgtttgaag tggaaatctt catgtttgtc ttacaaatac catctcagag tacattgctc 126780
agtataaaac ttgttttggg gggttgggta caaaaaacctg caaagatata gtccaggctc 126840
cttttcccaa agtccttcac tttcctactc ttagtataac cattattttg taaaatttaa 126900
taaggcccct aataacttgg ggtttgggaa tttgatttga ggtaacatgc ctcagagtat 126960
cacctatttt ttattaaacc aacaaatttc tatctgacaa agatgtgcat ttatgtgggc 127020
cttaataatt cccccaaata aaactattcg taagttctaa cagttccaaa tacttttggt 127080
ttcagcacac taataggatt tatagctgtc ttagataagg agcagtatct tctaaagctc 127140
atgaaaaagc catatcagaa tgccatgtgt tcaggtatat ttccttttct ttatggtatc 127200
aagaataaaa tctcagctta tgttttcact caagtgttgt gtgattactt tttcccatta 127260
ctctttcgat tgagcctgaa aaatgaggtg aaaaaatctt tctctttcaa ggatgaacta 127320
gaaggatcta ggctggctgg tcaccaaacc actgactagt tggccctttg tctttttata 127380
acccctcatt gtctgggatc caacatcata gtgagtctca gacatgttcc acaagtctag 127440
atagccctca tccatgtgtt cagtggtcca gcccatcagc atccaagcca gcagggtgag 127500
gaggggaagt gtaggggatg ctcattgccc tgaaggatgc atatgccact tccattcagg 127560
tcctgcttgc cagaacatag tcatgtgacc acagttagct gcaaggttgg ctgagaaatg 127620
cctttcactg ggttctatta ctaactgaaa atgggaagag tgaaagttgg ggataactag 127680
taaatattag ttagtccaag tcatggattg tggtattaat tccatgtgct aggaaggtca 127740
tttaaatgtt ttatgcagaa ggatgccatg atgataatta tgtttcaaag catatttgtg 127800
tgtgagagag agagactgaa agagaaagtg agataaatgg attggagaga atttgtctga 127860

-continued gtgttaagag gccattctca aacccaagtg ggaaatggtg gctagtaaca gtagtgagga 127920
taaaggggga tggaatggac tcaaaagata cagaagagat aacatcaaaa gatgaaacag 127980
gggcagagga ggaagaaaag acatccagat aactcctagg tttctgattt atactgcaaa 128040
ttctggggat caggtgttta tggaccactg agtttagttt tagaaacgtg atttagaggt 128100
atttgtcaga taggtggttt ctacacattc aaaataagat ttcaaaacat attagccaca 128160
attcacaatc agcaaaattc tcaaatctag tcattgtcaa ctaaactatt aaaatgaatt 128220
ttcccctcta agtgtttctc atcttaaagg gtttgtatgt attacatgtc acagtatggt 128280
ttattgcata taaacatggg aaagcaagcc aggcagaagg agtcttgtaa ccagctaaag 128340
gcccagctaa ttcttgaagc agtcataaat catgaacggt cttcttgtgt taatagtgtg 128400
gacaggactg ttggtcacac acaggaaaat gagtcacaca gtcttgtgtg tacagcaact 128460
cactccacac tcaatgatgg gaatggtcat gattgttcta actgtgtgag cagctacaag 128520
aattatggca aagctccaga gctagaaagc tggttttttt tttatgtcac ccgagtatgt 128580
aattcactaa atgtttagta ttttatacct tttagttgac ttgtgagccc tttctaaagg 128640
agatctattt ccctctacta gaaggtaatc agaaaaaccc taaactacgt tttctaaatg 128700
ctgtgttctt ctgcccaatt gaccaaaata tacttagttg attaggactt tgaagggatg 128760
agatgagggg actaaattaa gatgcaggaa tttcagtttt ctaggggttt tctgtaaact 128820
actttatact gctgacaaat ggttaaatgt ttccaatgaa actaagtatg ctaggatttc 128880
taatgagcaa tgaaatttta gaattcattt actcattaat ttcttcattt acaagatgta 128940
caatgtgcta tcttctgggc atttggggta ctttaatgag gtagcagtga gtaccacaaa 129000
tggtcacttc tgcctttgtt cttatactcc ttagagaagg gaaaggacca gattcagata 129060
ccctatcact gctttctacc catccagatc agagcctttg ctgagttcta acgcttagcc 129120
ctcttctcag ctgatttggc tgcctccatt gtaataggcc tcatgagact ccagcctagg 129180
cctggccttc agttcagcag gcagagccca gagatgtact gggcaaaggt caggggattt 129240
attatatgag acaatggtct gatgtgattt aatttactcc tctggtacca gatatgtgtg 129300
tgtgtgcatg agagagagag attgagaatg actgatttgg gagggatttt gtgaaggttt 129360
atatatcaaa gcagaaagac caagaattta gagattaata catgccaagt ggtaaccaag 129420
aaacttctgt gggatcccac ctccaacccc tccctctctg tcagatttta accaaatcag 129480
tgtgatgtga tctgcttgca tatatgagtg aaagaaaaag gaaatttaaa aagttcttga 129540
tataaagcct ggaggaaaca atacgaaaat ccagcctcta tttcagcaat atctgccgga 129600
ctattggtta gtattccctt actgttactt attgtttgat taaaaggctg atagtcaggg 129660
tttttttttt cttactttg cattttttag atataaatct ttaatatatg gctgtggcca 129720
gatgttttcc tttctcctcc cacttcgttc ttccctcttc tgggttaatt tctcattgtt 129780
ctctcttccc cttacttctc tgccctttc ctttctactc taagcgaaac ttcttttttt 129840
ctgtgctgga gtttataaag tattctttta ggcaaagaaa gcctttggct gccttcctcc 129900
ttgtctggtc accatcaaga tataattttg gttttcaaag gttgttctct gaaggaagga 129960
ctagttttct gagcatttag agagcagata cattttgaga aagtcaacag agatagtaat 130020
ttgcactcag gaaatactta agggttttaa ttctgttcca tgtgttacat ttcaacagtt 130080
tacattaaga aaagtattgt aaagagaagt gataccacaa ttgcatgttt attttgcatc 130140
tttagtctga gagatggtca gtactttgaa ggaaagagaa atagggcttt gtctccttct 130200
gcttcttgct atacctcttt tcagattaac tctgatgctt tgggtttctt actgcatgcc 130260
tgattaaaac ccatcccata atgcctgatg tgatgggaac caccacttat tctatctcaa 130320
tggaaagtat tcacatgagc tttcaacaga aggacattct cccacctctt ccaaacacct 130380
ctttgaaaac cgtgtccatg ggcctttatt catgtcttca acaatttgtt taaaactggt 130440
tgtgctaggt agtgggcaat ataaagatga gccacaggag agagatgaca atatcactga 130500
ttccttatag tgctgtaata agggtttatt aaggctgtga tagaagtaga gaggagaggc 130560
acctgacttc acttgggagt ggggttgttg ctaaggtgtt tctaagttga aatgtccttg 130620
agctgaggtt taggggaatg agtagcaaag atggattaag tgagaagagt ataggaggca 130680
gcagggccag aggtgtgaat agcccagaac cttctgagaa gattcctttg tggacggaag 130740
aaaggggagg tttgtggaaa tggtggaaga taaggtagga agaggccaca tcagatcaca 130800
catggctgga tgtacctctc taaaagtact ggggggtttg aaacagaggc tataaattgg 130860
cagtttaaga aaatcactgt ggtgtcagtg tgaagaatac atttttgcaa gattctaacg 130920
aggattattt tcagaaattt aggcccaatt tagtccagat gtcagggcta gtttggagta 130980
aatttctttc tttaattact ccagggctct tgtattgctt caaagaaagt agaaagtgga 131040
actcaccctc attcagggag ggtgggcaag cgaccagcca gctggggaag gccaaagagc 131100
caggtcacct tgtgcccgca cttgttatga tttgtttgta ttgtctgcct gatgatcaat 131160
gatattagct atgacagcac gtatgagcct ggggtaagtg tgtcttcttg ctacttgaag 131220
tgcttcttga aaatagtggc aggctgaaga caacaaggaa tactgaaaaa gcccattgga 131280
ctggggacag gagacctggt gctgctccca gcttggccgg caccagctcc gggggcttag 131340
acacattact tcacctctct gggcttaact taccccattt gtaaaatgca acctttagac 131400
taacactgtt ctcggggcca tgttcagcct ctggcttctg tcattgtgat cctgcctccc 131460
caaggttccc ctgggcccca tcactactaa ccctaggctt ctagacattc tgattcatag 131520
agaaatagga aagcccattt atcttaagtt aatgtcagcc agaagtacag ttgtgtctta 131580
aggaatctaa tctagtgaac atggaaaata attttctaag gaaaaaaatt gtgattggtg 131640
ttctgtcctg aactgatggc aaaagggaag cagaaccact tcacacatct caatctctct 131700
gttttttcct ttttatcctc ttgaattttt ctgcctgttt gtctttcaaa agtagagagg 131760
agtttgaatg gggatgctga ggagactgag ggtagccacc gatgggggaa gctggactgt 131820
gggaagccga gttctgccac ctgacaaagg ggcacgtgtt tagtgtttat ttggcatagc 131880
agctgttcag gtggagccca ggcagaattt tgatgtcgtt gggaccttcc atacctttct 131940
gaaattctct tgcaccaaca cccggcaccc tcaggttatg ttctgctgcc caaagcctga 132000
ggctcaactt ctagccctct cttttctctt ttaccggaac taacttctaa aaatccagaa 132060
atgacaagta gatggtggtc tggatgttcc tgaggtggaa agagaacctc tagtgcctct 132120
ggctgacatt atatccactg acagatcccc tcccgcacgc atacatgtca catgtttctg 132180
ctcatttatc aaatacagcc catgctttgg tgattgagag cagagtgggg attataagtt 132240
gatgcagtag gcctgtgtct tgcccttaga agtttacaaa cagcaacaca ggcaccaaga 132300
gctcatctgt tacacccaca gggatttatc atcttgtgac ttggatattg tggaatgttt 132360
tatagtaaag gttaaaaaaa aacaatgtag gcacagagga gttaacagct aagttgcggt 132420
ggggagtctg gaaggcttca tggacgtggt gatatttgaa cgtgactttg aagggtaggt 132480
agagtcctga tttgtctaac agtagccttg aaagtaaagg aaacttgacc atgaagaagg 132540
ctgttgaaag tctggagaaa agagaaggta ggagactaag actctaggag aaggtactac 132600

-continued gttccaggga gaatgcagag gtagaatcct ccctcatggt gacaagttaa atgtgagaag 132660
ggatggagta accaactggg tgaaccctga tctcattaag caaaataaga aatagaagaa 132720
atgaatctgc atgctcataa tgtagggatc agaagcaggt aggaaatgct gactttattt 132780
tagacagagg ttattttagg tacctgtgga catccaggtg tattatttcc ctatgtctga 132840
agcacatgtc ctttggttct ttagcatttt gatgatgatg ctccatgtaa actgcccccct 132900
aggattttct ataagttttc ttcctcattt gagagtaaag ttttaactgg taacatgatc 132960
acaagtggtt gaaaagttaa aatgttattc atatagcttt ccaatgaggg gagcatgaat 133020
ggtttggtac tgttttacaa gatgtgaaaa ctgatttcac ttaagtagac tgtaacataa 133080
agtttatgtg tctgtccctt tggcttcctg gtaggtggac agtctctctg aatcaatagt 133140
ggctcaggct tctgatttca aacctctttg gccagccaac tggtttagga gaaacatggc 133200
caggtcattg aattataatt tcctgagtta tgttgtggtg gtcccgtagg acagtaaaca 133260
taagcctcct gggaactgaa cttttaattc aggaggactg aaaacaagct cttctgagcc 133320
aagatttgca aggacatgtt acaaagatag actggccttc ctgcttccac accatttttt 133380
cctccataaa tacatgctcc ttttccgtat ttttcttcta ccctagtctg ttgtagattt 133440
tgaccttggc tgttactttc ctaccaacac attgcctatt tttaagtttc ctggtttgac 133500
ctgatgttaa gatggaaagc aaagctagca aactgatgga gatagggcct tccagccttt 133560
ctaactttcc ctgggatcat cttatgttga tttacatgtt caaaaaattt ttaaaaataa 133620
ataaattgta tcagttgatc cagaagtgat tagactctag ggcctgattt tatcttagcc 133680
aaacttaaga gatgagccaa tacaccaaaa tgccaatata tttgtttgtt ctctatggca 133740
ctgtcaagca atttcatttc atctgattac tgtgttcatt ttcctgaaag atagtgaacc 133800
cagaaaacaa gaatcagaag gtcatttgac aactgtggag ttggaataga gggaactgaa 133860
tgaccctcta ttgggtcatg agggagagca tcatcaagct ttgagaaatt attgcacctg 133920
tctctgtgtt gggacatttt tttggtccca ggtagttgga agagacaaag ctgtaaatta 133980
tttactagtt tttcaacatt tccttatcac ttatcgttaa ctgatggaac taagttttct 134040
ctaaagtccc ttatgaataa aattgctaga cattgcaaaa atgcccctct caatattgac 134100
atgcttcagt ggtgattatc ttcctgatta atgtttacag tcaatctcaa gctctataat 134160
ggactcttaa aggctgtagt agttttctat tgcttccata acatattacc acaaacttag 134220
tggcttaaac aatacccatt tattgtccca cagttccata tgtgagaagt ctgggcacac 134280
catggcccaa ctgggctctt gcttagagtt tgcaaggcag aaatcagtgt tgttagggcc 134340
tctagggatg aattttcctc caagctcatt ccagttgttt tcatgaactg agttccttgt 134400
cattgttgga ccatgttccc catttccttg ctggctgtca gctgggagcc agtttttgct 134460
cctagaggct atctgcattg catctcatgg tttctgtgtg ccccccttcca gcaacaagat 134520
tctatgtacc cccttccagc aacaatattc tatgtaccct cttccagcaa cagaagatca 134580
agtccttttc aagtttctag tctctctgac ttccccttct gccatatctc attctgcttt 134640
tacaggctca ggtgattaca tcggtttgtg cagataatcc aagataatct ccctgtttta 134700
aagccagtgg gttagccatc ttaattacat ctgcaaaatt ccttcacagc agtacctaga 134760
ttagtgtttg aataacccag gatggtaatc ttgcgggga tcttttagca ttccatctac 134820
ccagtctcat cagcaacact ttgaaatatt gtcgttgagt gatcatttct gtggccggct 134880
gatttcatct atacaagtgt attcttttta tttgccattt tataggataa tattttctga 134940
tcttaattcc atatttcagt attaaaatta cttgacatag atccataaat catcatctgt 135000
tgcaaaaaag cacattaatt gattggttga atggggagat tgagatattt cttttctctt 135060
cttctgctca ggtgggggca acttttgggg gcagatgagt tctgttgcca caaaagttat 135120
atagcacatt tggtttgcac tgaatcagcg attctcaatc ctggccatgc tttagaatta 135180
tacaagaaaa atcttcaagt atcaatactc agtccctatc ctactgatcc aattcatcta 135240
tgataaagcc agagcattga tttttaagtt ctgcaagtga ttctaatata cagccaaggc 135300
taagaactac tgatatgttc caaacactct attttggaga taaagaagtt gaggctgagg 135360
atgagaactt agtcacataa agttccataa ctagtaacag acagaagttc tgtcctacaa 135420
aaaaaaaaaa atttgatgct ttaattgtat gtagagttca gtgctcagta attatgtaca 135480
aagtgagtgt tgagacgatc tggaacaccc tacttcttgc tttagtagga agactatttc 135540
tttctactac tttaaaaaat tatcagatct tgcaaaataa ctgtatgaag gtctcttctc 135600
agcagctttg gcctgccttg tgagtaataa taaacacaga tctattctac actaactagg 135660
gagctggccg cttggacttc tactacctct ctgtgttcca gagcttcatg gtacaatgca 135720
gtagccacta gccacatgta gctattaaac acttgaaatg gaactagttt caactgagat 135780
gtatgtgagt gtaaaaggca tactagaatc aaagatccag tatgagaaaa aaggtgcaaa 135840
atatctcatt aatacttaca ttgattacat gatgaaataa tatttgaata tattgagtta 135900
aataagatac attattaaaa ttaatatatc aatttttaac ttttttaatg cagttgctag 135960
agaatttaca actatgtatg tggttggcat ttgtggctca cattatattt ctgttagcac 136020
ttttctaggg agtattttct attaaagcta ttaacaatga atggtccaag tccaagctat 136080
tacacctcct ttgatcctga agagtgaagg ggtacactgt aaacttcctg gagatgagac 136140
atgatattga tctgccctgt gtttgccatc tatctggcag ccagtcagtc tggccaaata 136200
gacttctatt tttacataga agcttaaagg aggcaggata atgccccatg tcatggagag 136260
agcacactgc atagctcttg agtaatgtac ccaaaagtag accaggtgct attggaggtt 136320
ctaaggcata gcgataaata ttacatccct tgagcaatgt aatacagccc ttgaagaaac 136380
tgccatgtca gcacttatga attatcactg tctttgacag gccctatgca ctgaaaatat 136440
tatggtgtct acctctcttt ataattcaca tccaaatatt actctgtctt tttcttgctc 136500
cctgtagttt gttctgattc actgctaccc tgattgtgtg tttagtttgc ctagttcaca 136560
attgaagaag catgggaaag taaaggcagg ccttggaaag atcaagcaca gttcgaaacc 136620
ctacccagaa ttattctgtc tgtgtgagct tgggagattt acttaacctc tctgagctcc 136680
tctaaacttc cattttctca tttgtgaaat gagccttttct cttgcaaggt ctgtctgagg 136740
gttgaatgaa ataagaaggt acctggcaca cttatttttt gggtagatgt tgtagtgaac 136800
atctactctg tggcaagcct atggctaatt gttaggatgt aatcgtgagt gagacacagc 136860
tactgcttcc agctaagaga agagaaagac aaggagcctg gtaacgtcgg gacatgaata 136920
gccgtcaatg aaaggcagct attattacac tgcacagtgc aggatttggc ttataacaaa 136980
attttagaag ggtgttcagg tgagggaatt gagacccata gtgattaaat gactacctga 137040
gtcaccagct cggacaatgc tgggctgatg tcaggttacg ggattgctga ctcctcctct 137100
agtaatgcct ttcctgggag atcacattgc ctcactcttg gtttcccaac ttgtttacct 137160
tcaaagaata actttaccat gttggactcg ataaaaggaa agaggggttt cctccaattt 137220
ttgctccatt tgttattagg gcatgctagt aactaactgt ctttgaaaac ctacgcttct 137280
gttaactcca aagaaggcag gaatacatgc acttctttaa gatataaaaa gtatttagta 137340

-continued tactataaat tattatagta atcattgtta gattatatct caccaagata atgaatgttt 137400
ttgtttgaag acttcactgt atgagaaatt gtctcctata ccttatttat ctccttttag 137460
attaggtaaa acaaaatttt caaatttgag tctgaagaaa attccaacat ctttaaattt 137520
gtttaaggaa cattttccat gatctatatg atctatcata gtaatttaaa aaatcagatt 137580
ttagaatgag ccacgtgtag aaagagaaaa aaagtagaaa gtcaataaga ggtttcattt 137640
ttcaaatttt gttttggaaa aaactacttg gtagggacaa tggtgtaaag taagatataa 137700
gaaggaatat actgttcaaa taagcggcca tgcaattgat tttctctttc atgtaacaat 137760
cacatctgca ttgtgaatcc gttagtgcac caagtgaatc aagcttagtg agttgacaaa 137820
catccacagg gatagttgcg gggaggcatt ataaagtgca atgtggtcct agtgaaacag 137880
aatgcttcgt tctttgagaa agttccactc tgaatagaat aacggtgcat accaatatcg 137940
gagtatggcc aagcatttgg ctactgacat gccccttctt ctttcactcc tccataaagg 138000
aagagacaga gactcaggtt cttgtaactc agttgccttt tttgagttct cccaagaaaa 138060
gttctaactt caagccaagc gtcttgtcac tgggatttct gtatctaatt tttagttcta 138120
gaaatccatg atttcacaaa acaaattatc caaacctaac gacaaccaca tagaactttc 138180
ttaaagtaga cgagggagga attagcccct aaagtatttc ctgcacaatt ggaactcact 138240
atagaagatg tacaattgcc tgtacaccca agcacaaata ggctgtatta ttgccttatc 138300
ctaggagata tacactttac attatgatgg tccttccctt tcctggacct tcatatgatg 138360
taagtgcttg atttaggaat agggtcttac atattgtggc tggcgaagag cacatttgct 138420
gattgctcta ccacatgcct agatgtcctc ttcatgatat ataaatgagg gtccctactc 138480
tcaatatacc ccataggaac ataataaaac ataaatagtc tatttgttac tactaccaag 138540
aagacttcag taagtgtaat aactaaccct tttggataca tgcagaggga atgccaaatg 138600
ctttaaataa attatctcat ctaatcctga ttttttatt aaaaagggaa aatcttatca 138660
tatgaatatt agagatgagt aaactgaggt ttggtagagc tgggatttga acctagccct 138720
ctgtgactcc aaagcacatt cacttaaccc caagcccacc ctctctgtaa atgaagatta 138780
atgatagcat ctgtggtaga agctaatgtc tcctgacctg ggaaaatatc tttcaatgat 138840
tattaactaa atgtgatcag ctgccagtgg atcagatgtc atcaaataaa atcgagtgtc 138900
cagggtttac tcaacagtac tgtctcttac attttttatc aatgttagta gattgcttaa 138960
tctttgtacc tgttacctca catgaagcct agatagcatc agtcccttcc ccagccagtt 139020
tgtgctgggt tcagcttctg gcttgtgaat ccagtcagtg aattaatgtt ggtagcttaa 139080
aaacagccct gagagaggta tttacatcac agaaattggc aaatgataca aatcatgacc 139140
ctttttttaa attccaggga gacaggtgtt aaacatttac cagtacacca ctgtctatga 139200
ttcaaatcgg gacataataa ttgtatttct gaaggtaaac aaatgcacac tgagtaccct 139260
tggaaaaaag caaccttcca cagatacaat cacacctaag tcacctaagt ctttagtgaa 139320
ttttttgtcc ccatcattct gcatttggga ggacctttta caacataacc ataatgattt 139380
tatatgtcat ttgaaatttt aaaaaattac tttatttgtt catttttgtt atgaaagcaa 139440
atatgcccat agtaagcatt taatgttttt gaatgtaagt gcagacatat aaaccataaa 139500
atgtatatac gaatgctacc agtagaaata aaatgcaagc cacatatgta atttaaaatt 139560
ttcaactata gtcatgcacc acgtaatgac ttttcaatga tggactggtc ccataaaatt 139620
ataaaatcat gtttttatga catcttttct atgtttagat atgtctagat acataaatac 139680
ttaatattgt ggtaaaattg cttatactat tcaatagagc agtaacctgc tgcacaggtc 139740

-continued tgtagcccag agcaataggc tatcccatat agcctaggtg tgtagtaggc tataccatct 139800
aggtttgtgt aaatacactc tgtggtgttc acagaaccat ggaattgcct aatgatgcat 139860
ttttcagaat gtattcctgt cattaagtga tgcatgactg taatcacatt taaaaaataa 139920
gaaatatttg ttttaataat ggattttatt taattcagca gttaaaaata tgatttcaac 139980
ttgtagtcaa cgtgaacatt atcaagatat tttgcatctt ttcttcttgt actaagcttt 140040
caattctgtg tatattttat acttatagca catatgaatt tagatgctaa attttaatca 140100
taaatacttg atctgcattt acatttcata aaatgtaaag cttaaaaagt gggttcatat 140160
atccaatctg ttatagactt acatatttaa ttaaattaaa tttaaattgt cattgaattc 140220
ctcaattgca ttagccacat tttaagtgct caatagccac atgtgactta ttgtaacata 140280
attggtcatt gcaggtacat accatatatc cttattttat aaaattggaa acctaggctg 140340
gatgtggtgg cttatggcta taatcccagc actttgggag gccgagacgg aaggatcagg 140400
tgaggccagg aattagagac cagcctgggc aacacaccaa gaccttgtgt ataaaataaa 140460
caaataaata aaaatagcta ggtgtgttgg cacatgccta tggtacaagc tatttgggag 140520
gctgacgaag gaggatccct tgagccaaag agttggagac tgcagtgagc tatgattatg 140580
ccactgcact cccaacctgg gtggcagagt gagacccatg tctcttcaaa aagtaaaaat 140640
acaaataata taacaaataa ataaataaaa ttggaggcct actatatata caactcccaa 140700
aagtcttttc ccccctcaca cgttacacat ttaaaattcc catcctgcat tccctgctgg 140760
atctccaaga ggagagaaat ctcagcaaaa gtagttatat caaaactgtc tgtgagcttt 140820
ttcttcctca ctcataggaa ggaaataaat tcacataagg cattttggat ctgaccattt 140880
tccaaattat catcaccata aaaagttggt aacaacatga actctgaaag caagctgttt 140940
caatgcatgc ctggtgctaa tgaaaaccag cagttttaaa tgccctttttg ggttagcttc 141000
ttcctttttc tgtgctgtat tattagaaaa gcttcaccaa ggagatcaac tagatataat 141060
ttcacaatat ttcttagtaa tcaatgttgg catttactct tcccatatat taatttatta 141120
acatcatgct tctaaggatg ctttaatcac ttttttaaaa aaaatacttg atacaaatta 141180
gagggtgtta gttattttag gtggtgattt gttttgtttc tgcaaaatta caaaccagat 141240
atgagcatat tattccctgt gtggcttaat aaactgtttt ttctttttttg agacagagtc 141300
tcgctctgtt gccaggctgg agtgcaaggg cataatctcg gctcactgca acctccgcct 141360
cctgggttca agcgattctc ctgcctcagt ctcccgatca gctgggacta caggtgtgcg 141420
ccaccacacc cagctaattt ttgtattttt ggtagagacg ggtttcacc atgttggcca 141480
ggatggtctc aatctcttga ccttgtgatc cacctgcctc ggcctcccaa aatgctggga 141540
ttacaggtgt aagccaccac gcctggccaa tacactttta atataatttt tgataaaggt 141600
gttatggaga cttgtcacca aatagtctag tcttcacatt aaattcacat gatactcctc 141660
atctctattt agctctctct cacctccagt aatgacctcc cttgtctctc agtctttggt 141720
ctcttacctt cagcttccca ctagccgttt ctcacatttc caaaagtctt gtaattgcct 141780
taaaacacca agtatccaaa gcagtcctat gaccttctcc tcctgctaac caactcagat 141840
ccccaaatcc tgatttcttt cactagcact atctctcatc cacacatact cagttatttg 141900
tgatagacat gtctctatca tctctcatat ccaatcatca ccaaatctta tcaatacttc 141960
tcagtgatat taagttaaga agtcatgaag ggcggctgta ccctaaggaa aacccacttt 142020
tgcacaaatc tgagtttctg atcaatctga gttcagaatg ctgttttaat ctggtcctac 142080

-continued ctcgccaatc taattttagg cccttttatt cgtgaatttg aaccttgttc tctattcacc 142140
agcttcctca gaatattgtc caaaacatac tcagaattca tactcatatc cagaacattt 142200
gctctgagct tttaccatac aagttcacca cagtttctct cccttttcca tatccaccaa 142260
agccttatct gtcatttagt tttaatttta agcccttcag tttgatagct gatttttccc 142320
tagtctgacc ttctattttc gggtatgctc cttcttttca cagtttcatg tgtttgtact 142380
gccttattct tgaagaacca ttattttgat tgcttttgca ttaatctcca tagtgccttg 142440
ctcagtgtta gcaggaacta gtagtttaac aaatacttgc taattctaaa ttaaagagca 142500
tgaaacatat tgtttctttt gcctggagtt ggttatagca tgctggaaaa agtattatat 142560
ctaaccttca tcttttctca tgtgtttatg aactgtttta tagccaaaga ataagttagt 142620
atatcatggg cctaattatg taatttggag gcctcctctg ctgggcagtc tacagattta 142680
aaattcatgc cagctgcatt acgctggttt tgaacttgct ttttcttgag aaagatgggg 142740
agcagacaaa atgcctcagg ctttgagggt agaaatggtg tgagttccat tatgcaagaa 142800
tagaacccca ttttttaatc cctcctgctg aaaatcttgc catgaggcta tagccaaaga 142860
atgtgtaaat atcaaaagaa atttagagag ggattttccc taggaaaata ttgcaagctt 142920
aaaaaaccca gtgggctaag gtccaattta gtagattcct ccgaacaatg ccatcctcta 142980
cttagattgt tacagaactt cttatgacag catttgagta gactcctgta cctctgggtt 143040
aaaaggtaca tgtaataagt ttaggtacct gggcaaaaag ggcttggcag aggggaatag 143100
agggactttc ttattctcac atctagtata tcattacatt gtaatgttag ataacattaa 143160
agttccaaac ttcatgtgtc cgcactctga cgtttcctag ggacattttg tctcagctag 143220
aatctaatag agaaggattc cctcatctag aagcttccat atggggctct gtgaagatga 143280
tgtggacagt gtacaatcca attgaatgtc acgtctcgtg gcctggctca tgtgagggca 143340
ctagagagag ttctccagag gagtgcagat ggggctactt ttggaatcat tcccactgag 143400
ccaacatcag tggaagagaa ggggaggagt tagattctaa taaagccctt atcttctgct 143460
gaatccatcc acattttttt atcctcctcc tggcccctgc acttagttag agtcgggtcc 143520
ctatgcagtg ttccaggcgg cagtgaactg cattcacctc ctgtttggga gcatggcaat 143580
tttaaatact tttttctgct gtaagagtat gcaaacagat ttctggttaa ttttgtgttg 143640
aggattcttg tttgtttttt gttttgatag agcacattct atggacatat gttcagcttg 143700
taaaggaagt gttatagttc cttttttttt tttttttttt tttttggaga tggagtcttg 143760
ctctgtcacc aggctggagt gcagtggcgc gatctcgact cacttcaacc tccacctccc 143820
tggttcaagc gattctcctg cctcagcctc ccgagtagct gggattacag gcatgcgctg 143880
ccatgcccag ctaatttttg tatttttagt agagacgggg tttcaccatg ttggccagga 143940
tggtctcaat ctcctgacct cacgatctgc ctgcctcggc cccccaaagt gctgggatta 144000
caggcatgag ccaccacgcc ccacctagtt ctttatttgg aagaagtgaa gttcatttgc 144060
aggcagctgc tttcaaaagt ttggggattg gaggaaggtc atcttctatt caactgaagc 144120
aaatgccact tgtttgtggc atctgccagg catccttgag atgtctgaag aggtgacttc 144180
caaaccagag gatgcagcct tccgagaaat gcaaacctgt tcacattctt gctcagatgg 144240
gaagcagaaa aggctgcgtg ggaattgggg atttactgtt atactctggc attggaatag 144300
caggtgctac tggaaacttc tttacctgac actaagtgtc ttgggagata acaagtaaaa 144360
ttaacacagc atccagttct tcagtgcttt ctccacttaa aaagaatcag gctgggcacg 144420
gtggctcata cctgtaatcc cagcactttg gaaggccaag gcgggtgggt cacttgaggt 144480
caggagtttg agacaagcct ggccaacatg gtgaaacccc gtctctacta aaaatacaaa 144540
aaaaattagc cgggcgcggt ggcgggcgcc tgtagtccca gctactcggg aggctgaggc 144600
aggagaatgg cgtgaacccg ggaagcggag cttgcagtga gccgagattg cgccactgca 144660
gtccgcagtc ccgcctgggc gacagagcga gactccgtct caaaaaaaaa aaaaaaaaaa 144720
aaaaaaatac aaaaattagc tggcatggt ggtgcacacc tatagtccca gctacttgga 144780
aggctcaagc aggagaatcg cttaaacctg ggaggcggaa gttgcagtga gctgagatcg 144840
tgccactgca ctccaggctg ggcaacagag tgaaacaaaa aaagaaaaga gacagaatca 144900
aatgcaaagt aaatatttag ttaccaacag gatggcattt ttagcctata actttttttc 144960
agccttttaa tatatttctg ctggaggttt ccagctttga ttacatagcc tgttcaccta 145020
ggagtaaagg acattgggag ggagagatgc tcagtggttc tcatttgcaa agtagacgag 145080
gatgatgaaa ggccatcagc tcaaggcctt ccaggttagg aattaaaaac atgaatgttg 145140
taaaaaccac aactcatatt tatttgaaat ctcacaaagt gtgagattta tttgaaatct 145200
cacaaagtgt gagatttatt tgaaatctca caaagtgtga gatttatttg aaatctcaca 145260
atgtgtgaga tttatttgaa atctcacaaa gtgtgagatt tatttgaaat ctcacaaagt 145320
gtgagattta tttgaaatct cacaaagtgt gagatttatt tgaaatctca caaagtgtga 145380
gatttatttg aaatctcaca atgtgtgaga tttatttgaa atctcacaat gtgtgagatt 145440
tatttgaaat ctcacaaagt gtgttcatct gcatgtttct cacgtgaaat ctcacaaagt 145500
gtgttcatct gcatgtttac actcaatcct atgaacgact ccatgaagta gtgtatgaag 145560
gagagttcct catgcatgtg gatttgcaca tggggattca gatacaagaa gacaatttag 145620
tttacataga gatgtgcttt tttaaagaaa tttttaagaa tacaaaatta tatggaacaa 145680
aaaagatagg tcctctgctg tctagaaatt aaagtacgtc aagaatttta tccctatgta 145740
gaattacaca gccattgccg ggggccacat ctgtaggccc atggaaaaaa acatctttgc 145800
tcattatttc agcctgatta gggataccat gaagggctat tccattaggt caggtttgca 145860
cagtaataaa aatgaagcca gtagaggatc tcgtggagct cctggtatga tgataagtct 145920
ctgagtaact tgtaaatagt gcaattttat ggaaatgttg cagctaagct ttaaagtagt 145980
tggcattagt tgtcagacac agcaacagct ctacaaaagg caatacgctg agttcatttt 146040
caaccagccc aaacttgcct cagaagatcc gggatgtgga caccctggta tatttttttct 146100 agaaaagctt atttccttcc tccagataaa ggtgtatggt cactgaggtg ttgtgctgac 146160
agaagtgttg atctactctc tccgttagac tgaagggctc caggtgtggc cacactgggc 146220
ttctaaatgg ctagcaaagc cacagacgca tccctcttgg tgtctgaggt gttcacattc 146280
ctgggtcttt cagatctgta ttcctcatga aaataaaacc tctctacgac acactgtgtc 146340
cttgtgggtt tttagtttta ctagggagtt tttgtttcct tttgcttccc tccttctttc 146400
tgcttccctt ctagttaaac ctctttagga tggctcatta gcaactcgtt ttgagtggtt 146460
tgagctcttt tgttcactgg gaaacagatt tatgaaatgt tactattacc atgattgtta 146520
tgtttttcct tttatggcct gtccagctca aggccccatg ctttctgata ctgctgataa 146580
ggttttctat ttccagatca aattaaagca aaccttactg gccctgttac tgaagctgtg 146640
catgggggtc gtttgctgtg aggtgtttct atggctttga gccagggtat gaacatctct 146700
agtgttcatg ttatttcctg agactagcac tcacgggaag tagaatttat tacaacctgc 146760
tgtttgagtt catgaaaagt aggacaatat gagactctgg ggcagtgaaa gacttaccag 146820
gattccttct ggaactgact cgtcagctca ttcatgtctt acccagtctt taaacagtat 146880
ttcatgataa tggtctgctt ttaattgctg ggctttacct taccctttt gtgattgcag 146940 gtcctacagg tatggatctc tggcagctgc tgttgacctt ggcactggca ggatcaagtg 147000 atgcttttc tggaagtgag ggtgagttct gcttttccat ttccaccctc agtgttttga 147060
aacaacactg aactgtattc gctacatcca agttttttgg atgattttat taaaagatgc 147120
aagttttaca tagcagcaaa aaggaaactt gacttagctt taaaatcaga aactagtagg 147180
acttttctgt ggatgtttag gaggaatgca gtagtcagtc aactttggca tctgatgttt 147240
tcatatcaaa aattaatact acaaatcatg ctgaggacat ttatgttgaa gacaagccag 147300
gtctcttgtt ctcaggcttt gggagagata ttgaaattac actgaagggt tattagctta 147360
ctgttcactc agctcatctg tgactaagga tatctaatct atttccagag ctcagaattc 147420
aggcttgtta atcatattct cagagaaaag aaattgcagg tttcaaatga atttcacttc 147480
tcactctctg ggtgattacc atttggctaa gttgaggaaa gagacacctg aaatagttga 147540
atgatatacc cagaaattat gagcttcctt ccccatctct ataattctcc ctcccttttt 147600
tatatccctc tccttgtaga gaagtctcaa tatgtttaaa ctatgtttca tagcagacct 147660
aactaaaaca aggaagagta atagaaggga aagggaagag gaacttttct gtcagaaaga 147720
aaactgtgct ctctaacggg tgggagactt ttttttttt aatgagtact tgatgttttt 147780
ccttgcctgg gcttctacag aagaaagaaa gaatatattt ctcccatgct atgacactga 147840
atttagttgt tgctttaaga gtgtcagact ccccttctca ccattcagct catgttggaa 147900
aacacagttt aacagcagac ttagcgcctt aagatgtcct ccctgacctt ctagccaaaa 147960
ataaatccgt agtagtgagc tgctgagggt gaccacagtc acttagaaaa tgagaagagt 148020
aaaatatgtt attttatctc ttaaagcaat ttaaaaatat ttatagaaaa gagtcataat 148080
tgttggaaat attttttggt ctctctggcg ttataatgtc aacattatgc aagtcaaaca 148140
tggagagaat tgcaggctcc atttcagcag cttttcccat ggctggtttt agaccttggt 148200
tctgagccaa agaattgcag ctgagatcct ctgctgttcc aaagtcatgg tggcttaatc 148260
tctcgtttct tcattaaggt gactttcact ccactgggca agatttgagg aatttaaaaa 148320
acttgtgaaa tgaaaagtat ggcataggaa atctttaaag aaaattaaaa atgcatcccc 148380
agctgagaga ttagagctca aattacattt tagaactaga aagtctgcaa ggagcatctg 148440
tttcagctgc ttcgacattt tactaaaact ttgagttcct gagtgaagag aaaacatcac 148500
tagttgcttt taatgtttgc tttttgtttt tctttttaat agttttgttt gattcattta 148560
tttgttcagg gagagcagaa tataagcaaa tgcaatagtt tatactaaac acaaatcaca 148620
tatcctacca gtacttacgc ataagaagta atttaacaaa gaagaacatt tttgtctctt 148680
ttttttttgt cttattgaac taaccaatat ttctttttcc tttggaatat gtgcatattc 148740
cagaatcctt tcttaaaatg gtctaaggat taaggatggg gcatgatgtt tatgtaagaa 148800
ggcatatgta agcacgttcc agtgtgtgtg tgcatgcttg gctctgtgtg tgtgtgtgtg 148860
tgtgtgtgtg tgtgtgtgtg tgtgtgtgtg ttctagttct ggccacttat ctaatgaatg 148920
ggttcatggg ttcagccaaa gttactgcat aacatgacat gggtcagtct cagataatat 148980
ttatggacca tgtgtttgtt tttctgccag gtctggattg tagccaaatc attttatttt 149040
tattgtgtct cctattgaat aaggcagact aaaaatatag attaaatttt taaaaagaaa 149100
agatactact attgaattca gtttgttcag tgaaagatgt ggcattgatg ggtaagtgat 149160
cttggaagca tcacctggag aaaagtcacc caggagctgg tagaagatga cagacctgta 149220
tgcgtaggga agggtagcac ttgagcaggg attttcttgc ttgggcagat gagcaattag 149280
aaatatactg gccctgaaag gatttttttt tattaaatct aattgccctg tgggaaattt 149340
aatgagaact aaatttgaac agtgccgtta ttgtgttagc taaagtgttg taatagatgt 149400
tttctgtctc tcatccttaa tatgaagttc tcatccttaa tatgaagctc tatatctgct 149460
cctcaaagcc agttacatag tctagaggag aatttttat tccaaaatca ggaatgatcc 149520
acaatgcctt gttttcaaag ggcttcacat ggttgaccta tcaactgatt gtatcaaaat 149580
tgctgctgct ggaataatgt tgctaatgag aaatgtgcat aaagatctaa tggatataag 149640
tattcttcca aggagtgcct gttataaatt aggtcgtata tctctactat ttcaatcagt 149700
ctacccttga atatacccct tgacctcagt aacctaaggt ggaagtaagc aagcccctgc 149760
cttgtagttc agtctagctg ggacatgagg aatgtcttga aattaatgag agcctgtata 149820
cctttaaagt ctagattgtg tgatgaagag aaatggtcaa gatgccctga aaaagaatag 149880
atcaaggtgg actagaatag ttaattcaac aaattcagtg tactgataat tcttaagagc 149940
ttcctatttt caaagcctgc acctatggct atgaggaata cattgattct tccctcaagg 150000
aacttttcat gggttaataa atcaggcatg tacaccaaga attacaatat caggcattgt 150060
atattaacta tcaaaatggc ttgaatcaca ctttatagaa gtgatgatga cgtgagggat 150120
acctcagctg tggtgaatta cagcttcatg aaggaggttg acattgtttc tctagagact 150180
agaatgtcag gtttaagatt ttaaaaggct gagaagaaca gaaggctatt acaggaataa 150240
cttatgtgat aaagcaacaa cataaacaga agtgtacaga tgtagatatg agatgtctat 150300
ggacaacaat tcattcactt actgtgctag tcaatggatg gttctatttt atgcatttaa 150360
cattcaacaa gcatttcttg agcacttact tcgtggaagg cataggatta atttggccag 150420
ggtgtgtggt acataggtgc tatatttgta attattccct ttggaagcaa acttaggtca 150480
gtaggtttga gtcaaattat agaaggccca gagatagcaa aggcattatg gaaaaggcaa 150540
gacttgctgg gcccttgaaa aatcggtagc atttggagag gaagaaaaga aagaggaagt 150600
gtatgccata tccagccagt aatagtcctc aatattggag gccagacaaa agcgctacct 150660
gcatgatgga atagtgtgtg tgtgtgcata tgtgtgatat tcatatgtaa catatatagt 150720
atctacatgt aatattgata tataatattt acatacaaca tatttatatt tgtatgtgtg 150780
taatacatac actatatgta cacatataca tatacatgta tatatatgta cactatatgt 150840
atatagtata tgtatgtgca caccagtgag gtgtggcttg caggcaaagc acataattga 150900
catcactcaa attctgcaaa aggtgttata tcattctgta ccattcaaag taagagactt 150960
aggaatgaga tgccacatcc taagggaacc aagagcccca aaataatttt ttctgtatat 151020
tttgaacatt tttcataaac ctatgcacac tgacaaaaca cttacttgaa aggaaagaca 151080
cccctgttct cattgctatc agacagcaac aatttatttt ttaaaataaa ctctattcca 151140
ccacagttga ggttccacag agctctgaga ggatgtcaag acatgtcaga tatatttcac 151200
acaagtatta gagtcatggt ttcagttagt aaacagtaat gaatgcatct gttaaatgtg 151260
ttcaagaatg aacacttcaa ggctttccat tcacagtgaa ggtggggaaa aaagccacag 151320
agcttttgat tgctgctgtc ttcaccataa tccagaggca agaagaaatc ttatggtgtg 151380
ttctagtgca atggcctgcg tccatgtaca tcagcaatcc tctgtcccct tgtcctcctg 151440
atattgcaga atttatttga tgttggagtt cagcaggtca cagcaagctg gattaatcta 151500
gatggtgcca atgtagataa tgacacataa aaagtctttc aagaagcttt tattaagtca 151560
ttttacagat tcaaggagga atttcatgta tttatttatt tattcattca attttgcatg 151620
catgcattta ttcatttttt tgttttagag ataggaactt gctatgttgt gcaggcccca 151680
aacagttcta ctagcttcaa acaatccttc ttcagcctgc agagtagttg gcattatagg 151740
tatgagccac tgtgcccagc ccaaggaaga attttgaatg tatattcctg cttttaagga 151800
gctcacagtc tttagaagag aaaacagaga aataaacata atttaattgt gatcctctta 151860
gattattaaa gggttttaat ctaggtaata atactgttag atttttactt tgtcagtaat 151920
actagtaata ggataaaagt gaatttgaaa gggatgaatt agaggaggaa gttgatgaca 151980
ataggtcagg agagagataa tctaagtgtg acagggatga taaaaaatag atggatcaca 152040
aacacgggga tgttaagaag acagaattac cagtactcag agtctaatta acctgtggat 152100
ttttgactcg gggaactatc agtgccttct tttccatcca tttctaagtt tctgcatttt 152160
taattaatgt gatcatcagc aatgactcac gtttaatgca gtgaagtcct ggtgcacagt 152220
tcagcctatt agcactaaag tggcacttgc acagaacaac tctgtagggg aggaaacatg 152280
ctgaggctgg atgacagcag agtgtctaag ctacgcttct tttgtactat ttctctgaac 152340
tcctcatgcc tgtgtctacc ctgggtcctg cagctgtctg ctcagctctg cagtatggct 152400
gtggtatggc tcaggctact atgcagtgag ggtctacagc aaggacaaag gtctgaactc 152460
cctcctcatt gtagtctctg gacatgtgtg actctatccc aaaaccttga caatccccca 152520
gatattttgt cattgctaga gtatgtactt actcatggga tacaataaaa tatatgcagg 152580
atgagttgag aacagcagag ccatgtgctg ggcagagtct gggaggttgg ttaggctccc 152640
acggaaaatg agtgacctac ccctacaaag aagctggcag tgtgagtgat tagatttgtg 152700
ccacagctaa ttagtaaatt gaaggagtgg gaccacccaa gaatactcag aaccctgaat 152760
gttagttaaa ttcacacatg ccagtgatag agtatatttc tggtcttccg ccttagatgc 152820
cagctcttac gggaacagag ccagtcctgg ttatataata gaatgtttcc acaccacttt 152880
ggttcagtat cctaaattgt ggctcttgtt atggggtaga caggaatgag gttgacataa 152940
cgtatttggt gtttggtgat ggcaaagagt acctgttcat agacacacct ggttgtccac 153000
ctctggctag agaccaaccc aagttcaact gtgcagaagt ccatgttggc ctttactggc 153060
ccagccagcc tctacctgag atcattccct acaacaaggg gcccaggatt cctcagtcac 153120
cccagcagct tttcccaagg aaaaccatct catgaagaat ttgccattga tgattttctc 153180
ctcactgtgc atcgaagtca atgggtttat tactgagagt tggttccttt taaaccttaa 153240
ccttacactg tatatgatat agaactgtag gcaggccagg gtcatcaata aagacatttt 153300
tggggcctct acttggcttg taaccacctg cttatccaca gtactgtgca cctagcttgt 153360
catcaggcag agtcaccagc agccacaaca aaagggtgca ccttcgtctt ttccaagcag 153420
caggcaatgt ggctccattt taacttttct ggcaatactc acatggattg ttaaataatg 153480
ctgtcaacag tgtcatcttc aaacccaaag caaacttcct catcatctgt agttagcagc 153540
atgaagacgg tgatgatgtg taacataaac acactttgaa atctgatgca attgacccta 153600
cgaagagagt attccttagt gccctgtctg gcaacttctg gacagaccag gaggccttgg 153660
ggcttagagc acttcttcag cctcagctgc aaatccattt tttcttgtcc cttgttccca 153720
ggatgaagcc acagtgtttc atcaggtaca tttatcagga atctctgttt ctgtttatat 153780
aacaatttaa cttaagcctc aaccttcaca gtgtacgcat cacatttcca tggaaggatt 153840
gcaggtatta gaagatggtg gatcatgtct taaccacagg ggaaatgttt caggatgttt 153900
ttatagaaac tttcactaac aagcaggaca caggattggc agagaggtgg gggtaggagg 153960
caggtgaagg gtggcatttg ttgtgtttcc ctcttctaaa tgaagttata atgacatctg 154020
tgtttcaaga gtgtggcaag tttggactga gcttgaaata aatacagttt aattggtttc 154080
aaataactga acaaaatgac cattccatgc cctgtgtaat aaaatgttat agaattaaaa 154140
cttattagac gttaaaatcc atgaaggata ttttgctgga tgcccatcct tcagcattct 154200
gatgaggatc ttcgtgtatt tgttcaatga ataagtgaat cagcagctaa atcctgacct 154260
ttgatttcct cagttctctc ctgcaattgt cactgatgct ctcatctcca gtcctgagca 154320
aggcaggagt tgaattagta tccccttata gtgggagggg tctagaaata gctgtgccac 154380
tttagaagct aggctttgtg ggcttttccg ggggatggaa tgatttcatt ttcctgcttt 154440
ctactccaca taccaccaag atcagaattc tgccctaaac actaatgtgt gggagcctga 154500
tgtcctgcct aagtcttgtc aacctctttc caggtgactg aactccgaac cccatgcacc 154560
agtcactggc caacattctg cattaagtga cccggtcacc cagcaccatc cccctgacac 154620
cacctttatc tctacaccac ctgcctcctg cctgattaaa tctcctcaaa tattgacaga 154680
cataatgata cctgaagatc ccaaatccaa attttcttttg ccccctttgga cattgaactt 154740
tagattacaa aagaccctga ctagggatcc tgtggatagc tgagtcaatt ttcttagccc 154800
cattccttaa atatcaagtc tttctaattt tccaatgaga gcacatgaaa ctctcaaggt 154860
taaaagtcaa tttatattaa taaaatcttt aatttcttga tttctgaata tgaaaaaatg 154920
atactttgtg tattttttaa ttttttggca aaaccttcca aatttgtgga aagagaaata 154980
atattgacta ctggataacc atgtgctatg tgtaaatatt aacggattca ccttagtggg 155040
cactgacttg atgatgtttg ccacattata ttttccagag ccttggctct cccaaaaaat 155100
gagaggtcat ttttcagggg aggaccattt tgtgtttggc taacatttag gacatataat 155160
ttcttctcct ctacatgcca ctgacccact gcatccctgg ttggagcaag aagagccatg 155220
ctttccttaa taatagctaa tggtgaaagg atgtgttgta acaagagcag aggaataggg 155280
aaacaggaga aagacagtca gttgaagagt cctgccctgt gtcagggcac cgtttggcca 155340
gctgggcttg ctaggagtag aatatagaaa gtacatgaag tgccatactc agacagctct 155400
ggctacgttg acaaactggt atatcatggt gcccaacttt ctttgttagc tgggccagca 155460
tcataccctc tagtatttgc tctgaacttc gtaagcacgg ttgactagct ttcttttcct 155520
ctgcagttat cattcagact gaatagtttc taagaggctc ttaatgagaa atagaaggaa 155580
gtaagttaac ttctgtgcat accttggcca tatttgcttg acaaactgat gtgtatacta 155640
aagccattat gggtgtgaaa ggcaaaagta taagtgctcc ccagtatgac ctggctattt 155700
tgtcttactt ctatatttga ttgctaaaaa tatatgttct tgggtcaaaa aactcacttt 155760
aagggaaaaa aatggaagaa tattaataac caaaatagaa gaatattaag aactttaaca 155820
tgagatgtat ttagatcaaa accatctctt tttggatttt tgcgggtgat ttctccaaca 155880
tgtttagaac tgggttgcta ttcacccaaa ggtggaaact tttgatgttg gggaatacca 155940
ctgatgcctt aaagcagagg gtaaaaggaa aagactgaaa ttccaggcta aaatgaggag 156000
agcatggcca ccactgagcc caaggtagca ttcaataaat actatataaa ttactgattt 156060
atttctacag ttggttgata gaagcttact atgatctgcc taagggtgca tcaaattcct 156120
ctggtactta tcctattctt gactatcact tccttggggg cagcagttaa tcaggtagag 156180
gcttatcctg tcaagagagt aaagggagct atggaggaac tcgctgggag gagaagctgg 156240
tcctcagaga tgcttagggt ttaggaccag taagaggcag tctccacacc acccacatct 156300
gattcttgtc tccttcttct ctgctgtggt caggagaaac agtttagatt agggatttca 156360
gagcagtggt gttgaacttt gtcaaaactg catttgaatc ccatttatga attgtgtgat 156420
ttttttaagg ttgagttccc cagaagtagg atgctgagac aaggattcct atgaaagtga 156480
attattagaa aatggtccag ggagaaagcg ataggagagt cagaaaatga gacggggaag 156540
gtaaagaaac cagacaagga tacaatatca agtagaatcc aacagtggtg tgggtgggta 156600
gaagtatctg tctcagcaga ttttgagttg tccagattat cctcagttgg tggttaaggt 156660
taaatttgca tcctcacgag gatgcaaatt tctacacact atcagttgtc caagtgcagg 156720
taaagctggc tccagcagcc tgagggcagc cgacagagag acacgggtcc tgggtgtggg 156780
agtgaaacca cacatgaagc ctgcatgtaa aaaaaaaaaa ggtaaagagg ggctgggcgc 156840
gatggctcat gcctgtaatc ccagcacttt gggaggccaa ggcgggtgga tcgagaggtc 156900
aagagtttga gaccagcctg gccaacatgg tgaaacccta tctctactaa gaatacaaaa 156960
attagctggg cagggtggcg ggcacctgta gtcccagctg ctcgggaggc tgaggcaggg 157020
gaattgcttg aacccaggag gcagaagttg cagtgagctg aggtggtgcc actgcactcc 157080
agcctggtca acagagcaac actctgtctc agaaaattaa aataataaaa taaaataaaa 157140
taaaataaaa taaaataaaa taaaataaaa taaaataaat aaaataaaat aaaataaaat 157200
aaaataaaat aaaataaaat agtaaagtaa aataaaataa aggcaaagag atcaatctac 157260
atcaccaaag cactgacagc atctgctaca gtgactttgg tagtttctta cattctctga 157320
gcctcagttt tcttatctct taagtcagag gaaaatgact tgtttaaaaa ggcttcaatg 157380
aggtaacaca agtaaagcat gtattgagat tactacacag gaaaagcagt tgctgaatac 157440
aattagtcaa ctggtaattg gtaataatta tgtaaaattc ctataattat agggagcgct 157500
atacaattat tatatataat tcctataatt ggaattacca ataggctaat tgtattcagt 157560
aactactctt attgtcctca agttgagtta ttattgcaag ccctgagggc tgaataaaca 157620
tgcaaactaa actgacatgt agaattttat ttataacaat atatgcctaa aagaagcggt 157680
ttatttgcac aaggaaattt tggaagctac agataatttt aataatgact acagaaaact 157740
atcttgaaga tgtttctaat gtttaagaca taatagcata agcctttata aaatgggata 157800
ctgttatgta gttatagttg taagaatcag tgtttaaagg atgggtttga tgaaattgta 157860
ctactctagt tcctgtgctt ctaataaaat taaatctgat taatacagca agtaggtctt 157920
tggtgagttg attctgatgc tgggagtgat tttcttaatt cttgctcaga aagccatcca 157980
tgagaattaa atgagatagc atgtacaata cctggtatag ttactggtaa gaggttttca 158040
gtagagacca atctcctctt tgtttacctt ctcatcaaga gaggaagaac aaggaaaatt 158100
aggttgcttt tttgagaaaa tactttaggc caattacaat tatctgaaag tagaatgaat 158160
ttctaggtta ggcaagacta gagttaaaac gtgggtgtgc agggctgacc tgccagggta 158220
ctctgtatgg aagtacatgg aaatgtatgc ccaaatacag cttcatataa ttgttttgat 158280
catacacagt ttccacatga gattatattt gaatgactaa ttcagcaaat ataaaaaagg 158340
agaaaaccag tggacaagat gattcctaag gttcctttct tcctggtcta tgccctagtg 158400
tattatgaat tgatattcac tggaacacac agttactgct ggagattgag ttataaaaac 158460
attcaaatgg gttactccat tatatctact taggaaattt ttttttaaaa taactgatag 158520
atgttcagtt atgcgaaacg aaaggtattt ctggctaccc ctttatagtt gtgtacatga 158580
ctgcagagcc atcatttcat gcttacttcc ccacattcat gtaccatttt ctcaaaggaa 158640
aattattgaa tgaacttgct agttttgatt ctggggtttg ttttaaacaa ctgatattta 158700
aatccaccta gtcctcttta gctgttctcc taggaacttt aatattaaca aacagctgaa 158760
cttatacatt ttgtaaaaga gttcagacaa tgaattcatt cttcttgaaa tgcatggaag 158820
tacccaggtg ctagctacac ccaagagcct tttctaaata caaaaaggat tgacaaacca 158880
agcattcatc ctgtctgcgt ccaacagttc ggaatcaaac catgaacttg ctgttcctct 158940
gtttgtggtt agcttgtttg tatattttta aggaagatga ttcaatgcaa gaagtagttt 159000
tatatagtac gttaagtaaa tttcctatac gatatactta atcagaaaaa tatttttgaa 159060
ctagagctca cagaacatat gattacaata gttttcagaa agcaaggggc taaatgagga 159120
tttctcaacc ttggcactat tgagatttta ggttaattta tctatggtgg gaggcgtgtc 159180
ctgtgcattg tagcatattt atcagcagtt gtgacctcgt acccactaga taccagtagt 159240
ccccccttctc agttgcaaca accaaaacaa ctatagacat tgctaagtgt tctctagggg 159300
tcaaaatggc tcctgcttga gaaccacagt ctagatctgg tagttgcata ttgaactgac 159360
agtccccagg attgttgtgg ggatcaaatt agataaaact tgtttatatt ttttaaaaag 159420
taaaactaat acatatagtt acattacacc tcttcttttc atttgttact catctaagat 159480
tttttgagcc agatgatgga gacccataaa taaattaacc ttaagaggct caaaggtttg 159540
ccaggtaaac aaagagttag aagaaaaaga gagatcatgt cagatgtgcc ttaatgaatg 159600
tgtgtgtaac atgtacaaaa agttatggga accccaagaa agaaaagact ccttttgaat 159660
gaaatcagag aaaaccaact ggaccataca gttgaagctc tataacagga attaccaatt 159720
aactaattgt aactaaatac tcttttatac aatgtcatat attcatgtag tttttaaatc 159780
tagaagtagt taaggttcat aattgtcatt tctcagggac actactgaag tggtatcaaa 159840
tctaaatgag caacttaaga attgaagttg tcagacagct gttaattccc ctttttcata 159900
cctgctccaa tgatagccaa caatcaaaca aaaataataa aataaaaacg aaagcaaaaa 159960
atacaactca gatttcacta cgtacagcaa taaatatcag agacattagg gaataataat 160020
aggtcaaagc agaaattcat tcctcagcat gttcttcaag tggaagaatt aggtctgttt 160080
tagttctgtt gattctaaaa gaaacattca ggctatcaag aaaacctgtt ttaaactcta 160140
aatctgacac tatagataga tagatagata gatagataga tagatagata gatagataga 160200
tagatagata gatagatgat agatagatat agatagatag atagatagat agatagatag 160260
atagatagat agatagacag atagatagat ataattctgc ctaagtaatt atctgctggt 160320
accaaagaga ttgacaaaga gattcactaa cctaccagaa tttcccaacc ttgttccagg 160380
gtattctaca ttaaatactc attaccaagg aaattccaca taaaagctgt catgcttgat 160440
ggagccatat ttacatgaaa cgttgcagca ttttcttctt taaacctctt ctacaatttg 160500
accaattcca tgttccaggg agtactcaga ggctgattag gacatgagtt gttagcatgt 160560
gctgcactaa tggttatgag tcacatttgt tttggaagat caccccttaaa gcctgtcact 160620
catgcttgtt tatgggaaat acaacaactt aaacatcagt taacaaatcc ccatgaatgc 160680
atggtcatat ttgagtgctt ctaacaaatg cttcctttca tttctccctt gacagcccta 160740
agaattaaag gctggtagag caaactggga gacatccatg aacatttatt aaaggaagca 160800
taggagagta tgataactgc aaagccagct gtttatatta ttggtgtgag attaaatttc 160860
atcagtctta aaacctgctt tttaccacta gagaaatcaa tctgccatat ttaaggttac 160920
attaacgtgg aacattccac gtactgaact gtcacatgcc tttaaaataa ccatgccatg 160980
ctgttttttt tttttaaaat cattacacat gaaacaaaca gctgacaggt ggggatctat 161040

-continued tggtatattc aagtttttca tgtgaaaatt tcccccaata ttagtggtaa tcacaatttg 161100
attatgagaa acaaacatac catatatagg cagaactata tatcagtagc ctttatattt 161160
gacagctcac tgtaaaatcc atactatgat tcagtgaaca tatttatgtc ttatatctgg 161220
gttgatctgg ttgccttcag ctttcctcac ttgaaaaaac tatacttaaa aaactgtaat 161280
ttaatgttaa agttaattaa cacagcaaat acttattgat gacctattat ttactgggta 161340
ctattttcgg tgcttgcaat gcctcaatga acaaaagaga taaaaacctc tatggtcatg 161400
ctgcttgctt tagtgagata tatgtgtgtt tgtggggtgg aggacatgaa tgtgaggcag 161460
acaataggct acaaaaataa taaattatct agtattttat aaggtggaaa gagctatgga 161520
aaactgcccc atttgttcct catctgagta tacccaaaag ttgatcttta atattttata 161580
tgagtctcct aggttctaaa tgttagaaac taattaaaaa taaattgaaa ctaaactaaa 161640
tatctttgtg atctctctgg ctagaagcct caggaccagt cctcactgtt tactgatgag 161700
gaagccgagg cccagagaat taaacgatgt agccaagatt tcaagcagtt actgtcagag 161760
gtaggaccaa gacacacaac ctccttctct agtgtgtttt tctcaatcgg ttggcattta 161820
acagcaagtg ttttagttga aaaaatttat ttgaaaatct gtttgaaaca tgacaaaata 161880
ggaaatacct gcttattccc tcactgcaga gtggtcctca gcagaaagaa gatttgaag 161940
tttatgaatt atgttcagac aagaccctta taaaatcact ctcctctctc cagtggcaga 162000
agcgtggccc ctgactcctc acccaccttc attcatcttt cgtattcctt gaaaattacc 162060
actgagtatt ttccttctgc ttcctgcagc accagcagaa aagatgagga tgcgtctctt 162120
gattgccatt acaaatctct ttcttatgct tgtttccatt cttattctgc acataacttg 162180
gacttggcca tcattcttag agctcctcta aattgtttga ttaaaagatt gtttataagt 162240
ccagagtcag aacggaattg aaaaggcact gcacattatg atggagagga ataaactcca 162300
gtcaaaagtc atggcttctg gactcaccac cctaaggcag cctcactgga acttgctttt 162360
ccaactgtca gtggagtttt agaattttcc tacttgcaag cttgttgtga ggattaaacg 162420
gttaagagag attgtgtctg ttatggaatt gtgaaaactg taagttgcag tccacactgt 162480
agaaatctta gttacctctg ccctttcttt ctctagagac aggttgctag tggaatagac 162540
aagtttgcca ttaatttgaa ggttgcatta agcatatatt atgttagtga agttggtctt 162600
ctgaaagttg gaagggacct cagaggtcct gtattagacc aactgtggct gttccttaga 162660
ataagctgga agttttctga aaaatacaaa ttctgaagcc tcatacatag agattctgat 162720
gtggaagatc tggaattgat ggcagcagcg gcccatctgg agccgctgct gtgaagatgc 162780
cggctgtagt gggggaggtg cggctgtggt tgtgccctcc acagagctgc caggtgggaa 162840
gcctgaccct tctgagttgg caggtctgaa gcccagtgct cttcaggcac agttgcagct 162900
gcccatctgt gcctctagac ctgggcatcc ccgtgctctc gggggcccag gaagcacccc 162960
ctgctcctgc aggcttggaa gtgcctgcta tcactccctg gcctctccct gcacctgcac 163020
ccagcacccg ctccggggtg aagcaaagtc atggccaagc ctggatgctg tcatgacctg 163080
gtcaggtgtg cacacactcg gagcagtgct gacacaccag ccccctggca cataggcact 163140
ctctggactt tggacaccaa ccagcatggg agggagactg agagggcact aaggggtggt 163200
tcagcgcagg cctgcaggcg ccccttggca tgaacagcct gggtgctgtg gatgacatgt 163260
agatggtggc agaaggcaga caggctcctg ggcagaaaga ggccagtccc cagtgaagct 163320
ccaccttcaa gccagggatg gccggaagcc ttgtggctga gctatcagtt ccaggtggag 163380
tccttggctg ggagtgagaa cttatggtgc tttatccagg ccttcccata gccacccatg 163440
gaccaataag cacacccttc ctcccttctg atctcataaa atccctggac ttatccaaac 163500
tcgggcagat gtcgggatga cctgcctatg gataagagct acccacttca ggtctcctga 163560
gaactgtact gtcactcagt aaagtatttc ttcaccttgc tcaccttcca gttgtctgtg 163620
tatctcattc ttcctggatg tgggacaaga actcaggacc cacttaatag caggactgaa 163680
agagctgtaa cacgaacagg gctgagacat gccttccctg cccaccacat tgtaggtgac 163740
aagaacagaa gagctacagc cctttgggga gcccagacct gtgtgacacc ctctttgggg 163800
gctctgcggt ttctgtcatc tccatgctcc caggcgtcac cacattcccc tcgtccagat 163860
gcagttgccc acggtggaag ccatttgcgt acatcagatg cagccgcagg cttgcatgga 163920
gctggtgcct gtgctggtgc ctggagctgc tcaccccacc acggcagctg gtgtacctgg 163980
ctgtacacag tggctgaacc ccatgcttac ccactcacgt atccctcatt gctccacgcc 164040
tggcttgccc ttggcaggca tggggtccag gctggtagcg caacccgagc atagcctacc 164100
aggccgttgg cagaacaagc ccattgggcc cgagcaaaac ttgggcaaat gtgccaccag 164160
ccacaaaaag gaaacacaaa agtttccagc tggaaaagca agacctgaag aatcctgcaa 164220
cagaatgatg ctctggagtg ttttctgtgt taggtgtgct tgtttgtttg actaaacctc 164280
caaacatgag tctgaagatt aaccagtttg ggaagccttg cttcagcttt ctactgacat 164340
taaactcctt ctcctctccc atttctgtct tcacttagaa atggaaaccc actaattact 164400
caagatctta ccttttccat tcagtcaact aggcccttgc acccccatta ctttgcgttc 164460
caccttgaca attgctattg ccaaacatcg gcattaatct attttgacat cttctttcca 164520
cctgctgccc tctagtggaa gtgctgacaa gcagcaaaat atttaactgg gaacagcagg 164580
aaagtgacca gtttgagctg gccagttcac acaagtcagc gcaggtcccc agcatgatgt 164640
ctacagacta cagctatgcc agaaatcgtt aggatggcct ccagctgttt ggacactatt 164700
tgcacacaag ttacatttag agcagaactt tgtaaagacc ctggcattta ttcaagggct 164760
ttttaaaggt ttcaaaaatc tacctggaaa acattaccct tgggatattt ttgtttcttt 164820
gtccctcatt ttcttctttt gtcatttacc caaattcttc ttcttgcaaa agaaggtggt 164880
tctttcctgc cttccctaac ctttgaattt tccaaatctt gcaaaaaata aagatatata 164940
tatctttaaa taaagatata tatatatata tataaattct tacagtttag aagcttccag 165000
tcaccaggtg aaaggaattc acatgaactg aaaattgaca atgtaaagga cactgtgttc 165060
tcctactgtt cctccaagtc tctttgcggt ccgttagtag tcttcttttt tccaggagac 165120
actgaagtta agagagttta agaagattgt agtatgtcac aaagcaagtg gaaaagctag 165180
cactagaact caggtctggc tgatggaaaa ccccttatgta tttttttaa tgtgcttctt 165240
tggtgtttag tgattattta gtcttccgtg aagtaataaa taataacttg catggtaaat 165300
gttattaagg ctcgaggtac taaatttata gcaaaagtca ttcagctttt ttttaaatga 165360
atgtttaata atcagtgtgt ctctgcataa tctccaatta ctccttttag cagaggaaca 165420
tggcaggaat gcaggtaagt ttgggtggga ggaaaagaca gcaaaagcca cagcactgat 165480
gcaaagttga gactagattt cacagggcag atgccgtata ctccctcaag ctttgaagaa 165540
actaaatagt tatctatgtt aaccaatagg gcagaactcg tactccaaac accgacataa 165600
accgtgtgtg tgttttgtgt atgtgtgtgt cttcccccac agcattctgc acaattatta 165660
acccttttg tgtagtggtt tttcataatt ttatccttga ttgttaatat catggtaagt 165720
gatgtgttat aaatatattt ttccttaagt atcataaaca atctaagatt tcatttggct 165780
gatttttctt ttcttagtat tgcatatcat tattgctgtt agaacactca tacagattat 165840
tcagcttctt aactagaatg tatacacaca cacacacaca cacacacaca cacgtgcatg 165900
tacagaactg ccttctttct ctttgatggt agaaaataca gctctctata gtaagcaaat 165960
ttgctttcag tctcagacat acccttcatt ctctgcatga ctggtaaaga gcggaaagag 166020
taatacttag gatctggatt ccagttccct gttctctgac catttaaaaa ttttgttacc 166080
ttggccaggt aaatacagtt ctatgaacgt cagttgtgcc tcaattgagc aggcttgtcc 166140
aaaggattcc tcaaggatga ggtatccttt cagctgtatg agctgaacct tgatttgtgc 166200
aatagtttaa gcccctgaat agtcagataa aaatcatgtt aattaaaatt aaatagctat 166260
tggtaggatc tggttttcca ctggcttgca tgaatgatgt tttgccctcc tttctgatac 166320
tcagctcaga ggattccttc cattgggttt tctttcttgt agtttttctg gttcataaat 166380
agcctataga caaacactaa actgttacag gtaaaaggac cctagattaa gccttttata 166440
aaacaaatag tcctgtgtaa ataatgacat cttattttat gtgtgtgaat ttgagtttta 166500
ggatgtaggg catgtctgac tagatagcta aaggctgagc tccaggcagc cagctgctat 166560
ccaatctcca cacctggaat gttccaaaaa acctcctgtg ttttctttct gcagctaagc 166620
actgatgagc aggatttaag aagtacagcc acacactttt tgctgcacgt tttttaaagt 166680
ttgttatttt tgtcatagat tacttgtttt gaatcaaaaa tttttaaaga aaacttaatc 166740
tcccaaattt taaccccctt gaagtttcag gattccaagg aatattttta ttttaagatg 166800
cataaaatac tcagtacatg tacaaaggta atgcttataa gaaacttaga aaaaaaaaag 166860
gagctagtaa gattgagaag gggaagaata tctaagctaa cattactaac ctggcaacta 166920
ttataggtgg ctggatagca tgaaggcata aagctgaagg cagttaagaa aatagactgg 166980
atttgaatcc tggctctacc tggattagtt ttgtgacctc agagaagttg cttcccttct 167040
ctgtgcctca gtttcttcat atgtaaaagg agataactat agtgtctaac acacagaatt 167100
attgtgagga ttaaataagt taatacatat aaagaaagtc caaaactatg gcacacaaat 167160
gtttaatata tgtaagctat tattgttata aaactaaaga aagagaaccc agaagacatt 167220
cagtttggtg ggattcagat atatgttttc ctttcctcct cctcctcctc ctctccttct 167280
ctaaccccac tatgcttgcc tcccaatcta tccctgactc ctatttttct tcctcccaac 167340
ttaagaattg tcactaaaaa tatttagaag aaaagaaaat gtgcatactt caggggggtgc 167400
caagcttttg ggtaaagtac acttttcagc taacatgact gtatccaaca gtaatgggct 167460
ttatggcaag aaaaagcttt tttctcaata aatgggtttt aactttgtaa tggattattc 167520
tctttgcatg ggtaattctt ctggaagatg gaaattggct cgatgataag ataggacagt 167580
tggatttagg gatctagatt aagggactat catgtatgct tttaggagag aagtttaatc 167640
tgcaaaacct acttgtctta tttaattaat tgttgctctt agctgctcaa ttttgtacag 167700
gtgacttgca tgaaagcaaa atgtatgtca aaatccaaaa gcagagtgaa gcctcgggac 167760
ttcagtgctt ttgggtgtct ttccagacct ctgctcttcc cccaccctca ccaaggcccc 167820
actgacctca aagggccctt cttgccaggc cgtgaattac gtctgagcca gagggctggg 167880
actacagcca aagccaaatg aaggtgcaga atttaggact aaaaaaagcc tgagcacgtg 167940
gcactgggta tagcagataa atttgttgga gaaatggttt ataaataaca tgaaaaggga 168000
aaggggatag agggtcaaaa tattgagctg ttgagagttg ttcaatattt gaggtcagtc 168060
tcaccatttt taatactgaa cccaaaagta atacacactg aaaaaaaaaa aaaactcact 168120
gaataaaatt aactacagct gggcttattt tttcttatca agacatttgt aagtttggca 168180

-continued

```
gcaagcattt ttaaacagga tctctattat atgaaataaa tttaaaaaca tgtgtctaca 168240
gtcaggacaa acaagtgaac aaaaacaaag caaaagcaat aaagaagccc catgaaggca 168300
ttatgctttt ctgaggacag tataaggcta ggatactgca gaaactgaaa tacttaggga 168360
tcttattgaa atagttttct tttcctccaa acaaagcaac catctcagag ggatagatgg 168420
gctaaaagac aaggaataaa gtaaacagaa gattggtaac ttgggaggtt ttcttttccc 168480
ctttctcttt ttggttttga tttgcttttc ccttgttaaa gccagaaagg ataaattttg 168540
gtccagaact cccaagacca gagggtcagg gaaagccacc ccgaggctgg aagctatgaa 168600
cttatcgcta gtctaaactc cacctccttc ttccctggga gtcctgcaca aatataactg 168660
cctgatcttt ctgtttactg gcaaaggttt tgctcccttc tctttcgtat cggaatgtga 168720
acttggggaa agatttgggg tttttttgt tttttttttg ttttttaag aaacagagac 168780
ttgacttatt cctcccacaa actcttaccc tggcacaggg agaccacaaa ctaagtgaaa 168840
acaaggtaag aagcttagag aaatgggacc atatgccctc cccggagctg aaccgtgttc 168900
cctgtccacc atcaccttgt cttcccatgc tactactcca ctcctgtctc ttccacactc 168960
tgggtcacat gtctacccct tactgtgagt tataatcgcc caggaagggt aacccattga 169020
ctgagggcca agcttctgat aagtgaatga acttgtcttt tctcctggcc agatatctgt 169080
ctttgccaga gagggctgag tcagggagac taagattttc aaggtcaaat tgtatattgt 169140
ttaaaattgt gaaaatttgc tttgtgcatt gaatctcatt ttcaaaataa aattatgcct 169200
taagtcagat catactgatg cagattctgc agatgttaag aggcttccat gattgtattt 169260
gccagctgca ggtcaggcag tggtggatgg tggtaagaag taacctatac ttttggctgg 169320
gagctgtggt tcatgcctgt aatcccagcg ctttaggagg ctcaggcggg cagatcacga 169380
gatcaggaga ttgagaccat cctggctaac acagtgaaac cccgtctcta ctaaaaatac 169440
aaaaaaatta gccaggcttg gtggcacacg cctgtagtcc cagctacttg ggagactgaa 169500
gcaggagaat cgcttgaacc tgggaggcag aggttgctgt gagcgagatc gcgccattgc 169560
actccacact ccagcctggg cagcaaaagc gaaactccat ctcaaaaaaa aaaaaaaaaa 169620
aaaaaaaagt gacctatagt tttgcagtag aattttgaat tcaaactcag gctttatatt 169680
ttctccaaag taaattgtat tttgttcatt ttaatccatt ggttgactct aatgagatct 169740
ttctgactgg aaattctgcc cttttttcc tccataactg tattaccagt tatctctcat 169800
ccatgtgttt gataaatcca tatgaatgtc tttttttgtt ttctaccaaa acctttataa 169860
caaaacaaaa ttcatagctt tgtcaactac acttgaaaat tatgccccag gcttttcagg 169920
attctgtaat taacttattg agtcatttgt ttaaccattg gtgaattcat ttatctttac 169980
tcgggccaca gtaatgtatt ttacttacaa catattatga gaaactacat cacctgcttc 170040
accgaaattg aaaaacatta gatgaacaac actgccctaa accatatttc aataatcctt 170100
tcatgaaagg aaaggaagta catttcctat aatgatttgt tcttagtgaa gccatgttga 170160
ctccaagtga cctgttgttt cctttctggg ctcatagaaa taatctaacc attctaaaat 170220
attgatgggg attcaggtca aaggtatagt tttaaaaatt caccatattt aacctgttaa 170280
acattcagta tctcctacct tctgtcttcc aaaaatccaa agaaataacc atttattgtt 170340
ccgtttatgc tttcagtgtc taggacatag ctaatctgat actgaacatt tgaacttatc 170400
gttagctttg aaaatatgcc ctattgtcct attggcttta tactaaagtt ttattaatac 170460
attccctcaa tagtctccag tctttgccca agaagaagaa aattctgtaa gagtttcttt 170520
```

ttaccttcct ttcttctctg agtggaataa tcttttttgt tgtcttcata gtattttaga 170580
gttttgtgag atcagacaaa atttacctca gcttataact ttatctttta agtggaaaaa 170640
ctctgaacta ttgattattg tgtcatcttg aaaaaatagt ctatggaata tatataagta 170700
gttgtgttat ttttttcagt gttaagttga cctttttctt ttagtgcatt gtgaatattt 170760
aaaaggtcat ttgtgcaaca tataagagga ttgacaggtt tccatgcatg atgcttaatg 170820
tggagatgat ttctttccat caagttatta tgcttggaat aagtaacaca tcttaaaatt 170880
acaaccttga tgtagcaaat catcagatgg gttaccatta catggaaaga gccagtgaaa 170940
taaagaccat taagttcagg tagacagaga tggcggtgag aaattcacag ccaaagaggg 171000
ccatatggag gtgaaaacac tggtaaatgg ctctgggacc ctaggagtct acagtaagtc 171060
attgggaagt tggagtggag aaaggcaaca ttagctaggt atttcattca ttcctccata 171120
aatgcttatt gggagcatgt tgtgtgcctg gcatcatcct agcttcactg aaaagaatga 171180
ggaacatata aaatgtgaag gtgagaataa gtgagaagta attgctcttt actctcaatt 171240
atagctgggc aagtacatat atgaatatgc ttttgtgttc tgaacacaca ctaagcagtt 171300
ggtcaaagta ttaagctaga gacaacttct actttcaaat gtagtgtttc aaaataataa 171360
taataataaa gatttcagga cagtttacat ataaccattt agagatttaa ggattaaaat 171420
caggagggaa ggagaaatgt ctctgctggg gaaatttttt taaactagtg ttttctactc 171480
agctactcaa tgtgatttct tttattttct tccttccatt gcttattggc atttattgtg 171540
gggaagactg ctgtgttggc agcatgagag agatgggaat caagaaaatg gaaacaccat 171600
tcaatattca aaagccacta tccccttaaa agcaaccaca gatcattcag ttttgccaca 171660
tactcagatt gcacactaac tggaggatgt taaaaagtgt tctattacaa ccagttatcc 171720
agtttttgcc acttaaactc tgctgtgaga aatgtgactg tagagcagcc ttaaaaagag 171780
atcatcttga tattaagcag tgttactcat acatgcttgt tgacattcta acaggtgact 171840
ttgaatggat cttcaggctc agaaacatgg ttgtgtccct agaactggtg aggctggaac 171900
aaggtgtaca gaagtgaaat gaccacttgc tttctctatt ggatttcttt atccagctgt 171960
gcaattgttt cagggactac agttgatttt cctgatgcaa gcctagcaac ttgtttttca 172020
gttcagcaca gtaaaatatg aacaggagag aactccctgt tggccaccca cctcacaatc 172080
tttaaaaggg aactctgtac agaagcattc tgcattaggc aaatgtacac ttctgcaatc 172140
aaaatgaaaa acacttgagc tgaatcgttt ttcgttagct ttagtttcca gccctgatta 172200
aaaagaacac agggaaccct gcaagtttaa gcggttttgg cagccgagga aacagctgtg 172260
acattgtcaa gggttgtctg taggagctgt gcaggctgct gacagcactg ataatgccca 172320
gaaatggggc agacgctttt cgcatttggt catcaaagga gtggcagcag ctaggttcaa 172380
gaagtgaact tttgaccctg tctgagacaa ctggctctcg tggatcttgt tctgtcattc 172440
tccagtctga ttttctcttt cagaacaagt gggtaggatc tttggttttt aaactgtttg 172500
actgttatta aaagtaagct agttcttata gctgcgattg gaagggatgg aaggtgagga 172560
agaagagctg gtatttccca ctatcctgca ggggtgggga aatctatcaa cgactgttcc 172620
actaatctgc ggatgagtta tctagggaat atcatgcagt tgccaaagtt ttcagcatct 172680
aaaagcctcc aaagttctct ctgtgagggt ctacctcccc tgtctccaga tccttcccat 172740
gcccctcaga ctcagcactt gtccactgtc cttgctacca gggaatccct ctgcagcccc 172800
cttaccctcc tgcccctccc aaaagagctc cagactttga cctttctctt ccacctcaac 172860
atctgtttgt gtcttaaact gatgtccatt gaaagaaaca gataaactaa ttaatgctga 172920
gatatgactt atgaagtatt atgaatgtgc taactctctc aggggtatgt gcattttaat 172980
agaggaccag cagtccaaag gccggtctca ctccactgtg cccctctaac agcaccgagt 173040
ctatttccag gcagccagag accaggcctg agaacttgcc ccagaccacc agcgtcccca 173100
ctgagaaagc aagcagactc aacagttttt cagtgtttca gggagcctgc agcagcaata 173160
cagttccttc aaagggtctg tggattctct cagctttcct agtaggttgc tgtggtagtt 173220
tttggagcaa aagttcacga tgtgaatctt cacatgctgc tctttgtgcc gagcaggtgc 173280
ttgcaagcta gttctgcccc tatctgccat cttaatccta acatctccca tgttttttta 173340
atttaacttc tattttggtt tcagaggtac atgtgcaggt ctgttatata gataaattgg 173400
atgccatggg agtttggggc atacatgatt tcatcaccca ggtaataaac atggtttcca 173460
ataggttagt ttttatgtcc tcacccgcct cccatcctcc acccccaagt gggtgccagt 173520
gtctattatt cccttatttg tgtttatgtg tactcagtgt ttagctccca cttataaatg 173580
agaacacgca gtgtttagtt ttctgttcct gtattagttt gctcaggata atggcttcca 173640
gcactatcca tgtggctgca caggacatga gctcattttt tatggctgca tagtattcca 173700
tggtgtatat gtatcacatt ttctttatcc agtctactgt caatgggcat ttaggtttat 173760
cctgtgtctt tgttattgtg aatagagcct cagtgaacat acgtgtgtgt gtgtctttat 173820
ggtagagcag tttatattcc ttggattgtt gggtaaaata gcagttctat tttaagttat 173880
ttgagaaatc ttcatcctgc tttccatagt ggctgaacta atttacattc ctacaagcaa 173940
tataaatatt ccttttctc tgcaaccttg ccagcatctg ttattttttt gagtttttaa 174000
taatagccat tctgactggt gtgagatggt attcattgtg gttttgattt gcatttctct 174060
agtgaatagt gatcgtgagt attttttcat atgcttattt tccatgtgta tgacttcttt 174120
tgaaaagtat ctgttcaggg acatcattcc tatgaaaatg ctagttaatt atacaagtat 174180
tacttgtttc caataatcga ttttttaaaa aaccttataa tcaatattgc attaaaattt 174240
tcagctgtgt gattccttat cattttcttg gatgcaaatg ccttgtgtca cgtactatat 174300
ctcataaatc tatattgcat ctaacaaagt gctttgtgta aagtaggcaa ttaataaatg 174360
cttgtttaat gagtagattt gtttttgttt tattttgctt tctatgtttt cctaaggatg 174420
tggggcatta ggccaatgga aactgtctct caaaagttct tatatataaa tattgatgtc 174480
aaagtcacta tttttgtaca aataaacaca tttacctaat ttggtgagca tttatagagt 174540
cctgcctata ttcaaggtcc ctgtgctgat cagtgggcaa ctgaagaagt atgaggcact 174600
gttactgctg tcttccttcc ctaattgggt cctataccttatcttggtac agctacctcc 174660 taaggaggcc catctgtgct gttgagggta catctgaagg cagtgcactg gaatgtatag 174720
cctaggactg gaatttggag tgaggccctg agagatcata cacatttttc acttgtgggg 174780
gaatgtcctt aagtagaaat agatggtgat ttcagatatt tgatccaaac ctaacttcct 174840
catttgaatt gagtatgcta ataactattc ttgaggctct ggaatagtga tgacatttcc 174900
tggttgggaa atcagatgct gatttctgaa gcagagtttt aaagttgaaa gatgaaaagg 174960
gaacaaaaca ataaacacaa ccttagactg aagggtcatt tttctagtcc aacttccctc 175020
cacctagctg ccacccaaga ttgtccctca gccatcctta gaatattaaa ataaatccat 175080
tgcagtgctc aaatgacttg tttctatttg aaaatccttg ccattggaga atttttctat 175140
atatcttacc ttaatggctc tccacgaatt ttgtcaacag tttgtcagca atgtactcat 175200
gaaaatatct catatctatg tatattctat cactttagcc tccttgactt ctagaccagc 175260

-continued agttcccaaa cttttcaaat gtgacccctt ttagtatcaa cttctgttta taaaagtaca 175320
aaagccctca catcttatac tttcttttat gcttttattt attgagatat tagacaacac 175380
atacttgtag gtgacatgga ttcttagatc taaataactc cactctccat ggtcactgtc 175440
acttcaacac aggttgatgc agtccttagt ttggaaaaca gttttggcat aaataatccc 175500
aaaccttcct atcacttctt ggagcttttt tcttcatgct ttccttgcat ctttcttaaa 175560
atgtgaagac tacattggat atattattaa aataatgtca ttattagtgc tatgtttaaa 175620
gctgaccttt tcttcctagc cactgatata gcagtgccaa ctgtggactc tctttagaat 175680
gaacacttta gtaataataa gtccttagaa cacaaacact gtcacttgta aaacactttt 175740
ctatacttgg taacctacac agaacagcgg ttcccagact ttttcttttt tttgtcttgt 175800
gggtccttta tatattctta caaattatta aagactccaa agagcttttg tttatgtgag 175860
gttttgttat tgatacttac tgtcttagta attaaaacta agaaaattgt aaaacaacac 175920
atcccattag ctgtcagagc atcatcatgt cttgtaggct ctggaaaact ccactgtaca 175980
ctcatgaaga atgagtgtga aagagccaaa tagtagctta atattattat aataatagtt 176040
taactttgtg agctcaccaa tataatacat attcatgaca cagtccctaa catctaaaaa 176100
cttacaatct aaggcccaac ataaatacta atagatgatg ctaaattctg gcttcacagt 176160
gcttcctaca ataatactaa aaatatatga atttagacag aggccaaaat gtgtttatta 176220
accacttggc tttgcttagt attttgttac ccaccttgga gaattgcctc tgctgattta 176280
cactttataa gaagcagccc tatgaaattt tttatcataa gtttaacaat gatgtagaac 176340
atactgtttc attttataat gatccttggg caaaatgtat aatatctgtg ggagaaatgc 176400
tcaatgctgc agtaaaaact atacttctcc tcagaatcag gtatgttctt atatggtcag 176460
tataaatctt ataactgtgc tttctgatct cctttggcca ccaggaagac aggagctgac 176520
aatccaactt actataaatt cttcagggtc tgatgtcatt atttctataa gattttccct 176580
ggcattatct tatttctcag gtctcacttt tcctttgttc tgatttattt ttcttaatat 176640
gttttattgt gtatttgtta atatgttttg ttgtgtattt aattgccaat ggggatgaat 176700
gaataagtga gaaagaaaga tacttgatcc atttgagtgg gactgcttga gtacctggag 176760
tggtgcagac caagcagggt aactgtatca ggtttcatta atgaaatggg tcttaagtgg 176820
agattaggaa ggaaaggaag tgggttgctg gagaggcggg gtgtttttatg tgacagattg 176880 gctgtaataa agatgcagct gtggagtgag tgagtgatgt cctgagcaca gtaaggagat 176940
ctggctgacg tggcactgca cctcattgcc ttaatatctt ttcatttgat tgaagaggca 177000
gctgagggat aggtgctctt ggaaagtgga gtaaccattt ccaattaagg aaggactctc 177060
acttcagttt ctaaaataaa ttagaaggga gaaaatatga agtctgagag atcaattagg 177120
agaaagttct ggtgctacat atagaaatag gcttatccgc atatgcaggt gagagtacga 177180
agaagaatct gtgaatggca gtcatttttt gtagctggtt ccaattaaaa ttgattctct 177240
ataatgacta cttattggct gctgctcacc aggtctgcct ttttcatcat tgtctgcaga 177300
acatatcaca gtatacagca tagagtaggt gcttcataat gtgttaaatg gatgaaatgg 177360
gttcctacct ccaaaggaga tggaaaaaaa aaaacaggca agtaaataaa gtaaaatatg 177420
tataaattgc tttaagaatg ttttataaaa aaggacagta gcccaacagc attcacagta 177480
ggctggctgg agtagcagtc attgaagaaa cccatgaaaa cagcggcaga agcaaatgtg 177540
cagctgctct gccttttcac actgtagggc agcacacgaa tagtcctgga gcaccagggc 177600
ccttagactg tgggattttt aagttaccta gttggcacag cattgactcc tcctctggtg 177660
tgattagggg ccaggataca ataaacatat gttatgttgg aactttgatg ccagcctaaa 177720
cttgccagtt cagtgtttgt ggttgcaggt agtatcagct cctctcctga tatgattgag 177780
agactgaggt ccaaggcttc aggttgaaca gaattgatgg ccctaaggat tgggttagaa 177840
ctcttccaaa gcacttagca ggaagccagt ttacttttct tggatgccag cttccaagaa 177900
aagatcagtc ttgagcaaaa tagtccttca ctctcagctc agaagcctaa ttgagagggt 177960
atcctataag taacacagcc cactctgcta gtaacctgtt ctacttcaac ctgtaaggcc 178020
catgaggcta gccagtgaca tcactacagg acacagtgga ggatgtttag gaatggctgg 178080
gtgatgacca gggtgcagat tgtgtttact caaggctgat tgagaaatac tgttttcagt 178140
ggtgtgctta taaatgttta acagtggtgg gtggaagggg ggctctggct tgtagcattt 178200
ttctagtgcc catggtgtaa atactcccaa catgaccaac tttaagttac caatgtgatt 178260
gaaagtagag tttggaagcg aggcacagta gcccactgtt atgtagtatt tttgccatac 178320
agatgcataa gagacataag taacctgaag aacatagata attattaaat gtagtaaaat 178380
gatcatgaag tgacagatct tgagtgtttt atcacatttg tttttaatat aatttaattt 178440
taagttgcca taatttaatt tgtaattaag actatgttaa taattggctt atggaatttc 178500
tgagaattca aaaaccagtg cccataggtg gatccagtac accactaggt aagaacagcc 178560
tagaagtact tctaggctct tgttctgaaa ggtgccaaga ctggcatcca tggttccagt 178620
gccagggtcg aggaaagact tactaggtcc tgcagtattg ctcccaaatc tctttcagtg 178680
gccagggaaa ttatcagcct gaaggcaggc tgaatggctt gcttacattc aggtcccagt 178740
atctacgatt gacaatcggc ttcatttgta agtaccagat agtgcaactc catgtatcca 178800
ggaggctggg aggtactgag agcagactga tagtgtcaag agacactgaa atgactgcca 178860
gctctctcct gccatatcca ctactaagtg agaaattcag tgacatagtc actgaggact 178920
ccaccactgc tgggtgttgg ggagggcaca ctgagtattt caagacaatc cgggtaagat 178980
ttttcttgga gggattcaag tacaaaatag ttaatatgca gaaatgaagc agaaattatt 179040
atacctcaga aatgagtcag ataatactaa agaaaggaag aaaggaaagc atgacttgat 179100
tcatgtcttt aatgatgacc aaagaagttg ggtctttaaa gatgacaaga gaagactgat 179160
caggtagcag tgaggtggaa ggggaaagat gagagagggg acattcctgg tagaggaagc 179220
aaggtagaca aagtgtagga atgtgaaaga gcataatgta tgtaagtatt gttcaggtga 179280
cttcttgggt acctagatag tagagagaaa ttagaggtaa gaatggagga aggggagact 179340
cagggccagg ttgttgaggg cattttatgc catgctaagg agtttccaat ttttcctttc 179400
agtaatagca agaaacttaa aatgagcagg ggtttgtgtt tttgaaagaa ctgggaaaac 179460
acctctgggc aatccattac ctggggataa tgggtgaaat ttcccaagtt agtgcacagg 179520
ctgctgggta gggcttgagg ctttcctctt gcctcctatt tcaacactgt ggtcttttag 179580
gacttgtcct caacatgttc ttaaaaggaa tgtttgctaa ctgccaaaac agtagtcttc 179640
atatttattc tgttcctttc caaaaggtaa attgaaaaag caacataccc tcagccaaga 179700
gaattaatct tttatcacct aagttactgc ccactgcctt tcagttttaa agttaattta 179760
gtgtgcataa atggctatga gcccctggaa ctctctttat gtttgcatct taaatttacc 179820
agaccctcct tctgcctcta gttccagaat tttctttgtc ttattttctt caagaaatgt 179880
atttctttaa attggattgc aaatttggaa tacacacagt caaagccttt taaaaccatt 179940
cttttaaaaa aggacaagtt tcttgagaac atttttaaag gaaaaagtta aaatagatgt 180000

-continued caatggaaga tgcaaatatg aatataaaat atgaaaagca tctataggct ggagcttctc 180060
agtagagctc tacttcattt aaagtcatat tatctggcac catttcaaag cttttggtta 180120
cttgattttg tagttagaaa aaaagtataa agttgaaata ttgggctctt tacatgacca 180180
ttttgctagt agcagtggat gaagcttttc tctaagagat caatagcttt agtgtaaact 180240
tggtcaatac cttattggaa gaggtgacta tgtcagatta ggtagaaact ttaaaagcca 180300
gcaagtttcc aaatgtcctt ctggaattgg cctcctaggg ccatgtggac cagagagatc 180360
ttatcacaga agtcataaac tgatatccgt gagccaaatc tagctcatgg gcatgttgtt 180420
tggcctacag cacatttttt tttttttttt tttttttga gacagagttc actctgtcac 180480
ccaggccgga gtgcagtggc acaatctcag ctcactcaac ctctgcctcc cgggttcaag 180540
caattccctg gctcagcctc ctgagtagct gggattacag gtgcccacca ccacacctgg 180600
ctaatttttg tatttttagt agagatgggg tttcaccatc ttggccaggc tggtcttgaa 180660
ctcctgacct cgtgatccac ccccccgcct cttggcctcc caaagtgctg ggattacagg 180720
cgtgagccac cacgcctggc ccacaccaca tttgtaagca gatgaattgg ttatttttaa 180780
aaatttgaag aatttaacaa caaaaacaac aacaacaaca acaaactttt gtgtccagct 180840
tctttttttt tattgtccca atagttaagg acaatcctgg gcctgcattc tttgaacagt 180900
tggctagact taagtagctg ctgccccttt tagatggggc aaacattctc tactttttca 180960
cagtcccctt caagggtgct tcagccattt ttgctactca cttgtcttca ataaaccaag 181020
gtcatgttta aaagattaaa taacagttat tgcatgctca ccaaaccgtc acaaggaacc 181080
agacttgtgt accagaacag agtcctggag catatctctg ttaggctaga catcactctt 181140
ttagttatgg gatcatggaa aggtgcagaa agttccaggg aaggggtcgg gagggatttg 181200
gtgagtgagg cacttggagg catgggtcaa tagcttttca ccagctagca tggaagtact 181260
tttagtgttt aaaaacctat ggcacagtgg gatcttctag gaaagtagac cctggagatg 181320
gagattcaca tgtagcacat ttattagggg atgccactag gatcaatatc tgtaaaagag 181380
agagaaagga tgtaagagtg ggcagaggga gaagttgagc tgcaaagcag gcccagtgcc 181440
agcctcaact ggctccataa ggagctctgg ctctggaatg cccttttata tttgtttccc 181500
atgggaccag gatggctagg ccattctact ctgacatgca tcactcactg aaagtgggaa 181560
gagtcttgct cttgagtgag gaaatcccct gctactgagg caatccctca aaggagtaag 181620
aagtgaaagc tcctggcctg gagcacctgc aacatctgaa acaagaaatc cttcattgaa 181680
caggatctgg gcagcacacc agagtgatca cagtcagcag ctataccagt gacaacagat 181740
gaatatcaac tctgccttta gcccctaggg tatgacacct ggcctaccaa ggctgtgcct 181800
aaactctttg gactgattca gaatcaagca agtcctagcc taaagagagg agtttaatgt 181860
catgctacgc tctagcccaa tatttgctga cttgtaattc agtcattaaa aaaattcttt 181920
ttatcttcac atagttttag attgtcaaac tgttaccgtt ctgtgtccag aaattaaaat 181980
ctattctttc tattcttttt tttttttttt tttttttttt gtgacggagt tttgctcttg 182040
atgcccaggc tggagtgcga tggtgcaatc ttgtctcact gcaacctccg cctcctgggt 182100
tcaagcaatt ctcctgtctc agcctcctga gtagctggga ttacaggcgc atgccaccat 182160
gctcagctaa tttttgtgtt tttagtagag atgaggtttc atcatattgg tcaggcttgt 182220
cttgaattcc cgacttgagg tgatccgccc cgctcagcct cccaaagtgc tgggattaca 182280
agtgaaatct attcttatat tttattgtaa cctcagaaaa gaatgctttt ttgaggacta 182340
gagttctgtc tcttttattg tcttctcctt tctctttccc aaacctataa ctctattttg 182400
cttagcacac aatgaataat cagatgtctt aaattgtggc ttacataatt actagtataa 182460
ctttttgct tttttttatt tcattttaat ctgttcatga ggactgttac ccaggtattt 182520
aaaaaatctc actccattgt tttaaggtta gtggttccaa agggatttta gagaccctga 182580
cccaataata gttatatttt tctaagtggt tctgaagcaa tggtcacaag taagaaactg 182640
cagttcaaaa cacatcatag gtttgttatt ttccaaattc ttattaaagc attaatgcaa 182700
atggaatttt cctactagta ttctgctttc tctaatcctt gacaggacta attgctaaac 182760
tataatatga tttattataa ttttatgttt atattaaaaa tatagaatat gattgccctt 182820
tgatgtcaaa tactaaagat cctgctacta ttttagttgt gctggttctt ttcttcctta 182880
tctttcattc accttttcaa ttcatctcat aaacatttaa tgaaaaactt attgtgtatc 182940
aagggttgtt tattatatga tttgtaattc aaaaactttc tttctctggt ctgagaattt 183000
tagaaacatg aaaagaaaga gggagggaga ccaactgaga gtataaaaat aaatctggca 183060
tttattaaca gttaaccaat ttcttttttc tataataatt tatctactaa actgtatttt 183120
ttaaattatt gttttagttt ttgttgcata tatttaaggt atacaacatg atgtttttta 183180
taattactag agtgaaacaa attaacaaac tcatctccta catagttatc ttttgcgtgt 183240
atgtgtgtgg taagagctcc agaaatctac tctattaaca aatttccaat atgcaataca 183300
atattattaa tgatagtctt tctgctgtac gtcagattcc tagacttatt catccttcat 183360
aactgctact ttgtaccatt tgaactacgt tttcacatcc cctgtgaaaa tgggaggggg 183420
gccgtaccat ttgcatggaa tatctttttc catcacttac cttttactgt atgtatgtac 183480
tcagatctaa actgagtttc ttgtggaaac catacagttg gatcttcatt ctttacccat 183540
tcagccattc tgtatctttt ttattgagga gtttagacca tttacaattt aagtaattat 183600
tgatagggac agatttaagc ttgccatttt gtcaactgtt ttctatttgt ttataattct 183660
tttttctctt gctctcttct tcagtgtttt gttggatttt tatgctgata ggttttgatt 183720
tcttcttttg tgtaacttct atatattttt tctttgttgt caccaaaggg cttacataaa 183780
atattttaga gttgtaactg tccaatttat gctgatagca acttagcttc ctttgcttat 183840
aagaactctc tgcttttacc tcttctcccc cattatatgc tactaatatc ccaatgtaca 183900
tctgtttata ttgtgtatgt agtaacataa tttagttata gttgttttaa tacttgtctt 183960
ttagttttta tagtagaatg aacatattta cctaccactg ttatagtaat acagtattct 184020
gtattatttt ttaccaatgt gttccctact ctgctgcttt ctttttgttt caattttaag 184080
agctatcttt ggcatttctt ataaggcaaa tctagataaa ctctctcaac ttttgtttgt 184140
ctgagaaatt atttatcttg cctttatttt tgaaggacag gattgctggg tatagccgtc 184200
tttgttgtta ggttttgtgt tttttttttc ttttttcagc acttggaata tatcattcaa 184260
ctcccttcag gcctgcaagg tttctgcaga aaaatcgtct gataatacta cagagatttc 184320
attataagta gcaagtcact tctctcttgc tgctttcaaa attctctttg tcttcaactt 184380
ttaacaatta taatgtgtcc tggcgtgggt ctctttggat tcatcttact tggtgtcgtt 184440
tgggcttcct ggatctggat gtttattttc ttcccgggac tggaaaatat tcaaccatta 184500
tttctttgaa tttttttctc tctctcttct ccttttgtat attccgtaat atgtatatgg 184560
gttcacttga tgttattcca aaattccctt aagctatctt tacttctctt cattcttttt 184620
tctttttgct tctctgactg gataatcatc aataatctgt ttttgagtta gctgatcttt 184680
tcttctgttt gatttagtct tctcttgaat accttctgag taaaaacaaa caaacaaact 184740
gtttttcctc tgctttcaca gttcaacagc aatcagtaaa gaagcccttt gtgacaaaat 184800
gtgtgtttag ggaaggggtg gtttccttca cacaacaagt aagcaatcag ttctgcagta 184860
aataccagtt tggtgtcctc taattcaatt ccaacacttc tactgagaga tcctacagat 184920
tgggggctca gtccccgaga ctgtcttcct caaccaactt ccaatgccaa ttgcaaaccc 184980
caggttattt tgcctgtact tcttactgac tggctataaa ctgaggttcc cacaaccccc 185040
ttctgaggtt caattaattt gcaagagtgg ctcatggaac ttggaaacac ttgcttatgt 185100
ttatgagttt attataaagg atattttaag ggatacaaac aaacagccag aagaagagat 185160
gtctagggta aggtcaggaa gggtcatgag tacaggagct tctgtccttg tggagttggg 185220
gtacacaacc cttcggacat gtagatgagt tcttgttcac cttcctgtaa gccttcacat 185280
gtatagctgt ctagaagctc tctaaatcct gtactctttg gccatttatg gagacctcat 185340
tggataggca tgattgacaa tcatgtggaa atgtgattgg acaaaaagag tattagctag 185400
tgctaacaga ctgaatggaa aacccagaaa ggcctgtctg ttcagattct tcctggtctc 185460
tctctgcagc attctttcct ccagggaatg gggcaggacc tttttgaaa tgaaaatctt 185520
atgacctaca atcagacaaa gtaggtcaga gaatttcttt atggccagag gcaggggaag 185580
acttaagtgt atttttagtt tctgttgcct gccttatgga gaaaaaggaa caggtgaata 185640
gagggtaaga gaaagtcata gagagatttc tgtttttttga ggcctgcttc taatgtctaa 185700
agcaccccag cattataata aaagactgta ataagagcta aggaagttat gagccaggaa 185760
ctgtggacaa agtaatatca cacccctcta tttttttttt ttttttagtt tacttactgt 185820
attatttatt tccatgattt ctgtttggta ctttttaata ttttctatct ttttgttgaa 185880
atctcacttt gttcatgcat tgctcacata aactcagtga gcatctttat ggctgttatt 185940
tttaattctc tgtgaaatca gttacctcca tttcattagg gtcagtttat agaggattta 186000
tctagttctt ttgtttgaaa tatattttcc tatttcttta ttttccttga ctacctagag 186060
ctttctttaa attatatgaa atagccatct ctcccagtct tgtcaaactg gctttgtgta 186120
gcagaggtac ctcaccaatc aacttgacca gagatttgtg gtgcctcttt tttttttttt 186180
tttttttttt tgagacagag tttcactctt gttgcctagg ctggagtgca atggtgccat 186240
tcagctcacc ccaacctcca cgtcccgggt tcaagtgatt cccctgtccc ctgtctcagc 186300
ctcccgagta gctgggatta caggcatgca ccaacacgcc cggctaattt tgtatttttt 186360
ttagtagaga tggggtttct ccatgttggt caggctggtg tcgagctccc gacctcaggt 186420
gatccgtctg cctcgacctc ccaaagtgct gggattatag atgagagcca ccgcgcccgg 186480
cctggggtgc ctcttaaact tttgtgctta ttcaaaccac cagttttgtt cttagtggcc 186540
ctcggtagga atgtcccaag tcctaagtta gtgaccaagg tagagaaacc tgtccctcaa 186600
gaagcagcta gaaatattgg ggctctagat gagtggtcca tcttcctctc tcctcaggga 186660
taagctggga gctggacttt ataccccact cactctgcag tccagataga ggatctgtgc 186720
caaatgcttg tgctctattt cagacaatgc tctctttaaa catttacttt gctctctcaa 186780
atggcaggtc tcattagctg tcctggataa gtgaattagc tggaagcttg gttatgtttc 186840
tggagtgagg agctgcagga agtgccctca tgcctgttca gactcccgga gttctactaa 186900
ttgcctgctc catcagctcc ctgatgcagg ctaattaata gcttaatcca cggacagcag 186960
ctaggaaagt cagaatatta tgtatgcagt ctaactccgt ccagggagaa actgagagct 187020
gggtgttttt gcttgctcac tcttcactga gcttggggaa ctagctgctg gtagtgcaca 187080
tgagctcatt taaaaccact tctttgttcc ttgtggtctt gggggacaca taaatgccag 187140
tcccccatag ctcccagagc taggtgattt cagagccagt ctctcaggtg ggagctgtaa 187200
aagttggggt gctcaatgta tggacaaact ccttccagga gagattagat gcttgatttt 187260
atcattggat tgagctgggg gagaaggcac aggaagtgcc cacacactag tgcccacata 187320
catacccttt caagctccca gaggtcttac taattacctg ccccactggc tcttagtcca 187380
cttagtaatg ctataaggaa tacctgttgc tgggtaattt atgaggaaga gaggtttatt 187440
tggttcatgg ttctgcaggc tgtacaggaa gcatgatgct agcatctgct tccagtgagg 187500
gcttcaggct gtttccactc atggtagaag gttaagggga gttggcatgt agaaatcaca 187560
tggcaagaga tgaggcaaga aagaaagagg agaaggtgcc aggctctttt caacaatcgg 187620
ttctctcgta gaaactaaga ctgagaactt aaccactgcc ctgacaaggg caccaagcca 187680
taaatgagag atcattctta tgacccagac acctcccaca aggtccacct cccacactgg 187740
ggatcaaatt tcaacatgaa gctttctggg gccaaacaaa ctgcatcaaa atcgggctcc 187800
cagttttaga ctatgtagaa ctttaatcct tgggcagcag ctgggaaagt gcaataaaac 187860
ccctaccaga gagaaactag gagttgggca atatcgcctg ttcactctgt actaagcctg 187920
agggaattgg ggtaggaagt tcttgcacac ctgtttaaaa ttgccacctt gttctctgtg 187980
gtccagagat aattgcaaat gctgagccta tctgcttcca gagctaggtg aattggtgat 188040
tatggtttgg ctctgtgtcc ccacccaaag attgatcatg gggacggttt cttccaagca 188100
ttctcatgat agtgagtgag ctctcacaag agctgatgaa gttttaaagg tgtttggcag 188160
ttccccctttt gctcactttc cctctctcct gccaccatgt aagatttgcc ttgcttcccc 188220
ttcaccttcc accatgatta taagtttcct gagccctccc cagccatgtg gaactgtgag 188280
tcaattaaac ctctttcctt tttaagttac ccagtctcag gtagtttctt tctagcaggg 188340
tgaaaacaga ataatataag gagcaagtcc ctcagggagg agctgtaaaa gttgaggtgc 188400
tatatgtgtg gtcccaaccc tttaacttct aagaaggtaa agctaggagt tgggtttcct 188460
tcctgattac aaagtgatgt gcctgggtgg tgctattggt gtgaattaac caatttctta 188520
aacatcaact aggtgttcca aactgtgcta agggctaggg aaaaggcttt gttatcctta 188580
ttctgagaga gcttatagtc tgattaggaa taagaaaact gacacaaaat aacagcaaat 188640
aacaaggcaa cataatcagt tgctacatgt tatggtggta tataaatgat ggtagaattt 188700
agaaaactga aaggggacag gatagacaag agtggtcagg aaggctgcat ggaagagaag 188760
gaacttgatt tgggatagaa gaaggggctg ggatttggga agacaaaaca aaagaagagg 188820
gccattccag tatccaagta atgacagata gaggcacagg gcatgtatta acacgagaat 188880
agcagaagtt tgatgttggt tagaacttac taccaacttc ttacagaact ttcctctaag 188940
aattatgagt ttgaaaacat tcaacacctc aatctacttt caagatttcc tggcaaagtg 189000
aaggaagcaa ataccttttat tattttacaa ctgaagttac ctgttttgtc agttatgatc 189060
taggctgatt ctaactacct atgggcaacc tagaacagtc aaaagagcta ggaattcatt 189120
caaaagacca aaatctgcat tgtctggtag tgtgagcatg agcaaatcac ttcatctcct 189180
tgagccccag ttttctcatc taggaatgaa aagtagagcc ttatctatct gaccaggtta 189240
ttatgctatt aagttatata agtaaatgtg aaaattcttc ttaaacaata aaacaatata 189300
aattttagtt ggtacttttg ttaacatcta cactagacca cgtttatata ggtaatttaa 189360
aaataaaaaa gaatggggaa ttcattctta tgtcatggat ttatattttt tttgtagtac 189420
aaagttaatc gctcagcagt gtttgttaca tttcaagtag caaccatcat attgccatga 189480

-continued

```
aatttattta gtaacccccta actacttttt ttttaatgaa atagcataga atgaaagtat 189540
agtgtatatt gtacttttta gggcagtaga ttatatcatt tgtcataaag atgagtgtcg 189600
tttagtgaca cacaaaggca taagtgacat acacactggt caaaatgtaa aatatatttc 189660
tttttgtgga ttgttgtcaa agaagattga aagacactaa ttaataatat agtatttcaa 189720
atataaaatc ctcagtcttc atattttgaa ccctcaaatt aaactaacca aaaagataaa 189780
tttcagagaa aagttatttt atgtaaagaa agtgagattt tgatgaaatg agacatgcta 189840
ccacatattc tttattttct tcttatgtct cttgctgaaa cccaaattct gtcttcactt 189900
ctgctgccca agtatacaaa gcaaagggat tttttgtgtg tgtttccatc aaaagctaca 189960
tgcctagaaa ctcattgtac tctatttttt ctggtagctc ttgagttgtt tattttaact 190020
atcaatcaat attatataat ttaaaaataa aaacttaatt tgtgacaaag taagttttca 190080
gtctgggttc aggaaagaaa gggatggcat atgcaaaaat gatgtaacca ggaagaatgc 190140
aataatatgt ctatgtacaa gaggggtgat agaattaagg aaaccaacca aagatggtga 190200
agaacccaga gctaagaaaa gggtactagc tcccaggcct gaaaggtcac agtgttctag 190260
gttccagaag tgacactgag cagtgggaga ggagcaatat tactagtgcc atcatgggaa 190320
accagtcttt tcaggaaaga gagaggcatg gaggggacag gtgccaatgg ctgaacccaa 190380
tgaagaccaa gggttctggg caatgtcatc tgtaatggcc aacttcctgg ggcacagagc 190440
agggaagacg agagtggaaa atgagtgtgg agcaacaaat ggggagtaac cagcaaccta 190500
ttatatgaat gatcattttt catgtcagat ggtggcatat agcttttcta ctcaaattca 190560
gtttccttcc tctgtttgct aactggccta gaccaatcct gatctagccc atggtagttt 190620
actttggttc ctagctgttg ggtagccaac cagtggtgtc ttcctgcagg aacttcttag 190680
aagggccaaa gataaaggat gaagtgtcct cattgatttc atagacacaa ccagttctag 190740
atcactggtt caaagagggt aataaattag taaagtggga gaacacgaaa ttaggaagat 190800
tcatttctgc tttattgtga actgggtcaa tttttgcttt cttaatatta atcttgaaaa 190860
agatatcctt tgaaatctca aaatcctttt ctgtaattta aaaacaacct taccatctgt 190920
gtcctctgtc atatggtaca atattcaaga gggtgaaata atggtccagt gactaagaaa 190980
aaccttaaag gataaattgg ccttagtgac tgtcactaaa atgtaaacat ggctttaaaa 191040
agtaaatcag gaggcatgaa agggccttga cagctaaggc tctcaggaag ggtctagaaa 191100
gacatgaagc acaattttat aagtgtgata taggagttac tcttcttttt ttattcatgt 191160
gtcatagaag ggaaaggaaa tttctaaagg agtaagacca gccagatatc acaagaatat 191220
acaggaatgt aaggatagca tgttcaaggg caacatgagg agtcaaagaa aatgtcctgg 191280
atgccaagac tagctgtgtt cttgcagctg ctggctcctc cttggcaaac acaccattgg 191340
caatgaactg atctgatgtg aacccctcta agtccttgag actctctttt tattgcaaag 191400
cttgccagcc tctttaccca gtacatgtac tccactctaa gaagaaaaaa caaaactaag 191460
tgactgctaa gctcatggac aatgtttttg ggtctctcca gcagccagct agtggctgac 191520
taggtaaaat catttatttt tctcaagatg ttgtgattct gggaatgcag ggtttggctg 191580
ccatgttagc ctggattttc tgagatgcat ccctgcaaga gattcactgg gaaattagat 191640
gtgcaagaga tttatctggg gaaatgccta tgagggaaaa tggagaagga gctgcagaag 191700
gctggaagag atgaccactg cagtacaggt ctaatcccag tggaaaaaaa aaaaggagag 191760
aaggaatgag aaaagggaaa gagagaagga gggaagaaag gaaagaggta gggagggagg 191820
gaaagtctta gacatcagtg cagtgccaag aaagttttgg caaggctgat ggggagtctt 191880
```

caaaccaaag tcacttgaaa gaggaatccc ctcatcatcc ctctaggaat gggcctgcct 191940
tggtgtcctt gtcatgcaaa gtcactggct gggtggattt cagagcatag cagctgaggg 192000
cataggccag ttacactctg ccataggagg cttgagagat gcattttcat agctgccaca 192060
tttgccactg aaaccttctg ggagtgatgg gttgtgctgg aagaatttga agatactatc 192120
ttatgctcca gataaagaaa tgcattgatg aaggcccttc actattagat ttatttttgt 192180
gtgtcccaac tattatataa attcccctat caaggaattt tcagtgtttt ctccttgccc 192240
ttagatatgt gatcttatat cccaggtttg ctgagacatt cctcttacag atagttctac 192300
tggctcatga gtgtaatgtg tctaaatgta tggttggaaa aatgtggtta ttagatctaa 192360
attttaagtc caaatttcct tagcctgaag tttagagtct tccacagtct agtcccaacc 192420
actttttcca accttaatta ccattgcact ttatcctgta tttcaattca tttgaaatat 192480
ttgctccttt ctaaattact cttgcttacc caccactatc tctttgttca tactgttctc 192540
ttcaactaag gttaattaat caacatgtat ttattgcccc cttcccatgg gccaagccct 192600
gtgcttagaa ctgtatgtta ggggacaaaa cgcacatggt ttctgtcttc ttagagtttg 192660
aatttagtag aagaggaaca gacaaataca caggtcaatg gacagtgcat gcttacaaat 192720
catgtgacag tgtcaaaagt aaacaaagag ggttccctga cagagaatta gaggaaggtt 192780
ttattttaga tagagctatc aggaaagaaa tggcatttca gctggaactt gaatgataaa 192840
gggaatgtag ttactaagga cttaagtcct gcaggtacca gttccatcat cttcaagata 192900
ttgccatgat cttcacaaaa tctttactga ctcatcattg gactctcaac caattttagc 192960
cctgtgctat ctgcatcttt tatatcacag aaagtgttga agttcatact atatactaaa 193020
tgtgtttgtc tccaatcaga ctataagatt gtggaatgtt agacccatgt gtgatgtatg 193080
cctttgtatc ctatcagatt atatgatttt ggaaggttag agctatgtct gtatccagca 193140
taatatttat ctctgtatct gcatgatact taggataata gtatgtggcc acatccaaca 193200
aatacttgtt gaatgaataa acagtattcc actctctgca aatttggtct ttctgacatt 193260
tgtctgaatt atagaaggag aaggaggctt tacataatag ttgaaaatta ctgttcatgt 193320
aatacagagt tctgaacttc aaccagaagc aagtctacag cagatgaaaa catttgtaat 193380
gagggaatta gctgtggata actttcggat aggatgttat aagtttagca tttgtattaa 193440
aatccattat tatatgcata attaagtttt aggaagaaaa tctggctgaa tagtaaacaa 193500
ttactatttt caaacagttc ttcagcagtt agttaccact ggcttctaga atttaactgt 193560
tgttttttttt aatatatcaa actagcatgt gggttgagac acaacatcac attacaaatg 193620
ggtagtccct tcacttgtag atcaatcagt aataatatag atactgattt ttacagtttg 193680
taaaattatt gtcatttctt tctcttatta tctgtattct cagaaacaaa gagtataaac 193740
aaagagaaag ggcatgatgt atttttgata ggctaccatc tcaaattttc atttcaatgt 193800
ttatttggag aaacactttt atctaaaatg gacctttttcc attttacaat tgcacttgct 193860
ctcagaatga gaactgcacc ttccaggaga gatttcaatc tgactccaaa gccttgaccc 193920
tcacaaacag tgttgtttgt aatggcccct ggttagaaac tctcagccta acaagcatgc 193980
agcatagccc ctgaagtctc tcctcctatc tgcataaatt ggggatgtag aactcctgca 194040
tatccagcct cacttactca taaaatgctg ggaatcattc caaattgctc ttccagagga 194100
gggtttgttt ttaaaattat ttcagataga gatgtttcaa attctacata aatgcataat 194160
attatttctg attgtgcttt cttggtattt ctcttcctgt aacacctact tagccattct 194220
ccagggacca cttcaaggac ttttgtaatc catatagctt tcctaagctg ttctaacttt 194280
cagcaatccc aaccacatca ctgaccgagt ttgtaatgac tcaccagaca atgtgttggg 194340
tcctctagta atactttgtt aattccaagt tatccttgct gctgttgttt ctccgtgtgt 194400
gtttctatct gcgctctcca gttaagctgt aatcaactta accactgggc tttgtcttat 194460
actctacttc tcacaaccct tgcctcttaa attggttaat gtatgtttga tgactaattg 194520
tacacataat agctacttga taaatgttct taagaaaggg acaaattaag tattttccct 194580
gataatcctc tataccaggc atcgctgtgg aaagctgcac agttgggaaa gcgtcatttc 194640
aaaaacagga aaaatcacct gtaaattatt tcagggattt gactttgaca ttatgttgac 194700
ataaaagagg cttaagaaca gctattagaa aatagaaaca gataaatgaa tgagtgaatg 194760
gcatacctaa atggcatgaa atgtgaaaat gatacaaaat gttaaggtaa tcctttttttc 194820
ttctctaatt aatctccact gggtatgggg aatagggaac aactggggta ttcgtaacag 194880
gcaaacattc ctgattcttg ccctactaaa ggtagggaca ttaggagaaa ggatcatcta 194940
cttggaaaat aaactggcat tgctaagtct aaatgattga gtcaagtgca aattttatag 195000
gccaaataga attttcacaa gtccattgac tgttgaaaac tacttgtacc ctggctcaaa 195060
ggacatttttc ttgctgtctg tagtaagcgg tctgtaaact gtgtttagga cctgaaccga 195120
atgctggcct ttcacttctc aaactatagc ttagtaatcc cagctcagaa gtccctccat 195180
acacaattta gtaaaattaa catcagagca taaccatgct ttgttccctc cagaagtaaa 195240
atgtgaagtt tcttcccatt ggaagtctat ttattattag tttcagatgt tgtgacaccg 195300
ttttcatcca aatgttagag aacagaaaga agcctttttt aaaagcgtaa ctttcattat 195360
tcatctaggt ttttttcagg gtccttgaga aatgctaaga ttatgccttg tgtttgagaa 195420
gtagaaaagg aaaaagggag gaaaaccacc tagagaagtg cttctcaaac tttaaggcac 195480
acatgaatca cctggggacc ttgcagattc tgattctgaa ggtcagaggt ggggcctgac 195540
atcctgcatt tctaacgagc ttccagggga tgctgatgct gctggcccac agaccatact 195600
acctagagca gcaagcttta taggccatag aggacatttt tttttttttt tttttttttt 195660
ttttttttgc atggagcaca gattactgct ctactctagg ttacaattcc aaggaaataa 195720
tgactaaaga aaaatactgc tgtttcaaca tttctgagtc atttagtaag aatggaaggt 195780
taacattagc aatttaacat ttcaaatgtg gtgggagtat ttattgatgt actaatttgc 195840
attttgttcc tgccaaatct ttttactctg ttggctccag ggagtttgaa agtctaggac 195900
agaatttttc ttcctaggtt tgtttacata ttgtggaaaa gaagtgagca tctttggagt 195960
taaggagagt taagacccaa ggagaagaaa gaaaaagact atgaaagatt tttaaaatgt 196020
ttatccctgt gtaagatctc caaagcccct cccttgaccc agtagtagca aatggagcca 196080
cagtgatggc tgaaattgaa tatcccacta acttggtaaa agttgggcag gctcccagtc 196140
agacttaaat cattttagag aagtacaata atgtggcatt ccttgcaccc tggtgatatg 196200
cagaaaatac atacctgctt ccgacgaaat ttaaacatgg actgttaaca agaatgtacc 196260
cttaaagttt tgtaaactct acagcaaaga aaaaaaaaac tgctacagaa aaaataagga 196320
ttttttttct agctttacca gcgacctata ctttcatttc ttcatgttac taattacaga 196380
aactttcagc agaaatgtat cactcttggg catcagttag ttctaaacat tttagctctt 196440
aggagcctct gatgacatct gttctgttgt tagttttgct ccctgactag attgtaactt 196500
ctaagctcag gaatcatgtc tgcaactact tttctttagt cctaacctaa ccaagagcta 196560
ggcatttagg aaatgctcac tataaatgta ttgacaaatg attatgtata attagctctt 196620
catcacaata tttttcatca tcaagaaata gatttaaagg agatattttc aaacagtatg 196680
gatgtatcat cccccttacct ttatgtatgt gtctggttgt gaatagtcag cacatattat 196740
ggttaaactc aagaaacaag ggaggttatt ttctaagcct gcatcatagc agtagaaatt 196800
tggaaaaaaa caaaaaacaa aaaaaaaaaa acatagaatt aattgagttg taatcaaaga 196860
aaattatgtg actataaatt gtaatatttc taaaatatac ccacatatgc caatctattg 196920
taagaaaatg ttcgcagagg gaaaacaatg gaaattccta gaagctttag atagattcta 196980
atgattggaa ataagtatta caaatggtcc acattttaat gtgacttcta gaattttttta 197040
gaagtcatag tatcctttca cgctcttatg ctgcttgctt acaacataca cttgggtcac 197100
gtttttctgt taggaaatat catactaatg atttgtgatc atatttacca cttggggatc 197160
ttggtggcca tgataaggaa tttggacttt attctgatta catgggaagc cactagagaa 197220
ttttagccag tgaggtagca tgatcttact tatgccttaa aaaggttaat tgttttggta 197280
gttaattgaa ggaaggcaaa agtggaagta ggaagtctag ttaggaaact atttgattgt 197340
tcgggaaaaa ggtgctggat gcatgggcta taataatagc aaaggagatg gagagaagtg 197400
aatggattga gatggaactg aaagaacttg ttgatggtta aatgagttgg aaggagttag 197460
agaaagcaaa gtgacaaaga tgactcagaa gtgtttggct taagtacctg agtggatggt 197520
gaaacaattt tcagacatag agaagaattt aggaagaaca gttttttttca gacattgctc 197580
gagagttctg tgttaggatt gagataccta ttagatacca actgaagata ctgaagaggc 197640
tgagtagagt ctgaagttca atggagaggc tcagactaag atagaaattt ggaaccatca 197700
atgtgtagat gatatttaaa gccatgagac tcgatgagat tccctttgca ggggaaaaaa 197760
aaaaaaaagc tagaatattg gagggaagag ttttgtaaca ggacaatatt tatgggtcgg 197820
gcagaggaaa agaagccagt aaaggagacc aagaaagaac agtcggtgag ctagaaggga 197880
caccaagtgg ctcaggcatc ctcaaagcta agcaaagagc atatttttaa aagacagtaa 197940
tgtactgggt caaatgcctc tgagaagtta agtaatataa gaaataagaa gggactattg 198000
aatttgatat gaacaggttt agtggaatgg aaggattaga agtaaaacca aagtagattc 198060
agaagaggag aaattaggaa gtagagacag ccattcagac aaggacttaa aagatccagg 198120
aatggaaagg aaattcctgg gagcgcaacc cctaagaagc caaaaataga gtatgctttc 198180
catgtaggtt tttaattctt ttttggtggt gttctttaga aagagaaatg tctgttggga 198240
ttattgtttg aaatggtgtt gggggcccaa ccatttctgg cttctataga tccccttttt 198300
gtacatgctc attcccttaa aaaaaaaaaa gaagaagaag actagatttt ctaatttagg 198360
gcaaggggct aatagcaaac caaactcatt tgtaatctaa atggtcacat attattttgg 198420
ttgctcttca gtggcactag ctgctgctag gaagttcatt ttacacacac acacacacac 198480
acacacacac acacacacac acagcatttg ctgcagatcc taaacttgaa gccctggatc 198540
ttccttacat catttaccca gaagtatctt tgtcaacctt cttaacttac atccaccaga 198600
aagtagaaca aggcagaagt tgtgtgggag ttctgttcct ccccatttcc cccctcacct 198660
gctggcgtca gcacaataaa tactgtgttc agaacttggc taactgcttc ttttcccaca 198720
ttcgatcagg gaatacttaa agccatacag tgtccttgtt ctgccaaaaa gcatatgggg 198780
caggttgccc cttcaggctg acacaaagac acactgtgca agacatctat ggccagtgga 198840
gtggccgtgt atgggttatc aatgagactt ttgacttttt tctttatgtc atattgtcat 198900
cacattaaat agaattcaaa caaggaaaca aaatttatat tctagacttt taaggcattg 198960
cctgccctat agctatgaaa cttttctttt tcatacctgg tataattttc cactttaaac 199020
aatgttgtgt gatttgatta ccgttttgac tctcatttaa ttgtccattt taaaaatttt 199080
aactgaagtt agatttagat ttaaagttca atacccataa aggatacttc tcaatagagc 199140
cgagaacttc agaaggcaca acaaaaaaag ggcaaagttc aaaaaactaa gcatcaggta 199200
gctacttttt actgcccagg gacatgtcta ggtaaactgt caccatatcc atctacattt 199260
gcttgctagt agagcttcca ttttctactg caaaatagtt tctggaacca cttccatgtt 199320
ggccaaaaga gagtgtcaac aattcctttc caaaattgac ctttagaaag tgaatctaaa 199380
atgtttgatt caagtatgtg aggggagctg catcaaagtt ttcattttta ctacatacaa 199440
aagtgacaga taaatccgta aaatgtatgc atttttctgc taagactgct aattaattta 199500
aaaagagatt gttagaataa aaggtcagag agtaaacata ttacagatat ttattgagag 199560
cctgctgtgt gcagagttgg aaaaaataaa atgaggttgc tcctttcaac agacttacaa 199620
tctaattgag ggagcgacag cataaatgta tgcaaagcaa ataatgcaag atacagcata 199680
agacataatt aactatcaga tgagtgacat atataataaa taccattaat tcacaggcaa 199740
tcgtaatcag aagcacttaa cttactatgt gccaggcatt ctgctcagta cttcacatac 199800
attatttcat ttttttgaaa tattatttct actttataga tgggaattgg ctctgatctt 199860
ccccctattc tggagaaagc aaggataatg gtgtaaggta gacaaagacc caagcagaca 199920
tgttggtctg gggcaaaggt ccatttaagg gaatggagag aaatgaaccc tggggccagc 199980
attagtctgt ttacaaccat atcccagtgc ctagtatagt gccttgcaca taataagtgc 200040
tcaataatat gtcttgaaaa aacaaatggc cctctggtct gtgcctgtaa tccagatcaa 200100
gtaccatgga ataaagttaa ttagtgaatt aaagccacat accacatagc ttaaggaccc 200160
atccccaaga cctcccaatt cccaactatg acaataaagg attgcagtgg aaaagataca 200220
tcataagggg aatagcaata gcaattccag ctcactgggg tctatttcat ggaatctgac 200280
atggtgaaca gttcataagt ttatttccag gctgcaagac cctgcaacat ctggcctctt 200340
gcacctccac aacctcaaat ccttctattc ttctctcact ctctctactc ctgccacaca 200400
tacctccctt ctactcctca aacccatttc agggcctata ttcttgcttc atattgcctg 200460
gaatgttctt ccacaaaaca tctgtgtggc tcattaccat accttcagat ctataacagc 200520
cactctcccc acatcttccc agctgcctga cattataata cacatctatt tccttatgtg 200580
ttcatccccg tacacactag aacatgggcc caggaaggca gaattccatc tgctgttttt 200640
gccattgaat gcccagcaac taggacagtg cctggcacat tgtaagtact cacacacagc 200700
aactctaact caggattact ttttctagct ctgaaatacc tacttccaag agaacgaaat 200760
ttattcaaga aatgttggat ggaaattgaa gagtgagctt ggaaacgaga cacagagtgg 200820
caggagccca gaccaacctg tttatgaaag atgcctttgc ccatagaggg aaaaatacac 200880
cttaaaacct ctgccaaagt atatgctttc ttaggacacc tctgacatgc tgaattgcac 200940
ctggtctgaa caagatctat gaatttgcca aaacaactaa ttcctgtgat ttaagagtca 201000
ctactaccag tatcagccta gtaaacaagt accaagcaac gagcaccaca tatgtcagta 201060
tccaaagaca aacatgctgc tgcatgcaaa accagacaaa tgcattcacg cgggtgacag 201120
tgagtggaag aaattaatct tatttttatt attttttccc ttatcaaaca ctagcaaggg 201180
actagatgtc ataaatctag ttaaaatatg ttgactttgc ctcaaatttg agcattcatg 201240
gttccaaaag gacacttgtt ataggatctg atgatgtact ttagaatctt cttttgtgca 201300
aattgagact tcagagaact caaaatatat ggtaaattca aagtaatatt ataagtaaaa 201360

-continued tcataatgcc tcacaacatt ttttgaaagt taaatattta gtaattttac aaatatgtat 201420
tgagcactcc ctatatttaa ggaactatgc taatgctgtg atggatcaaa aggagaataa 201480
gccatgatcc ttaccttcag acttcaagct tattattcat tgggcagtta gataactaac 201540
atatcagaca tggaataata agtgccattg tccagatatt aaaaacaaaa ttggtgttgt 201600
ggaagcaaaa agaatgtaga gatggatccc aactaggaga aagaaaaatt gcttcctaaa 201660
gaagacacag attgaccatg aaaggtggat ggttctacac aggactagaa ggtaggaatt 201720
cttcatttgt tggacttgct aatttttttt ggtgtaaata tacccactgt tgttgattta 201780
aagttgataa cgtgatgcaa ctgaacacag aactgggaag agaaggtggc tccagcacgc 201840
tacctatgag tcaccagctg agctccagac ttaattaaat caacctcctc actactattt 201900
tgaatgagtg aattcacaag tcttaaaaag atctatgata acattataag ggaagagata 201960
gtcacttctg tcattctccc ttacatctcc atctcacctt ccaatattct gtttgaatat 202020
ccttccaatt tcagtcatat gttcctggct ggcctaccta ggattaatat tggcccagtg 202080
ccaaaatgtg attctattta ttccttttag cattgctgtg attaatctgc gctcctgtta 202140
tcccatggca tagcaaactc tcttactgat tatggcctgg tattgacacc tctgctgttc 202200
tccataacga aaagcagctt ttggggtggc tagctgggca ggatgttttg ctgctcttgt 202260
aacagtagga aggaaaagct ggaggaatta ctgggaagct ttgcagaagg aagatacagg 202320
ccagctgaga gccagcattc atattgcctg ttcctttcag tattctttgt gaaaacacca 202380
ccaccaatgt gttccctgga cgtcactact gcacctttaa ctggccttat tatgctaggg 202440
actgcatttg aaaagccaaa ctctagtatc tgtctgtaat tgcaagcgga tatctcagca 202500
catgcacaag cttatgtcag gaggatgttt atgaaaaact caccaagcag aacactgcta 202560
gacaggaaat aaatatgtga agcttgaagt tgttaggaaa cttccacatt tgtccctcta 202620
agccagagat aggacctgtg agaaaagaag gtctttatca ttgcgcattg attcttgctg 202680
aacccctgct attctcaaaa tacatttaca gcaaaatgtg gctactgcag atgtatttaa 202740
acatgtgctt ttttaaatga cactggttta tcttccaagt ttgttatcta ctattttact 202800
gtaaagcatt aaaaagtgtt tgaaaccacc agcaccattt cacagttcct gttttatttg 202860
tttaaattct ctagctcatg taatatgctg tatgatttac tgttcaagta gagaagaaat 202920
acactccctc atggagatgt ggggaggtaa tactgtctct tggaagggct cagagatttc 202980
ctgtttagat tacacaggct tctttagagc tgccaagagt cataacatgt acgagataat 203040
acactttggt tcaggaaaaa ctatggatag gaatgtaatt aattcactga gccacaaaag 203100
atattccagc ttagaaatgt cactgcactc aggcctggtg gactcagtat gccaaggggt 203160
agccatgacc aaaaagagga ttgctgcctg aggacccact gagtagtatc caaccacaga 203220
gcaaaaggag ggggcctggc tgctaaggac atcacacgtc tcacctgctt ctttgagaat 203280
tgatccctga agggtatttc tgcccaaagc ctcagcaacc tggcttcatc aatataactt 203340
tgtgatgctt gtgacattga gatcaatcaa tcagcatgta ctttatcaag tgcctcctca 203400
tgagtaccaa ttgtggcaca tagtggggaa accctagagg cagagccctg cagaggatat 203460
ggtgattctg accagagcaa gaaggtatag tgaaaagttt cctaaatata ttttgtgtct 203520
tgtcataaga atcacctggc agggaggggt atggaagggc aaggtaagca tacacattcc 203580
caggaccttt ccaaaatgta gagtgaccag ggacttagag attcagactc tatcaatctg 203640
gggcagggcc ctagacttgg tatatttaat aactgctgtg tgaggccctt tacatgcatg 203700

-continued acctcctgta attgtatagc ttggttgctg tatatggtac tatgtttact tgtgtttgca 203760
ctgtctattc aggggtgttt ctaaatgcca ttgctacaca actggtgaat tatgattctt 203820
gccagaacat tgattctcct actcttgctt ccttaatgac acactagaga actgggattg 203880
gctgcattta gtctcaggat gaatcattgc cataagtaga tttccatccc ctactccacc 203940
aactcatttg ccaaacaccc ttaaagaaca gaacccactg cctacatgca gcctgcacca 204000
ggagggccta aatggtctag ctgggtttat gacaacatcc cgtcttcaca tcagcaaaac 204060
cctaagtgca caaagtctaa tgtaaacaca atgtcaagtt ctccatagga aaagacatgt 204120
ccctgctgtc aaggtagtga ctagcaataa taataatgac aaaaacaata acaatgataa 204180
gcatatataa cacttactta tcactaatta tattgtaaat gaaatgattt gcatgtacta 204240
actgatttaa atcttatata tatatagata cttttactct ctcaatttta aacacagaga 204300
aaccaagacc tagatacgtg tttctgttga gaagttgagt acaaggttga gtgtaagtag 204360
ggaaagttca actgcagtca gttctagtct tggtaagtac actgtgaggc gctccacccc 204420
aagcatagca aattaatggt tccccagtgt ttgcagaatc aaaattaagt tctttggcta 204480
ggttctccct gatgtgcccc tgcttcttcc ctaattcaac acatccccag ctccatccat 204540
gcattcccaa cacatcacag ctctttacat gcccaggctg tgtcttctgc acctttgtac 204600
cttctgcacc tttgtttcct tggccccaac tgccctttct tttcctccac attacccttt 204660
atcccaaatt tagcacctgt ctcaaggagt caccttccca aggaagtttc tccaaatttg 204720
ttaacagata ttccattgtt cctccaatgc ttgaccactc ttcctttata gatccctgcc 204780
tagaaaaatg tgggctcact gaggccaggg gctgcagcta gtttatttta taacccagca 204840
tttaaaagtg cctatttatt gatttgttgg gaatagttaa taaatggagt ccttgcagat 204900
cataaccaag accacagttc gtaatggttt cattaacttt gttactattg gatgtgattc 204960
tctgcttatg gtcttccttt acttgttttt cccttactgc tcagcacctc tagacattag 205020
gtacatggct ctgatgctaa ttaaaattga tgactgagaa tgacacttcc atttgctaag 205080
ccagcgcagt tttgttcatt gtgctttact ttttaaccag caccccttagc ataaatctgt 205140 agtctttcca tgagggtacc atttgttcct tttatgtctc gattcattac atattttcag 205200
gactgttagc tgactaagac tttttgcttt gtgaaaatgt caccaaatgc acgataaagg 205260
caaagtcaca agatgtctgt ttgcaaaaag aattaaatgc tggtttgtga agattcaagg 205320
ctggccaggg ctccccaagc atttccaggc cagagctttg gctctgcact ctccttagga 205380
tctcataact gacccccaca ttccatttct gccatcgtgg aaaaatttgt caactttact 205440
gctgatgtta ggcctggaaa ttgtcatcca ttagttttct cagattcaag ctgaaaattg 205500
agacaaactt cctacgtaat tttgaccaaa ataacacata tgtttatgtg ctatcccatg 205560
attaacatat ttttaaaacc actttattga ggtatggttg gcatacaaaa atctgtgcat 205620
atttaatgta tacagcttca tgaatttgga gataagtata catccatgaa attattactg 205680
catgtatgcc ataaacctat cacctacaaa aatttccttt cactttgtta ttattttgat 205740
taacttaatt tttttcttcc tttgaactat caaaactttc tcaagtaata catagttgtc 205800
agttatacaa acttactgaa ccttgaccaa aggtcctctt ttagtgctca tcttagagaa 205860
agaattaatg aaacaaagtg ttctctgatt tgtagcaaag atctgtgatg gtggtgggaa 205920
tggttctaga aaataatggt aataataaaa acttagagta tcaaagcagc aagtagattt 205980
gaaggaattg ttacaatgca attttgcttt cccgccactt taaaatcaag gtgtagtact 206040
ttatttactt taggaaaatg tttgcttttt gtcataattc cttattgcat atgagagtaa 206100

-continued atgatctata gatgaagata ataataaaat ttagagagag aataaaaaag aaacactttc 206160
acagctgaaa ggctgcttcc cagttagcta actgggagga gttactgaaa aagtacattg 206220
aaaagcggct caggggcagg tgaattggac tcaccaggct ctgacattca gagagatggg 206280
aatgagtcag ctcactgtcc agcacatctt tattttattt ctctttcttg ttttatatca 206340
gaaatagatt tcttggcatt gttactgtgg gtttctatta aggactgaaa caaaagtatt 206400
aataatctga gagtatgtaa aaaaaaaatt cattttctcc tactatactc tcataacaca 206460
gaatattttg gtgaccagag atcaccaaaa tgtgtgtggt gtcaacgaaa agagtcaaac 206520
tctctaaaat atttgaagag attttttctg agccaaatgt gagtgaacat ggcctgtgac 206580
atagccctca ggaggtcctg agaacatgtg cccaaggtgg tcagggtaca gcttggtttt 206640
atatatttta gggaggcata agacatcaat caaatacatt taagaaatac gttgatttgg 206700
ttcagaaagg caggacaact caaatggggg gcttccaggc tataggtaaa tttaaacatt 206760
ttctggttga caattagttg agtttgtctg aagacctggg attaatggaa aggactattc 206820
aggttaagat atgtttctta ttggacctaa aactgtgcct ggctcttagt tgattactgc 206880
ctggatctgg gaaggaagga aggaaaacaa agggggaagg ggattctcta tagaatgtgg 206940
atttttccca taagagactt tgtagggcaa tttcaaggca tggcaaggaa atatactttg 207000
gggctaatat tttttccttg tctcataatg ttatgccaga gtcatattga aaagcaagtc 207060
acaatataca aggtcaaata aaacccatcc tgatgagaac ccatggtttg tagggcatga 207120
ctccccagaa ccccttaggta ggaatttggg caagataaaa aatcggaact tagtcctcgg 207180
tgggaatctc tccccacaca aattctccaa cagattcttc agtgggacac caactgggtg 207240
ttctcaaatt caattcaatt ctgacaatct acctatctac ctggaaatag catcagataa 207300
ccacaggttt acggctcatt ccaacaatac tgtcccccac ttcagatgcc aactgcaagt 207360
aataggttgt tacctatact tctagccagt cagctgtaaa ttggtgttcc cacaacctcc 207420
ccctccggtt tgataatttg agacagcttg cttacatgta ccagcttatt agaaaggata 207480
ttacaaagga cacagatgaa gagatggata gggtaaggta tgtgggttgg agttgcagag 207540
tttccatgac ctctctgagt gcagcatctt catgtgttca gctatccaga atctctcgga 207600
ttaagacatt ggccactggt gatcaaatta accttgagtc cctctcccct tcctgaggtt 207660
ggagagtggg gctgaagtgt ctcaacctct aatcaactct tggtctttcc tgtgaccatg 207720
ccccatcctg aggctctcca ggagccccca ggcatcagtc aactcattag catacgaaag 207780
acacttatca ctacagagat tcgaaggatt ttaggaactg tgtcaagaaa cggagacaag 207840
gtcaaatatg tatttcacaa tatcaccagt agtttcactg ggaggtaaaa ctcagtgttt 207900
actgtgggcc tgagccatgc tgaccctcta agaataactt agaggtaacg tgatcagatg 207960
tggggaattc tggagaaaca cctttcacca ccaagcccag acaagagatg catacttttc 208020
tagctgggat gcttacaaag caacccactc taatacttca aggtagagtg acactacatt 208080
catcattttt catttttttcc tgttttttat gccatctact actaatgtca atcaaattac 208140
gactgtgttt atagtggatg aattatggac catctcacac cataaagttc tgtttctctc 208200
atgttgagct tttcacctcc cttcattccc tccctacttc caggatcatt cacatgttta 208260
tttctaaaaa taaacttttt ttactgaact ttttttcata ctgtttaaaa agaatttata 208320
tttctcttca ttcttacaga taagattcaa gtttaaactc aaataatgta ggaaatcttt 208380
ttttaaaaaa ttgttcccta ctgtgtctag gcgtgagacc aaaagtaatt aagaccaggt 208440

-continued

```
tttcatttgc tgtgatttgt gtgagttctt tttagaggtt aggtgcaatt ttaattttta 208500
aaagggggat tattatgaga ggagaaatca tactttatca tttgaaaatg atgccataac 208560
aggtgttagc agaaaaatca aactgtaaaa tattttaaag agatttattc tgagccaata 208620
taagtgactg tggccccatt gaaatgagcg agttccctga tccctctcac agagcttgcg 208680
acagggatgt ggctcacctg ttcagttgcc ccactgctca aacccctagg gggagaatac 208740
agacggtcag gtgcaaaggc tggggcaagt gccttggccc cttggcccct tagccccgag 208800
gtagtgtcta ggggtggggt gcctgcaacc ccagtgttac aaagttcttt cagctttgca 208860
gtccacggac agcttgagtg ttaatcagct caatggaccc tctgccttat agcaaaggca 208920
gagggccagt gtgacagctt tctgtatccc aagctcttgc ccagtgtcct agaaaaaaca 208980
gatcatacag gggctcgaag gatgagtgca aggttttatt gagtagtgga ggtggctctc 209040
agcaagatgg atggggagtg ggaagtgggg atggagtggg aaggtgaact tcctctgaag 209100
tcgggcagcc cagtggctgg actcttctcc aacctccccc aggcaagctc ctctcagcgt 209160
ccagatgttc ctcttccctc tctctctctg ccgcatcatt tcaccatctg tctgctggtc 209220
agctggcttg ctggtgtgct ggtctgttgg tctgctggtc tgcttctgga acctcaggtt 209280
cagagtttat atgagtgcac gataggggt gttttgggcc aaaaggtagc tttttggaca 209340
tgaaaacgga aatgcctgtt cccatttagg gctgcaggtc ttcaggcttg agggtggggc 209400
ctttgcccag gaactaccct cttctaccca gtgtttccct gtctcctgtc catatcacca 209460
gtattcacag tctcaaggag tcttgagaaa gtgtgcccaa ggccgtcaga ttcagtttgg 209520
ttctgtatgt ttcagggagg caggaattac aggcaaagac ataaatcagt acatggaagg 209580
tatacattgg ttcactctga aaaggcagga tgtcttgaag tggggacttg caggtcatag 209640
tttggttcag agattcttta atctgcagtt ggttaaagga acaaaaactgt acagaagctt 209700
cgagttagca aaaagaaata tttaaattaa gataaggatg ctatgtcaga gtcagccaca 209760
aaatgacctg tttagcaaga ttaatggcct ataggtgtga cttaaccctt gccttgcatg 209820
gcctaaggtc ttgtttataa tttagtatct tattgcccaa agagtctatt tagtcagtct 209880
tatgatctct actttaacat taatgctggt cacttgtgcc taaactccaa aggggaggta 209940
tatccaacct gccttcccat tgtggccagg aacctttctc tggagtcccc ttggccaaga 210000
aggggtccat tcggttggtt tgggaagctg aggattttgt ttttagttta cacagggtca 210060
tatcagattg ttttgatggg gatgactaat ggttttcttc tctttctgtt tcagccacag 210120
cagctatcct tagcagagca ccctggagtc tgcaaagtgt taatccaggc ctaaagacaa 210180
gtaagaattt cagtcctttt tcttccttca atgatatttt ccatgtttta gtgtaattaa 210240
gctactatcc tttctctatt ttatttggga tggtagtaac tggaatagtg actgagttga 210300
aattttatag gcaagcaaaa catttttttaa ggatttattt tttaacttct gatatagttt 210360
ggatgtttgt cccttccaaa tctcatgtaa tccccaatgt tggaagtgga gactgggagg 210420
agatgtttgg gtcatgtggg cagattcctc atgaatggtt tagcaccctc ctctttgtgc 210480
tgtcctcacc atgagtgagt tctcatgaga tctggttgtt taaaagtgtg tggcacctcc 210540
cccttcaatc tcttgctccc actctcgccc tgtgagacac ctgctccgct tcaccatgat 210600
tataggcttc ctgaggcttt caccagaagc agatgctaat acagcctgca gaactgtgag 210660
ccatttaaat catttttctt tataaattac ccagcctcag gtactttttt atagcaatga 210720
aaacaaacta atacaacttc tgtgcaaggc tgcttttttt tctatttttt gcttgtgctt 210780
ggaggttaag taaggccaaa ttaatgaagg aggaaaaaag aggaaatgat acatcatgga 210840
```

tcaacaatta tttattgaat ttaggaaact gcctcttttt ataaattctt tttaaaatta 210900
ttttcattat tatcttgaag tatttatcta aggtttacac tggtagaaag ttaaacttgt 210960
ctctccaacc aaattgcctt aagcttcaaa attatgcctt attgtaagct ctttcttaac 211020
cttaaaatga ctttacacat tccccgctgg tcctttgaca atctcctctt caaccacaag 211080
acagaacccc accatcaact ctgtggggaa gcgtctccaa attctctagt cctgaacaac 211140
attctgcctt ctctgcttcc atggaacttt gtcctttaca acatgatagc gtttgcctcc 211200
tgacatttta gtgtgtgtgt tagccctgca tatagaactc accagattgt gtggactgca 211260
tgaatgaatt aattctattg aactttaagg caaagcctaa actttatgct tcttctaaat 211320
cccttacatc tcctaaaaaa attctgatcc atagtagtag gtacttgttt aattaaattt 211380
tagggatgga tatttttcat cagtggaagt atatgctaga gtccatatta tgcaataagg 211440
gaagggaaga cagtgtacct aaatcagtta agatattgct attcttgttg ttattctaga 211500
gtcacgaaat cataatttga attttatgac taaattgcag aattaatttc caatgtgaga 211560
ttttaacatt atttccttgg aggtgaccaa aaaggagagc tggtactgtt tttaacaact 211620
gtcattcaat tgtcagttgt gccagaccac aaatccttta tagccctcct gtttaagaag 211680
catctgacat gttaagctgc tccctaatta acacagaggt tgtaaaagaa gtggctgttt 211740
ggttctgttt gggtttccca gccagtatat tccaaagcct tttttcactc aacagatgag 211800
ttatgtgctt tatattctgt aaggaaatga gaagtaatca gttgaaaatg tgttactaat 211860
ggtacatgct tcacattgaa accatcctcc tgacacaaac ataatacttt gccctccact 211920
gtcccccaaa gtggcagtag gatttctcta agtaattttc tttacttata tgagtgcagg 211980 ataggggggtg ttttgggcca aaaggtagct ttttggacat gaaaacggaa atgcctgttc 212040
ccatttaggg ctgcaggtct tcaggcttga gggtggggcc tttgcccagg aactaccctc 212100
ttctacccag tgtttccctg tctcctgtcc atatcaccag tattcacagt ctcaaggagt 212160
cttgagaaag tgtgcccaag gccgtcagat tcagtttggt tctgtatgtc acagggtcta 212220
agaagcgtaa acattgtgtc ttgttgaaat acagcctcta ggtatggagg atgtgttgaa 212280
caacttccta ccagtcattt ggcatatgtt gatttcctgt cttcatgata cgtaagacga 212340
ctagctaatt atcattcata tgtggtaagt cacatagata ctgacttccc ctatctttcc 212400
agctttttct tatcaaaagt cacctgctct ctgtcccagg aacgactggc taaagtaacc 212460
tatatcagtg tctgtaacag tgggcaccta tcatagtgca catgcttgaa catatcattg 212520
ccttttatca tcacgagcct cacatccaga tgtgacagac tcaagtgctc acatcacctc 212580
actctgtcac tgtatacatt gttaccgtgt cacaaatatt taacagtctg ctgtgtactc 212640
agtctttagc tgtgtgccct gagggagaca gagtaagata ctgccttgac atcaaggagc 212700
tcacattctc cctaaagaga taatttcaca tgaaaagtta gtgtttaata tgaaaagtta 212760
gtgtttaaca tgaaatgtcc tgagaatata caattataat ttacacgttt cctgtgtgta 212820
cttttctaag ttctcagact caaaacaaag ccccatggaa gaaaaaatga aataaaaacc 212880
ctgtcaggac aaatcctagc cagaactgac caaacataaa aaataaatgc cactgccctc 212940
tccaagctac ctttacttta tacttgggtc caagaagccc aaacattgtg cctcattgaa 213000
atataacctc taggtatgga ggatgtgttg aacaacttcc taccagtcag tgcagtgcag 213060
tgaccattta gcagcatctc cctcctctct ccttccaccc cctgccccat ctctccttcc 213120
ttgcatctat cttcccctgc caacaataat tttcttatgt tctaagtaaa tatctttagt 213180

-continued

```
gctctcccta ctacctaaac attaaacttc aaacctttcc caagaccctg aacacccacc 213240
ccagcttgta agttcaggct acttaccatt ccccaggcac actgtatttt ccctcctctg 213300
gtacactgct catgtcatcg aatctatctt cctcccaccc catcctggat tctgtaaata 213360
taaatcagtc ctgcccacct ttaagtttca gtcaaaacct gatactcatg gcctgaagca 213420
atccctccct tctccatgct ggtctgagag aggtcatgat atttcagtag ctctggagag 213480
acacatatgg tcaaaccaga ccagctaaaa ttaacccatg ctatgcacaa cctaaagaat 213540
cacctcttgc tgtaacctct ttcttctctt gctcaccaaa aactgtctgt cacatttgct 213600
aagtaagccc ttagggcttt gctgtgctgg caaaaggtct taatccatgt gaatgtgcat 213660
ttttgtgtta gtgagcacat gctaacatgc cttccacaga ttagtttctt aagaaacatt 213720
ttctgggggga aaaaagacct gtttttggtt agtaacccca aaaggacctt tcagttcaca 213780
tacgtggtag cagcatactc cacttatgca aaggtcagcc cagggtaaat atgggcaaaa 213840
acacagactt aggataagaa gaatgttaag ggagtttaca gtttaaagag atatccaaac 213900
aacttttttta tattttaaag aagtaatgct ataattttac tacaaagaaa acttctttat 213960
atttctgggg agaagaatag gaagagttac aatctcctag agaaaagcaa aacattttta 214020
gtattcccaa ataagacagg cacctcaact agggtgctgt ggttgcacgt tctttgtagt 214080
ttttcaagaa ttttatttct ctgtcatgat tatttattgg cagaagattt gttgggccaa 214140
acatgtaaga ctttcttaaa cacatataga gaaaaaaatt agatgattgc acatctttct 214200
gagggagatt tttcccctat ttttaaaagt cattgctttt cactgaattt gtcttgtatt 214260
cctataaaag tgtaaatttt gtgattgata gcatttttac ctcaaaatga aatgaatatc 214320
caactggagc aagttttatt gactgcttat tggagcataa attagtctaa gttttcatga 214380
aaataggcat ttgaacatga gtattaatgg ctgagatcag aggcaagttt tgaaaggatt 214440
ccaaaatatt atcatattag ataggcaagc aaatgaattg cttgaatgct agaagttcac 214500
aaacattcaa acaattgtga gttacattaa cttcaataaa aacttttgca ggacaaaaat 214560
ttaatatagt aaacttcatc ttgcttgtcc aggtccgtat acattcttag ctggactctt 214620
gtcctagctt cctaattttt cttcctatct cctattttttc cctattccaa gccaccatac 214680
tctgttcttg attaattctt cctgcctacc tctgattcag tgattcatct gcccaatcat 214740
ctatagtagc tccaaactct tttctaaatt atgaataaac ttatctccct ggcattcaga 214800
aaattcaaca gcattcatct tacacacttt tctagcctta tctccctttt ctcttatgta 214860
ctcctatgtt tatattccct gcagtcttgc ttcattatat ccatttacaa tgaccctttt 214920
accagtaatt tcctcttctt tcctctcagt ctgaaacaat ccttcataga ttttgtcctg 214980
tgagccatat ttcaaataca actttatcca caaagcttg cccagttccc acaagaggat 215040
tctgcttttg ctttagaatt gtagcctttt tttcctctct cgcaaggaga gagagcgtag 215100
caccgcagtt taagtactca gcctctggag taagctttag tttaagaccc agttctactg 215160
cttacttcct gtatgatctt ctctaaattt tatgatctct ttgtcttttt tttttcatct 215220
ctaaaataaa gatgctaata gtacctacct cataagatgg ttgtgagaat tataagtgtt 215280
gatatattta aagtagttag aatagtatct ggccctacag taagcttacg tggtatttat 215340
tgtattctct tatggctctt attttattcc aatgtgtatt aaattgaacc gtatgaaatt 215400
gcccatgtca actctatatt ggaccctaaa atcattatgt cttttggttc aaccaaatgt 215460
agtgcttttt gcaccccccc ttaataaatt gaactatctc taaagatagg gacaatatct 215520
tacacatcat tatatcctac agtacctgct acatacttga catatgctga gtatttcacg 215580
```

gatggttatt gaattttgca cacacacaca cacacacaca ctgcaaaaaa taaacagaag 215640
ccaagccctc cccagtatct taagtactct ttggctacca gggagtttac tccatgctgt 215700
tcagcagtca tttatgaaag gagagtgata aagatataga ggaggagaat tttatcttgt 215760
ctattgctga gtataaatac tatgcctttc cgaaaagcct tccacagaac ctttccttca 215820
ggtcagggac ctagtgtcat gggtcggtct tggataacgt tgcaggacat atcagttcaa 215880
ctgccaaggg aatcataaat agtcctactc ctgcctgcgg cccaccactg cctctctgct 215940
ttcattcttt tttatcagat attttcaaca tcaagaactt attagctgat aatttaacta 216000
aattaagtat aacataaggg aaatgtgtcc tggcagagat ggcatcttag agtgaatgca 216060
cagtctttat tggttaccaa aaacaaaaaa aaaaaaactt gagctttgga caagcagtag 216120
agagcagatt tgatactggg ttctgacatg gaagctgaca ttaaattatt gacagtctac 216180
ttgtttataa actattcaat aaacaattta gtaagtaaac atagattctt gcaatcccctt 216240
ttaaggaaac agtgtttatg ttggctctct cttgtaccca acctagtgct cagcctttcc 216300
tgactcacat aagcactaat ctccagataa caccaagcac cctagggtta ttatttatcc 216360
cccttccttg ttctctgaaa taagagaaag gcaggttaaa ttatgcactt tatgtaagaa 216420
gaaatggagg tacagagaaa acagcttaag tctcttaaca gcccaagaga gtgaagaaga 216480
tattgccaat gcaatgagtt gtatctgtcc ctaggtaagt aaaatattaa ttaaagcata 216540
caactatatt aataattaaa acaacagtct ttacttatat ggactttgca gtgacttttt 216600
tccagcctga aatactcaga taatgactgc cattagtttc acacgttagt gctttattat 216660
atactgcttt gttttcacac aaaatcgttg agaggtaaga attttttgaa agaaatattt 216720
ggtcttaact tttttatccc ccttcaactt caagcaattt tctgagcaat gataagtggt 216780
aagtagatat ttaccactta gtttacaaga gacctgtttc tctctgtgca ttgacttagg 216840
cactattaat gaaacctttg gaatgcaggt cccttctggt tgtaaacata tactgaggtc 216900
ttctatttct tttggaactc aaacaataag aaaatagtta gaaatctgtt tgtgggcata 216960
ggtctctaaa agccttaatc ttagaagtga gtaaaaaaaa ttttaggcca gacgcggtgg 217020
ctcatgcctg taatcccagc actttgggag gccgaggtgg gcggatcacg aggtcaggag 217080
atggagacca tcatggctaa cacagtgaaa tcccgtctct actaaaaata caaaaaatta 217140
gccgggcgtg gtggcgggcg cctgtagtcc cagctacttg ggaggctgag gcaggagaat 217200
ggcgtgaacc cgggaggcgg agcttgcagt gagccgagat ctcaccactg gactccagcc 217260
tgggcgacag agcgagaccc cgtttcaaaa aaaaaaaaaa aaaaaaaaaa ttagagccta 217320
agaaggatga ttaagcatct tacttaaatt ttcagtatgc ctatgtacac tctatatact 217380
gacttctagc atggtttctt tgccaaagca taacacacat tttttaaagg gataattcaa 217440
gacaaacatt ctttcaccct gggtgacccc aatgggtggt gaacactttt tagtaactct 217500
tgaaagttaa agcatccaac agttggttgt gaccttttttg gttgtgacct ttgagttctt 217560
ctagcttgta gcccactgat ttgctgctta attccacagc ttcaaaacca actctaatca 217620
ctgctcccga gagagcccta gcttctgcac acatgagtct ctcaccagga aaggatacct 217680
gaagtccaga aaagcccttt gttcacactg gctcctccta gtggggaaca gttttttttaa 217740
ataatgtaca tttatgcact gggaaaatat cttgaattta ttatttaggt gtaaccagac 217800
tttaatacaa cttaacctac acactgagaa agcagacatt tacaaaaaga tttatggctt 217860
tgacaaagcg ttcaaatgta gttaccatta aatagtagtt caagtaattg tgtgtctcat 217920

-continued ggcaaataca tgcaatataa ggtaatatat atttaagcca aaaataacaa gaggtgatca 217980
tttgctaaac aaagaactta ttacttagga aaaaatgtta cacaactttc aaaggacttt 218040
tgaaaatata gtatgattta taggaaattt atttgcatat aattcacaat atctggtaca 218100
aggtaagcta cctctgtgtt ttttttcttt aggtcaacaa atatttaaac caagggttgg 218160
caaacaggcc ctcagaccag atgcttgttt ttgtaaataa agttttattg gaccacaccc 218220
atgcctgttt gtttcagatt gtgtttactt tagggctaca gtggcagagt ggagtagcta 218280
agacacagag cataggtcca caaacctaaa atatttactc tctggccctc taaaaaaaag 218340
tatgccaaac cattctaaac agcaaagcaa ttaattcttt tttttcaact cttattttag 218400
atttaggggg tacacgtgca ggtttgttac atgggtcaat tgcatgtctc tgaggtttgg 218460
tgtacaaata atccccttac ccaggtattg agcatattac ttgatgtttt tcaactcaca 218520
ccccgctccc aatcttcacc actctagtag tcccctgtgt ctactgttgc catctttata 218580
cccatgttta tccagtgttt agctcctgct tataagtaag aacatatggt atttcgtttt 218640
ctgttcctgc gttaattcac ttatgatgat gacttccaca tacatccatg ttgctgcaaa 218700
ggacatgatt ttgttctttt ttatggctgc atagcttttc atggtatacg tgtaccacat 218760
tttctttatc cagtccacca tcaatgcgca tctaggttga ttttatgttt ttgctgttat 218820
gaatagtcct gtgatgaata tatgagtgcg tgtgtccttt ttgtagaatg atttattttt 218880
ctttgggtat ctacccagtt atgggattgc taggttgaat ggtagttctg ttttaatttc 218940
cttgagaaat ctccacactg ttttccacag tggctgaact aatttacatt cccaccagca 219000
gctataatat ggttgtttgt ttgtttgttt gtttgagacg gagtctcgct ttgtcgcctg 219060
ggctggagtg cagtggtgcg atttcggctc actgcactct ccgcctccca ggttcaagca 219120
atttgcctgc ctcagcctcc tgagtagctg ggattacagt cgtgcaccac cacgcccggc 219180
aaattttttt tatttttagt agagacggga tttcaccgtg ttggtcaggc tggtctcgaa 219240
ctcctgacct cgtgatctgc ccccctcagc atcccaaata ctatactgcc ccctcagtat 219300
aatatagtat tttaaggaac taatcatcaa gtttgtactg gttaccctct tttagtctcc 219360
tgttatcttc aatttcataa ttggcattaa tgacaataca gtgttcactt tataaatttg 219420
cttcatagta aactcttctg aaataaatta cagtcatgca tcacttaaca gtggggatag 219480
gttctaagaa atgcataatt aggtaatttc atcattgtgt aaacatgaag tgtactcaca 219540
caaacctgga tggtacagtc tgctgcacac cagcctttat gatatagtct attgttccta 219600
ggctacaaat ctatacagca tgttactgta ctgaatattc tcagcaattg taacacaatg 219660
gtaagtattt atgtatctaa acatagaaaa tgtacagtaa acatatagta ttgtaatcgt 219720
atgggacgac tatcatatat gcagtctgtc gttgaccaaa acatcattat acagcacaag 219780
actatagttg aaaattttaa attacatatg tgggttgcac tgtatttctg tttgcagcat 219840
tgatatatac atttaatggt ttgtatgttt gtgcttgcat tcataaatat taaactgtta 219900
cagggagcat attttcttgt gtaaaaaaat aaataatttt tatttctaat gacatataaa 219960
attattatgg ttatgtttaa agaggcttga agaggtatta tggttatgtt tgaagaggca 220020
acggaaacgt cacctttgtc attgaccaaa acatcattgt gtggctcacg actgtaatag 220080
tgtaaagtaa ggattcaatg tatcggctaa tcaatgtgga catatcattc agtattatta 220140
aagatactcc atccaatgaa gactgaacac ctgtaaatgc ttggtgatgg atggaaaggg 220200
caattatttg cagctggact gtctgagacg tgtcatcatt attgcataat atttatttaa 220260
tgaaggatca atgcaccata cagctccagt ttgagaacac acttgacatt gtagtttgta 220320
gatcttttat aaactaactg ctatcactga atttttgctg aagaataaag acaaaagatt 220380
ctctctttag gaaattgtgc actttaaaga ctcataaacc tgaaacctca cagaatcata 220440
atagatgtat tttcagagac aatttctgag tccttgacat attctcaaat gtcattcatg 220500
tcttcactgc cgcaggttat ctttttattt ttatctgtca tggaaaagca gccttttttc 220560
ttttttatc tcctactatg ccttaataaa tagaatttaa aaccccgaat ttgaattatt 220620
gtgaaagcca atatttgtag caaatccatc tatgctctgt gttgtcagca catatggttt 220680
tgtgtacctg ctaccatgaa actctgccag ggttatcctc agagaaatgg agagacacct 220740
gatgccatcc ttactctgac agaagttttt ctttctgtga attccaaaaa cttttgaagt 220800
tatgcatctc ttgcattgaa cttcagtggc ttgtgtacac atggtatctt cctttctaga 220860
ttgtaagttc tttgagggca gggactgaac ctttctcatc tttatatgct ctgctcctcc 220920
acccttggtt tagccagggc cttacaaaaa gtagaagctt aaataatgtt tattaggtga 220980
atatcatact aagttccaga aattacctga gagcaattga agaagggaag tgtggaggga 221040
gaggtgttag catagatttc atagtgtttg agtttggcag tttggcatcc ttttcctcaa 221100
cactaatact gacacagata agtaacctaa ctgccttctc aaatctgaga gcagtagatg 221160
cattttctct tttgggactt ttctatctca tgtgggaaaa gcaaacaaga aggtcctgca 221220
aaagtcttgt gggtatttat tcttatcagt ggttgtggca aactctctta ctggtttcaa 221280
ttggtcccac aggctatgtg atgaggactt tggggtttgg ggagctggga accatgagtt 221340
gtctcttaag tatgacctaa catactgcta ataccccaca agcttcaatt tatccatctc 221400
gaaatggaga tactaacatc tatctcaaag ggtcattgtg aggagcgagt aggaacatag 221460
aaaagttcct agcacaaagt agatatggaa gatatggaat aaggtgttag gtattttatt 221520
atttttactg ctgctgctgc tgttactact actgctatta ttattactac tcctggaaga 221580
gtaggacttg cctgggacac tgaccctact taccccttca cctcattcac caaaacttat 221640
ctcctatata aattcatgta tatttttctg gaaggataag aaaaatcctt catctaggta 221700
gcgtattttg tatttgaata gtttatgttt caaatcccag agaaggccta tacagccaaa 221760
tttggaaaaa aaataaattt aaaaataaat attcagtgtt tcatatataa taaaatacct 221820
aacatcttat tccatatcat atatgtgtgt gtgtgtgtgt atcttttaat tgccatgtat 221880
ttctaccaaa aaatacaaaa cttaattttg cgtcctgaaa gaccctcgtt tgagaatccc 221940
tgcttttatg ttctgcttta gtccaggcaa cagatagctt aggttgtcac tttacaactg 222000
gagcagcagg tagggctgag aggctcgcca tactccaaat taccagtgcc agtcccatgg 222060
caccaagaca ggaaaggcag gcactcaaac agaaaggtag tgcaattaat tgcttcaaat 222120
tctttactca gggctgccct tagtcatgat caaataaaat gtacacattg tttggcactt 222180
ggtaaaatgt tgtttccttt ccttcctcct tcccctgata gactctcctt aggtacaaaa 222240
aagatgaggc tgtacacaga gctaaaagtg tacacctttg aaaaaggtgt ctttttcaaa 222300
gagcaccttc accccttact ggactaaact caatccaaag ctcttttctc taagctttat 222360
aacacttact gcctggatga gtcatttgtc aataaataca gaatgtttgt ataggtgggg 222420
ttcttgtata tatgtacgag cccctagagt ctctaactta aaatttattt ttgctttaga 222480
agttcaggaa taaggaggct ttgatgatca attttaacaa ccgcaatata taatacagta 222540
actaatggtt aggtgtccag gctagcccag ggcagcctgt gtgattcatg ctgctggtga 222600
accatggctg gctgggcgaa ctagatctgg aattctgtgg tgcctaaggg agggaaggga 222660

-continued atatttccca cactatctca tcctgccctc actatcgcta cccccaatct ctctctacat 222720
tctaccccac ctactttgct ttttctgtga aagaccagct ggggcaaata ttttggatta 222780
agtaaaattt gtcttgggta acttccctaa aatttagttt ttaattgaat aatcttggtt 222840
aatccatgag taaataagct tgtagagtat agtcagcctc actgtgagaa gctgacaaac 222900
cagaaaacca gaggaatata caccaattcc ttcctgtcct gcaaacctct gcttcttgag 222960
gtttttaaag agtgggtgcc taattgatta gtcattagtt attgacagga ccaaagagat 223020
atgcctggct cctcttggaa aaaccaaaag actgagaggg aaaagtacac caaaaagata 223080
cctaaggagg cagactgcta taaagaaaat aattaggaga agaaatcata tgttttcaga 223140
tgaaaagaat ctgaggatga aaaaagcagc cttttcaggc cgatgatgga aagatagaaa 223200
ctaaattcag aaggatcaga agacgattag aagggcaaga agtcatagaa gaccaagatt 223260
tcccaaatta ccaaaagaaa tcaagcccag tcttgttcag gctgcagaat gagaacgccc 223320
ttctagtaag atccgtacaa tgaatttcac aaatgttgat ttctttctgt cctctttgag 223380
cccataatca cctccttcta cttgcacaac cttgaccatc accactacct ataactaata 223440
accagttctt atgttcccct caaggcataa cacaaaaata ttttctttat gattactttc 223500
tctacaaaaa agagggagag agagagaaac aagtcagggg acttcgttgg tgagtgtaga 223560
ccacagcaag aacctaaaat cctagtgggt tgttagtata gacaggctga aaccactatc 223620
ctgaagtggt ggttctaggt aggtatgccc atcagaatca tctgtggata agtattttca 223680
gtaaatacac atgcaggacc tctacctcaa atgtactgaa ttgaacttca ttgctggagc 223740
ttaggcattt catatttgtt tcctaagctg ctataacaaa ttaccacaaa cttggtggct 223800
taataagaga aatgtattct gtcacagttc tggaggccag aagtccaaag tcaaggtatg 223860
accaggattg gttccttctg gaggctctga ggaaattctg ttccatgcct ctctcctaga 223920
ttttggtgac tgccagcaat ctttggtgtt ctttgatttg cagaaacatc attccaatct 223980
ctggttctgt cttcacttga ccttccctat gtctgcgatt ggtctccttt ctgtctcttt 224040
taaggacacc tatcactgaa tgtagagcct atcctaatgc acaaggagct caattatacc 224100
ttaattatat ctgtaaagac cctttttcca actaaagtca tattcacagg taccaaggtt 224160
taggacttgg gcatatcttt ggaggataca gttcaaccca ttacacatat gcattgaagg 224220
gaaaaattca cgccacaact gattatccta taaagaatgt tggcttaact taacgcattt 224280
aacgcaccat ttctccagca cttaggaaat gctaggagat gcaaagctga agctaaatag 224340
gcttctttat tgcagaacct ctcagaggct ctcatctgtt tgtgtgcatt ataaatgtcc 224400
aagagaaaga aaagaatcac aacatttcct ggaaatactt gaccagggaa cttcttttca 224460
agggattacc tgttaactac ctcaatggac actaatgact aaaggaatac atgctgctgg 224520
tgatcatggc acttccaaac tatgctcaat ggtgtgggca tgagtctacc acagtgtcta 224580
aacactaaga ttgttaatgt ctacacgacc tctccctgga tatgagcaca catccttcat 224640
caaatatcca cagtggtttc cctagaggat ttgcatatgt gcatggattt ttagatgtct 224700
agtctctact cttgtcttca gccatttttg tagagagaaa ttggcaaaat attagcatga 224760
atggaaggga aaggtggcca agataataca ttatgccttt ttttttttcc ctgaaaacag 224820
cccagaatat ctgaaaaggg agaagtgact taatcatttc tattcccaca attctggtcc 224880
tacaaaattg atatcagtat atgattcatc cagagaagtt cacagtggta ttttttttaaa 224940 aaaaactttt agaggttacc agggcatctc actattttaa aatttaatac ctcaagggaa 225000
ataagcaact accttgaatt tttgcatgaa ttgcatttga gaataactga atagttggtg 225060
gaataaagtt gtttttttaa aagtaggcat attctagtta ataaatataa aagaaatggt 225120
aggattagaa aaatcactac attacaaact ctaatgacat aatagattta agcaagatga 225180
tcagtgaatg ataaaatatt taggtatgct gtcttctagg tgaatcaagc tgacaatacc 225240
ttggacccac gttaatctta ccacatgata ttatatgtct cctgatactt aaaataaata 225300
tcaaataaat cttgataatt gttgaaaatt gttgatgaac atatagttca cagcaccacc 225360
catgatgtat tctttccatg agaattgatc tgaatcaaag taagcctcta ggtctaactg 225420
ccagtgtgta ggaaatacca gggatagaga aacattttta aagtctttaa gattgcagta 225480
agctgaaaga aattgtctgg tttctgcaat aacagcaaca aagttatgta ataagaagag 225540
agagggagaa tcacggattt atacaaactt aagagacact gtgtgaatct agtttgtatc 225600
ctgatcaaac aaattaactg tcaaaagatg tcttttgaaa catgatggga aatttgagca 225660
taaactaagt attctacgat attcaggaat cattaccaat ttgttagata tgatgttggt 225720
atgttttttt aaatgagaaa gtttttagct tttagagata catacctaga tagttatggg 225780
tgaaagcata tcattaaaaa aaagatagtg gaagtacaca aaacaggatt gctatatgtt 225840
gataattgtt gaaccttggt gatgaacata taggaattaa ttaaaccata ttttctattt 225900
ttatgtttat tttgcaaatt ccaaaataaa aatagaataa tccctcatga acagatggtc 225960
tcaaatttca tcctcaagta aacacaattc acattctcag gggaacccat gagaatatta 226020
tgaagtatat gtctatctca tttcattata tatggaatcc taccattcct tttgtcttta 226080
ttactagtgg ccagagttct atcttgaaag gtgggaaatg tccttatatg aacagattag 226140
tttagagaat tattgtgaga aaaccagaaa atatttgagt tctagctaac tggatattga 226200
atgagttgtg ctgaagtatg tggtcataaa gggttgataa tgaaatactt gctttccagt 226260
ggcaaggaaa aataaatgtc ttagaattta caaggtcatt cttgaaatca atcaacgtgg 226320
gctgaagatc tcattgcttc tgttatctgg cacgatggta tttgtttgtg cacagctctg 226380
ttgatgtgag ctatcaaata tttcttagag ctgaaatcat ctaatagcaa acattgctat 226440
gtcccaatgg agattccaag actctttggc catggaacat ttacattcta tccccttca 226500
tcactcctga acaaacaaaa acaaaaaaag gaaagataac caataggctt tttatttaat 226560
tgaaaaccaa agagagagag aggaaagaac cagttagttg ccattttcta aatgcaggct 226620
tttgtttgtt tctgccttct aattctttgc tcttgaagct atagctttca agcttgtgta 226680
tacaggccca gagagaacat ttgaaatgtg gccaccctac ccatgtccat gccactcttc 226740
ctgcctttct ctctgcctac ttctgctcca ccatcccagg tcaggggctt ggaggctgac 226800
agcattacaa gtaatatagt cgttcaagct catataaaca agatgaaatc caaataataa 226860
ccaaaatgta ttttatttca aggactggac tactcagttc cctcagtttc gctgaccgat 226920
ttctaggagc cctaggctca gctcttggtt gtctcagaac tgaggagagt actcatttgc 226980
accatatgca tctgcttgtt agcctgtgct accaaaattg attcattact tggccttctc 227040
tgaaaagaaa aatgaaaaca aaaatgcact cttaaaaata attattaaaa tacaaccagg 227100
aggtatgtgc ctagacatgg ctcaccttct accaaatcat actttatgat tttccacaat 227160
attatcttct attcctcctg cccctaaggt tccatggagc agagcaagtt gaagaatgtt 227220
aaggttttac taaactttta gaacagaggc tttggggaag caagagagag gtacactgaa 227280
aatgaagtgt ctgtctctgc ttctattaat gtcataggac tagaagttga cctcatagct 227340
gattacaaat gaaccctgca aattgaaccc cagcacatgc ctctcattat ccattcttct 227400
ctttgcagga tggggtccat gctcacatat caagaaaatg gtgggtttca gtctggctca 227460
ctgggtgagg ttttggcatg aaaactaata cgggttagtg tacatcaccc ataataaaag 227520
taaaagcttt ttttttattt tacccaggta aataagcaaa aggcagatct aaaatacatt 227580
agagttaagt tccatgggga cagaaatgtc tgctttgttt gttgttatac aattgacacc 227640
tagaatggtg gctggaccat agtgactaca aataaaatat ttcttaaggg aatgaatggt 227700
tctgcaggat agatgttctc tgcatttgga taagtgatga tactatagac tcagagccta 227760
gatagaaaat attgtcccac tttcagttct gcaaactgac ttgaggtgct tggtgacgtc 227820
ctgcagcaag caaaccaaat gaaggcatct ctgagacccc atagtcacca ccagcatgct 227880
agcctcccat taccttgccc accctagatt ttcaaattgg gaatcactgt ggtaccagac 227940
tgggaatcgt gacttgcata ctttctcata ttggggcttg ggattttgag atcttatttc 228000
ctttttggc ttcttgagat ctgaaattgt tgttcagaga aggatattaa gacaatgact 228060
cttccattac catgcatttc tgttaccaac agaggaggta agtgaatcac ttaaaatgat 228120
acaattccat ccacttcagt acaccataaa catatcctta gctttgacta taattatagt 228180
atgtgggtga tgccgctgag aaaatggtat aattataaca ttatggttga gaattgtctg 228240
agtagaaaac actgagctgt actgtgcaaa gtttaaggcg gaattgtggg tccctttca 228300
atatgaataa aattgattag ccaattgcaa ctgagagctt tgtgcaatga tattaataat 228360
ataaaaatcg gccgggcgtt gtggctcaca cctgtaatcc cagcactttg ggaggccgag 228420
gcgggtggat cacgagatca ggaaatcgag accatcctgg ctaacacagt gaaacccctt 228480
ctctaataaa aataaaaaaa tatagctggg cgtggtggca ggtgcctgta gtcccagcta 228540
ctctggaggc tgaggcagga aaatggcatg aacccgggag gcagagcttg cagtgagctg 228600
agatcctgcc actgcactcc agcctgggcg acagagcaag actgcgtctc caaaaaaaaa 228660
aaaaaaagtc aagggccaaa gtaacaatgt aggaaaaatt tgatgacttt aatttcattt 228720
acttctagga gtcttacatg caagcctaat gcagagtaga gaagctcacc aacttgaagg 228780
aagcatgaat gaaattacaa ggaaatctag cttagaaaaa ttaaccctgt agcttggttt 228840
ttccactctt tgctcttggc aaaaggatct tacgtatgta taccaaatgt ctatttgaaa 228900
attttgtttc tctgaatata gctttctttt ctctttaaca cactggtcca gtggttctag 228960
attttatgct cccataaatt aagtaagaca gcattctata tcatgactga ggtgttaatg 229020
acattatgca gttgtcacat tttgaaatat aaacttaaat gcgagctttt cactgtgtgt 229080
aaagtttctc tgtatttttt taaaaaattt ttaaagacca gagattttca gcaacaagaa 229140
acataaagaa gtaaaaagag cgtagaaacc ctgccctaga ggacctgctc caccacttaa 229200
aagccatgta cctcttgaag cctgtttcct ttatttccaa cacaggaatt tttatattta 229260
caccctaacc atcacatggg tcacatgtga taacaatgtg caagtttctt acaagtgttc 229320
taggaatctg taagtcttag agttctgagg tttattccca aaggacagga aattgtgggt 229380
tacaccaaac agttaaacag ggtggcaggg aatccctgtc acgtacccag gcctttgggt 229440
tattttctag ggtgagggga catggccagt agtacaaaga gcatgtgaac gcatggatgt 229500
gggtgtgtga ggtcatgagt gggtgtgtat gtttatgtac aacacatgta ttggaggata 229560
aaagggaaaa taatttgtct tcctgacttc ttctctattc ctggcttttc ttagattgtt 229620
attcctctct aaacaaagct tcaaaacaga aacccctccc cttctttatt atatcggaaa 229680
tctgggaatt cagttatcct tgtcttatcc tactccctgt tctgttctaa atatataata 229740
acaataagta atagtactac tactagtact agtagtagta gtagtagtag tggtggtggt 229800

-continued agtaatggta gtaatagtaa gaggatgaaa agatggagga ggtgaattgg aaatagggag 229860
gtttcctgta gctgactgac agtttatata gcaaccgcct gcagatttag gttttttctg 229920
actgcgctta ttttatagca acctcaacaa gctgtgacaa cctgcaatat ctttagccct 229980
taagatactg tctcttaaac ctgaccaata tttcttattt ctcaaagagt aatgatagtc 230040
ttttctgtct gataagttca aaaggcacaa ctgattttcc taacattttc ctcaaatgaa 230100
gggagtattt gaaaaatgga actcaaatga ggagccacct cagaagccta actggagcat 230160
tcagactgca tcagacagac ttggcttcag ttctgacact gatacttact agctgtggga 230220
tttttggaca agcttctcat ctgtaaacaa gtataaatac tacctacttt ataagctcgt 230280
atgaaaattc ccacaaagtt tgatgttagt ttcctttctt tttgtgctca gctctaaaaa 230340
tatgcagtgt agtgagtcac taatatttca ttaacataag ggaaaactat atacccaacc 230400
caaaagctga gattcttcag aacatttttt aaagaggttc taattaggaa ttttataaat 230460
ggaatacaga gtacttttta aataataata acaatgatta atttaagtta ctaaacaaaa 230520
taccttaatg aatttgagaa aaataaactg aagataaata ttaattatta aaagagaaaa 230580
ttattaaagt aataacatgc aagtcacttg atacttgcaa agtaacacag aattagacat 230640
aaagccacat ttaagaggca gcaaagccaa aatggctggc cccctttaaa aggctcttgg 230700
caacagacat atggaaaact gtcatctctt ccctgggcct ttcttcctac tctggataag 230760
cagcatcctt cacacaaaag aacatccagg ataactaaga aagagatgaa atgatttatc 230820
ggaactagtt aaaataatta aatcttaaaa gcatgttctc ctgggcatag agtggggtga 230880
tttctgcaaa cattttgaaa ataaagtacc cctaaaacaa ggatttggtt taactgctag 230940
aaaacaaggt gacaggttga gaaaactgaa aattttctta aaatcttgtt tacttgaatg 231000
gtgagccagc cacccaggga agaaaccaga gctctttcct ttaagaaata tagacttcag 231060
ttggaagaaa aaattagtag gttttaacct tcaaccttct agtgaagtga gaatattgat 231120
tgagcaccta ttattagaat aaatttatct taagtgaccc agggaagggt cgtgggtgac 231180
gggaactgtc aagaaagaaa aaaaatatgg ctgtggatct taagtactta aaatctactg 231240
agggctcttg tctccatttt ccttagaccg tgatgttgct caaagtcaca taagagggca 231300
cataaattta ctgaatagta ttacagaaag cagcagtgac actgaaatgc ttgcattata 231360
ttcactatcc cagtcatctg cagttgcctg agggatttgc aagcaaggac aggaaaatgc 231420
tagtaccaac cagttctaga taaagaattt atttgctcca aaaactttca ctgtattaaa 231480
ttaaattaga ttggctggaa ttaaaaggta ataaggccca ttttcttatg taggtcatca 231540
attaatttaa ctctaaagat aattccaaaa gaagaggttt aaaaattgtt tgagtagtag 231600
taacatcatt ggaatttatg taaaacttcc caatgtactc acttttacag ataacatata 231660
tatatatata tatatatatg tatgtctatg actgctggca taatgatcaa aatgatcagt 231720
tttattactt tgtaatcaca tcaggcggca ctgatggttg aaataaaatg tgttagatga 231780
gtgaatgcaa agataacata tagcaaatga aagtctttgt ctatgaagca catgattgtt 231840
ataattgttg ctgccctttt gggatcctga accagattcc ccaaataagt aggtaacaca 231900
gaatttgtct tgagcacttt ttcaagcatt gtaatccatg cattgaagta ggctttatca 231960
gcctacagct ataaactcca aggtgatttt aaagtctgaa ggtttatagg tcttcattag 232020
gataagctgg gcttaccata taaatctatg aggactttgc tagaaaaata gtggaattgt 232080
tgaataggga aaagagataa tggtaacggg atttgcctga tgtcttcatc ctagaaaaaa 232140

-continued agatttctgc ttgggcatta aggaccccag tgatgattct gggagacttt caggaatgct 232200
gacaaggctg gagctactca ggatttgatg ccaaagaagc cacactgcac atgtgttcct 232260
ctaaggtgta cttggttctc atctgagagg caaaggctct acttcttttt aattgtttgg 232320
tcctaagtta ccttcaaact ccacctaacc acatctctaa tcctgtgtat agcctttcca 232380
acatcttgta aattccaagg ggttggggga acctttaggt tccaaggctg agctaagtta 232440
taaatgaata ccctgtgcag tgttgagaat gaaacagaag ctttggtgcg tggtagccca 232500
ctgtgagtgg ggtttcaaag gagcagtcca ggggccctac atgaataggc atatatgggc 232560
caagagacag gcttctctca gccataccat agtatactgg aacaatgaga aatgggagag 232620
gacatacttc ttaaagtgac acactgacct gttttcattc tctcctctct ctgcttctcc 232680
atttccactt attgccccta ttgcatctgt ccagtaactg tttctttaac agttttccaa 232740
actgacatta ttaatccaga agatggatgg tggtttttta attaaaagag aaagctgatt 232800
ttatttggtg agacttctgc tatcatcttc agtgttatat cccaatatga gtactttttt 232860
taatgttcta ctaaatccaa tagtatattc acctcactct cgagttaaac tcttggcttt 232920
aaaaaaatta gccagaaaaa cttcttaaga aaaaatacag tattttaaat tctataaatg 232980
aactatatct taaaatattt gggggcataa ttcaattgta tccattttac tttaagatca 233040
tgcaaaaagg gaaaggtata gatgctattt tattgatatg ctgctccatg gatttcaaat 233100
tcaacatcat aagccaagat ttgtgggacc agaggaatgt tcaaaagtat aatctgatac 233160
attatctgct gcaggaatta agtaaaatat tgcatacatc tcacttccta taccaaatag 233220
agagaatgaa agtactagat tttgtattac agatagttta gacaactata gggaattctg 233280
aactttcaaa cttttatatc ctaaactcaa gatttgggcc ttgaaaaata aaactgataa 233340
aactgctaca gtgtagattt ttaaaattac attcatgtgg tgaagttgac actttctgtt 233400
ggtatggcta gaagtcagat agatgcttaa tttgaaagac catgttttta tttcttctct 233460
ttttcttacc ctatgatttc attgacctga agtggctttt agtgccattc aattcacaca 233520
gaagccaaaa ttggttactg tgttaagaag aaaccaagat gttttattta gtttatgaaa 233580
cactagcaaa attactattt gatgcaaaac tgtgaggaag ttttgtagtc attgaaagga 233640
gcaagaatat agactgcttg cagttccagt gtcgagacat tcattatcag atttaccact 233700
tgaaaatatt atcaagatag tatttatatt gtgtttacca ggtaaactaa gcactttagt 233760
tctgagcact ttacatattt taaatcatta atagtgctgt aacaagcctc tgaggtaggt 233820
actgttatcc ctctttaaca gataaagaga ctgaggcaca aggaagagaa gtgacttgct 233880
gaaatcacac acagctgaat gtggaccctg attcaaatcc acacatcctg actcaagcat 233940
ccttgctctg tactactgtg ctacagtgcc tctttacatc ctcctgatgt agaaatcttc 234000
ttctagaata atgagaagca gtgtgaactt tgaagtagga cttcctgggc atggtgcttt 234060
ccatctctgg gccaaagttt tctcatcttt acaaaaggat tacgatcaac ccccatctca 234120
tactgtggtt aggagaattg agcaagacca tatactaaaa gatgtcagaa cagggcctga 234180
cagatcatag tgcccaataa acattggctc ttgttatcat cataaatatg ttaaaatgag 234240
ctttagtatg tggataatag tagcagaatt tcctgaatga gacatgttaa acatttatta 234300
agcaggcact ttttggagtt tatcttataa taattcagta aggttactct tgtcatccct 234360
atttcactga atttgaggaa tctcaggctg caagataacg tattagtttt ctagaatcaa 234420
ataagcaagg attcaaactc aggatatatt gaccccaaaa cctcagatct ttctgccatc 234480
cctatcttgt tctaaacccc aggtttgctc atccgggccc tagtcattga tcaaaaagca 234540
ccaatacaaa tcagagtaga gaaagtcata ttgagcttgt gaggttgtat tatgggcatg 234600
gtaacaaatg taattcagct gtattggcac agtgcataac aaccacactt aatttctgtc 234660
ctaagacctg tctgagccca taaataaagt tacattaata attacggaat ggtaagggac 234720
cactcagaaa atcttggttg atataggaag tggcatctgt ggcttctaat tgagagatat 234780
tgcttcttga atcagtgcta gaccattgct ctagggggat attaagcctt ctctgtccat 234840
ggaagatgtg aaattcaaca gctgacctga ctgcttgtcg ctgttgatga tcctataaaa 234900
tttcctctaa gatacgaact ctgtgttcta gtccaaatca agtgaatatt tcctgttggt 234960
tgacctacaa cttcaagggt atgaggtcat aagtttaaaa agattccttt tctccccagt 235020
gttgtaagag ttattttagt tctatcaaat gctcccagtg agtactgcat atttcctttt 235080
tgccagatac attagctatt cactcttttt tcctatctct tctatgcttt tattttttcc 235140
ctcatctgtt taaccaatgg taccctgaat tttagaacca gacaggtagt aggacaaggc 235200
aggtgaaaat gcacaggttg taaatttcag aatgcacatt caaattccat cgttgtctct 235260
tactaactga atgaatgtag gtaagatgct ttacctctca gagtcttact taccccatct 235320
ataaaatgag aataatacaa actgtcttct gtggttttct tgagcattaa acgtctctat 235380
ttatggaaca tagtttcaca tagtaactga ttctgtacca atgccctgcc ccccatgtag 235440
gcaaatgcat gtcccgaaag acccaaaaca agttgtccct cttttcaaga tgaagatttg 235500
taatctctcc ttaaacttat ccagttctgg tgtttaattt cctttataag ccagaagttg 235560
ttttacgtct caccaaatct tataacatga atattacact gtcttccaaa tgtgagcctc 235620
taattacctt aggccaatag cagagcctct gatcttgtct tttctccttt tccgcttacc 235680
agacagcaca ttctgcctga gagttgagac ccaaaaagat ataaatcaac tagggggcaa 235740
aaatggagtt tcctaagctt gtcccagagt ttgactcagt agcctgaggt ggagttcagg 235800
ggcttgatgt taaaaacaag ctaccccagt ggttttgctg caggtggacc agactcccaa 235860
gaccacattt tgcaagcact ggcatttagg aagagcacgt acctactcta gcagagttta 235920
tgcagactat gattgcagcc tagtttgtgc agactattga ttgcagccac ttggcaaggc 235980
tctataagaa aaagcgagcc aacatgtaag taaattatca tggccttgaa actcctcatc 236040
tgaaagggtt tcctctcatc ccctcatccc cttgtgtctg cccctgaatg ccagactatc 236100
ttctccagcc ccaagtcaac ctctcatttt taagccattc ctcattctcc tatatagtcc 236160
aaaatagcga atacattttt aggaattctc ttgctttatg gacgttcatc caaaaatatt 236220
tcattatgag aataagtgct tagcttatcc tgtagtgtct ttctgctcta atatttgggc 236280
ccttcctttc cacatagttg cattttcttt gacgggcaga tgctgctcct ttaatatttt 236340
tcacaccttt gtgcttctaa cagagcaatt atttcaggat gagggcactt ggagagctgt 236400
aagaggataa ggagcccagg gctctgcctt ggatttgtgt acctaaatgt tacctaatta 236460
gataaacctg aggaagatgt ggaagcaaag tagaatggaa cagaaagtgt ttgaataata 236520
agaatttgga cattgctgct ccgtggtgac attggcagac tctaagcctc ttgcctcatt 236580
ttattcattc atgtatgacg gggttatgct cagtcataag tcactaaaat ttgtattcta 236640
catcccatta gtaaagtaat ttttgaacac atgatacata tgtttacata tttgtaagtt 236700
atatatatgt acaaggttct aatatattct gttcattgtc aaacataaaa tatatataaa 236760
tttggtttaa tataaaatat aaaattggca ttagtagaca ctgtctaccg aaatgagaca 236820
ctgtctcatt tctgaaaaaa gcacaatgta tactaagtta aaggttcatt cttaacagca 236880

-continued gtaggagtag atctttattt caaatagtct ttgggataat ttcctatttt ggaagacagc 236940
ttatcagatt tggttagagt tgatgaaagc ttattctagg gttaagaaaa gtattagccc 237000
agccattttc ttattgttga tttgggcttg cataattagt tttaccttca gtatgaagtt 237060
tctttacatg aatcttttta actcacttat ttgttataca attattagtt aaatcaattt 237120
taaatcagta taatctatcc acaaaatcag tcatacagaa cctgcaaaaa acatgttcta 237180
acatgttaca tgaagaggta actaaagata ctacaaacaa cccctctgaa cggtaacact 237240
cccactcttc ctgcaaaatt cctctcatag caaatgcaac atgtgactca gacacaggct 237300
gactgaaggc tttatgcaac tcttacatgc tcaatattag aaaactttca tttgtttcct 237360
attttatata aacaacacat ataaataaac attttagtat cttctcatta cccagtggat 237420
tgtcttgcat ggtccatttt gaagacagta aactgtagcc tctattttta tttaatttca 237480
aatacctgtt tgccaatatt cacagccagc tcttgttaat gttcttttct gtcctgtgaa 237540
tcctgatgtc gtatcttgca acatcacctc taaagcctat ctttgcactc ctgtccatcc 237600
cccattctct attattatgc tgcctctgat ggccagagaa aaaaatcttg aaaatatata 237660
ttgtattgcc ctacctggcg aggaatcagc agttatacaa ttcaaagttg cagcaattca 237720
ccacattgtt tagcacccta ctatgtgtaa ggaggaagct tgatttaaaa aatatataca 237780
atcatgcctt cttcaagaat gttttggagc atgcaagagc ttaatgctca tggacattta 237840
ctttattcca gcaaatttag acccaatctc tgtgtagttt cattttgttt tccatttcct 237900
gattaactga ctatatatct agctacttat ttgctgccat ctagtgtaat aaagtatgtt 237960
gattatacaa ggaattttga gcccattatg tagttgaata tcagtactca aaatgattct 238020
ttttttctgg tttcttataa gtttacaaaa tgcctagtca gggacctttc ttatcactgt 238080
aaccctgaac atggtcttaa tcttgtgtca tagaatctag ggctcaggat caaccttcgt 238140
tcattttcta taaatgtgac atttggaaac tgggtagggg cttagcagtt ggtggatatg 238200
aagtaaatat ataagagtaa tcattaagag atcatctcag tttagtgacc atgatttttt 238260
cctcatggag gcagcaaaac acagcatgga ttcttaccag tagtgtgacc atgggcaatt 238320
tatttctctc ttggaggcat cattttcttc atatctaaaa tgaaatggta ggtccaggtg 238380
actgttaagg tctcttctag ctctaagagt ctgtgtctac atataaatga ttttctctgc 238440
caaagtagtg tttttagagt ccttttttaat gccagaaatg aatacggctt ctctagttct 238500
tctaagtggc catctatcct ttggtgatgg ttagaagtaa gcagagatcc tggctagaaa 238560
gagagagagg aaaatgtgga ccatgatttt attcctttta ttcttgagag ttgtccaatg 238620
ggatattgtc cactagtgga taagtagata cttgccaata tgcacctgac ctcttctctt 238680
cactcataat gggaatttag aagtataata cctgttataa tcaacttcct aatctctatc 238740
cctttttgt cactctattt cctactgtaa cttctctatg aagtactata agtctacagt 238800
aacatactgg tgtttccctt tccttatgaa gttttatata gctactccag tatatcctaa 238860
aatgttcctt tttcttgctt ttatagtgga gtcttgcttg ttggccaggc tggcctcaaa 238920
ctcctgagct caagtgatcc tcccacctaa tagtagctgg gtattcttct gagtaggtgg 238980
tcctaaaatg ttttattttc agcttatttc ataggtataa gtcttatttt cccaaccagg 239040
ctgaaaactt ttcagaatca ggacttgtct ttagtttctc attttttatg aggggatgtg 239100
gcattattgc ttagggaatt cagatatttc tgataataaa gatgcttttc tgtttgttca 239160
tataaattag ggtaaaagag gaagtacaaa actatctcaa atcaagtaca ggactcttaa 239220
ttattactag ctatctaaca gctcatagaa accgataagt ttctgaacct aatgccaaaa 239280
aaaagcaacc ttaccataaa aagaaaatcc aaataaaact gaaagaggca gtgggcagtg 239340
ctacctatgg gaagaaaact ttgaagtggg aaaaatctgg attcacatcc cagctttgct 239400
acttattacc tttgtgtttt ggctaaaaat tatctaactt tcctgaagtt aagtttcctt 239460
ctctgtaaaa tgagggttat aataatatat acagcatact ccacagaaga gttgtgaaga 239520
tggaatgaga aagcaaatgg caaaaactta gcacaaagta ggagctcaat caatcatggt 239580
taaaaagaac ttttatccat tgttattttt gcttatatac agtaagaatt atccaatgca 239640
aatgtaatca gagcatctgc aattgagctt tataaagtga attataattc tcataccata 239700
gtggttctca tcaagggtga ttttttttccc cccaggggac atttggcaat gtctagagac 239760
attttacttg tcacactgga aaagaggggg tgctactggc atctagtagg tagagagtag 239820
gaatgatgat aagcattctc taatgcacag gacagcattc cacagcaaca aatgatctga 239880
tccaaaatac caatagtgtg gaagttgaga aaccctacca taaagcctag ggagtccatt 239940
acttctgacc taaatttgtt ttatatttaa gagtggatgt ggattaaaag tagcttccat 240000
tttggtaggt tatgaagaga gttgtctaat ctgtgcttta gattctaatt ttgaggcata 240060
tttttaggct aaggcattgc aatatataag gctttctaag tttcagacat tttcttggag 240120
gtcaacaaat gaaggcttgg ggatctatta acccactaga gtagtgtaat aatggtggtg 240180
gttgtttatt gaagactaac caagtgccaa gtactctata ataatctgat ttatttttca 240240
gcaactgtat aagcaggtat tttgctctca ttttacacag gggaaaactg gagcttagag 240300
aacttatgta acattactag caagttgcac agctgggatt caaactgaaa tccagctagc 240360
ttcaaagact gtgttctttc tgctgctgca tactacccct acctaccaag gctctgagat 240420
tagaaagcag gatgggtgtg ttttaaagga aataaggtag gaaagttttc aaatattaga 240480
aactctgcac aagaagatta ggtcaagttt cccactgagg ggcccttgag tatctatgaa 240540
ctcgatgaaa actctgagct tctcaggaag gtagaccaaa gggaaaggat tcatcaaaat 240600
ggatgttagc actatgccat gtgtattact ccatcctcac acggccaaaa ggacatacct 240660
gagactgggt aatttgtaag gaaaaagagg tttaaaaaag ttctcttcga tggccaaata 240720
ggaacagctc cggtctacag ctcccagcgt gagcgacaca gaagacgggt gatttctgca 240780
tttccatctg agctactgca ttcatctcac tagggagtgc cagacagtgg gcccgggaca 240840
gtgggtgcag cacactttgc aggagccgaa gcagggtgag gcattgcctc actcaggaag 240900
cgcaagggga cagggagttc cctttccgag tcaaagaaag gggtgacaga tggcacctgg 240960
aaaatcgggt cactcccacc ctaatactgc gcttttctga cgggcttaaa aaacggcgca 241020
ccaggagatt atatcccgca cctggctcgg agggtcctac gcccacggag tctcgctgat 241080
tgctagcaca gcagtctgag atcaaactgc aaggtggcag caaggctggg ggaggggcgc 241140
caggcattgc ccaggtttgc ttaggtaaac aaagcaggcg ggaatctcga actgggtgga 241200
gcccacaaca gctcaaggag gcctgcctgc ctctgtagac tccacctctg ggggcagggt 241260
acagacaaac aaaaagacag cagtaacctc tgcagactta aatgtccctg tctgacagct 241320
ttgaagagag cagtggttct cccagcatgc agctggagat ctgagaacag gcagactgcc 241380
tcctcaagtg ggtccctgac ccctgacccc tgagcagcct aactgggaga cacccctcag 241440
taggggcaga ctgacacctc acacggccag gtactcctct gagacaaaac ttccagagga 241500
acgatcaggc agcagcattc aaggttcatg aaaatccgct gttctgcagc caccgctgct 241560
ggtacccagg aaaacagggt ctggagtgga cctctagcaa actccaacag acctgcagct 241620
gagggtcctg tctgttagaa ggaaaactaa caaacagaaa ggacatccac accaaaaacc 241680
catctgtaca tcaccatcat caaagaccaa aagtagataa aaccacaaag atggggaaaa 241740
aacagagcag aaaaactgga aactctgaaa agcagagcac ctctcctcct ccaaaggaac 241800
gcagttcctc accagcaacg gaacaaagct ggacggagaa tgactttgac gagctgagag 241860
aagacttcag acgatcaaat tactccgagc tacaggagga aattgaaacc aaaggcaaag 241920
aagttgaaaa ctctgaaaaa aatttagaag aatgtataac tagaataacc aatacagaga 241980
agtgcttaaa ggagctgatg gagctgaaaa ccaaggctca agaactacat gaagaatgca 242040
gaagcctcag gagccgatgc gatcagctgg tagaaatggt atcagtgatg gaatatgaaa 242100
tgaatgaaat gaagtgagaa gggaagttta gagaaaaaag aataaaaaga aacaaagcct 242160
ccaagaaata tgggactatg tgaaaagacc aaatctatgt ctgattggtg tacctgaaat 242220
tgacggggag aatggaacca agttggaaaa cactctgcag gatattatcc aggagaactt 242280
ccccaatcta gcaaggcagg ccaacattca gattcaggaa atacaaagaa cgccacaaag 242340
atattcctcg agaagagcag ctccaagaca cataattgtc agattcacca aagttgaaac 242400
gaaggaaaaa atgttcaggg cagccagaga gaaaggtcgg gttacccaga aagggaagcc 242460
catcagtcta acagctaatc tcttggcaga aactctacaa gccagaagag agtgggggcc 242520
aatattcaac attcttaaag aaaagaattt tcaacccaga atttcatatc cagccaaact 242580
aagcttcata agtgaagggg aaataaaata ctttacagac aagcaaatgc tgagagattt 242640
tgtcaccacc aggcctgccc tacaagagct cctgaaggaa gcactaaaca tggaaaggaa 242700
caacaggtac cagccactgc aaaatcatgc caaattgtaa agaccatcaa ggctaggaag 242760
aaactgcatc aactaacgag taaaataacc agctaacatc ataatgacag gatcaaattc 242820
acacataaca atattaactt taaatgtaaa tggactaaat gctccaatta aaagacacag 242880
actggcaaat tggataaaga gtcaagaacc atcagtgtgc tgtattcagg aaacccatct 242940
cacgtgcaga gacacacaca ggctcaaaac aaaaggatgg aggaagatct accaagcaaa 243000
tggaaaacaa aaaaagtcag gggttgcaat cctcgtctct gataaaacag actttaaacc 243060
aacaaagatc aaaagagaca aagaaggcca ttacataatg gtaaagggat caattcaaca 243120
agaagagcta actatcctaa atatatatgc acccaataca ggagcatcca gattcataaa 243180
gcaagtcctg agtgacctac aaacagactt agactcccac acaataataa tgggagactt 243240
taacagccca ctgtcaacat tagacagatc aacgggacag aaagttaaca aggataccca 243300
ggaattgaac tcagctctgc accaagcgga cttaatagac atctacagaa ctctccatca 243360
caaatcaaca gaatatacat ttttttcagc accacaccac acctattcca aaattgacca 243420
cgtggttcga agcaaagctc tcctcagcaa atggaaaaaa acagaaatta taacaaactg 243480
tctctcagac cacagtgcaa tcaaactaga actcaggatt aggaaaccca ctcaaaacca 243540
ctcaactaca tggaaactga acaacctggt cctgaatgac tactgggtac ataacaaaat 243600
gaaggcagaa ataaagatgt tctttgaaac caacaagaac aaagacacaa cataccagaa 243660
tctctgggac gcattcaaag cagtgtgtag agggaaattt atagcactaa atgcccacaa 243720
gagaaagcag gaaagatcca aaattgacac cctaacatca caattaaaag aactagaaaa 243780
gcaagagcaa acacattcaa aagctaggag aaggcaagaa ataactaaga tcagagcaga 243840
actgaaggaa atagagacac aaaaaaccct tcaaataatt aatgaatcca ggagctggtt 243900
tttggaaagg atcaacaaaa ttgatagacc actagcaaga ctaataaaga agaaaagaga 243960
gtagaaaaat aaaaaatgat aaagaggata tcaccactga tcccacagaa atgcaaacta 244020
ccatcagaga atactacaaa cacctctaca caaataaact agaaaatcta gaagaaatgg 244080
ataaattcct caacacatac accctcccaa gactaaacca ggaagagttg aatctctgaa 244140
tagaccaata acaggctctg aaattgtggc tataatcaat agcttaccaa ccaaaaagag 244200
tccaggccca gatggattca cagccgaatt ctaccagagg tacaaggagg aactggtacc 244260
attccttctg aaaccattcc aatcaataga aaaagaagga atcctctcta actcatttta 244320
tgaggccagc atcatcctga taccaaagcc tggcagagac acaaccaaaa aagagaattt 244380
taggccaata tccttgatga acattgatgc aaaaatcctc agtaaaatac tagcaaaccg 244440
aatccagcag cacatcaaaa agcttatcca ccatgatcaa gtgggcttca tccctgggat 244500
gcaaggctgg ttcaatattt gcaaatcaat aaatgtaatc cagcatataa acagaaccaa 244560
agacaaaaac cacatgatta tctcaataga tgcagaaaag ttctttgaca aaattcaaca 244620
acacttcatg ctaaaaactc tcaataaatt aggtattgat gggacatatc tcaaaataat 244680
aagagctata tatgacaaac ccacagccaa tatcatactg aatgggcaaa aactggaagc 244740
attccctttg aaaactggca caagacaggg atgacctctc tcaccactcc tattcaacat 244800
agtgttggaa gttctggcca gggcaattac gcaggagaag gaaataaaga gtattcaatt 244860
aggaaaagag gaagtcaact tgtccctgtt tgcagatgac atgattgtat atctagaaaa 244920
ccccattgtc tcagcccaaa atctccttaa gctgataaac aacttcagca aagtctcagg 244980
atacaaaatc aatgtgcaaa aatcacaagc attcttatac accaataaca gacaaacaga 245040
gccaaatcat gagtgaactc ccattcacaa ttgcttcaaa gagaataaaa taactaggaa 245100
tccaacttac aagggacatg aaggacctct tcaaggagaa ctacaaacca ctgctcaatg 245160
aaataaaaga ggatacaaag aaatggaaga acattccatg ctcatggata ggaagaatca 245220
atattgtgaa aatggccata ctgtccaagg taatttatag attcaatgcc atccccatca 245280
agctaccaat gactttcttc acagaattgg aaaaaactac cttaaagttc atatggaacc 245340
aaaaaagagc ctgcatcgcc aagtcaatcc taagccaaaa gagcaaagct ggaggcatca 245400
cactacctga cttcaaacaa tactacaagg ctacagtaac caaaacagca tggtactggt 245460
accaaagcag agatatagat caatggaaca gaacagagcc ctcagaaata acactgcatg 245520
tctacaacta tctgatcttt gacaaacctg agaaaaacaa gcaatgggaa aaggattccc 245580
tatttaataa atggtgctgg gaaaactggc tagccatatg tagaaagctg aaactggatc 245640
ccttccttac accttataca aaaattaatt caagatggag taaagactta aatgttagac 245700
ctaaaaccat aaaaacccta gaagaaaacc taggcattat cattcaggac ataggcatgg 245760
gcaaggactt catgtctaaa acaccaaaag caatggcaac aaaagcaaaa attgacaaat 245820
ggggtctaat taaactaaag agcttctgca cagcaaaaga aactaccatc agagtgaaca 245880
ggcagcctac aaaatgggag aaaattttcg caacctactc atctgacaaa gggataatat 245940
ccagaatcta caatgaactc aaacaaatct acaggaaaaa aacaaacaac accatcaaaa 246000
agtgggcaaa ggacatgaac agacacttct caaaagaaga catttatgca gccaaaaaac 246060
acatgaaaaa atgctcacca tcactggcta tcagagaaat gcaaatcaaa accacaatga 246120
gataccatct cacaccagtt gttagaatgg cgatcattaa aaagtcagga aacaacaggt 246180
gctggatagg atgtggagaa ataggaacac ttttacactg ttggtgggac tgtaaactag 246240
ttcaaccatt gtggaagtca gtgtggcgat tcctcaggga tctagaacta gaaataccat 246300
ttgacccagc catcccatta ctgggtatat acccaaatga ctgtaaatca tgctgctata 246360

-continued aagacacatg cacactatgt ttattgcggc actattcaca atagcaaaga cttggaacca 246420
acccgaatgt ccaacaatga tagactggat taagaaaatg tggcacatat acaccacgga 246480
atactatgca gccataaaaa tgatgagttc atgtcctttg tagggacatg gatgaaattg 246540
gaaatcatca ttctgagtaa actatcgcaa gaacaaaaaa ccaaacaccg catattctca 246600
ctcataggtg ggaattgaac aatgagaaca catggacaca ggaaggggaa catcacactc 246660
tggggactgt tgtgggggtg gaggaggggg aagggatagc tttaggagat atacctaatg 246720
ctaaatgacg agttaatggg tgcagcacac cagcatgcca catgtataca catgtgacta 246780
acctgcacat tgtgcacatg taccctgaaa cttaaagtat aataataata aaagaaaaaa 246840
aaagaaaaag aggtttaatg gactcacagt tccacatggc tggtgaggcc tcacagtcat 246900
ggtagagggt gaatgaggag caaaagcatg tcttgcatgg cggcagaaaa gaaagcatgt 246960
gcaggggaac tgccctttat aaaaccatca gatctcatga gacttattca ctgtcatgag 247020
aacagcacaa gaaaaacctg cccccatgat tcaattacct tccaccagct ccctctcatg 247080
acacatgcgg attatgggag gtgcaattca agatgtgatt tgtatgggga cacagccaaa 247140
ccatatcacc atgacataca atttgccgat tcagcaacag ttttcaggtc ttctattttt 247200
aagcctaatg caatatattt tatgaattct tcctatttat gtttttcctt ttaaataagt 247260
tctactatct taactatcac tttcaaatat aatgcaagct acatatgcca ttttaaattt 247320
tttagtagtt acatttaaaa agagggtgaa attaatttta acaaagtagg ttatttatcc 247380
caatatatcc aaactattat cattttgaca tgtagtgaag ctaataaaag cattcattgt 247440
taatgatcta tctcttacat tattttttcc taataaatct tcagaatctg ggtgtgcatt 247500
ttaactttcc agcacatctc aactgggatg tgaaattttc agcaattaaa gtgaaatata 247560
gccctatcaa aactattaat gttgcattta ggaaaaagat atttttcact ctttttattt 247620
ttaaatttga gtttaaatta attaaaatgg aataaaattt aaaattcaat tctctgtcac 247680
actagccaca tttcaagtgc tcaataccta cgaaagaccc atggctacca tattggacag 247740
cacagatcta agctcttatt gctcagaatg tggtccccag agcagaatca acagcatctg 247800
tgaacttatc aaaagtgcag tatttcagtt cacacctact gaatctgcat tttaacacaa 247860
tccccaggtg atgcttgttc acatgaaagt tgtgtctctc taaatcgcag atcttttcaa 247920
caaagagccc agaaaaagca catgaatcaa taactgtgag gaataaggaa acttgccaca 247980
ggagaatggt gccagggttg gcattaatga tgtgctctgg tgaaaagtcg taggtttccc 248040
acaaaggcaa ccatggctat tctattgttt gaactgacac agagccattc tagagcttgg 248100
agttggctct gctcccagaa tctacatcaa agaatctaac actaacttcc atgactacca 248160
caattaaggc agctgcacac cccaccacta tatatatttg aaattgcaac tttagaaccc 248220
ctgtaacaca gccgtgagca tgtttctgct atacacaagt ggaatttaag gtcgaacctc 248280
cctgggagac cccaggaaga tcacccacaa gagtggcttt tgttgtctgc ctcactgtca 248340
tcctctgaga gctaacacag acacagtcaa catcctctta tatggaggtt ggcccagatg 248400
cccctgggga ttcaatgtat tctgcttcac ctcactaatc cttatttggt ttgtttttca 248460
cagaactcag tatttgatgg gcctttcaat attttccttt aaggaattca ttgtactaat 248520
ataacataga agctcattgt tctaataagt ggtccccaat gttggctgca cattagaatc 248580
acctggggca ttttgaaaaa taccaatgcc caggcatcac cccaatctaa ttaaattaaa 248640
cctgtggaag gtattttgtt aaagatcccc aagtgattac aatgtgcagc cagagttgaa 248700
atccactggt ccaattagaa ggaggcctta gctagcggtc aggtgcccaa ggaaaggcat 248760
ctcaagtttt aatgcgcata cagatagctt gggatttgtt aaaatgcaga ttctgatcca 248820
gtaggtatgg gtggaaataa acccatgttt gtgtacagat gtttctcttg tggtatgtgg 248880
ttggtaatca tcctcagtat gtttccattt ccggcaaact gggttgagtt gatgacccta 248940
ttcttactcc tccctgaaac ctttgtctct ccctcaggct cccagttctc attaatcact 249000
actttctgtg atattctgaa gcaattatta tctttaactg cctttttca ttagctactt 249060 ctctatctgc ttatgtacgt gagttatttc ctctactgga ttacgatctt caaggtagat 249120
ccaaatatca tgtcattttt ataattctca ctgcacctaa agagtgcctt acacacaaat 249180
gccacttgtt gattaattga aacagggaat agctgatgtg atcatctcaa aaaatatcca 249240
aaagacttaa aaatgcaaga tatttttctt tgttggacag aaaaagaaag tttagatagg 249300
caagggggta ggagatattg aggctttcaa tttttatttc actcggtaca tatttaaatt 249360
ttgaagaatt attttgtaat ttagtgattt taattatttg ttgggaatag ggcactattg 249420
acattttgga ctagatcatt ctttgttgtg gctgtcatcc tgtgcattgt aatatgtttc 249480
acagcatccc tggcctcaac ccactagatg ccagtatcac cctttacccc agtcttgaga 249540
accaaaaatg tctccagtca ttgcaaaatg tctcctggga aactcattca tggttgagaa 249600
cccttagttt agaaaaatgg aagtgtgaca cagctgtctt accgcactaa tatagacctg 249660
aaaaaaataa aaaattaaaa acatgcacat aagagaatga caagctatgt tctgagcaat 249720
atgtgtatat ataaatatta atataaaaat gttctctgtt cctgcgtttt ggaggccatg 249780
tgcttgtaga ccatatttat ctttgtattt gtcatcttgg tcattctctt tataaaaata 249840
gaggtatatt gcatgccaat gctcctcagc ttatgaggtt acatcccaat aagcctgttg 249900
taaatttaaa aaatcataag ttagaaatgt caaaacttga aaatgcattt aataccctga 249960
taaacacatc ataaagttga aaaatcctaa gtcaatccat catgagtcag gaactatttg 250020
tatatgaaac atttttaaaa tctgaacata gacttaggaa ttttaatatg tagtggtagt 250080
aattccacca agcaagagaa tacatagagc aaaaatcatt aagaaacagt gactgagatg 250140
attctcattc tcaggaaact ggtccagccc ctttacataa aatattctgt tcagtgtgct 250200
gtgatccttg gactgaatat actgttttag caagcagagt tgttaagcta aagcctgcac 250260
atcaacaggt gttcaatgtc tgctgaataa atgaagaatg aatgaatatt aactgcacct 250320
ctaaacccta aaattaaaaa gctttaatgt gctcatcaca aaagacccta ttttgttgca 250380
tttgaaattt caagcttcaa aaatgaaatt acatgcaaaa gtatattatc atcaatgaga 250440
ataaatggcc tcaacaaaat tacaagatag aaaacaaagt ttcatttgtc agttggtttc 250500
ttctggcaat agaaggctcc ccttagactt cattagcttc agatatttca gtgacagaaa 250560
tttaatgttg gcaaagcatt gctatacttt caggcttgga ttggaatgcc ccacatttac 250620
tttttcctac cattcctggc taaaaacttg aatgtgagaa ccagacacaa ggctctagtg 250680
gtagcaagca gaatgtctcc taagctccaa ggggaaaaaa tgatataagt cagtggttcc 250740
caaattaacc atcaaatgct acccattaaa atcactgggg aacttttaaa aattaaatgc 250800
ccaactaaca acaaactgta tgaaaaagaa atttagaaaa caatcctatt tttaaaagca 250860
gcaaaaaagt aaaatactta ggagtaaatt taaccaagga agggaaatat ctgtttactg 250920
aaaactatga aatgttgatg aaagaaattg aagatggtaa aaataaatga aaagataaat 250980
atgtatggat tggaagaatt aatattgtta agagatctat actacccaaa gcaatctata 251040
gattcaatgc aatcctatca aaattccaaa gtcattcttt atagcagtag aaaaaaatca 251100
taaaattcat atggaaccac aaaagactct gaatagccaa agcaatcttg accaaaaaga 251160
gcaatgctgg aagcatcaca ttatcagatt tcaaaatata ttacaaagct acaatattca 251220
aaatagcatg ctactggcat taaaacagat ctatcaacta ctgaaacaga atagtgagcc 251280
cagaaataaa cccacacatc tatgatcaat tgattttcaa caaagatacc aagaacacac 251340
aatggggaaa gacagtgtct tcaataaatg gtgctgagaa aactggaaat ccacatgctg 251400
aagaatgaaa ttagatcctt atctcatccc ttatacaaga atcaactcaa aatagattaa 251460
agacttaaac ataagccctg aaactataaa actaatgcag aaaatatagg gggaaatcta 251520
catgatatta atctaggcag aagtttcatg gatatgacct caaaagcaca gacaacaaaa 251580
gcaaaaatag acaaatggca ttgcatcaga ctaaaaaact tctgtacagc agatgaagca 251640
acaaatagag tgaagagaca acctacagat taggagaaaa tatttgcaaa tcatatatta 251700
gataaggggt taatattcca aaaggtacaa ggaaatcaaa ctactcaata acaagaaagc 251760
caattaccct attaaaatat agggatagca ttgggagata cacctaatgc tagatgacga 251820
gttagtgggt gcagtgcacc agcatggcac atgtatacat atgtaactaa cctgcacaag 251880
gtgcacatgt accctaaaac ttaaagtata ataataattt tttttaaaaa aaagcaaaaa 251940
ttaaaaaaaa aaaaaaaata tatatatata tataggcaac aaacttaaat agacatttct 252000
caaaagaagc aagtatcacc ctgatttaaa acctggcaaa gacacaatga gaaaacaaac 252060
tacaggccaa catctctgat gaacatagac acaaaaatcc ttgacaaaat actagcaaac 252120
tgaatacagc agcacatcaa aaagttaatt tgccatgata aactagtgtg ttagggtgtt 252180
ctagcatgct attaaaaaat acccaagact gagtaattta taaagaacaa aggcttaatt 252240
tgttcatggt tctgcagcct gtacaagcat ggtgccagca cctggccagc ttctggggaa 252300
gcctcatgaa atttttattc atggcagaag gtgaaacagg aacaggcaca tcacacaggg 252360
gaagcaggag taagagagag tgtgagggag gtgccacaca cttaaacaat caggtctcac 252420
aagtactcac tcactactgc aaggacagca ccaagccata agggcccacc cccatgattc 252480
aaacacctcc caccaagacc cacctccaac attgggcatt atatgtcaac atgagatttg 252540
aacagataca aatattcaaa ctatatcaag taggcttcct tcttgggatt caaggttggt 252600
tcaacataca cagatcaata aatctgactc accacataaa cagaattata aacaaaaacc 252660
acatgatttc aataggtgtg ggaaaagctt ttgataaaat ccaacctccc ttcatgttaa 252720
aaaaaaaaaa aaaaacctta agaaactagg cggccgggcg cggtggctca cacctgtaat 252780
cccagcactt tgggaggccg aggtgggcgg atcacgaggt caggagatcg agaccatccc 252840
ggctaaaacg gtgaaaccca gtctctacta aaaatacaaa aaattagccg ggcgtagggg 252900
cgggcgcctg tagtcccagc tacttgggag gctgaggcag gagaatggcg tgaacccggg 252960
aggcggagct tgcagtgagc cgagatcccg ccactgcact ccagcctggg cgacagagca 253020
agactccgtc tcaaaaaaaa aaaaaaaaag aaactaggca ttgaaggaat atttctcaaa 253080
atagtaagag ccatctgtga caaacccaca acaacataat aataaatggg caaaaactgg 253140
aagcgttccc cttgaagaca agaaaaggat gccttttctc acctgttgta ttcatgacag 253200
tacttgaagt gctagccaga gcaatcaggt aaaagaaaga aataaaagac atcaaaatag 253260
aaaaagaaga aatcaaacta cctctcttta ctgactatat aattctatgc ctagaaaaac 253320
ctaaaggctc caccaaaaaa gctcttggaa ctgataaaca acttcagtaa agtttctgga 253380
tacaaaatca atgtgcaaaa atcagtagca tttctataca gcaatagtgt tcacattgag 253440
agccaaacca agaatgtaat cccatttaca gtagccacaa aagaaataaa gtacaactag 253500

-continued ggatacatct aaccaaggag atgaaagatc tcataatgct gcacaagtac agccatttaa 253560
tcttcaacaa agatgacaaa attagcaatg gggaaaggac tctctagtca gtaaatggta 253620
ctgggataaa tgtaaatgtc agtaaatggc tagtcagtaa gtgatactga ctagctatat 253680
gtagaagaat gaaactggac ccctaccttt caccatatac aaaaattaac tcaggatgga 253740
ttaattattc aaatgtaata tctcaaacta taagaatgta atattcaaat atatctcaaa 253800
tgatatacaa actataagat atatattata tctcaagcta tatacaaact ataagaatgt 253860
aatattcaaa tgtaatatct caaactataa gaatcctata agaaaaccta ggaaacacca 253920
ttctggacat cagccttgga aaagaattta tgactgagtt ctcaaaagca atttcaacaa 253980
aaacaaaaac tgacaagttt ttctgtgtag aagctcttag tttaagaaaa agaaaccagc 254040
aacagagtaa acagcctaca gaatgggtga aaatcttcac aaactgtgct tccaaccaag 254100
atctaatatc tggcgtctgt taggaactta aacaattgag caaacaaaaa acaaccccat 254160
ttaaaaatgg gcaagcagca tgaacagaca gttctcaaaa gaaggcatat aaacagctaa 254220
caaacatgaa aaaatgtctc acatcactaa tcatcagaga aatgcaaatc aaaaccacaa 254280
taatatgcta tatcacacca gtcagaatag ctattatcaa aaagtcaaaa acaacagacg 254340
ctggcaaggc tgcagaaaaa aaagtgaacg ctcatacacg gttgctggga atgtaagtta 254400
gttcagccac tgtgaaaagc agtttggaga tttctcaaag aacttgaaac agagttacca 254460
ttcaacccag caatcccact gggtatatat ccaaaagaaa gtacattgtt tcttttggat 254520
attgttctac ccaaaagaca catacactca catgttcatt acaacactgt tcgcaatagc 254580
aaagacatgg aatcaaccta ggtgcccaac aaaggtggat tggattaaaa aatgtggtac 254640
atgtccacca tgggatacta cacagcaata aaaaagaatg aaatcatgtc ctttgcagca 254700
acatggatgc agctggaggc cattatacta agtgaggtaa tacaggaaca gaaaaccaaa 254760
tactgcatgt ttttacttat aagtgggagc taaacattgg gtaaacatgg atataaaggt 254820
ggcaacaata gaaactgggg actaacagag tagggaggta gggagcagag agaggactaa 254880
aaaactatta ggtactatgc tcattccctg ggtgatggga tcaatcatac cccaaacctc 254940
agcatcgtgt gatataccca ggtaacaaac ctgcacattt gttccctgaa tctaaaataa 255000
aagttgaaat tacaattttt aaaaggatag aaactagtca tcagcgtgtt ttttaatttt 255060
ccaggtgact ctaacattca ataattattt taaataatta tttctgtctg tagaccttct 255120
gccagctact aagtttcagg aattttgatg gtctcattaa agagaacctg acaaccccac 255180
ttacaagtgc ttcagctaag tttcatttat aatattttca tattgccaag gatccagtag 255240
tgtctttttt acagtgagtt acaaattcct gtttttgtga cagtgacagg ccaaaattaa 255300
tgagctgtga tttttaaact gaaaaagtga ctgtccaata gaggctaaaa agaaaactaa 255360
aattatattt tgtcaatttt agtgttaagt gtgatttttt gctttgtatg ttttagatag 255420
ttttttttatt gagataaaac ccaaatagca taaaatccac ctttttaatc tcaaagtggt 255480
ttttggtata ttcacaatgt tgtgcaacaa tcactactat ctaactctag aacattttca 255540
ttacttcctc atggaaccct gtacccatta gtagtcactc ccagtttccc attcacctca 255600
tttcctggca accactaatc tacttttctg tctctctgta tgtgactatt cttaacattt 255660
catgtaaatc agatactata atatgtggcc ttttatgtct gacttctatc acatagcaac 255720
atattttcaa ggtcattcgt gttgtagcat gtatcagtat tttattcctt tttaagacaa 255780
tactttatta taggattata ccacatcttt tttatccact catcagttga tggacctttg 255840
agttgtttct acttttctgt tattttaaat aatgctgtta tgagcattct tgcacatgtt 255900
tttgtgtgat catatgtgtt tgcttctctg ggcatatacc taggagcaga attgcagggt 255960
catatggtaa ctctgtattt aacattttga ggaacccccca aattgctttc cccagtagct 256020
ataccatttt acattctgaa cagaagtgtg tgagggtttc tattacttca catcctcttg 256080
ctttctattt taattattta attatttaat ttaattatct aagatgcctt ttaccctaac 256140
caaccagaaa ataaacttga ctgaatttag tgctaattgt ttttgcatag tcattcagta 256200
taattgtctt tgacatctca aaacactgct tatgcagaat acactttttt aaaacagtga 256260
aatcatagca attctatttc ctaagtcagt tcttcttcag ggtagtaagt tataggtctt 256320
tgaggtcatg ttcctgtttc catcttccaa aaggcaacat tattaaaatc ttgttgctgt 256380
atctgccttg gcatatcccc ctctctatcc agagaaaaga tcactgacag aatagtgtcc 256440
ccacctttct atcttagagg tctcattacg agtcagtatg cttttaaaag aattaatgga 256500
taaagagcta gacatcaaga agaagagaga aaattttaaa taagacagag gagtgtatga 256560
tcactctttc taagatgatt aaatgaaata atttgaaagg caataaacta actgcaccaa 256620
gtaaatcttg tgaaagcgaa aggaaagagg agaaggaaga tttgagtgct gaaaaccagg 256680
ataaattgta ttcaaccacc agcattaagg gaagttatac aatacatttt atgaagaaag 256740
tgttccatga aaataaaaca acaaaaagaa agtttggtga aggtttaaat gataaatgcc 256800
aatagtagta tatgtgcaat tatctactga cactgctata caaatgagct atctatatag 256860
gctgtgacca cataacctca cctgccaaac cacagtacta taaataaata cttttcccag 256920
acactacaga gctcagttga cttgagattc atcttatggt aactggaaat gtagactgtg 256980
cctttatttg ggtcaatcct acaattttct ttaatgtacc agcaattcat tatttaaagt 257040
ttactagagt ttaatttaaa attataaaaa aggaagaaat tggctgggta tggtggctca 257100
cgcctgtaat cccagcactt tgggaggcca aggcgggaag atcatgaggt caggagatcg 257160
agaccctcct ggccaaaatg gtgaaaccca gtctctacta aaaatacaaa aattacctgg 257220
gcatggtggc acacgcctgt agtcccagct actcaggagg ctgaggcagg agaatcgctt 257280
gaacctggga ggcggaggtt gcagtgagcc aagatctcac cactgcactc caacttggtg 257340
acagagcgag actccatata aaaaaaaaag gaagaaatta atagttcagg tgagaacttg 257400
tgaattttta ttctcaactc taagctagta agtgcttaaa tagaagactt tacaacgagc 257460
tgtaccttct taattctaca gagaatcatg aggaaaatca aatataaatg tgaatttctt 257520
atgttcagta ttgtccaaaa agaaaatatt ttattaaatt ttttgtcagt tgccatcatt 257580
atttaaagcc ttcctgccag tagcctatac tatttttgga atggagtgtt tgcagtttca 257640
taaccacttg ataacaccat aggttaaaaa aaaagtctac cagtcttttt cagatggcct 257700
ctttgacaat gcattattta tagggaagtt cagttacttt taacaataaa gacaagccaa 257760
aagaaattac agatctcttt taccatattt tgatatacta gcagcatcca ctcaggacag 257820
gacctttatt aaaagggggc ttaaggtact tttaattgga ggaattactg aattcctgaa 257880
gctcttcaaa caaaatagca cttgggatat gacaagagta ctttggagaa ggctgcttgg 257940
tcccaaagca gagattcaag aggaggactc cagctagctg ggtaaggggt tccttcctct 258000
caacctaagt gtttatgtaa gcctgctggg ggccaggaac tgcgtaaaac tcagtaagct 258060
cagtacttct cagcacagaa tccagtccca aggaagcacc cagcaaaaat ttaggttgaa 258120
ttttctttaa aataaaataa agaaaaaagt aaaattaaaa aaaaaataca attcaactac 258180
tcagcccatt ccattccggg tagttttggc tcagaatgct ggaagagttg gataggctat 258240
tagtgagaga actcaaaact ccccaaactc cacttcatta ctcttccttt atattttttc 258300
tgaaaagagt attgccaata tatcaataaa gctttttgct atgacttcag agtgcccagg 258360
tcactaggga aaagtatcaa gtagcatcct gaatccacaa atcctttgag agccagccac 258420
acagtatctg cgtgagtgtg gtaattctct acccttacga gtgtcatcac agaattgcag 258480
cattctcttt tcattgtttc tcaggaaaac atagacaaag gctctgcttg gatttttttta 258540 atttaacact aatatgtaat aatatagcaa catctcctag ttatctagaa ctcaggcttt 258600
gatagctgtg actgtctaga atacaaccac agaaaatcac ctctgaacag tgagggaaat 258660
agctgccaca gtatcaccac ctactccaag cttgaacctc tcaacccgca accaacagac 258720
tgcaagtagt tcagtacagc tttgaatgca gcccaagaca aactcgtaaa ccttcttaaa 258780
acattatgaa atttttttgc aacttgttca tcagctatcg ttagtgttag tatatttttt 258840
gtgttgctca agacaagtct cttcttccag tgtagcccag gaaagccaaa agattggaca 258900
cctatacttt ggatgtttca tctagtaccg atatacttat aattacatgt ttcaactagt 258960
actaatgaac ttatagttac aggatgaaat ttcaaattag caatgttcat catttgctct 259020
tcctaggtaa caacagttaa caaatcatag gttgacaatc acaactgatt gtgaggatgg 259080
aaataataac aatgagcatt tatataatgc ttactctata ccaggcactt ttctaagaac 259140
tttacataga ttagctcact taatctttac aataaccctg tgacatacca ttattatccc 259200
cattttacag gtgaggaaac tgaagaagtt aagtaatttg cccaagatta cagattgtat 259260
gtgattgagg taggatttga actcagcagt ctggcaccaa aatcagcact ctcagcctct 259320
acccagtatt atcaaaagta atttcctggt agcttctttc aattgtcatg gcaactctca 259380
agataaagaa ttattgtttt taataaataa tgtcattccc agaaatgaat tatgtgtgaa 259440
tcatactaag ctgcagtgag agaatgaata tcaccatcac agtggtgaat ctacttagtg 259500
taggggtaaa aggccagtct ctcccagcag ccctgcacat aggtacaccg taattcacta 259560
ggataatccc tgatcgccat gctgtcataa aaaaacgtta aatgatgttt aacaggtttc 259620
attaatgatt cagagaatct tataatatgt cttaggaaaa ataatttcag gagtaacttt 259680
cagttagcta gacaatacag ttctgttgag catctcataa tctatgccag acaaaggaaa 259740
cattcttgcc tttctttgag ggaattatag accaacaatt ttattaattt tcaactttca 259800
tcgaggcaag attagcttca tgaacaatgt ttctcaaact gaaagtagtg acctgtatta 259860
gtaaatcaat ttatagggtt gcaagcagca tcatttataa actgaaatca gaattcattg 259920
caggcagtaa ttttgagaca ttttatttta catgtgcgtg tgtatatcta tcatataaat 259980
aagtatgtga gaacatttta aaacatttaa aatatattta tatatctaaa gtttaaatgt 260040
aaatatatat ttatattaat aatataatta atatgaatta ataacatatt aattcatatt 260100
aacttatatt aatttatatt aacaatatgt aaacaatata ttaattagta atatattata 260160
ctaatattag tatgtattaa tatattatta taatatatta tatattaatt aatatattat 260220
atattgtata ttatatatta attaatatat tatatattgt atattatata ttaataacat 260280
actattatta atattttaaa tatattttaa tatacttaaa tttatactta aaatttacat 260340
atacatataa ataattttcc tgaaagtcac tttcaaaaac tttgaaagcc accagtgcag 260400
tggttaagaa tacaaatttt gggctgggca tggtggctca cacctgtaat cccaacactt 260460
tgggaggccg aggtgggtgg atcccgaggt caagagattg agaccatcct ggccaacatg 260520
gtgaaacatt gtctctacta aaaatataaa aattagctgg gcacggtggc acgcacctgt 260580
agtcccagct atgcaggagg ctgaggcagg agaatcactt gaacccagga ggtggaggtt 260640
gcagtgagcc gagatcatgg cactgcattc cagcctggcg acagagcgag actgcatctc 260700
aaaaaaaaaa aaagaataca aattctgaag cacagctgtt gagttggaat catggctgtg 260760
ccacttaata accaagtgac tttgggccag ttattttact tctctatgcc tcagtgtcat 260820
ctattcagta gtgagaataa tagtacctaa ctcattctag ttttgagaat gaacactttt 260880
tatattacat ataaaatgtg taggacagag accccaaaga agccgtagtt gctgtcatat 260940
tgttattctg ttcctgctta agaaggggac ttggaaaaat aatgatgttg aatgcagtaa 261000
cttctttcac tcatggaaga attacatatt cacatcttct ttgctcatca aacctttgaa 261060
gatcatgcat gtctcattct gtaacatcgc cttaaccaaa tataaaggct aaatacaaag 261120
gtgtttttaa ataactgata catttaggcc agtcacacaa agattttacc caaagcctat 261180
gcaggcatag tccaagaagt agacttgttc tactgcaatc accatctctt gtttattatt 261240
tgtgaaagga acattatggt ttcaccacag ttggcctggc caacgtgctt atgcagtcct 261300
cagaacatat gaaagtgatt tcggctgaca ataagtattt cctcactttg gcttatgttc 261360
aataatagcc attctttatc cagatcaggg tgactgagca tgctgtaacc attcttctct 261420
tctaaaactg acccttgttt gactgcatat gcagattgct tagcagaacc catatccacc 261480
ataacgggcc aaaagtcatt tgatccaatg tgcttttctt tttttttctt tttttttaa 261540
ttccatgaaa ttttattaag ataaattaat tataaacatt gcaaaacact ttttttttta 261600
gacagagtct cactatgtca cccaggctgg ggtgcagtga cacgatctca gctcactgca 261660
acttccgact cccaggttca agtgattctt gtgcctcagc ctctctgagt agctgggatt 261720
acaggtatgc ccccaccagac ctggctaatt tttgtatttt tagtagagac ggagtttcac 261780
tatgttggac aggctggcct cgaactcctg gcctcaggta atccacccgc ctcagcctcc 261840
caaagtgctg gaattacagg tgtgagccac tgctcccagc cccaaacatg attttttgat 261900
tgaatgctta atgtctttct attattatta ttttttttta ttatactttg ttctggcatg 261960
catgtgcaca acgtgcagat ttgttacata ggcatacatg tgccatgttg gtttgctgca 262020
cccattaaaa attaattcaa gatggattaa agacttaaat gttaggccta aaaccataaa 262080
aaccctagaa gaaaacctag gcaataccat tcaggaaata ggcatgggca aagacttcat 262140
gactaaaaca ccaaaaacaa tggcaacaaa agccaaaatt ggcaaatggg atctaattaa 262200
actaaagagc ttctgcacag caaaagaaac taccagcaga gtgaacaggc aacctacaga 262260
atgggagaaa atttttgcaa tccgcccatc tgacaaaggg ctaatatcca gaatctacaa 262320
agaacttcaa taaatttaca agaaaaaaaa aaaaccatca aaaagtgggc aaaggatata 262380
aacagacact tctcaaaaga agacatttat gcagccaaca gacacatgaa aaaatgctca 262440
tcatcactgg tcatcagaga aatgcaaatc aaaaccacaa tgagatacca tttcacacca 262500
gttagaatgg cgatcgttaa aaagtcagga aacaacagat gctggagagg atgtggagaa 262560
ataggaacgc ttttacactg ttggtgggag tgtaaattag ttcaaccatt gtggaagaca 262620
gtgtggcaat tcctcaagga tctagaacta gaaataccat atgacccagt gatcccatta 262680
ctgggtatat acccaaagga ttataaatca tgctactata aatacacatg cggccgggcg 262740
tggtggctca tgcctgtaat cccagcactt tgggaggctg aggcaggcag atcacaagtt 262800
caggagatcg agaccatcct ggctaacatg gtgaaacccc atctctacta aaaatacaaa 262860
aaattaggca ggcgcagtgg cgggcgcctg tagtcccagc tactcgggag gctgaggcag 262920
gagaatggca tgaacccggg aggcggagct tgcagtgagc cgagatagcg ccactgcagt 262980

-continued ccagcctggg caaaagggca agactccgtc tcaaaaaaaa aaaaaaaaaa aaagacatat 263040
gcacacgtac gtttactgca gcactattca caatagcaaa gacttggaac caacccaaat 263100
gtccatcagt gatagactgg ataaagaaag tgtggcacat atacaccatg gaatactatg 263160
cagccataaa aaaggatgag ttcacgtcct ttgcagggac atggatgaag ctggaaacca 263220
tcattctcag caaacgatca caagagcaga aaaccaaaca ccacatgtgt gttccaactt 263280
aactcattgt tcttagtgat aattcactta ggggcaaagt taggctctct tgttaattgc 263340
aacattcctt tcagaggtgc tataaatgga tgttgaacta tactattttt agatttaatc 263400
tttaaaaatc ataagaaagc aagaaatatt actagttcag aaatgatttt ctgttcctgg 263460
ctaatcagag aagacctaag agtctatagt agtcatttgt tgtcttcgta gtaaaagtaa 263520
gattctaata ggatttttag acatagtgag aaaggtgttc attttaagat tatggtagtt 263580
cctctcagat ttagaaagcc ttaagatgac actaaggagt tggactttag gaatgctgag 263640
tgtcttcagc cacagcggca caatggtact agatgtgaca ggatgtgatt aaggagaaac 263700
taaacggcca ggcacaatat agttcttctt gcctccaaaa gaggagtcac ccactttctc 263760
acactcactg tgatacattc catttgctaa gaaaagtggc ttgtgtcatt cttgagcact 263820
acttttaagt tctgatatat taaattcatt tactctgtat taatagcatt caaatattta 263880
gtaaagttaa tatacctctc acactttttc caaagtaacc caccagctgt gtcctgtgct 263940
tcaagctatc ttataagact gcaatcaaag tgtcagccag ggctgtggtc tcatctgaag 264000
gctggatagg gaaagattgg ttcccatgct tatttacatt gttgttggca ggattcagtt 264060
cctcaaaggt ttttttattt tttatatatt tttttttgag atggagtctt gctccatcac 264120
cagactggag tgcagtggcg caatcttggc tcactgcaaa ctccgcttcc caggttcaag 264180
caattctcct gcctcagcct cccaggtagc tgggattaca ggtgcatgcc accatgccca 264240
gctaattttt ctatttttag tagagatggg atttcaccat gttggtcagg ctggtctcga 264300
tctcgtgacc tcatgatcca cctacctcag cctcccaaag tgctgggatt acaggcatga 264360
gccaccgcgc ccagccagtt cctcaagggt ttttatactg agggcctcta cttcttgctg 264420
agtgttggcc agaggccatg cttagttctc tgctgtatgg ttctcaccac acagcaacgt 264480
acttcatcaa aaccagcaaa agggtgagtc tgctagttaa aaagaagtct caatcttttg 264540
taacctaatc atagaactgc catccactcc atgctgccat attcttctga ttagaagcaa 264600
gttactcaag ggaaggaaat acataaggct gtgaatgaga gaagacagga atcattggag 264660
gctactttag gggctgtctg ccacagcact taacagcaca tacccagcca taaaatttaa 264720
aaaagccgga aagagagaag gagggtgcag ggtaaaataa agaaaagagg aaggtggaag 264780
ggaagaaagg aagggaaaga aagacattta aaaagacaag aacaaaacag ctctgctgca 264840
caacatctgt atcggagttc catgtgcaga cacacacgtc atcacatcag caccacaccc 264900
ataaatttcc tatttcttat ttacaatgag aaggtaataa ggactttcta tgcatctgga 264960
gttaaaagga aacaataaat ctaagaatac taagtttaag taatcaaaat gtgtttcaga 265020
ttagttattt tttcttttta agtttttttt tttgtttcag ctgacaaagt tttttatttc 265080
tttctgtttc aagttttgaa gttgagttta ttattcttgc tattatgtaa caggcatatt 265140
ttacagagaa tataggaacc tgattgacat ttgtatttgg tgttctattg ttgtttcaat 265200
tcaaatgcca aaattatgtt tttgttgtgt acgttattgt tcataattat atatgcctct 265260
taattgtaaa agcgaagctg taaaattgta aagtactttg tgtctcatct attccaggca 265320

-continued ttctactaag gaaatcaaga ccaaatggct tgggaaggtc aacgttaaat agtgtcagag 265380
ccagaactag agtacacatc tctcaatttc taatctagtg catttccttt tcttatttct 265440
gtgcaaacga acagttagaa tgtgaaatag tctcctcaga tataccagca ttaaaacagt 265500
tgtggtttaa atatttagtt ttaataatta ctaactttgt agaaggacct aaaatagtgt 265560
ttgttttcag tgcttcaact aatagtaaaa aggaatattt tcagtgcttt actgtatgag 265620
aggtgcttgc ctaacgaaat acacatcttt ttcactgtac tcatttgtaa cagataatgt 265680
gggctcgtac acctcagtgt tctgagaggg gttggtaaac actgaccaca tagagagagc 265740
tgcccatctg ccctcagtac caaggcacat cccatccatg ccctaaaact cttgtaaatt 265800
tctccattca tacaggaaaa tgagtatttc ttacaacaat atgaccgtgg aatttgatta 265860
caaaaacact cctgctatcc ccaacctgtg ctcccagggc taaagacata tttgcaactc 265920
aggattttct gaagattcac ttgtttgtac tattgagggc aacagttgtt ctcaaacaag 265980
gatgcagttc ctttcttctt accctgctta tttttctttt tattattatt attattatac 266040
tttaagttct ggggtacatg tgcagaacgt gcaggtttgt tacataggta tacatgtgcc 266100
atggtggttt gctgcaccca ccaacccgtc atctatatta ggtatttctc ctaatgttat 266160
ccctccccca gccccacagc cctcaacagg ccccagtgtg taaagttccc ctccctgtgt 266220
atgtgtgttc tcattgttca actcccactt ataagtgaga acatgtggtg tttggttttc 266280
tgttcttgtg ttagtttgct gaggatgatg gtttgcagct tcatccatgt ccctgcaaag 266340
aacatgaact catccttttt tatggctgag tagtattcca tggtgcatat atgcaacatt 266400
ttctttaacc agtctatcac tgatgggcat ttgggttggt tccaagtcct tgctattgtg 266460
aacagtgctg caataaacat acatgtgcaa gtgtctttat agtagaatga tttataatcc 266520
tttgggtata tacccagtga tgggattgct gggtcaaatg gtatttctag ttctagatcc 266580
ttgaggaatt gccacactgt cttccacaat ggttgaacta atttacactc ccaccaacag 266640
tgtaaaagcg ttcctatttc tccacatcct ctccagcatc tgtttttttcc tgacttttta 266700
atgatcgcca ttctaactgg tgtgaaatgg tatctcattg tggttttgat ttgcatttct 266760
ctgatgaccg gtgatgacga gcattttttc atgtgtctgt tggctgcata aatgtcttct 266820
tttgagaagt gtctgtttat atcctttgcc cactttttga tggggttgtt ttttttcttg 266880
taaatttatt gaagttcttt gtagattctg gatattagcc ctttgtcaga tgggcagatt 266940
gcaaaaatat tcccccattc tgtaggttgc ctgttcactc tgctggtagt ttcttttgct 267000
gtgcagaagc tctttagttt aattagatcc catttgtcaa ttttggcttt tgttgctatt 267060
gcttttggtg tcttagtcat gaagtctttg ctcatgccta tttcctgaat ggtattgcct 267120
aggttttctt ctagggtttt tatggttttg ggtcttacgt ttaagtcttt aatccatctt 267180
gagttaattt ttgtataaga tgaaaggaag ggatccagct tcagctttct gcgtatggct 267240
agccagtttt cccaacacca tttattaaac agggaatcct ttccccattg cttgtttttg 267300
tcaggtttgt caaagatcaa atggttgtgg atgtgtggtg ttatttctga ggcctctgtt 267360
ctgttccatt ggtctatata tcttatttgg taccagtacc atgctgtctt tgttactgta 267420
gccttgtagt atgaagtcag agacacaata aaaaaagaaa attttagacc aatatccctg 267480
atgaacactg atgcaaaaat cctcaataaa atactggcaa acctaatcca gcagcacatc 267540
aaaaagctta tccaccccga tcaagtcggc ttcatccctg gaatgcaagg ctggttcaac 267600
atacacaaat caataaacgt aatccatcac agaaacagaa ccagtgacaa aaccacatga 267660
ttatctcaat agatgcagaa aaagccttcg acaaaattca acagcctttc atgctaaaaa 267720
ctctcaatta actaggtatt catggaatgt atctcaaaat aataagagct atttttgaca 267780
aacccacagc caatatcata ctgaatgggc aaaagctaga agcattccct ttgaaaaccg 267840
gcataagaaa agaatgccct ctctcaccat tccttttcaa catattattc aaaactctgg 267900
cgagggcagt caggcaagag aaagaaataa agggtattca attaggaaaa gaggaaattc 267960
aattgtctct gtttgcagat gacatgattg tatatttaga aaaccccatc gtctcagccc 268020
aaaatctcct taagctgata agcaacttca gcaaagtctc aggatacgaa atcaaagtgc 268080
aaaaatcaca agcattccta tacaccagta acagacagag agccaaatca cgagcaaact 268140
cccattcaca attgctacaa agagaataaa atacctagga atacaactta caaaggatgt 268200
gaaggacctc ttcaaggaga actacaaacc actgctcaag gaaataagag aggacacaaa 268260
caaatggaaa aacatcctca tggataggaa gaatcaatat catgaaaatg gccatattgc 268320
ccaaagtaat ttatagattc aatgctatcc ccatcaaact accattgact ttcttcacag 268380
aattggaaaa aaactacttt agatttcata tggaaccaaa aatgagcctg catagccaag 268440
ataatcgtaa gcaaaaagaa caaagctgaa ggcatcacgc tacctgaccc agcttatttt 268500
tctacatagg atccccacat ccctgctttt gctagaatgg aaactagaca aggaccaact 268560
tttatcaact tgttcatttc tctattccta gaacacagcc tggtacaaaa tttgcgttta 268620
ataatgtttg ttgaatgaat ttgaatgatg gatttgttta gaaggtttat aacatcccat 268680
gccttatgag tttgttgcca gaggaaaaaa gaagcctgtt tttggttcat aacatcaggt 268740
atgtaacctg gaatttggaa tcatgagttt ttatgcattt gcttcatatt atttattttt 268800
aagagatctt tcaaagtatt gacaaagata ctttaagatt gagagcctcc ctgataaccc 268860
aggaatgaga gttttagatt aagtttacaa tatgattgaa ggctaatcat ataaggagaa 268920
aaaaataaga aaaagaagag aaatttgaaa agaaatctcc aaaatggcca tggacatcag 268980
aacactgaga attcatacac aaaaatgtgt tttgcttcat acctgtctgt tgcacatcta 269040
tacatttcat agatgcagag gaattttggc taaattccta acacatgaga ggcattctgc 269100
acttacttct caaattagaa ttaacacatg agtatgtata agttgtttag agtgggcatc 269160
tatttaatga gtttactggc tgaatctttt aaaagaatgc aaacataagt gccttttatc 269220
aaaaatcaat gaaaagataa aaggccctgt agtgcatgct gtggttccca cactacatcc 269280
cccacatcca cctgatgtca tcacaactgt ctatggtgtc catttgccac tatgcaccct 269340
gccgggcaga ctcaggtgcc tgcctcggca aagaccctca gctcatgtgc aggtacagcc 269400
tagaagtgca tgggggtgaa catctctgag gcaccccttca accagtgagt actgggagcg 269460
gtagataaat atcctagcct ctcatctttc tacacaacag tggtggtgca tattctacac 269520
agcttctcaa aggagcctca gagggattgg gccccattag ccactgtgat aaccagctca 269580
gaacacacac atattagttg ttctcccttt ccttcccacc ctccccattc cctgactgct 269640
agatccagaa gtcatcttcc agatgaacta cctatatcca aatcctaatc tctagctctg 269700
gtttcttaaa caggtcctat gaaatgcttg aaataaaagg caaaatggtt tgtgtctaga 269760
atcaaaggct gacaatggca agcaacaggc actaaaacta tgacccagga aaaatgcttt 269820
tctggaagac atcggcatta cctcctagac acggaataca ctggcttcat cccagtagtt 269880
tcttcacaca ctttagatac gtgtctcatt aggatcacat atgactcacc tgatttcatg 269940
ccttgccttt tctttttatt ctgcagattc ttctaaggag cctaaattca ccaagtgccg 270000
ttcacctgag cgagagactt tttcatgcca ctggacagat gaggttcatc atggtacaaa 270060

-continued gaacctagga cccatacagc tgttctatac cagaaggtgc caccatcatg cctttctgat 270120
tttcctctcc atggatgtac ctactaaagt acactgagtc agatgtactg tgggaatgga 270180
agtgatttgt tgtgatttat gcaatcaatg aatattcatt cactcattta ttgaaaaaaa 270240
tattaatcaa gcccatccta tgtgctgagt actattttag gccctggaga tatagcagtg 270300
attacaaaag acaaaatccc tggtctcatg gagatttcct tccaatgcag ggagacaggc 270360
aataaaaatt gaattaaatg tcagctagta atataggtta ttaagaaaaa taaagccaga 270420
aagcagcata tcagcagtgt gtgggagttt gtgtatgtgc atgagaatgt gtgagagtgt 270480
gtcaaagtgt gagtgagagc atgtatggat acacgtgggc atgtgcatgt ggatgagagt 270540
gtgtgtaaaa ggcttgaatg atgctgaaat gcgtggtcct aggaggcctc tctattgtgg 270600
tgtcctagac cagagacata agtgaaacgg gacaggccac gtgagtatct gggggaaagg 270660
ctatgcaggc agaggaaatt gcaagtacaa agtccctgag gcagtcttgg catatttgag 270720
ggatgaaaaa ggccagcact gaaggcacaa gattgaaagt gaggagagtg atatgggaag 270780
ggatcagaga gttacttagg gactgaccat gccaaacctc ataggcaagg gcaaggcttt 270840
gaattttact ttatttgtgg tggaaagctg taggtgtttt tgaaaagata tatgctttaa 270900
aagatgtagc tttgtttcta accagataat acactccttc tcttaaatat attcagtaaa 270960
agactgtagt actttttcat ttttaccagt gaccctctaa aataacagag gaagggtgaa 271020
acaaagacct ctcaatatag gtaccatcca agttgtttat ttcttcccct tcacctggca 271080
ttattttcat ttttgtttac tctcactgtg tatatttttc cctttttttac attttaggct 271140 taaacacttc attatctcct gttttccacc caacccccag agaaggccta agccaagatg 271200
cagggttagt gaggaccctt tatccttggc tcaaggtgtt cgttagtcag aggatgacat 271260
tgtctatcca accgaagagc tggaataggg aaggaagatg cagccagcag ttaagggtat 271320
gagctcaggg ctaacaaacc tgcacttcag tgtagttctg cactttctca ccaaggaata 271380
ctagggaaat tagccagttt gtgtacaact cagcctcctc atttgcagaa aggagataat 271440
ggacttgcct catgacttct tgtgaggatc atatgagata acccatgaaa aatacttggc 271500
agagtacttg acacataata agtactcact aaatggtagc tggtattctt cttatcggta 271560
gtatagtgat aattttaaaa taattatgat atagaaatcc agttcctgga ctataaaatg 271620
actataaatt gtataagacc atttatacca gtaaattgtt ataattattt taattattgg 271680
tataagagca ttttaatgca gagctgctgc ttaatttgca gataaaaaaa tacttggagt 271740
tagcaaccaa gcagaccttc ccccaccttc agtataagag aggtctcttg gatgaagtga 271800
agtgaagatg aaatgtttgg gcaccaagta tactatattt ttccttaagg ctgacaccac 271860
agagaggttg gggccagtaa acagagttga tttctataaa tacattcaga catgaagtta 271920
gtatgtttga tgacactttt gaaatgtgtg gaatcattaa gttatttgta caggcacaat 271980
tagccaaact gtaaagaaaa gtagcagaat aacctcttaa gctgggccca ctttatgaaa 272040
ataatttttt gctacctcaa tatttaccaa atttgatgag caaaaagaga aatccaaagg 272100
aatgaagcct tgataaatat atatcccttg ccctcatcaa tcagggtcac ataactctgt 272160
ccacaggcat cttatgcaca ctccagtcat ttcagcatct ctggttcaaa tccaggatct 272220
acactaccaa ggatgctgct gaaagtgtga ctgggtaaag ggaaacgttc agacatattc 272280
agaaagatgt cttagatttt gccctggtag tgtttggaat cccaggaggg taagtacagc 272340
ttcatgatta agtgccaacc caaacttaca aaattagata tttgtgtttt ttctataaaa 272400
tataactatt ttgaatatct tagccaaact actatgagcc cacagcccag tttatccaag 272460

```
aaggataaaa ctgagggatt aggagtatca ggactggact ggactgatta gtgtacagtt 272520
atatttgatt tctcattgcc cacttcacag agaagacaat acaaatgcac tttctgactc 272580
ttatcactgt ttcttagaac tcagttgcca ggcaactcct gaaactatag aaacatgctt 272640
ctcatccctg acacataaat aaaactctga gatgatttta tccaaagtca gagtcagtgg 272700
gcagtgcagt tgtttcagtt tgctggcctg gcctcagtat ctaaagcaca acagaacgtg 272760
aacatgtcag gctgtcaaca ggacagttca ggcacagccc tacaggcagt tgtgtgtttt 272820
gcctggctct gctccttgcc aggtggctgg cagaaaaggc agcctccaca tgttagagca 272880
gcagattcaa aacagtgtct gccatcctgt gatgacgata gtgccaaatt cagcctctga 272940
gcttgcaggg gactcaggat gaatgcacat tacaggcatg gtaaaaagag gctctgggaa 273000
gcatgttcga gctgctctgc tctcagctcc ttgcatgtaa atgctgtgtt tttaaaggaa 273060
gtgggcatgt gaacactcag tccttaaggc tgtatccccc acctcttcca tacccattca 273120
accccacttc aaaaattacc ctggtcttaa gagaaatttc attttctata caaggttgtg 273180
tggaaaatca gtagggagaa agggcattat tactttcatt tttctttaac aaaagtatta 273240
aatttaaagc caaaaacgtg cgctttctgt catgaaaaca gctgccctta aaaacataaa 273300
tgatgtttta tttttattac ttttatctag ttggttgtct ttagatgaaa aacatttctt 273360
ctgctcttta ttcttatttt taatgatagt ctctttctat ggttctcacc ccttccattt 273420
cacaagatag tctgggagca aacctaaagc acttaacttt tgggagtaag agcagagggg 273480
agcttccata cattgatttt ggtcatctgt agagacattc aacccagaga aggcaagtga 273540
cacagtatct gttttatgag ctaatttggg ttcttgtcta catttaatag tttaaaatat 273600
aagttataaa tatttattta aaatgaaatt caacattggt tcatgaagaa agaggttgga 273660
agtagtgttt tgaactagct gtttctgatc catcatgctt aaaataaatg ctctgtttgt 273720
cctgtggagt tcatggattt gggataatct aaacagggtt ttttaaacag tcctcatggg 273780
gaacaaggta ctgacatgca ctgttgagaa attctgtgaa tcatgaaaga gctaatcttt 273840
tagaaatcca gacctgttaa gcactaatct acatctttgg aatatcttaa tactttgagt 273900
tttctaactt ttatactatc acttatgcta agtacatttg atatcccttc tattatgtga 273960
aagcctcatt ttctgggcaa ttttcttaca actactctct ttaatgcact cttacttaat 274020
ttgaaagtaa atatcaaatt aagcatacta tagttcaatg aaccacccac ctattcctaa 274080
ttttttttaac atttctcttc tgactctaca tacacacata cttacacaca cacacacaaa 274140
cacaccttat cttttcttct gccttttgcc catttacttt ttgcatcaga gatgaatctc 274200
tcattcaagc atatgcaact tttttttttt ttgagatgga gtcttgcttt ggcacccagg 274260
ctggagtgca gtggctcgat cttggcttac tgcaaacttt gcctcctgcg ttcaagcaat 274320
tctcctgcct cagcctacct accgaatagc tgggattaca gaagcatgcc atcatgccca 274380
gctaattttt gtatttttag tacagatggg gttttaccat gttagccagg ctggtctcaa 274440
tctcctaacc catgatccgc ctgcctcagc ctccgaaagt gctgggatta caggcatgaa 274500
ccaccgtacc cagccagcat atgcaacttt taagagtctc aaccaaagca gcaattcact 274560
gtctcagacc ctggagtctc tgccatttaa atcccaattt ccttccaaca gctgaggagc 274620
agctgtctca aggaccctct gatactacac aagttttctc ctagtgccaa gcagaccagc 274680
ctgagaaaca gctataagaa ggaaataggc gtcttctccc agcttggcat cctttccttc 274740
caggccctgc cttccctaca acctgcattg tcttcattgt ccactgctgc ccagcaccca 274800
```

tcccacagag ggatggtccc aaacctccac agtctggcct gtgagccaca ggcgcctctg 274860
cctgcacagg gccattccta cctcatcttc cacaaccaca gattacatgg ttttatgtcc 274920
ctttgactta tatattgtct tctcaattaa taggctagtg aataacatgg agatgatgaa 274980
ctacctcacc caagtagcaa ttctaattta agaaaatttt cctgtcattc cattgccttt 275040
tacttccatt accacactca tgcccatact tccttacctc aatccctttg acctctctgt 275100
ttattccctt ccttgccgta ttgccatcta ttaaactttt acccatcctt caagaatgct 275160
aaaaacatac ctccaccttg aagccttcca tgaagagcca gagcaatcat tccctcttct 275220
gaacttttaa ggaccctaga gagcactact aatgagcact tacccacatt gctttgtaat 275280
atggtttttt actctttcct tctgaggcag gaggaattcc ttagacatct atgaatccca 275340
tagtgtctgt cattatgttt tagacataac caattctcat taaatgtcaa tagaatgaat 275400
ataagaggcc caaaaaacta ctcagatggg aatttgagtc ttattttagc ctgaaattag 275460
gggaccacat cttacttatc tttatatctg cacagcgttg gtgctggata taatgcatca 275520
ctctgcctgg agcacacatc aacttgtctc ctcagtttct ttcaccatag gctggtgaaa 275580
cagccaggtc taaaccttca ctgttctctg ggaatctcta gtttgggggt gattctctgt 275640
actgttttaa tgaacatttt taaaatgtcc ctaagtctca gaaccttcat ctatacaact 275700
ggcataataa agtacctacc ataggaatcg atttatgagc aggcatagca tattcattca 275760
ataaacggaa gttttaccat aggcagaagt accaaacggc ctcgtagcag tcgtcagaca 275820
ctgatgatac tgtccactga tgtgatatgt ctcggaaatg atgttactaa aatacctctt 275880
cacaaaatat ttgtcttcca atttattgaa tcagactatc aagcacctta cttggactta 275940
agctacaaca tgatttttgg aacaattaat ctttttttaa cccttcattt taggaacact 276000
caagaatgga ctcaagaatg gaaagaatgc cctgattatg tttctgctgg ggaaaacagc 276060
tgttacttta attcatcgtt tacctccatc tggatacctt attgtatcaa gctaactagc 276120
aatggtggta cagtggatga aaagtgtttc tctgttgatg aaataggtaa atcacaggtt 276180
tttgtttcat ttgacatagt tttagactaa ataaatgggg aagcctgcaa ggtccaagta 276240
taatcaagta ggaagacttt gtaacagtgt tctatagata catggagatc tgttttacag 276300
gagatgggat cagctggtga acaagaggaa aagggcaggg ggaacttaag ttgactttaa 276360
cataaagtag cctggcagta aatgttgtga agaagagaat aggaaccttg tggagtcttt 276420
tcctttagga tatctttgaa gctgcgttgt gtttttatgt tccactgcaa agggtgaact 276480
taatatattc ttaggatttc ttacttccta attatttgat aggatcctta tattcaaatt 276540
cactgaaata cgttggcctt tgacctctac cattgctgta atcaaagcct agattttctt 276600
tatcacaaag cataatcatt ctggaatttt acatttacaa aacagccaca gttactttaa 276660
agacatgttt attagatctc agaacaaata ctggagacaa tcagctcagt gaactaagtg 276720
aaagatccaa acagaggatc ctttgcccat catatggaca caaggtggaa acaaaacaaa 276780
taaaacaaac aattgtaatt agaatagtca tgtttatacc ttaatagtat aaatagcaaa 276840
atagaaagaa tcaaagaagg actttgagta gctgaaatta gtgcctcaaa atctatccac 276900
aaaagctcat ttgttgctta taggaatttc tcgttgcttc tcccaaatgt attgttcttt 276960
ttatgtggtt ttctaggcat aagctgactg gaagacatag gagtatgtgg ctagaactta 277020
cagatagaaa caaataaaat ctaataggct gactttaagg gagaagatta agagaactgt 277080
atcaagcagt aaagataacc caattgcttt gcaaagacaa tttagtatgt gtcctaacat 277140
cactgggtat agctgttgag ttgaaactaa atgggatagc agaatgggat agtagcaaga 277200
acactgggtt aaaacccatg ttctagccct gttctctgcc aatagccagt cctactcatt 277260
tacctggctg acatgcctgt catgtgtcac gcactgttct ggtggtggtg gttatagaat 277320
aagtacaata cagtcaaaga gggaagtcag gcatgttcac aaataattgc agtgcagcgt 277380
gataggtgtt agcctggaaa tacgtggaat gcagagctgc aaaggtggtg gccaaaggcg 277440
tgaatgactg acaggcctga gggatgagga agggctgcac agagatggtg acagtttagt 277500
tacctctgaa ctggaattgg actctcccta tttttaaaaa agtgatgacc cacagtggtc 277560
aaaagcatga gtgagtattg tcaggtacca cagtggactt gcctttcagt aactactaag 277620
ttccaacagt aacttagtag ttacttagta attacaacag taacttagta gtcccaacat 277680
gttcagggac tcaggagcag ttaggaagcc ctcctagtca gctggagaaa tcatcagtag 277740
ttgtttgtgc cccaaaaagg aatttggact ttaactgtca cgaggtacct ttgaggatgt 277800
ttaaataggg aaattacttg aggatactaa tagttaacag tcacaaaagt cttaccatgt 277860
gtcaggtata aaaaccatct tttgcaatca cactttacag ataatgaaac cgaggcacag 277920
agcagttaaa ggactagttc aagtcaaaca gctagtagat agagctggga tttgaacctc 277980
cagcctccat gctcttactc ttgaggcttt gcagtaccac ttgtctcttt attaatgctc 278040
agagaaatta atcttgttgc aatgtgaaac gtagattgga gtgggacgga ctagaggtag 278100
aagaggttaa aagactgaga tgatcaaggt aaaagattat gacaggtagc tacaactagc 278160
acaatagttg tggggcaagg tgctgagagt gaaagagaac aaagaactaa tgtaaccctg 278220
gtagatcttg agaaagttgt caatcattat aagcctcagc ttcctcataa aatatgtatg 278280
tatggtacta cctcacaggg ctattctttg gatttgaagt actatattag ttagacattt 278340
gtcattcatt caattcattc agcaaatatt tattatgctc ttctctcagg ccagtcaatg 278400
ttctccatgc tggggataga aactgtcttc cctggtggga tttaatccca acgaggatgg 278460
aaagcgacaa tgctatggag aaatatagga aaggagaata ggagtgttgg agaggttgca 278520
gtgttgagtt ttcaggattg gcatccctga ggcagtggca tttgaataaa gaaggattgg 278580
agaggataat tatgtgtgtg tctcagggaa gggcatttca gcaagggggc acgccagaag 278640
aaagatctca aagtaggagc atgcttttcc tcactcaatg aacagcaggc cggcggtgga 278700
gtgggcacag agtgagcgag gagactggta tgagaccaaa tcgcacagac aagacagtca 278760
aatctaccca accattgcca aagactttgg ctttcacttg gagtgaggta ggcagccttt 278820
ggagggtttt agatgatgag cgatgtgatc taacgtaagt gttaggataa tcactgtgtc 278880
agttcgcttg aggattgcat ggagaataga ctggaggggg acaaagacca aaggggtaca 278940
gtggggagac aaatgaagca agaagaatga aaaaggataa tggccaggac caggttatta 279000
gtggtgcagg cggtgggaca tggttggatt ctgttatatc ttgaaagtac agctgacgga 279060
atgtggatta gtgaggaaaa gatgagccaa ggacaagttc attgttttta tcctgagcaa 279120
ctagaggaat tgagtcctcg ttaacagaga tggaaaagag gaaaggagag caggttttgg 279180
agaggaagag caagggtttg tttggggata tattaagttt cagatatttt ttaaatatct 279240
cacaggagtt gtcaatatag catgtagatt tatgtataga gataaaggag aggtcattat 279300
tatgcctgta atggtatctc acaggaggtc attgttatgc ctgtaatggt ggtaccaaat 279360
cttttccaaa aggaccttgt ctcatatcct ctatttttca aatgcagcat aagtaatgag 279420
ttatagaaaa tcttccatta aaaacaattt tatagtttgg tcactttaaa cggttaagct 279480
ttgattatca ggattcctga atctccaaca aatccagaag ggtgaggaat tattgccatt 279540

-continued atatcggcat atgtagtttg gccattttgc atatccttcc aatttaattt tcaaaatgta 279600
gtcatgattc atcaaatttt gactctccct gtttttaaaa aggtggtgtc gaccccacag 279660
agggcaacag catgctcctc caccataagg cctgttttca ctgtgggtgc acacaagagc 279720
ttccctcttt ggccaacaga tttgacagcc agtaagagct cctcactgtg tatatctgta 279780
aagttatctc cagtcaacgc tagggatgca cactctgcaa cactctaggt ggccttctgt 279840
atatatggca gaaaaagaaa gtaaatttta ctctgtatct gcaagtgatt ttcaaaaccc 279900
tcagtaatga gatccaacta gcaaaaattt accaggaact ctctagaata taaatttaga 279960
catagttcct agctttggaa tccatatttt tcttcatcag cctctgagaa attgtggtct 280020
ttgaggtcct actaagcaga atgcaacaaa ttttcgtgga actgtagagt atatcaatag 280080
aacctgagga aaacaatgtt tcaagttgtt catgtgacag tcaaaaagac agaaaacact 280140
gaattgtcac catttgtgag actagcataa tgctttcttc cttcttatgt cagaagaaaa 280200
tatcacatgt ggctaggaag atcacaaagc tagggagcat tagcagagtg tgcaggaaga 280260
ttgtatgaga agattgaaga agagtaaaaa aggataatgg ctaggaccag gttatagtgg 280320
tgcaggcggt gagatatggt tggattctgt tatatcttga aagtacagct gacggaatct 280380
gacggaatat ggattagtga ggcaaagatg agtcagggaa caacacagaa atgaggtaaa 280440
cagggtctct gcccccaggc catacatagt tgcaagaaaa aaggtttctc taccccctagt 280500 tccgaagcag ccccatgtct aaattctgta agtctttctg actctctgtt ttttcagttt 280560
caagtgaaaa taaattcctt tgccaaaatc ctgatgcatt tatgatatca gagcaaaaag 280620
aaatatacaa catggcagat cttgtaaata gtgatcagat gttttactcc aaaaggaatt 280680
tttgtaaggg cttatttaga agttaaaaac aagtcatcct tgagttaaaa aaaaaagtta 280740
ctctcttata aagtgaaagt tataataaga aaaatattgg aagaaataag agcatgaatg 280800
atcaaaaatg tagaaagtaa tttggtcttc tgagaagaat gccttccatt aatattaaat 280860
tgtgtctgtc tgtgtactaa tgctctgttg aattgcacag tgcaaccaga tccacccatt 280920
gccctcaact ggactttact gaacgtcagt ttaactggga ttcatgcaga tatccaagtg 280980
agatgggaag caccacgcaa tgcagatatt cagaaaggat ggatggttct ggagtatgaa 281040
cttcaataca aagaagtaaa tgaaactaaa tggaaaatgg taagatgttg ctacacctta 281100
cactttgact tttctttcta tttcaacaaa ctctctctca tttatcatta gactttcctt 281160
tgacctaata ccacatgttc atgctgtatg ctccataatt tcttaattga gaaaacatta 281220
tttaaccggt aaaatattgt cttgaaattc tgtaagacag gagatgctta tgtatatatg 281280
gaggcctgtg gaaggaaagg aaaactattt ctccattcat tcttgctgtc cagtttaact 281340
ttagagcaaa attatagact ggccacttag ctgtctttgg ggatgtggat aaaaatggga 281400
aagtttgtga tccagtcaac agtgactatg gccaaatatt ttcccatgat ttcagttgct 281460
gctactcaaa ggactcccac taaaacaaat tcatacgtgt ctataggaaa acagagggag 281520
ggaatttgtc tcttagaggt ttcagaagga tgttttgtta catacctcag agaagaatca 281580
agctgagatt cttatgtagg caattagaga gcatggtacc agttgacctc tgaatccctc 281640
tcttccttac caagcatatg gaactcagca ttttgataaa tttcacatgg cacataacaa 281700
gaggaaaaac aggagtatca tgctgctccc aatataacta attctaaatc tgtctaacca 281760
cagccacagc cacagccaca gccaagccaa gcagtttctg gccactcatc aggtgatgcc 281820
cagcagcctg gcacagatca ctcccagaat tttgagacac caggacattc agtgagccac 281880
tgaaaaagat gccaattttg tcattagagg aaagttaagt ttggaggaaa tttgagtagt 281940
tacaatactg ggctttgagg ctctattttc tgaatcattt taatttagat atctgttctg 282000
taacttggta caaataaaat gcctgattgg atgctaagtc aaacaagact gtctaaatcc 282060
aagctacaat caaacattat ttaacaacag gtactgaaat aactactatg cagaaggcac 282120
tgtgctaaat gcctgaggtg gcggttctca aagtgggagc cacagaccct tgagggtccc 282180
tgagaccctt tcagggagtt cagtactatt ttcacaatac actaaaatat tattttatta 282240
actatgttga aatttaactt aatggcacaa aagcaatgct ggaaacactg ctggcacctt 282300
agcatgaagc aaggcagtag gatcaaattt tactaatagt catgcactcc caatgaagaa 282360
ggaagaaaaa gccagtttca cgtttgaagt tcttgatgaa gctgtaaaaa ttgttaattt 282420
tactaaacct cgacctttga gtacatagct tattaatatt ctgtgtgaca tatgggaatt 282480
acacattaag catgtctgct gcgtactgag gtattgtatt tgtcttgaag aaaagcgctt 282540
aaatgactga gttgccagct gaactagttg cttttattgc ttggagcacc atttttactt 282600
ggaagagcca ttgataaact ggcagatggt tattcatatt tgaattggca aacatttgtc 282660
aaaaaagaat gaggcaagct tgtcgcttca agaaaaacaa ctgacagtat tttttgcaat 282720
ggaaaaaatt tgacttttca aagcaattca ttttgccttt ttcgaaaatt tgtgtctcca 282780
accgtgagct tgatagtgtt ttaatatttg aagacttttc ttgaagagat tgatggtgat 282840
attaatgaaa gtgacttttt aattatattg tgtaataaaa tgtatgaaca tttagaaaaa 282900
tctacaactc agttaaccaa tattttccaa attactaata catgatgtaa tcaaatcatg 282960
catggggaaa tgatccattc aaagtactag atagaatcgt gaattttttt aatgatcaaa 283020
aatttttttg tatatttatt gtgtacaaca tatttttttg aaatatggat acattgtaga 283080
atggttctat cacactaagt aacatatgca ttaccacaca taccttttt tgtgtgttga 283140 gaacacttaa aatctactca gagattttca aaatacaata cataagcatt aactatagtc 283200 accatttgc acaatagatt tcttaaactc attcctacta actgaaaatt ttaattcttt 283260
catcaatatc tccttaactc tgcaccctgc ccacaacccc tgataaccac cattcaactc 283320
tctgcttctg agttcaactt ttttagattc tgcatataag tgagattatg tggtatttgt 283380
ttttctgtct ctggatcatt tttcttaata taatatcctc caggttcatc cacattgtca 283440
caagtgacag gatatccttc ttttttaag gctgatagca ttccattgta tatacctacc 283500
acattttctt tatccactta tccattaatg gaacataggt cgattctatt tcttggctgt 283560
tataagtaat gaacatggga gcccagatat tctggctcaa catactgatt tcattttcct 283620
tggatatata cttagtagtg gaataaatata atggatcaca tggtagttct atttttaatc 283680
ttttgaggaa gcttcatatt attttccata gagggtatac taatttacac tcccaccaat 283740
agtgtgcaag ggttcccttt tgtccacatt ctcaccaaca cttgttatct cttctttttt 283800
tgaaaatagc catcctaaca tctttgtgca ctctatgcct tctgtgagct gatagctcat 283860
tgtggtttaa atttacattt ccctgatgat taaagatgtc aagcattttt catatacctg 283920
ttggccattt ctatatcttc tttttaaaaa tttatattca ggtcctttgc ccattttttta 283980 attgggttat tttcttgtta ttgaattgtt ttagttcctt atatatttca gatagtaact 284040
tcttatcaga tgtatgcaaa tattgtctcc cattccatag agtgtctttt tactctgttg 284100
attgtttcct tggcagtgca gaagcttttt agtttcatgt aatcccgttt atctatttcc 284160
acttttgttg cctgttccca atggagtcat atccaaaaaa tcattgccca aaccaatgtc 284220
atggagcttt ttcctatatt ttcttccagt agttgtacag tttcaggttt tacatttaag 284280

-continued tctttaatcg attttgagtt tatttttgta tatgaggtaa aataagggta taatttcatt 284340
cttctgcata tggatgtcca attttcccaa caacatttaa agacagagtc ctttccttac 284400
tgtgtattct tagcaccttt gtgataaatc aatttactgt aaatgtgtgg atttatttcc 284460
gaacacttta ttcttttaca ttggtttatg tcatttttat gccagtacca tgctgttttg 284520
atgactatag ctttgtatta tgttttgagg ttggtagagt gatgatttca tccttgttct 284580
tcttgttcaa gattgctttg gctattcata gtctattgca gttgcataca aattttagaa 284640
ttgctttttc tatttctgtg aaaaatgaca ttggaatttt gataaggatt gcattgaatc 284700
tgtagattgc tttaggtagc agggacattc gaacaatatt aattcttcta atccatgaac 284760
atgggctatc tgttcattta tttgtgttgt cttcatgttt tacagttttc agtgttcaga 284820
tctttcacct ttttgtttaa atttatttct aggtctttta ttttattttt atttttatag 284880
atattgtgaa agggatttct ttatttcttt ctcagattgt tccttattag tgtatagaaa 284940
tgttactgat ttttgtatgt tgactttgta tcctgcagct ttactgaatt tgtttatctg 285000
ttctagcaat tttttgttga agtctttagg gttttctata tataaaatca tgtcatctgt 285060
aagcaaggac aatttaactt tttccttctc aattttggat gccttttatt tctctctttt 285120
gcttaattgc tctgactagg attttgaatc gagtagaata gagtagagga gttacattga 285180
ataaaaatgg caagagtagg catctttgtc ttgttcctca tcttagaaga aaagctttcc 285240
acatttcact gtttattatg atgtgagttt gttatatatg gcctttattg tgttgaaata 285300
cattccttct atatctaatt gttaagggtt tttatcatga aaggatattg aattttgaca 285360
agtgcttctt ctgtatctgt tgagatggtt ccatggtttt cgtctcggtt ctgttaaagt 285420
gatgtattat gtttatgtat ttgtgtgtga tgaaccatcc ttgcatccct ggaataaatc 285480
ctacttgatc atggagaatg ttccttttag tgtgcttttg agttagtttc ctagtatttt 285540
gtttaagatt tttacatctg tatttatcag agatattagc ccataatttt cttttcttgt 285600
agtgtccttt catggtttgg gtataagggt aatgctagca tcaagaaata gtttggtagt 285660
atcccctttt cttccacttt ttggaaaagt ttgagaagga ttggtgttcc ggtgaagctt 285720
ccagtgaaac tgtcaggtcc tggacttctc tttgatgaca gactttttat tactgattca 285780
atctccttac ttattattgg tttattagat tttctatttc ttcaagaaag tcttagtagg 285840
ttgttgtgtg taggaattta ttcatttctc atgcatataa tttttcagaa tggtctctta 285900
tgaacatttg tatttctatg gtattggttg taatgtctcc tccttcattt ctgattttgt 285960
ttttaatttg ggctttctct ttttttatta tttagtctag ctaaagattg gttgattttg 286020
tttatctttt caaaaaaact tgtttcatta atcttttcta ctgttttaat gtgctaactg 286080
aaaagcacat taaaaggatc attctccatg atcaagtagg atttatccca gggatgcaag 286140
gatggttcat cacacgcaaa tacataaaca taatacatca cattactaga accaaaaaca 286200
aaattatgga accatctcaa tattttctat tctctatttc atttatttct gttctgatct 286260
ttattatttc cttccttcta tgaactttat gcttagttta ttctttttct ggtttcttca 286320
ggtaaaatgt taggttattc atttgagatc tttgttttct gatggaggca tttattgcca 286380
tgaacttcca ttgctcttag aacgactttt actgcattcc ttaaggtttg ctatgttgtt 286440
tccatttttg tctcaagata tttttgattt tattttttac tttttaacta ttttttttagg 286500
ttcagagata catgtgcacg tttgttatat aggtaaattg catgtcacag gggtttacca 286560
tacagattat ttcatcacca ggtaataagc atagtaccca gaaggtagtt ttttgatctt 286620
caccttcctt ccacccacta ccctccagta ggccccaata tctgtggttt cagtcttcgt 286680
gtccatgtgt tctcaatgtt tagctcctac taataagtga gaatatgtgg tatttgtttt 286740
cctgttcatg cattagtgtg cttagcataa tggcctccag ctccatccat gtgactgcag 286800
aggacatgat cttgttcctt tttacgcctg agcagtattc catggtgtac atataccaca 286860
tttcctttat ccagtgtacc attttcttta ttccatgtct ttgctattgt gaatagtgct 286920
atgatgaaca cacgcatgca tgtgtcttta tggtaaaatg gtttatattc cttcaggtat 286980
atacccaata acgggactgc tgggtcaaat gacaattctc ttttaagttc tttgagaagt 287040
tgctaaactg cttgccacaa tggctgaact aatttgaatt attaccagca ggatataagt 287100
gttccctttt ctttgcaacc tcaccagcat ctgttatttt ttgacttttt gataatagcc 287160
tttctgactg ctgtgatgta gtatctcatt atggttttga tatgcctttc tctctaatta 287220
ttagtaatgt tgagcatttt ttcttacact tgttggctca tgtttgtgtt cttttgaaaa 287280
gtgtctgttt atgccttttg tccatttttt aatgggactg tttgtttttg gcttgttgat 287340
ttaaagttcc ttatagattc tggatattag acatttgtca gatgtatagt ttgcaaatat 287400
tttcagccat tctgtagatt atctgttttt tcagttgttt cttttgctgt gcagaagctc 287460
tttggtttaa ttagatccca tttgtcaatt tttgtttttg ttgcaattgt ttttggcatc 287520
tttgtcatga aacctttgct aaggcctatg tccagaatgg tatttcctag gttttcttct 287580
agggttttta tagtttgggg ttttgcattt aaacctttaa tccatcttga gttgatagtc 287640
gtacatgttg aaaggaaggg gtccagtttc aatcttctgc atataactag ccagttaccc 287700
agcaccattt attaaacagt gttttcctca tttcctgttt ttgtcaactt tgtcaaatat 287760
tagttggttg caggtatgag gctttatttt ggggttctct gttctgttcc attgatctat 287820
gtgtcttctt ttttaaccag taccatactg ttttgattcc tgtagccttg tagtataatt 287880
tgaagtcagg taatgtgatg cccctgggtt tattcttttt agttaggatt gctttgacta 287940
tttgggctgt tttttgcttc catatgaatt ttacaattgt tttttctaaa tctgtgaaaa 288000
attacattga taatttgata ggcattgcat tgaatgtgta gattggcttg ggcagtatgg 288060
tcatcttaac gatattgatt cttctaatcc ataagcatgg aatgtttttc catttgcgtt 288120
atctgtcatt ttctttcatc agtgttttat agttctactt ataaagatat ttcacctcct 288180
ttgttaaatg tattcctagg tttctgtgtg tgtgtgtggc tataataggc tatgttaacc 288240
tgataacaat ttaactttct tgcataaaaa actctacact tttactccac ataccgcccc 288300
cccaaacaca ttttaaattt ttgatgtcac acttacatct ttttatattg catatttctt 288360
aacaaattat tgtacctagt attattttta ataattttat cttttaacct tcattctaaa 288420
ataaaagtga tttgcatatt accatgaaaa tattagacag gtaatgtgat gcccctgggt 288480
ttattcattt tagttaggat tgctttgcca attgggctgt tttttgcttc catatgaatt 288540
ttacaattgt tttttctaat tctctgaaaa attacattga taatttgata ggtattgcac 288600
tgaatgtgta gattggcttg ggcagtatgg tcatcttaac aatattgatt cttctaatcc 288660
ataagcatgg aatgtttttc catttgcgtt atctgtcatt ttctttcatc agtgttttat 288720
agttctactt ataaagatat ttcacctcct ttgttaaatg tattcctagg tttctgtgtg 288780
tgtgtgtggc tataataggc tattttaacc tgataacaat ttaagtttct tgcataaaaa 288840
actctacact tttactccac atactccaca cacacacacg ttttaaattt tcgatgtcac 288900
acttacatct ttttatattg catatttctt aacaaattat tgtacctagt attattttta 288960
ataattttgt cttttaacct tcattctaaa aagtgatttg catattacca tgaaaatatt 289020

-continued

```
agactacttt aaattggact gtgtacttac ttttactagt gagttttata ctttcatatg 289080
tttttatgtt actcattagc ctccttttct ttcagctaaa gacctccctt tagcagttct 289140
tgtaagatag gtctgttggt gaggaatggt taatttaaat ataacaaagt acaaaaagtt 289200
catcagtaga gtttcaggtt tcatttttcc actaacctgt aagaatttat catttgagtt 289260
ttagtctatt gttaaacaga aatgttcaca attatgtgaa aagtttatta aaatattcct 289320
cattttcctc attatttatc tgtgtgaggc caggttttat tcatttacga aaatagcaca 289380
ttctaataga tttaattcag aagcagttat aaaaatacag tcatcttcct ttaagtctga 289440
cattaaataa atttgcaaaa atgtaaaaca gtatcactct tctcactctc tttttgttg 289500
tttgggaaag tacaataatt tttatgaaaa tatattattt aacaaaatca atttattatt 289560
ttcagtttaa aaataaggat tttaaaattt tttcatttca atttctaata ctgtaaatag 289620
tgataggtat aacccaacta aaccaaactc tttaagattc tcaaattttt aagagtgtaa 289680
aggagtcctg aaataaaaaa gttaaacaac ctagaaaaaa acaaagatat aaatcagcat 289740
gttagcattc atcaattcag ttaccatcat ttcatcccta aaagccatgg catatagtta 289800
cgtctcactg agccaccact ttgaaactcc caccctgtgc caggtacttg tgagcatgta 289860
actttgttaa tcaactgttc agggctatat cccaacatgg ctttgttgca cttttcgtgg 289920
cacctctgct aaatctcgtt aggtagacca aaggggtcag ttaacttttt ctttatacct 289980
tttattcatg atatttataa gtttggtaat ttacaaaggt cttggacaaa gaccaggggc 290040
ttatatataa taatttattt atctcttgaa gaaacaaaca atataattgg ttatgaagca 290100
caggcgtcat aagcagaaaa caggtttata ggtaaagggg gaagacctag tgtgtgtcgc 290160
ttgcatcagg aattcatgtt accatttggc aatatgaatt tgcttagcag tgtgcttttt 290220
tttctccccc ccacaggatc ttgctctgtc cccaggctag agtacagtgg cccaatctcg 290280
gctcactgca acctccacct ccagagttca agtgattctc gtgcctcaga ctcctgagta 290340
gctaggatta caggcgcaag ccaccacacc cagctaatac agctaatttt tgtattttta 290400
gtagagacag ggtttcatca tgttggccag actggtctcg aactcctgac ctcaggtcat 290460
ctgccaacct cggcctccca aagtgctggg attataggca tgagccactg tgcctggctg 290520
ccctttttag taaatacatt ttgcatgacc atgtggttgt ttacagctat ttatctagta 290580
aaccaataac ttacagcttt ttaaaggctt aatgaatagc atggaattat tcatgatatc 290640
tgtgccatat cttgaggacc cactgtatac ctgatattgc actggacttt ggaaatgaaa 290700
aataatgagt gatcttgggg aatttacaat gtaacataga aaggtgtgta tcactaaatt 290760
tgcacaatga aacataatta ataatagaag aagtatatta tctggcagaa tagagtgggg 290820
aaaagtacca gcaaagactt agaataccag ctctcctcaa tacttgcact tagacttgga 290880
tgagaaacag ttccccgcac aggcagatga cagggttagg tatgatagga gccacgtaag 290940
taggagccac tcgaaatctg agtttggtgt ggctggtgtg gagggttgag ggaatatgaa 291000
gagaggacca caacttgaat cactgagggc cctttttga tcctattagt gaaatcttta 291060
aagaaattgt attggtgaca ataacagaga aataagggct ttgaggatga aaacataggc 291120
tttaaaaaaa aaacttaaga aaaaaataat aaagtaagtt cagtattcag tgtcctgcct 291180
taaagaaagc attttaggca tgcaaatatc ccatatattc agaggcttct ataaaaaata 291240
caaacaaacc ctgtcatata cacatgaggc aaaaaaagat actttgtgag tagaaactat 291300
tgaggtaaaa gaaaaacttg ttttagaagc tgaaggccca gctgctgact taataaaaca 291360
aattatgaga attttgttta tgcgaaaatc catgctgttg aaaacgcgag tgtttaaagt 291420
```

tttctataaa caggaacaag gtgttctacc aaaaaaaagt ataaaagcac attgaataac 291480
tgctttgagt atttgacttg gaggaaacta ccatcactag ttgagtatac ctctttgata 291540
gcaatatgtg ttaaaagtct aacagtctca ctctacccct ccccgagaag gtaaaggaat 291600
atcctgacct taagggttgt gagacctaga tgtttcttac caaagaactc cggtgacttt 291660
tctttgcaga ttttaaatag caaactattt tatggtggct ttaagccttc cagagcaagc 291720
agattaggta tgtagttcct tttaataaaa gtatttggaa gttcaataaa ggcaattatg 291780
atttttctag gacctttttcc aattctgtga ttatgtgaat gactacccgg aatttccatc 291840
aaacactgat atacaacttg ctatggctac aatttatttt ggtgtgaaaa catgtttgct 291900
tttctgttct tatgtctccc ttcatacaaa agtataatat cccagatatg taggcatata 291960
gttctgccat tcagagtaat tctaatatac tttaatctta ttaactatct ggaagactaa 292020
tgcacagtta tagctgcatt tctttaagca agtctatcat atctttgggt ttatgccaaa 292080
ctaaatttgt gaactattat ccatttacaa aatgattatt tacatcaatc ttcctttaaa 292140
taacaaatgc tcacaatgca ttttaaaata ttacctactt tataaaaatc cattctgaat 292200
aaaaatggga gaatacctgt agtgttcatt gcattgagtt gttgactctt tggccaatat 292260
gcgtttatat tttgtcttga aagatggacc ctatattgac aacatcagtt ccagtgtact 292320
cattgaaagt ggataaggaa tatgaagtgc gtgtgagatc caaacaacga aactctggaa 292380
attatggcga gttcagtgag gtgctctatg taacacttcc tcagatgagc caatttacat 292440
gtgaagaagg taaaagaaat aaaagattaa aatagtagct aacctggctt ttgtcaatat 292500
aacagttgat tcacccctgc actggtagtg tgttgtccaa atcaaaatat attaacatca 292560
gatatcagga tgagagacct tgagctcact atctgtaaca gatattgttc attgcaaaag 292620
cagaaggaag atttagtttc caaatttttc attcaggaga agtccggggg gcaggtggaa 292680
gtttagagac aggaatttgg tggcaatctc cggatggtag aattcagatg attcttttct 292740
ttatatattt ttatatttct gaaattttct atagtaagtt tgttttgaat ttataatcag 292800
gaaaaaaagc tgtactgatg gttagggaag aaagtatgta tctatatgga tggatagata 292860
tgtgacatct aagaggaaac ccaatattga gtcagcatag gtagtcaaca gcaggtgcat 292920
acggttttag aaagcggagg tgtggctttt acctagagga atgcctaata agtagtgtgg 292980
cagtcatact taaaggagac gtggaacatt tgaaaaccct atgtaggaga atcacaacaa 293040
tgattaaagt ttttaaaaat gggacctatg aatttagaat aaaagaatta aaacttttag 293100
atacagaaat aaagaaaact gattaatgat gagcagaaag tatagagtat tattattctc 293160
aaatgggaaa tggctctatt ccatcttcat tgaaaacaga agtttacagg gctatatgtt 293220
tgttaatgaa acaaccacaa gctacataga aaataaattt atatttctgt atttactata 293280
caggtagaat ctcatgatac taaatagcat taggatgaaa atttctatag caccattttc 293340
tctatactct agttaactga attcttgttt ccaaactatt tgatattatg caattctggc 293400
cttaaaagta caatagctat acacccttaa gcttagtgta gtggcattta attcacttaa 293460
catatatttt ttaaactgcc ttttccttct gttactaaca aaaaagaagc tctaacttta 293520
tgttattttc ctgaatatgt cattgatatg aaattataga cactacaaga caaaaaatga 293580
ttttttctcc cccaccaatt ctttaaaatg cttataatat ctccctaggg gattttaata 293640
actttttaaa taagaaaaga ctatttcagc ataaagacct acattttaaa tggcaatgtt 293700
aaggtaaatt tcatctgtca tttttataaa aaagtggtta gcctctgcct ctgtggtaag 293760

-continued aatactgggt accaactgca aagtagctgg caggtactca atcttaagga atgaaataga 293820
agttttacaa acaggttccc ccaagtctca tacaaagtat actaaaacct gaagatggga 293880
gcctcagtag tgatctttct gtcaatttta tgtatataat atacatgaga tatatttatt 293940
atattttaat aatttaattt attgatataa atacgtatat ttatagctgt aaaatatatg 294000
ttatttgtgt ctaagaagtt tctgtcatga tttatcaata aaaactctgc cttcatcttt 294060
ttgataaatc ttcaatctgg aaactaagaa aatcaccaca cttaaaaaaa aatagaaaag 294120
aaaccgagtg ggcattattt aggtagtgtg ttaataagca acactttttt actgaagctg 294180
aaacctttat gatactccct ggacacatag tatgcttaaa gcagattgtt tgttttcata 294240
aaacacacat tgattttgaa ctatatgctg tttctttatt ttgaagtttt tttttaatgt 294300
gaggagattt gaaaagtgga cagagatgtt cataaaacag aaaaaaaacta agtcgttgca 294360 ttctgtttca gtggttatca agagaaatca ctgactttat tagatgaata caaattatga 294420
attttttgtg aaaagggaaa gggaaatgta aactgtgctt caactattcg taattctgaa 294480
agcgaaatat tcttgtgtgt ttcagatttc tactttccat ggctcttaat tattatcttt 294540
ggaatatttg ggctaacagt gatgctattt gtattcttat tttctaaaca gcaaaggtag 294600
gtgtggagta gtattctttg gtattttgta ccagttgttt agatttccat atgtgtttct 294660
atttgttatt tgatattttc tttgtcaaat tatgagtgga aattttagtt aacctagtac 294720
acttttatct ccagttatat atttaccatt catataaaac tcaatttgtt gtatttatct 294780
tagacaattt agaggtttag attctatctg gagacttgta caggacatta agaggcttag 294840
gctggtgact atgcatacct tgtgatatgt acctctttat ccaagagcta gctctttccc 294900
tcaagtcctc aacaagttga cccattcatt ccaggacttc aaagtatcac tgagcctttg 294960
gctgagtctg atacagtcct tatatacaga caattttttt ttttccttga gacggagtct 295020
tactctgttg cccaggctgg agtgcaatgg cgcaatcttg gctcactgca accgccgccc 295080
cccaggttca agcaattctc ctgcctcagc ctccagagta gctgggatta caggcatgcg 295140
ccaccaagcc cagctaattt tgtattttta gatacagttt caccatgttg gtcagactgg 295200
tctcgaactc ctgacctcag gtgatctgcc cacctcagcc tcccaaagcg ctgggattac 295260
aggcgtgagc taccgcgcct ggccccattt aaggtatttt taaagtccca atggttaatc 295320
ttgttgcttc tcctagaatt aaggtgacta acactcccag gttgcctaga actctcctgg 295380
tttttagcaa tgcaagtccg gtgtgccagg aaatccctca gttccaggta accaagacag 295440
ttgatcccct tacctagaat tgaaaatacg ttctccagct gaagccaaga ggcatctata 295500
aatcaaaatg agatctatgt taatatattt taaaagattt tactttgttt tgtaaggtag 295560
tatagcactt gtaaacttca aaacagaatt ttgttaggaa gaagaattat tgggacgcta 295620
gatttctata gtgtcaagca tgctaaaagt ctaactgaat gcagaaaggg ttattttcag 295680
tagagcttca tgtccaattt tataatataa accaattgga aagtaaaatt cattctgaat 295740
tccattttgc acctaacttt ctggcaacat tcctgttttc caaaaaagca gctatcataa 295800
atcacaacac aattttctat tgtttcagga aaataaataa atatattttt agaattttaa 295860
tttgtgtatt taagtaatgc caacaacaaa aaagccaaat tattctgttg attaatttca 295920
gtttattaat ctatatattt ggtgggaaaa tttatacata acttcagtag ataaactcac 295980
gaggtatgta aagtaattag ctcttagtat tagctgtgaa tttctagcca ttgtgaaggc 296040
caagtcaatt tgttatgttg tttagttata ttagttaaca atattaggaa gaaaaaatta 296100
tcctctcaaa aagtaggatt tccaagaaaa catattactt ctaatacagt gcttttttata 296160 aataatgaaa tgcttaacta taatgtttag tcaaaatcac caaattctac aattgatttg 296220
aaatctttat tgttctccca aatttcctgc actaaattga attttctgta ggaaagaatt 296280
aactttattt tttatttgcc cattaaaaac gcttatcatt gtctaaattt gcatgttcta 296340
ctgaaagtgg gaaatagtag caaatatttg tcagcaagta tggacagaac atgtagttcc 296400
aacaattaaa ttgatactgc aaagaacgag atttttccta gaactgtagg gctgtaaagt 296460
ggcgtcaggt cctacatgcc tttgaaattt tctgagtcca caattcatta tccaacccac 296520
ttcaccctgc tttaatccag ttaattgagt caactctagc aaaatttata attttatttg 296580
tatctgatac aaaaccacaa acatagtttc aagtcaggct attattatac tggttcctac 296640
cacacaaccc tcccagcctt tgagctgtta ccaattgagg aaagaaataa ctgaatcagc 296700
ctaaaataga atttccaaac cagtagcgaa attcagccta cagattcata ttttgttatt 296760
ttattttaat tagttttgat ttcagagtga agattttcct acaaagtgtt tgtaaaatag 296820
agaattttca cacaaaaatc cagatttggg gattatcttt taaaaaatga aagatgtagt 296880
gaaactaaac aaggcagcat atgctgcagc agacaaccag ctatcctatt tgggattggc 296940
tcacattctt taatttgcca ccatcctcat tcctcctaat gactttgcaa ctggcttgct 297000
ttattcctct gcatgacctg cttgggcctc ttagatttat gctctgccac tgtggcataa 297060
ggtcactaca accactagaa aaccactagc gcatgcctga atgcatcatc ctatttaaaa 297120
aggaaaagca cacgtcacaa agtcaaacat cagccatttg gaaacctttg cttcctgtaa 297180
ttagaattat gttccatctt tttatgtttt tgggaatttg aaataccaat ttcgagatgc 297240
agaatcaaaa aaaaaaaaac aaaacagcga aacagcagca tgacacaaag aacctgggtt 297300
ttgatttgga gtcaggttct ctgggtttga gccccaactg tgccaactat gaatgcatga 297360
tttgaacatg ttgcttaatt ttccaagttt ttgcacagat atatcatctg cctccctggg 297420
agtcataagg attaagtgaa atgtttagtg caggggtcac aaacttattt catagagtta 297480
gagtacattt ttaggctttt caagccatac agtctctatc acagctactc aactctgcca 297540
ctgtagcacg aaagtggcca taaacaaaat ggaaatgaat gaagatgctt gtgttctcat 297600
aaaattttat ctacacaaac atgtgacagg ccagatttgg cccacagacc ttaatttagt 297660
gacccatagt ttagtgcaaa gtatatccca cagtgtctga tttatcagaa gcactaaaaa 297720
atgatagtag ttattattaa taatttgtat tacttatttc tatatctgta attcatcagt 297780
aacaatatgc tttaacattt gccccactga gtagtagagg ctacttaatg caatttataa 297840
aatggatttt tgcttattac ttggattagg taaaatagca agtggaaata ctgagaaaat 297900
gtactcctta tggaatggac tggactgacc attcacactg agtggaatag taactgatat 297960
ccaaaaatct ggttaccacc tcttcatgac agtgtcatct ctgaatagtc aggagttttt 298020
taaaaaatta aatgaattgt ttggaataat ctctgagcct ttttccagtg ctataatttg 298080
attttaaaaa ataaactcca ggccagatac aatggcttat agcatataaa tccagcactt 298140
tgggaggatg gggcgggagt attgccctga ggccaggagt tccagacagc tcgggcaatg 298200
actagagcaa gactccatta caaaaaatga aacaacaaaa attagcacac cctgtagtcc 298260
tagctactta ggaggctgag gcaagaatat cgcttggccc aggagtttga ggctgcagtg 298320
aattatgatt gcaccactgg actccagtgt gggcaatgaa gtaagaccct gtctcaaaaa 298380
gttttaaaaa aaattaaaaa caccataaat tccaattaca ctattaattg tacaaaatag 298440
atacatgatt tattcatttt tatgaccaaa aaataattta aagatttgga acaaaaaatg 298500
taagtgcatc ctagaattgt atatataaac ccatactgat tagttagaga tagttaaaat 298560
ttaatctgtc ccatctgaaa tgaaccctgt agtaaaaccc tggttaataa gatcatctta 298620
gataatttca taattaatat gaactatatg gctaacctac ccaagtctac cctttttcaa 298680
gggtgtaagt aatcttggct ccatgtggat tgactctttt ttctttcttt cctgtacaaa 298740
ttactgatga gatgtacact agaattgcct tatagctgaa atggaaatca gctttagatg 298800
aaattaaatt tctttctttc aaatactaaa tctggctgaa aataaaaagc attaagaaaa 298860
aaacaattgt gggaaaacca cattttcttt taatagactt cagatgaggc tttttgggtt 298920
ttttagttgt tctttttttt ccttctacag tttttctttc tcatttactg tctaatattt 298980
tcttctgttt ctcacactcc aattatataa agtaccagaa tatttggaaa aagtaatagt 299040
attgccaata ttttatttct atcttttgct ataattgaga atatgtagct tttaagatgt 299100
caaaaccaaa attttatatg ttttcaagga ttaaaatgct gattctgccc ccagttccag 299160
ttccaaagat taaaggaatc gatccagatc tcctcaaggt aactaataat tttatctaaa 299220
ttgtagctag tactaattaa cacctgaaga ctcctgtcat atgttgaagg ttttctgtaa 299280
gctatatata tcacattcaa ttttcttgtg tctcttctcc tggagaaaat ttttttaaat 299340
attctatttc ttaaaaataa gaaaacgtca tatgtattta aaaagttaca cactaattta 299400
tgttttttta tatgttttgt tactgttgtt cttattgtaa ccataattaa tctctgaaca 299460
ttatttgcta attcatttaa ttattatgag tttcttttca tagatcttca ttttctttct 299520
attttctagg aaggaaaatt agaggaggtg aacacaatct tagccattca tgatagctat 299580
aaacccgaat tccacagtga tgactcttgg gttgaattta ttgagctaga tattgatgag 299640
ccagatgaaa agactgagga atcagacaca gacagacttc taagcagtga ccatgagaaa 299700
tcacatagta acctaggggt gaaggatggc gactctggac gtaccagctg ttgtgaacct 299760
gacattctgg agactgattt caatgccaat gacatacatg agggtacctc agaggttgct 299820
cagccacaga ggttaaaagg ggaagcagat ctcttatgcc ttgaccagaa gaatcaaaat 299880
aactcacctt atcatgatgc ttgccctgct actcagcagc ccagtgttat ccaagcagag 299940
aaaaacaaac cacaaccact tcctactgaa ggagctgagt caactcacca agctgcccat 300000
attcagctaa gcaatccaag ttcactgtca aacatcgact tttatgccca ggtgagcgac 300060
attacaccag caggtagtgt ggtcctttcc ccgggccaaa agaataaggc agggatgtcc 300120
caatgtgaca tgcacccgga aatggtctca ctctgccaag aaaacttcct tatggacaat 300180
gcctacttct gtgaggcaga tgccaaaaag tgcatccctg tggctcctca catcaaggtt 300240
gaatcacaca tacagccaag cttaaaccaa gaggacattt acatcaccac agaaagcctt 300300
accactgctg ctgggaggcc tgggacagga gaacatgttc caggttctga gatgcctgtc 300360
ccagactata cctccattca tatagtacag tccccacagg gcctcatact caatgcgact 300420
gccttgccct tgcctgacaa agagtttctc tcatcatgtg gctatgtgag cacagaccaa 300480
ctgaacaaaa tcatgcctta gcctttcttt ggtttcccaa gagctacgta tttaatagca 300540
aagaattgac tggggcaata acgtttaagc caaaacaatg tttaaacctt ttttggggga 300600
gtgacaggat ggggtatgga ttctaaaatg ccttttccca aaatgttgaa atatgatgtt 300660
aaaaaaataa gaagaatgct taatcagata gatattccta ttgtgcaatg taaatatttt 300720
aaagaattgt gtcagactgt ttagtagcag tgattgtctt aatattgtgg gtgttaattt 300780
ttgatactaa gcattgaatg gctatgtttt taatgtatag taaatcacgc tttttgaaaa 300840
agcgaaaaaa tcaggtggct tttgcggttc aggaaaattg aatgcaaacc atagcacagg 300900 ctaattttt gttgtttctt aaataagaaa cttttttatt taaaaaacta aaaactagag 300960
gtgagaaatt taaactataa gcaagaaggc aaaaatagtt tggatatgta aaacatttat 301020
tttgacataa agttgataaa gattttttaa taatttagac ttcaagcatg gctattttat 301080
attacactac acactgtgta ctgcagttgg tatgacccct ctaaggagtg tagcaactac 301140
agtctaaagc tggtttaatg ttttggccaa tgcacctaaa gaaaaacaaa ctcgtttttt 301200
acaaagccct tttatacctc cccagactcc ttcaacaatt ctaaaatgat tgtagtaatc 301260
tgcattattg gaatataatt gttttatctg aatttttaaa caagtatttg ttaatttaga 301320
aaactttaaa gcgtttgcac agatcaactt accaggcacc aaaagaagta aaagcaaaaa 301380
agaaaacctt tcttcaccaa atcttggttg atgccaaaaa aaaatacatg ctaagagaag 301440
tagaaatcat agctggttca cactgaccaa gatacttaag tgctgcaatt gcacgcggag 301500
tgagtttttt agtgcgtgca gatggtgaga gataagatct atagcctctg cagcggaatc 301560
tgttcacacc caacttggtt ttgctacata attatccagg aagggaataa ggtacaagaa 301620
gcattttgta agttgaagca aatcgaatga aattaactgg gtaatgaaac aaagagttca 301680
agaaataagt ttttgtttca cagcctataa ccagacacat actcattttt catgataatg 301740
aacagaacat agacagaaga aacaaggttt tcagtcccca cagataactg aaaattattt 301800
aaaccgctaa aagaaacttt ctttctcact aaatctttta taggatttat ttaaaatagc 301860
aaaagaagaa gtttcatcat tttttacttc ctctctgagt ggactggcct caaagcaagc 301920
attcagaaga aaaagaagca acctcagtaa tttagaaatc attttgcaat cccttaatat 301980
cctaaacatc attcattttt gttgttgttg ttgttgttga gacagagtct cgctctgtcg 302040
ccaggctaga gtgcggtggc gcgatcttga ctcactgcaa tctccacctc ccacaggttc 302100
aggcgattcc cgtgcctcag cctcctgagt agctgggact acaggcacgc accaccatgc 302160
caggctaatt tttttgtatt ttagcagaga cggggtttca ccatgttggc caggatggtc 302220
tcgatctcct gacctcgtga tccacccgac tcggcctccc aaagtgctgg gattacaggt 302280
gtaagccacc gtgcccagcc ctaaacatca ttcttgagag cattgggata tctcctgaaa 302340
aggtttatga aaaagaagaa tctcatctca gtgaagaata cttctcattt tttaaaaaag 302400
cttaaaactt tgaagttagc tttaacttaa atagtatttc ccatttatcg cagacctttt 302460
ttaggaagca agcttaatgg ctgataattt taaattctct ctcttgcagg aaggactatg 302520
aaaagctaga attgagtgtt taaagttcaa catgttattt gtaatagatg tttgatagat 302580
tttctgctac tttgctgcta tggttttctc caagagctac ataatttagt ttcatataaa 302640
gtatcatcag tgtagaacct aattcaattc aaagctgtgt gtttggaaga ctatcttact 302700
atttcacaac agcctgacaa catttctata gccaaaaata gctaaatacc tcaatcagtc 302760
tcagaatgtc attttggtac tttggtggcc acataagcca ttattcacta gtatgactag 302820
ttgtgtctgg cagtttatat ttaactctct ttatgtctgt ggattttttc cttcaaagtt 302880
taataaattt attttcttgg attcctgata gtgtgcttct gttatcaaac accaacataa 302940
aaatgatcta aaccactctg tatactgtga attatcattg taaggagagc ttagcaccac 303000
tggatcaaat acatcagcat tgggtatgga gatttttatg tgctgagata tagagaggga 303060
aacatatccc ccttccctta ttttttgaga agacaaaagc ccaactcaga aatatcccac 303120
tggcttggcc ctccccttag gctgtgactc cccataggca aaggttcata gagctgtgta 303180
tttgatgcat catggaaaat aaatgacatg ggtgttggat gagggagagt gatatgtgag 303240
cattatcttt acatttccag cttgagcatg ttgtctggaa ggaaggaaag cagctcttcc 303300
tctgccattc acccattggc ctaagtcagt ttattggact agctgcttgt tatcatggga 303360
atcagctaat aagtcaggct tgggaggaag gctgattagg taagttgtgt aggagcctga 303420
gagagccatg aagtttagat tcctacagca ggaggcagga tgcaggtgag gtagctgctg 303480
aaccctaggc tcctgagcag gcactggatt ctgagatgta ggaatctggt gaggacattg 303540
ataaacctac taaacaatga cgtattgctt cagcaagtca aatgcaaagt gccacaactt 303600
tttataatac tcaagtgtta tgttaaaaaa aaaaaatgtc ttcacctgct gccctctgcc 303660
ctgtgagcag ccattacctg aaagaaccat ggagtgaagc ctcagggctt cttcatatag 303720
atgctttaag atatgaggag tacagggaaa agaaagcctg cctacttcca tggattgaaa 303780
taacacaatt ctatttcaga agattaatgg tgtgttgaaa atggctacac acatctttca 303840
gcatttcaat ttctcaaagt ttctactaac actttattca agtgctataa tatttacata 303900
tttacatatt tgtataccaa aatatgtctt gttatgtgct tgttttaggg taagaaatag 303960
tgaccagaaa aaccagaagt tacttaaatc taaacttttt agtttggaat ccaagatccc 304020
acataatttg ccccagtctc ctttgagagt ttaaaattta agacctagat gtaaagggca 304080
cagcttctga ataagaattt gatgtttggt taacattcaa actctattgc tgtggaaatc 304140
taatgagcat atgatgtcag ctatgttaca cgggaaacat tgctcatagt ttaaatgatc 304200
tctgactgat aaatgacatc tggataggga gaaactataa ccacctggag ataagttata 304260
ctttggactt gagtgtagtg acttgtaatt aagcatttcc cctatagaaa ctctggaagc 304320
tatgtttctg gagatgtaac aagagtaact ggctccagtg aggcatagag cttctaagcc 304380
tgggagactc ctttacctgc ccaatacctt ctctgaatct gagctgccag ttgtaggagg 304440
agaggaagga aaagaccttc tggatagcta tataaacagc tgtttagatt gcttcatgca 304500
ctgttatcat tactgtgact ctaaagcaga aagcctgatg ctgtatccct tctgtcctac 304560
atccctctga gtagactgga accaagtatg gtgaatctgg ggaatgtgtg gttgagccta 304620
agaagatccc cttgcatatg tagcaaaaga cacttgccat ttcttgaaca aagtttgtgc 304680
tttcccatct ctatgttctt ggtcatgcct cctccttcaa ctaaaaagct cccacttacc 304740
aaccctgcct gtcaagattc ccttcatcct tcatggccca gctctaatgc ctccttcatg 304800
aactctcctc tgattcccac catccaatca gtgatttttt cttctgaacc atgtttaatg 304860
gtgtttatca cattactttg gtagctcacc tgacaaacgg c 304901

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
tcagggcatt ctttccattc 20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
cataatcagg gcattctttc 20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cctttaatct ttggaactgg 20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
tcatcaatat ctagctcaat 20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
cttagaagtc tgtctgtgtc 20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
cctgctggtg taatgtcgct 20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
atgtaaatgt cctcttggtt 20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
tggtgatgta aatgtcctct 20

<210> SEQ ID NO 14
<211> LENGTH: 20
<212> TYPE: DNA
<213> ORGANISM: Artificial Sequence
<220> FEATURE:

<223> OTHER INFORMATION: oligonucleotide

<400> SEQUENCE: 14
ttctgtggtg atgtaaatgt 20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
aggctttctg tggtgatgta 20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
tggtaaggct ttctgtggtg 20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
agttggtctg tgctcacata 20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
tgttcagttg gtctgtgctc 20

<210> SEQ ID NO 19
<211> LENGTH: 20
<212> TYPE: DNA
<213> ORGANISM: Artificial Sequence
<220> FEATURE:
<223> OTHER INFORMATION: oliognucleotide

<400> SEQUENCE: 19
gcatgatttt gttcagttgg 20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
tataaaaggg ctttgtaaaa 20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
catagcagca aagtagcaga 20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide

<400> SEQUENCE: 22
gctatttttg gctatagaaa 20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
gattgaggta tttagctatt 20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
gatccatacc tgtaggacct 20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ccagagatcc atacctgtag 20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
tgctaaggat agctgctgtg 20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
ttgtctttag gcctggatta 20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
ttagaagaat ttgtctttag 20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
gtgaatttag gctccttaga 20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
gctgtatggg tcctaggttc 20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
taacagctgt tttccccagc 20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
tttcatccac tgtaccacca 20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
ttgcactatt tcatcaacag 20

<210> SEQ ID NO 34
<211> LENGTH: 20

<212> TYPE: DNA
<213> ORGANISM: Artificial Sequence
<220> FEATURE:
<223> OTHER INFORMATION: oligonucleotide

<400> SEQUENCE: 34
gggtggatct ggttgcacta 20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
attgcgtggt gcttcccatc 20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
tagggtccat cattttccat 20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide

<400> SEQUENCE: 37
caatgagtac actggaactg 20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide

<400> SEQUENCE: 38
aactcgccat aatttccaga 20

<210> SEQ ID NO 39
<211> LENGTH: 20
<212> TYPE: DNA
<213> ORGANISM: Artificial Sequence
<220> FEATURE:
<223> OTHER INFORMATION: oligonucleotide

<400> SEQUENCE: 39
agcccaaata ttccaaagat 20

<210> SEQ ID NO 40
<211> LENGTH: 20
<212> TYPE: DNA
<213> ORGANISM: Artificial Sequence
<220> FEATURE:
<223> OTHER INFORMATION: oligonucleotide

<400> SEQUENCE: 40
tcagcatttt aatcctttgc 20

<210> SEQ ID NO 41
<211> LENGTH: 20
<212> TYPE: DNA
<213> ORGANISM: Artificial Sequence
<220> FEATURE:
<223> OTHER INFORMATION: oligonucleotide

<400> SEQUENCE: 41
attttccttc cttgaggaga 20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide

<400> SEQUENCE: 42
agattgtgtt cacctcctct 20

<210> SEQ ID NO 43
<211> LENGTH: 20
<212> TYPE: DNA
<213> ORGANISM: Artificial Sequence
<220> FEATURE:
<223> OTHER INFORMATION: oligonucleotide

<400> SEQUENCE: 43
aacccaagag tcatcactgt 20

<210> SEQ ID NO 44
<211> LENGTH: 20
<212> TYPE: DNA
<213> ORGANISM: Artificial Sequence
<220> FEATURE:
<223> OTHER INFORMATION: oligonucleotide

<400> SEQUENCE: 44
ctggctcatc aatatctagc 20

<210> SEQ ID NO 45
<211> LENGTH: 20
<212> TYPE: DNA
<213> ORGANISM: Artificial Sequence
<220> FEATURE:
<223> OTHER INFORMATION: oligonucleotide

<400> SEQUENCE: 45
tgtgtctgat tcctcagtct 20

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
tatgtcattg gcattgaaat 20

<210> SEQ ID NO 47
<211> LENGTH: 20
<212> TYPE: DNA
<213> ORGANISM: Artificial Sequence
<220> FEATURE:
<223> OTHER INFORMATION: oligonucleotide

<400> SEQUENCE: 47
aaggcataag agatctgctt 20

<210> SEQ ID NO 48
<211> LENGTH: 20
<212> TYPE: DNA
<213> ORGANISM: Artificial Sequence
<220> FEATURE:
<223> OTHER INFORMATION: oligonucleotide

<400> SEQUENCE: 48
actcagctcc ttcagtagga 20

<210> SEQ ID NO 49
<211> LENGTH: 20
<212> TYPE: DNA
<213> ORGANISM: Artificial Sequence
<220> FEATURE:
<223> OTHER INFORMATION: oligonucleotide

<400> SEQUENCE: 49
ggacatccct gccttattct 20

<210> SEQ ID NO 50
<211> LENGTH: 20
<212> TYPE: DNA
<213> ORGANISM: Artificial Sequence
<220> FEATURE:
<223> OTHER INFORMATION: oligonucleotide

<400> SEQUENCE: 50
ggcattgtcc ataaggaagt 20

<210> SEQ ID NO 51
<211> LENGTH: 20
<212> TYPE: DNA
<213> ORGANISM: Artificial Sequence
<220> FEATURE:
<223> OTHER INFORMATION: oligonucleotide

<400> SEQUENCE: 51
actttttggc atctgcctca 20

<210> SEQ ID NO 52
<211> LENGTH: 20
<212> TYPE: DNA
<213> ORGANISM: Artificial Sequence
<220> FEATURE:
<223> OTHER INFORMATION: oligonucleotide

<400> SEQUENCE: 52
gatgcacttt ttggcatctg 20

<210> SEQ ID NO 53
<211> LENGTH: 20
<212> TYPE: DNA
<213> ORGANISM: Artificial Sequence
<220> FEATURE:
<223> OTHER INFORMATION: oligonucleotide

<400> SEQUENCE: 53
cagtcgcatt gagtatgagg 20

<210> SEQ ID NO 54
<211> LENGTH: 20
<212> TYPE: DNA
<213> ORGANISM: Artificial Sequence
<220> FEATURE:
<223> OTHER INFORMATION: oligonucleotide

<400> SEQUENCE: 54
ctctttgtca ggcaagggca 20

<210> SEQ ID NO 55
<211> LENGTH: 20
<212> TYPE: DNA
<213> ORGANISM: Artificial Sequence
<220> FEATURE:
<223> OTHER INFORMATION: oligonucleotide

<400> SEQUENCE: 55
gtgctcacat agccacatga 20

<210> SEQ ID NO 56
<211> LENGTH: 20
<212> TYPE: DNA
<213> ORGANISM: Artificial Sequence
<220> FEATURE:
<223> OTHER INFORMATION: oligonucleotide

<400> SEQUENCE: 56
aagaaaggct aaggcatgat 20

<210> SEQ ID NO 57
<211> LENGTH: 20
<212> TYPE: DNA
<213> ORGANISM: Artificial Sequence
<220> FEATURE:
<223> OTHER INFORMATION: oligonucleotide

<400> SEQUENCE: 57
aaatacgtag ctcttgggaa 20

<210> SEQ ID NO 58
<211> LENGTH: 20
<212> TYPE: DNA
<213> ORGANISM: Artificial Sequence
<220> FEATURE:
<223> OTHER INFORMATION: oligonucleotide

<400> SEQUENCE: 58
caatcactgc tactaaacag 20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide

<400> SEQUENCE: 59
aaacatagcc attcaatgct 20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide

<400> SEQUENCE: 60
gtgctatggt ttgcattcaa 20

<210> SEQ ID NO 61
<211> LENGTH: 20
<212> TYPE: DNA
<213> ORGANISM: Artificial Sequence
<220> FEATURE:
<223> OTHER INFORMATION: oligonucleotide

<400> SEQUENCE: 61
gttttacata tccaaactat 20

<210> SEQ ID NO 62
<211> LENGTH: 20
<212> TYPE: DNA
<213> ORGANISM: Artificial Sequence
<220> FEATURE:
<223> OTHER INFORMATION: oligonucleotide

<400> SEQUENCE: 62
catcaaccaa gatttggtga 20

<210> SEQ ID NO 63
<211> LENGTH: 20
<212> TYPE: DNA
<213> ORGANISM: Artificial Sequence
<220> FEATURE:
<223> OTHER INFORMATION: oligonucleotide

<400> SEQUENCE: 63
gaggctatag atcttatctc 20

<210> SEQ ID NO 64
<211> LENGTH: 20
<212> TYPE: DNA
<213> ORGANISM: Artificial Sequence
<220> FEATURE:
<223> OTHER INFORMATION: oligonucleotide

<400> SEQUENCE: 64
tagtgagaaa gaaagtttct 20

<210> SEQ ID NO 65
<211> LENGTH: 20
<212> TYPE: DNA
<213> ORGANISM: Artificial Sequence
<220> FEATURE:
<223> OTHER INFORMATION: oligonucleotide

<400> SEQUENCE: 65
aatgctctca agaatgatgt 20

<210> SEQ ID NO 66
<211> LENGTH: 20
<212> TYPE: DNA
<213> ORGANISM: Artificial Sequence
<220> FEATURE:
<223> OTHER INFORMATION: oligonucleotide

<400> SEQUENCE: 66
acactcaatt ctagcttttc 20

<210> SEQ ID NO 67

<211> LENGTH: 20
<212> TYPE: DNA
<213> ORGANISM: Artificial Sequence
<220> FEATURE:
<223> OTHER INFORMATION: oligonucleotide

<400> SEQUENCE: 67
catctattac aaataacatg 20

<210> SEQ ID NO 68
<211> LENGTH: 20
<212> TYPE: DNA
<213> ORGANISM: Artificial Sequence
<220> FEATURE:
<223> OTHER INFORMATION: oligonucleotide

<400> SEQUENCE: 68
ctcttggaga aaaccatagc 20

<210> SEQ ID NO 69
<211> LENGTH: 20
<212> TYPE: DNA
<213> ORGANISM: Artificial Sequence
<220> FEATURE:
<223> OTHER INFORMATION: oligonucleotide

<400> SEQUENCE: 69
tctacactga tgatacttta 20

<210> SEQ ID NO 70
<211> LENGTH: 20
<212> TYPE: DNA
<213> ORGANISM: Artificial Sequence
<220> FEATURE:
<223> OTHER INFORMATION: oligonucleotide

<400> SEQUENCE: 70
cacagctttg aattgaatta 20

<210> SEQ ID NO 71
<211> LENGTH: 20
<212> TYPE: DNA
<213> ORGANISM: Artificial Sequence
<220> FEATURE:
<223> OTHER INFORMATION: oligonucleotide

<400> SEQUENCE: 71
agtcttccaa acacacagct 20

<210> SEQ ID NO 72
<211> LENGTH: 20
<212> TYPE: DNA
<213> ORGANISM: Artificial Sequence
<220> FEATURE:
<223> OTHER INFORMATION: oligonucleotide

<400> SEQUENCE: 72
aggctgttgt gaaatagtaa 20

<210> SEQ ID NO 73
<211> LENGTH: 20
<212> TYPE: DNA
<213> ORGANISM: Artificial Sequence
<220> FEATURE:
<223> OTHER INFORMATION: oligonucleotide

<400> SEQUENCE: 73
atagaaatgt tgtcaggctg 20

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74
ccaaaatgac attctgagac 20

<210> SEQ ID NO 75
<211> LENGTH: 20
<212> TYPE: DNA
<213> ORGANISM: Artificial Sequence
<220> FEATURE:
<223> OTHER INFORMATION: oligonucleotide

<400> SEQUENCE: 75
ataatggctt atgtggccac 20

<210> SEQ ID NO 76
<211> LENGTH: 20
<212> TYPE: DNA
<213> ORGANISM: Artificial Sequence
<220> FEATURE:
<223> OTHER INFORMATION: oligonucleotide

<400> SEQUENCE: 76
agttatgtga ccctgattga 20

<210> SEQ ID NO 77
<211> LENGTH: 20
<212> TYPE: DNA
<213> ORGANISM: Artificial Sequence
<220> FEATURE:
<223> OTHER INFORMATION: oligonucleotide

<400> SEQUENCE: 77
ttgagtgttc ctaaaatgaa 20

<210> SEQ ID NO 78
<211> LENGTH: 20
<212> TYPE: DNA
<213> ORGANISM: Artificial Sequence
<220> FEATURE:
<223> OTHER INFORMATION: oligonucleotide

<400> SEQUENCE: 78
atggaggctg gaggttcaaa 20

<210> SEQ ID NO 79
<211> LENGTH: 20
<212> TYPE: DNA
<213> ORGANISM: Artificial Sequence
<220> FEATURE:
<223> OTHER INFORMATION: oligonucleotide

<400> SEQUENCE: 79
tagggtccat ctttcaagac 20

<210> SEQ ID NO 80
<211> LENGTH: 20
<212> TYPE: DNA

<213> ORGANISM: Artificial Sequence
<220> FEATURE:
<223> OTHER INFORMATION: oligonucleotide

<400> SEQUENCE: 80
tctccagata gaatctaaac 20

<210> SEQ ID NO 81
<211> LENGTH: 20
<212> TYPE: DNA
<213> ORGANISM: Artificial Sequence
<220> FEATURE:
<223> OTHER INFORMATION: oligonucleotide

<400> SEQUENCE: 81
tccaaatatt ctggtacttt 20

<210> SEQ ID NO 82
<211> LENGTH: 20
<212> TYPE: DNA
<213> ORGANISM: Artificial Sequence
<220> FEATURE:
<223> OTHER INFORMATION: oligonucleotide

<400> SEQUENCE: 82
tattagttac cttgaggaga 20

<210> SEQ ID NO 83
<211> LENGTH: 20
<212> TYPE: DNA
<213> ORGANISM: Artificial Sequence
<220> FEATURE:
<223> OTHER INFORMATION: oligonucleotide

<400> SEQUENCE: 83
attttccttc ctagaaaata 20

<210> SEQ ID NO 84
<211> LENGTH: 20
<212> TYPE: DNA
<213> ORGANISM: Artificial Sequence
<220> FEATURE:
<223> OTHER INFORMATION: target sequence

<400> SEQUENCE: 84
gaatggaaag aatgccctga 20

<210> SEQ ID NO 85
<211> LENGTH: 20
<212> TYPE: DNA
<213> ORGANISM: Artificial Sequence
<220> FEATURE:
<223> OTHER INFORMATION: target sequence

<400> SEQUENCE: 85
gaaagaatgc cctgattatg 20

<210> SEQ ID NO 86
<211> LENGTH: 20
<212> TYPE: DNA
<213> ORGANISM: Artificial Sequence
<220> FEATURE:
<223> OTHER INFORMATION: target sequence

<400> SEQUENCE: 86
ccagttccaa agattaaagg 20

<210> SEQ ID NO 87
<211> LENGTH: 20
<212> TYPE: DNA
<213> ORGANISM: Artificial Sequence
<220> FEATURE:
<223> OTHER INFORMATION: target sequence

<400> SEQUENCE: 87
attgagctag atattgatga 20

<210> SEQ ID NO 88
<211> LENGTH: 20
<212> TYPE: DNA
<213> ORGANISM: Artificial Sequence
<220> FEATURE:
<223> OTHER INFORMATION: target sequence

<400> SEQUENCE: 88
gacacagaca gacttctaag 20

<210> SEQ ID NO 89
<211> LENGTH: 20
<212> TYPE: DNA
<213> ORGANISM: Artificial Sequence
<220> FEATURE:
<223> OTHER INFORMATION: target sequence

<400> SEQUENCE: 89
agcgacatta caccagcagg 20

<210> SEQ ID NO 90
<211> LENGTH: 20
<212> TYPE: DNA
<213> ORGANISM: Artificial Sequence
<220> FEATURE:
<223> OTHER INFORMATION: target sequence

<400> SEQUENCE: 90
aaccaagagg acatttacat 20

<210> SEQ ID NO 91
<211> LENGTH: 20
<212> TYPE: DNA
<213> ORGANISM: Artificial Sequence
<220> FEATURE:
<223> OTHER INFORMATION: target sequence

<400> SEQUENCE: 91
agaggacatt tacatcacca 20

<210> SEQ ID NO 92
<211> LENGTH: 20
<212> TYPE: DNA
<213> ORGANISM: Artificial Sequence
<220> FEATURE:
<223> OTHER INFORMATION: target sequence

<400> SEQUENCE: 92
acatttacat caccacagaa 20

<210> SEQ ID NO 93
<211> LENGTH: 20
<212> TYPE: DNA
<213> ORGANISM: Artificial Sequence
<220> FEATURE:

<223> OTHER INFORMATION: target sequence

<400> SEQUENCE: 93
tacatcacca cagaaagcct 20

<210> SEQ ID NO 94
<211> LENGTH: 20
<212> TYPE: DNA
<213> ORGANISM: Artificial Sequence
<220> FEATURE:
<223> OTHER INFORMATION: target sequence

<400> SEQUENCE: 94
caccacagaa agccttacca 20

<210> SEQ ID NO 95
<211> LENGTH: 20
<212> TYPE: DNA
<213> ORGANISM: Artificial Sequence
<220> FEATURE:
<223> OTHER INFORMATION: target sequence

<400> SEQUENCE: 95
tatgtgagca cagaccaact 20

<210> SEQ ID NO 96
<211> LENGTH: 20
<212> TYPE: DNA
<213> ORGANISM: Artificial Sequence
<220> FEATURE:
<223> OTHER INFORMATION: target sequence

<400> SEQUENCE: 96
gagcacagac caactgaaca 20

<210> SEQ ID NO 97
<211> LENGTH: 20
<212> TYPE: DNA
<213> ORGANISM: Artificial Sequence
<220> FEATURE:
<223> OTHER INFORMATION: target sequence

<400> SEQUENCE: 97
ccaactgaac aaaatcatgc 20

<210> SEQ ID NO 98
<211> LENGTH: 20
<212> TYPE: DNA
<213> ORGANISM: Artificial Sequence
<220> FEATURE:
<223> OTHER INFORMATION: target sequence

<400> SEQUENCE: 98
tctgctactt tgctgctatg 20

<210> SEQ ID NO 99
<211> LENGTH: 20
<212> TYPE: DNA
<213> ORGANISM: Artificial Sequence
<220> FEATURE:
<223> OTHER INFORMATION: target sequence

<400> SEQUENCE: 99
tttctatagc caaaaatagc 20

<210> SEQ ID NO 100
<211> LENGTH: 20
<212> TYPE: DNA
<213> ORGANISM: Artificial Sequence
<220> FEATURE:
<223> OTHER INFORMATION: target sequence

<400> SEQUENCE: 100
aatagctaaa tacctcaatc 20

<210> SEQ ID NO 101
<211> LENGTH: 20
<212> TYPE: DNA
<213> ORGANISM: Artificial Sequence
<220> FEATURE:
<223> OTHER INFORMATION: target sequence

<400> SEQUENCE: 101
aggtcctaca ggtatggatc 20

<210> SEQ ID NO 102
<211> LENGTH: 20
<212> TYPE: DNA
<213> ORGANISM: Artificial Sequence
<220> FEATURE:
<223> OTHER INFORMATION: target sequence

<400> SEQUENCE: 102
ctacaggtat ggatctctgg 20

<210> SEQ ID NO 103
<211> LENGTH: 20
<212> TYPE: DNA
<213> ORGANISM: Artificial Sequence
<220> FEATURE:
<223> OTHER INFORMATION: target sequence

<400> SEQUENCE: 103
cacagcagct atccttagca 20

<210> SEQ ID NO 104
<211> LENGTH: 20
<212> TYPE: DNA
<213> ORGANISM: Artificial Sequence
<220> FEATURE:
<223> OTHER INFORMATION: target sequence

<400> SEQUENCE: 104
taatccaggc ctaaagacaa 20

<210> SEQ ID NO 105
<211> LENGTH: 20
<212> TYPE: DNA
<213> ORGANISM: Artificial Sequence
<220> FEATURE:
<223> OTHER INFORMATION: target sequence

<400> SEQUENCE: 105
tctaaggagc ctaaattcac 20

<210> SEQ ID NO 106
<211> LENGTH: 20
<212> TYPE: DNA
<213> ORGANISM: Artificial Sequence
<220> FEATURE:
<223> OTHER INFORMATION: target sequence

<400> SEQUENCE: 106
gaacctagga cccatacagc 20

<210> SEQ ID NO 107
<211> LENGTH: 20
<212> TYPE: DNA
<213> ORGANISM: Artificial Sequence
<220> FEATURE:
<223> OTHER INFORMATION: target sequence

<400> SEQUENCE: 107
gctggggaaa acagctgtta 20

<210> SEQ ID NO 108
<211> LENGTH: 20
<212> TYPE: DNA
<213> ORGANISM: Artificial Sequence
<220> FEATURE:
<223> OTHER INFORMATION: target sequence

<400> SEQUENCE: 108
tggtggtaca gtggatgaaa 20

<210> SEQ ID NO 109
<211> LENGTH: 20
<212> TYPE: DNA
<213> ORGANISM: Artificial Sequence
<220> FEATURE:
<223> OTHER INFORMATION: target sequence

<400> SEQUENCE: 109
ctgttgatga aatagtgcaa 20

<210> SEQ ID NO 110
<211> LENGTH: 20
<212> TYPE: DNA
<213> ORGANISM: Artificial Sequence
<220> FEATURE:
<223> OTHER INFORMATION: target sequence

<400> SEQUENCE: 110
tagtgcaacc agatccaccc 20

<210> SEQ ID NO 111
<211> LENGTH: 20
<212> TYPE: DNA
<213> ORGANISM: Artificial Sequence
<220> FEATURE:
<223> OTHER INFORMATION: target sequence

<400> SEQUENCE: 111
gatgggaagc accacgcaat 20

<210> SEQ ID NO 112
<211> LENGTH: 20
<212> TYPE: DNA
<213> ORGANISM: Artificial Sequence
<220> FEATURE:
<223> OTHER INFORMATION: target sequence

<400> SEQUENCE: 112
atggaaaatg atggacccta 20

<210> SEQ ID NO 113
<211> LENGTH: 20

<212> TYPE: DNA
<213> ORGANISM: Artificial Sequence
<220> FEATURE:
<223> OTHER INFORMATION: target sequence

<400> SEQUENCE: 113
cagttccagt gtactcattg 20

<210> SEQ ID NO 114
<211> LENGTH: 20
<212> TYPE: DNA
<213> ORGANISM: Artificial Sequence
<220> FEATURE:
<223> OTHER INFORMATION: target sequence

<400> SEQUENCE: 114
tctggaaatt atggcgagtt 20

<210> SEQ ID NO 115
<211> LENGTH: 20
<212> TYPE: DNA
<213> ORGANISM: Artificial Sequence
<220> FEATURE:
<223> OTHER INFORMATION: target sequence

<400> SEQUENCE: 115
atctttggaa tatttgggct 20

<210> SEQ ID NO 116
<211> LENGTH: 20
<212> TYPE: DNA
<213> ORGANISM: Artificial Sequence
<220> FEATURE:
<223> OTHER INFORMATION: target sequence

<400> SEQUENCE: 116
gcaaaggatt aaaatgctga 20

<210> SEQ ID NO 117
<211> LENGTH: 20
<212> TYPE: DNA
<213> ORGANISM: Artificial Sequence
<220> FEATURE:
<223> OTHER INFORMATION: target sequence

<400> SEQUENCE: 117
tctcctcaag gaaggaaaat 20

<210> SEQ ID NO 118
<211> LENGTH: 20
<212> TYPE: DNA
<213> ORGANISM: Artificial Sequence
<220> FEATURE:
<223> OTHER INFORMATION: target sequence

<400> SEQUENCE: 118
agaggaggtg aacacaatct 20

<210> SEQ ID NO 119
<211> LENGTH: 20
<212> TYPE: DNA
<213> ORGANISM: Artificial Sequence
<220> FEATURE:
<223> OTHER INFORMATION: target sequence

<400> SEQUENCE: 119
acagtgatga ctcttgggtt 20

<210> SEQ ID NO 120
<211> LENGTH: 20
<212> TYPE: DNA
<213> ORGANISM: Artificial Sequence
<220> FEATURE:
<223> OTHER INFORMATION: target sequence

<400> SEQUENCE: 120
gctagatatt gatgagccag 20

<210> SEQ ID NO 121

<400> SEQUENCE: 121

000

<210> SEQ ID NO 122
<211> LENGTH: 20
<212> TYPE: DNA
<213> ORGANISM: Artificial Sequence
<220> FEATURE:
<223> OTHER INFORMATION: target sequence

<400> SEQUENCE: 122
atttcaatgc caatgacata 20

<210> SEQ ID NO 123
<211> LENGTH: 20
<212> TYPE: DNA
<213> ORGANISM: Artificial Sequence
<220> FEATURE:
<223> OTHER INFORMATION: target sequence

<400> SEQUENCE: 123
aagcagatct cttatgcctt 20

<210> SEQ ID NO 124
<211> LENGTH: 20
<212> TYPE: DNA
<213> ORGANISM: Artificial Sequence
<220> FEATURE:
<223> OTHER INFORMATION: target sequence

<400> SEQUENCE: 124
tcctactgaa ggagctgagt 20

<210> SEQ ID NO 125
<211> LENGTH: 20
<212> TYPE: DNA
<213> ORGANISM: Artificial Sequence
<220> FEATURE:
<223> OTHER INFORMATION: target sequence

<400> SEQUENCE: 125
agaataaggc agggatgtcc 20

<210> SEQ ID NO 126
<211> LENGTH: 20
<212> TYPE: DNA
<213> ORGANISM: Artificial Sequence
<220> FEATURE:
<223> OTHER INFORMATION: target sequence

<400> SEQUENCE: 126
acttccttat ggacaatgcc 20

<210> SEQ ID NO 127
<211> LENGTH: 20
<212> TYPE: DNA
<213> ORGANISM: Artificial Sequence
<220> FEATURE:
<223> OTHER INFORMATION: target sequence

<400> SEQUENCE: 127
tgaggcagat gccaaaaagt 20

<210> SEQ ID NO 128
<211> LENGTH: 20
<212> TYPE: DNA
<213> ORGANISM: Artificial Sequence
<220> FEATURE:
<223> OTHER INFORMATION: target sequence

<400> SEQUENCE: 128
cagatgccaa aaagtgcatc 20

<210> SEQ ID NO 129
<211> LENGTH: 20
<212> TYPE: DNA
<213> ORGANISM: Artificial Sequence
<220> FEATURE:
<223> OTHER INFORMATION: target sequence

<400> SEQUENCE: 129
cctcatactc aatgcgactg 20

<210> SEQ ID NO 130
<211> LENGTH: 20
<212> TYPE: DNA
<213> ORGANISM: Artificial Sequence
<220> FEATURE:
<223> OTHER INFORMATION: target sequence

<400> SEQUENCE: 130
tgcccttgcc tgacaaagag 20

<210> SEQ ID NO 131
<211> LENGTH: 20
<212> TYPE: DNA
<213> ORGANISM: Artificial Sequence
<220> FEATURE:
<223> OTHER INFORMATION: target sequence

<400> SEQUENCE: 131
tcatgtggct atgtgagcac 20

<210> SEQ ID NO 132

<400> SEQUENCE: 132

000

<210> SEQ ID NO 133
<211> LENGTH: 20
<212> TYPE: DNA
<213> ORGANISM: Artificial Sequence
<220> FEATURE:
<223> OTHER INFORMATION: target sequence

<400> SEQUENCE: 133
ttcccaagag ctacgtattt 20

<210> SEQ ID NO 134
<211> LENGTH: 20
<212> TYPE: DNA
<213> ORGANISM: Artificial Sequence
<220> FEATURE:
<223> OTHER INFORMATION: target sequence

<400> SEQUENCE: 134
ctgtttagta gcagtgattg 20

<210> SEQ ID NO 135
<211> LENGTH: 20
<212> TYPE: DNA
<213> ORGANISM: Artificial Sequence
<220> FEATURE:
<223> OTHER INFORMATION: target sequence

<400> SEQUENCE: 135
ttgaatgcaa accatagcac 20

<210> SEQ ID NO 136
<211> LENGTH: 20
<212> TYPE: DNA
<213> ORGANISM: Artificial Sequence
<220> FEATURE:
<223> OTHER INFORMATION: target sequence

<400> SEQUENCE: 136
atagtttgga tatgtaaaac 20

<210> SEQ ID NO 137
<211> LENGTH: 20
<212> TYPE: DNA
<213> ORGANISM: Artificial Sequence
<220> FEATURE:
<223> OTHER INFORMATION: target sequence

<400> SEQUENCE: 137
tcaccaaatc ttggttgatg 20

<210> SEQ ID NO 138
<211> LENGTH: 20
<212> TYPE: DNA
<213> ORGANISM: Artificial Sequence
<220> FEATURE:
<223> OTHER INFORMATION: target sequence

<400> SEQUENCE: 138
gagataagat ctatagcctc 20

<210> SEQ ID NO 139
<211> LENGTH: 20
<212> TYPE: DNA
<213> ORGANISM: Artificial Sequence
<220> FEATURE:
<223> OTHER INFORMATION: target sequence

<400> SEQUENCE: 139
agaaactttc tttctcacta 20

<210> SEQ ID NO 140
<211> LENGTH: 20
<212> TYPE: DNA
<213> ORGANISM: Artificial Sequence
<220> FEATURE:
<223> OTHER INFORMATION: target sequence

<400> SEQUENCE: 140
acatcattct tgagagcatt 20

<210> SEQ ID NO 141
<211> LENGTH: 20
<212> TYPE: DNA
<213> ORGANISM: Artificial Sequence
<220> FEATURE:
<223> OTHER INFORMATION: target sequence

<400> SEQUENCE: 141
gaaaagctag aattgagtgt 20

<210> SEQ ID NO 142
<211> LENGTH: 20
<212> TYPE: DNA
<213> ORGANISM: Artificial Sequence
<220> FEATURE:
<223> OTHER INFORMATION: target sequence

<400> SEQUENCE: 142
gctatggttt tctccaagag 20

<210> SEQ ID NO 143
<211> LENGTH: 20
<212> TYPE: DNA
<213> ORGANISM: Artificial Sequence
<220> FEATURE:
<223> OTHER INFORMATION: target sequence

<400> SEQUENCE: 143
taaagtatca tcagtgtaga 20

<210> SEQ ID NO 144
<211> LENGTH: 20
<212> TYPE: DNA
<213> ORGANISM: Artificial Sequence
<220> FEATURE:
<223> OTHER INFORMATION: target sequence

<400> SEQUENCE: 144
taattcaatt caaagctgtg 20

<210> SEQ ID NO 145
<211> LENGTH: 20
<212> TYPE: DNA
<213> ORGANISM: Artificial Sequence
<220> FEATURE:
<223> OTHER INFORMATION: target sequence

<400> SEQUENCE: 145
agctgtgtgt ttggaagact 20

<210> SEQ ID NO 146
<211> LENGTH: 20
<212> TYPE: DNA
<213> ORGANISM: Artificial Sequence
<220> FEATURE:
<223> OTHER INFORMATION: target sequence

<400> SEQUENCE: 146
ttactatttc acaacagcct 20

<210> SEQ ID NO 147
<211> LENGTH: 20
<212> TYPE: DNA
<213> ORGANISM: Artificial Sequence
<220> FEATURE:
<223> OTHER INFORMATION: target sequence

<400> SEQUENCE: 147
cagcctgaca acatttctat 20

<210> SEQ ID NO 148
<211> LENGTH: 20
<212> TYPE: DNA
<213> ORGANISM: Artificial Sequence
<220> FEATURE:
<223> OTHER INFORMATION: target sequence

<400> SEQUENCE: 148
gtctcagaat gtcattttgg 20

<210> SEQ ID NO 149
<211> LENGTH: 20
<212> TYPE: DNA
<213> ORGANISM: Artificial Sequence
<220> FEATURE:
<223> OTHER INFORMATION: target sequence

<400> SEQUENCE: 149
gtggccacat aagccattat 20

<210> SEQ ID NO 150
<211> LENGTH: 20
<212> TYPE: DNA
<213> ORGANISM: Artificial Sequence
<220> FEATURE:
<223> OTHER INFORMATION: target sequence

<400> SEQUENCE: 150
tcaatcaggg tcacataact 20

<210> SEQ ID NO 151
<211> LENGTH: 20
<212> TYPE: DNA
<213> ORGANISM: Artificial Sequence
<220> FEATURE:
<223> OTHER INFORMATION: target sequence

<400> SEQUENCE: 151
tttgaacctc cagcctccat 20

<210> SEQ ID NO 152
<211> LENGTH: 20
<212> TYPE: DNA
<213> ORGANISM: Artificial Sequence
<220> FEATURE:
<223> OTHER INFORMATION: target sequence

<400> SEQUENCE: 152
gtcttgaaag atggacccta 20

<210> SEQ ID NO 153
<211> LENGTH: 20
<212> TYPE: DNA
<213> ORGANISM: Artificial Sequence
<220> FEATURE:
<223> OTHER INFORMATION: target sequence -continued

<400> SEQUENCE: 153
gtttagattc tatctggaga 20

<210> SEQ ID NO 154
<211> LENGTH: 20
<212> TYPE: DNA
<213> ORGANISM: Artificial Sequence
<220> FEATURE:
<223> OTHER INFORMATION: target sequence

<400> SEQUENCE: 154
aaagtaccag aatatttgga 20